US010575834B2

(12) United States Patent
Baym et al.

(10) Patent No.: US 10,575,834 B2
(45) Date of Patent: *Mar. 3, 2020

(54) DEVICES AND METHODS FOR PROFILING MICROBIOTA OF SKIN

(71) Applicant: Elwha LLC, Bellevue, WA (US)

(72) Inventors: Michael H. Baym, Cambridge, MA (US); Roderick A. Hyde, Redmond, WA (US); Jordin T. Kare, San Jose, CA (US); Eric C. Leuthardt, St. Louis, MO (US); Gary L. McKnight, Bothell, WA (US); Tony S. Pan, Bellevue, WA (US); Elizabeth A. Sweeney, Seattle, WA (US); Clarence T. Tegreene, Mercer Island, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 545 days.

This patent is subject to a terminal disclaimer.

(21) Appl. No.: 15/370,668

(22) Filed: Dec. 6, 2016

(65) Prior Publication Data

US 2017/0079627 A1    Mar. 23, 2017

Related U.S. Application Data

(63) Continuation of application No. 14/091,762, filed on Nov. 27, 2013, now Pat. No. 9,526,480.

(51) Int. Cl.
*A61B 10/02* (2006.01)
*A61M 35/00* (2006.01)
(Continued)

(52) U.S. Cl.
CPC ........ *A61B 10/0283* (2013.01); *A61B 5/0071* (2013.01); *A61B 5/443* (2013.01);
(Continued)

(58) Field of Classification Search
USPC ........................................................ 600/476
See application file for complete search history.

(56) References Cited

U.S. PATENT DOCUMENTS

| 4,384,288 A | 5/1983 | Walton |
| 4,446,233 A | 5/1984 | Auditore-Hargreaves et al. |

(Continued)

FOREIGN PATENT DOCUMENTS

| JP | 2002-284618 A | 10/2002 |
| WO | WO 2008/059274 A1 | 5/2008 |

(Continued)

OTHER PUBLICATIONS

Adak et al.; "Bishydrazide Glycoconjugates for Lectin Recognition and Capture of Bacterial Pathogens"; Bioconjug Chem; Nov. 17, 2010; pp. 1-27; vol. 21; No. 11.

(Continued)

*Primary Examiner* — Pierre E Elisca

(57) ABSTRACT

Devices and methods for profiling microbiota of skin are described which include a microbe profiling device including a device head and a hand-held housing, the device head including an epidermis-engaging component and an access window and configured to dislodge microbes from a skin surface, and the hand-held housing defining an opening aligned with the access window, the hand-held housing including a motor operably coupled to a motivatable component, a substrate disposed in relation to the motivatable component and including a microbe-capture region, a location-capture component to detect a location of one or more regions of the skin surface as the epidermis-engaging component contacts said one or more regions, at least one sensor component to detect one or more signals emitted or reflected from the microbe-capture region, and a computing component including circuitry to associate the location of said one (Continued)

or more regions of the skin surface and the detected one or more signals.

41 Claims, 24 Drawing Sheets

(51) Int. Cl.
  *A61B 5/00* (2006.01)
  *A61B 90/98* (2016.01)
  *A61B 90/00* (2016.01)

(52) U.S. Cl.
  CPC ............ *A61B 5/445* (2013.01); *A61B 5/7271* (2013.01); *A61B 5/74* (2013.01); *A61B 90/98* (2016.02); *A61M 35/003* (2013.01); *A61B 5/0077* (2013.01); *A61B 2010/0216* (2013.01); *A61B 2090/3941* (2016.02); *A61B 2090/3975* (2016.02); *A61B 2562/0233* (2013.01)

(56) References Cited

U.S. PATENT DOCUMENTS

| | | | |
|---|---|---|---|
| 5,077,210 A | 12/1991 | Eigler et al. | |
| 5,728,028 A | 3/1998 | Dusch | |
| 6,255,461 B1 | 7/2001 | Mosbach et al. | |
| 6,379,920 B1 | 4/2002 | El-Sayed et al. | |
| 6,433,244 B1 | 8/2002 | Roe et al. | |
| 6,797,522 B1 | 9/2004 | Still et al. | |
| 6,802,811 B1 | 10/2004 | Slepian | |
| 6,961,517 B2 | 11/2005 | Merola et al. | |
| 7,215,976 B2 | 5/2007 | Brideglall | |
| 7,303,875 B1 | 12/2007 | Bock et al. | |
| 7,314,453 B2 | 1/2008 | Kuo | |
| 7,319,038 B2 | 1/2008 | Southard | |
| 7,349,857 B2 | 3/2008 | Manzo | |
| 7,386,333 B1 | 6/2008 | Birecki et al. | |
| 7,494,465 B2 | 2/2009 | Brister et al. | |
| 7,931,592 B2 | 4/2011 | Currie et al. | |
| 8,028,708 B2 | 10/2011 | Molema et al. | |
| 8,109,875 B2 | 2/2012 | Gizewski | |
| 8,358,348 B2 | 1/2013 | Mohammadi et al. | |
| 8,475,789 B2 | 7/2013 | Bisgaard-Frantzen | |
| 8,620,451 B2 | 12/2013 | Kennedy | |
| 9,028,846 B2 | 5/2015 | Eddy | |
| 9,186,278 B2 | 11/2015 | Baym et al. | |
| 9,289,140 B2 | 3/2016 | Ross et al. | |
| 10,434,126 B2* | 10/2019 | Jones .................... A61K 35/38 |
| 2003/0007942 A1 | 1/2003 | Koenig | |
| 2003/0108896 A1 | 6/2003 | Vogt | |
| 2003/0173525 A1 | 9/2003 | Seville | |
| 2003/0225362 A1 | 12/2003 | Currie et al. | |
| 2004/0111035 A1 | 6/2004 | Kondoh et al. | |
| 2004/0125996 A1 | 7/2004 | Eddowes et al. | |
| 2004/0202685 A1 | 10/2004 | Manzo | |
| 2005/0142093 A1 | 6/2005 | Skover et al. | |
| 2005/0154381 A1 | 7/2005 | Altshuler et al. | |
| 2006/0037197 A1 | 2/2006 | Hawes et al. | |
| 2006/0048278 A1 | 3/2006 | Pitsolis | |
| 2006/0052739 A1 | 3/2006 | Henley et al. | |
| 2006/0111620 A1 | 5/2006 | Squilla et al. | |
| 2006/0172318 A1 | 8/2006 | Medinz et al. | |
| 2006/0257993 A1 | 11/2006 | McDevitt et al. | |
| 2007/0059736 A1 | 3/2007 | Saito et al. | |
| 2007/0128589 A1 | 6/2007 | Sanders et al. | |
| 2007/0134337 A1 | 6/2007 | Villanueva et al. | |
| 2007/0134649 A1 | 6/2007 | Kolari et al. | |
| 2008/0060148 A1 | 3/2008 | Pinyayev et al. | |
| 2008/0139974 A1 | 6/2008 | Da Silva | |
| 2008/0262321 A1 | 10/2008 | Erad et al. | |
| 2008/0262576 A1 | 10/2008 | Creamer et al. | |
| 2009/0001012 A1 | 1/2009 | Kepner et al. | |
| 2009/0186342 A1 | 7/2009 | Bruno et al. | |
| 2009/0202045 A1 | 8/2009 | Guertin et al. | |
| 2010/0055161 A1 | 3/2010 | Ahn | |
| 2010/0068247 A1 | 3/2010 | Mou et al. | |
| 2010/0239625 A1 | 9/2010 | Puckett et al. | |
| 2010/0331641 A1 | 12/2010 | Bangera et al. | |
| 2011/0035898 A1 | 2/2011 | Marek et al. | |
| 2011/0040571 A1 | 2/2011 | Warren | |
| 2011/0117025 A1 | 5/2011 | Dacosta et al. | |
| 2011/0172591 A1 | 7/2011 | Babaev | |
| 2011/0212485 A1 | 9/2011 | Mitragotri et al. | |
| 2011/0245094 A1 | 10/2011 | Washburn et al. | |
| 2012/0017929 A1 | 1/2012 | Samain et al. | |
| 2012/0058464 A1 | 3/2012 | Ermantraut et al. | |
| 2012/0065086 A1 | 3/2012 | Benson | |
| 2012/0171193 A1 | 7/2012 | Blaser et al. | |
| 2013/0057866 A1 | 3/2013 | Hillebrand et al. | |
| 2013/0078298 A1 | 3/2013 | Av-Gay et al. | |
| 2013/0079605 A1 | 3/2013 | Bandaru et al. | |
| 2013/0084259 A1 | 4/2013 | Lee | |
| 2013/0218024 A1 | 8/2013 | Boctor et al. | |
| 2013/0224155 A1 | 8/2013 | Kaplan et al. | |
| 2013/0244977 A1 | 9/2013 | Lee et al. | |
| 2013/0338039 A1 | 12/2013 | Mazed et al. | |
| 2014/0309662 A1 | 10/2014 | Brewer et al. | |
| 2015/0054944 A1 | 2/2015 | Bangera et al. | |
| 2015/0054945 A1 | 2/2015 | Bangera et al. | |
| 2015/0148684 A1 | 5/2015 | Baym et al. | |
| 2015/0148685 A1 | 5/2015 | Baym et al. | |
| 2015/0339513 A1 | 11/2015 | Bolea | |
| 2018/0318313 A1* | 11/2018 | Sengupta ................ A61K 45/06 |
| 2018/0357375 A1* | 12/2018 | Cutcliffe ............... C12Q 1/6874 |
| 2018/0363031 A1* | 12/2018 | Becares ............... C12Q 1/6888 |

FOREIGN PATENT DOCUMENTS

| | | |
|---|---|---|
| WO | WO 2008/086596 A1 | 7/2008 |
| WO | WO 2010/093503 A2 | 8/2010 |
| WO | WO 2010/094976 A1 | 8/2010 |
| WO | WO 2011/103144 A1 | 8/2011 |
| WO | WO 2012/044794 A2 | 4/2012 |
| WO | WO 2013/070893 A1 | 5/2013 |

OTHER PUBLICATIONS

Alexander et al.; "Molecular imprinting science and technology: a survey of the literature for the years up to and including 2003"; Journal of Molecular Recognition; published online Jan. 4, 2006; pp. 106-180; vol. 19; John Wiley & Sons, Ltd.

Ammor, Mohammed Salim; "Recent Advances in the Use of Intrinsic Fluorescence for Bacterial Identification and Characterization"; J Fluoresc; Mar. 12, 2007; pp. 1-5; Springer Science + Business Media, LLC.

"Antibody Mimetic"; Wikipedia; Feb. 6, 2011; pp. 1-2; located at: http://en.wikipedia.org/wild/Antibody_mimetic.

Baddour et al.; "High Frequency Ultrasound Imaging of Changes in Cell Structure Including Apoptosis"; PDF created on Aug. 12, 2013; pp. 1-6; IEEE.

Barlen et al.; "Detection of *Salmonella* by Surface Plasmon Resonance"; Sensors; Aug. 7, 2007; pp. 1427-1446; vol. 7; MDPI.

Bhatta et al.; "Use of Fluorescence Spectroscopy to Differentiate Yeast and Bacterial Cells"; Applied Microbiology and Biotechnology; 2006; pp. 121-126; vol. 71; No. 1.

Blank et al.; "A force based protein biochip"; PNAS; Sep. 30, 2003; pp. 11356-11360; vol. 100; No. 20; The National Academy of Sciences of the USA.

Bouchard et al.; "Optical characterization of Pseudomonas fluorescens on meat surfaces using time-resolved fluorescence"; Journal of Biomedical Optics; Jan./Feb. 2006; pp. 014011-1-014011-7; vol. 11; No. 1.

Brennan, John D.; "Preparation and Entrapment of Fluorescently Labeled Proteins for the Development of Reagentless Optical Biosensors"; Journal of Fluorescence; Apr. 28, 1999; pp. 295-312; vol. 9; No. 4; Plenum Publishing Corporation.

Bright et al.; "Regenerable Fiber-Optic-Based Immunosensor"; Analytical Chemistry; May 15, 1990; pp. 1065-1069; vol. 62, No. 10; American Chemical Society.

(56) References Cited

OTHER PUBLICATIONS

Cady et al.; "Optimized linkage and quenching strategies for quantum dot molecular beacons"; Molecular and Cellular Probes; 2007; pp. 116-124; vol. 21; Elsevier Ltd.

Cao et al.; "Molecular Beacon Aptamers for Protein Monitoring in Real-Time and in Homogeneous Solutions"; Current Proteomics; 2005; pp. 31-40; vol. 2; Bentham Science Publishers Ltd.

Chawla et al.; "An overview of passive RFID"; IEEE Applications & Practice; Sep. 2007; pp. 11-17; IEEE.

Chen et al.; "Aptamer from whole-bacterium SELEX as new therapeutic reagent againt virulent *Mycobacterium tuberculosis*"; Biochemical and Biophysical Research Communications; Apr. 11, 2007; pp. 743-748; vol. 357; Elsevier Inc.

Cho et al.; "The Human Microbiome: at the interface a health and disease"; Nat Rev Genet; Oct. 1, 2012; pp. 260-270; vol. 13; No. 4.

Chung et al.; "Size Comparisons among Integral Membrane Transport Protein Homologous in Bacteria, Archaea, and Eucarya"; Journal of Bacteriology; Feb. 2001; pp. 1012-1021; vol. 183; No. 3; American Society for Microbiology.

Cole et al.; "The Ribosomal Database Project: improved alignments and new tools for rRNA analysis"; Nucleic Acids Research; published online Nov. 12, 2008; pp. D141-D145; vol. 37; The Authors(s).

Cowan et al.; "Developement of engineered biofilms on poly-L-lysine patterned surfaces"; Biotechnology Letters; Accepted May 23, 2001; pp. 1235-1241; vol. 23; Kluwer Academic Publishers; Netherlands.

Crowe et al.; "Candida albicans binds human plasminogen: identification of eight plasminogen-binding proteins"; Molecular Microbiology; 2003; pp. 1637-1651; vol. 47; No. 6; Blackwell Publishing Ltd.

De Château et al.; "Protein PAB, an Albumin-binding Bacterial Surface Protein Promoting Growth and Virulence"; The Journal of Biological Chemistry; revised Jul. 22, 1996; pp. 26609-26615; vol. 271; No. 43; Issue of Oct. 25, 1996; The American Society for Biochemistry and Molecular Biology, Inc.; USA.

Didenko et al.; "Horseradish peroxidase-driven Fluorescent labeling of nanotubes with quantum dots"; Biotechniques; NIH Public Access Author Manuscript; Mar. 2006; pp. 295-302; vol. 40; No. 3.

Doornbos et al.; "White Blood Cell Differentiation Using a Solid State Flow Cytometer"; Cytometry; accepted Mar. 16, 1993; pp. 589-594; vol. 14; Wiley-Liss, Inc.

Dwarakanath et al.; "Quantum dot-antibody and aptamer conjugates shift fluorescence upon binding bacteria"; Biochemical and Biophysical Research Communications; Received Oct. 11, 2004; pp. 739-743; vol. 325; Elsevier Inc.

Elston, Dirk M.; "Fluorescence of fungi in superficial and deep fungal infections"; BMC Microbiology; Sep. 24, 2001; pp. 1-4; vol. 1; No. 21; Elston.

Fan et al.; "Sensitive optical biosensors for unlabeled targets: A review"; Analytica Chimica Acta; 2008; pp. 8-26; vol. 620; Elsevier B.V.

Fan et al.; "Structures in Bacillus Subtilis Are Recognized by CD14 in a Lipopolysaccharide Binding Protein-Dependent Reaction"; Infection and Immunity; Jun. 1999; pp. 2964-2968; vol. 67; No. 6; American Society for Microbiology.

Fei-Fei et al.; "One-Shot Learning of Object Categories"; IEEE Transactions on Pattern Analysis and Machine Intelligence; Apr. 2006; pp. 594-611; vol. 28; No. 4; IEEE Computer Society.

Finkenzeller, Klaus; "RFID Handbook: Fundamentals and Applications in Contactless Smart Cards and Identification"; printed on Apr. 16, 2014; pp. 29-59; John Wiley & Sons, Ltd.

Freeman et al.; "Chemiluminescent and Chemiluminescence Resonance Energy Transfer (CRET) Detection of DNA, Metal Ions, and Aptamer—Substrate Complexes Using Hemin/G-Quadruplexes and CdSe/ZnS Quantum Dots"; Journal of the American Chemical Society; 2011; pp. 11597-11604; vol. 133; American Chemical Society.

Gaitanis et al.; "The Malassezia Genus in Skin and Systemic Diseases"; Clinical Microbiology Review; Jan. 2012; pp. 106-141; vol. 25; No. 1; American Society for Microbiology.

Gao et al.; "A Micro Sensing Probe for Detecting Individual Biological Cells"; Proceedings of the 25th Annual International Conference of the IEEE EMBS, Cancun, Mexico; Sep. 17-21, 2003; pp. 3348-3351; IEEE.

Gauglitz et al.; "Host Defense Against Candida albicans and the Role of Patterns-recognition Receptors"; Acta Derm Venereol; 2012; pp. 291-298; vol. 92; The Authors; Journal Compilation: Acta Dermato-Venereologica.

Giana et al.; "Rapid Identification of Bacterial Species by Fluorescence Spectroscopy and Classification Through Principal Components Analysis"; Journal of Fluorescence; Nov. 2003; pp. 489-493; vol. 13, No. 6; Plenum Publishing Corporation.

Gopinath et al.; "Aptamer That Binds to the gD Protein of Herpes Simplex Virus 1 and Efficiently Inhibits Viral Entry"; Journal of Virology; Jun. 2012; pp. 6732-6744; vol. 86; No. 12; American Society for Microbiology.

Graham, Anna R.; "Fungal Autofluorescence with Ultraviolet Illumination"; American Journal of Clinical Pathology; Feb. 1983; pp. 231-234; vol. 79; No. 2; American Society of Clinical Pathologists.

Grice et al.; "A diversity profile of the human skin microbiota"; Genome Reseach; 2008; pp. 1043-1050; vol. 18; Cold Spring Harbor Laboratory Press.

Grice et al.; "The skin microbiome"; Nature Reviews—Microbiology; Apr. 2011; pp. 244-253; vol. 9; Macmillan Publishers Limited.

Griffen et al.; "CORE: A Phylogenetically-Curated 16S rDNA Database of the Core Oral Microbiome"; PLoS One; Apr. 2011; pp. 1-10; vol. 6; Issue 4; Griffen et al.

Hagleitner et al.; "Smart single-chip gas sensor microsystem"; Nature; Nov. 15, 2001; pp. 293-296; vol. 414; Macmillan Magazines Ltd.

Harz et al.; "Vibrational Spectroscopy—A Powerful Tool for the Rapid Identification of Microbial Cells at the Single-Cell Level"; Cytometry Part A Journal of the International Society for Advancement of Cytometry; 2009; pp. 104-113; vol. 75A; International Society for Advancement of Cytometry.

Helm et al.; "Classification and identification of bacteria by Fourier-transform infrared spectroscopy"; Journal of General Microbiology; 1991; pp. 69-79; vol. 137; SGM: Printed in Great Britain.

Hildebrand et al.; "Acoustic microscopy of living cells"; Proc. Natl. Acad. Sci.; Mar. 1981; pp. 1656-1660; vol. 78; No. 3.

Hilton, Peter J.; "Laser induced fluorescence imaging of bacteria"; SPIE; PDF created on Aug. 12, 2013; pp. 1174-1178; vol. 3491.

Hornyak, Tim; "RFID Powder"; Scientific American; Feb. 2008; pp. 68-71; Scientific American, Inc.

Huff et al.; "Light-scattering sensor for real-time identification of Vibrio parahaemolyticus, Vibrio vulnificus and Vibrio cholera colonies on solid agar plate"; Microbial Biotechnology; 2012; pp. 607-620; vol. 5, No. 5; The Authors; Microbial Biotechnology—Society for Applied Microbiology and Blackwell Publishing Ltd.

Ikanovic et al., "Fluorescence Assay Based on Aptamer-Quantum Dot Binding to Bacillus Thuringiensis Spores"; J Fluoresc; 2007; pp. 193-199; vol. 17; Springer Science + Business Media, LLC.

Jaiswal et al.; "Long-term multiple color imaging of live cells using quantum dot bioconjugates"; Nature Biotechnology; Jan. 2003; pp. 47-51; vol. 21; Nature Publishing Group; www.nature.com/naturebiotechnology.

Jhaveri et al.; "In vitro selection of signaling aptamers"; Nature Biotechnology; Dec. 2000; pp. 1293-1297; vol. 18; Nature America Inc.

Kashyap et al.; "Surface Plasmon Resonance-Based Fiber and Planar Waveguide Sensors"; Journal of Sensors; Accepted Jun. 26, 2009; pp. 1-9; vol. 2009; Hindawi Publishing Corporation.

Kim et al.; "Lens-Free Imaging for Biological Applications"; Journal of Laboratory Automation; Jan. 27, 2012; pp. 43-49; vol. 17; No. 1; Society for Laboratory Automation and Screening.

Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.

Koening et al.; "Laser-Induced Autofluorescence for Medical Diagnosis"; Journal of Fluorescence; 1994; pp. 17-40; vol. 4; No. 1; Plenum Publishing Corporation.

(56) References Cited

OTHER PUBLICATIONS

Koo et al.; "Development of a Streptavidin-Conjugated Single-Chain Antibody That Binds Bacillus cereus Spores"; Applied and Environmental Microbiology; Jul. 1998; pp. 2497-2502; vol. 64; No. 7; American Society for Mirobiology.

Kumar et al.; "AnimalLectinDB: An integrated animal Lectin database"; Bioinformation; published Apr. 22, 2011; pp. 134-136; vol. 6; No. 3; Biomedical Informatics.

Kupper et al.; "Generation of human antibody fragments againt *Streptococcus mutans* using a phage display chain Shuffling approach"; BMC Biotechnology; Jan. 25, 2005; pp. 1-12; vol. 5; No. 4; Kupper et al.

Lee et al.; "Graphene-Based Chemiluminescence Resonance Energy Transfer for Homogeneous Immunoassay"; ACS NANO; 2012; pp. 2978-2983; vol. 6; No. 4; American Chemical Society.

Martin et al.; "Learning to Detect Natural Image Boundaries Using Local Brightness, Color, and Texture Cues"; IEEE Transactions on Pattern Analysis and Machine Intelligence; May 2004; pp. 530-549; vol. 26; No. 5; IEEE Computer Society.

Mateus et al.; "Adherence of Cadida albicans to Silicone Induces Immediate Enhanced Tolerance to Fluconazole"; Antimicrobial Agents and Chemotherapy; Sep. 2004; pp. 3358-3366; vol. 48; No. 9; American Society for Microbiology.

Meerwaldt et al., "Skin Autofluorescence, a Measure of Cumulative Metabolic Stess and Advanced Glycation End Products, Predicts Mortality in Hemodialysis Patients"; Journal of the American Society of Nephrology; 2005; pp. 3687-3693; vol. 16; American Society of Nephrology.

Modlin, Robert L.; "Inmate Immunity: Ignored for decades, but not forgotten"; J Invest Dermatol.; Mar. 2012; pp. 882-886; vol. 132; No. 3.

Mohan et al.; "Bokode: Imperceptible Visual tags for Camera Based Interaction from a Distance"; PDF created on Aug. 12, 2013; pp. 1-8; http://cameraculture.media.mit.edu/bokode.

Mohanty et al.; "Micro Electrical Impedence Spectroscopy of Bovine Chromaffin Cells"; printed on Nov. 14, 2013; pp. 1-5.

Murakami et al.; "A miniature confocal optical microscope with mems gimbal scanner"; Transducers '03; The 12*th* International Conference on Solid State Sensors, Actuators and Microsystems, Boston, Jun. 8-12, 2003; pp. 587-590; IEEE.

Nakatsuji et al.; "Antibodies Elicited by Inactivated Propionibacterium acnes-Based Vaccines Exert Protective Immunity and Attenuate the IL-8 Production in Human Sebocytes: Relevance to Therapy for Acne Vulgaris"; Journal of Investigative Dermatology; published online May 8, 2008; pp. 2451-2457; vol. 128; The Society for Investigative Dermatology.

Nitsche et al.; "One-step selection of Vaccinia virus-binding DNA aptamers by MonoLEX"; BMC Biotechniques; published Aug. 15, 2007; pp. 1-12; vol. 7; No. 48; Nitsche et al.

Oberreuter et al.; "Identification of coryneform bacteria and related taxa by Fourier-transform infrared (FT-IR) spectroscopy"; International Journal of Systematic and Evolutionary Microbiology; 2002; pp. 91-100; vol. 52 IUMS Ozalp et al.; "Antimicrobiol apatamers for detection and inhibition of microbiol pathogen growth"; Future Microbiology; Mar. 2013; pp. 387-401; vol. 8, No. 3; 1 page.

PCT International Search Report; International App. No. PCT/US2014/052081; dated Nov. 20, 2014; pp. 1-8.

PCT International Search Report; International App. No. PCT/US2014/052077; dated Nov. 28, 2014; pp. 1-4.

PCT International Search Report; International App. No. PCT/US2014/052086; dated Nov. 28, 2014; pp. 1-3.

PCT International Search Report; International App. No. PCT/US2014/051928; dated Dec. 1, 2014; pp. 1-3.

PCT International Search Report; International App. No. PCT/US2014/051934; dated Dec. 1, 2014; pp. 1-3.

Peppas et al.; "Polymers and Gels as Molecular Recognition Agents"; Pharmaceutical Research; May 2002; pp. 578-587; vol. 19; No. 5; Plenum Publishing Corporation.

Proske et al.; "Aptamers—basic research, drug development, and clinical applications"; Appl Microbiol Biotechnol; Published online Nov. 11, 2005; pp. 367-374; vol. 69; Springer-Verlag.

Quast et al.; "The SILVA ribosomal RNA gene database project: improved data processing and web-based tools"; Nucleic Acids Research; Published Nov. 28, 2012; pp. D590-D596; vol. 41; The Author(s) 2012; Oxford University Press.

Rucker et al., "Functional Antibody Immobilization on 3-Dimensional Polymeric Surfaces Generated by Reactive Ion Etching"; Langmuir; In Final Form Jun. 2, 2005; pp. 7621-7625; vol. 21; American Chemical Society.

Seidl et al.; "Opto-mechnical combination of a line scanning camera and a micro laser scanner system"; PDF created on Aug. 12, 2013; pp. 1-6.

Selinummi et al.; "Software for Quantification of labeled bacteria from digital microscope images by automated image analysis"; BioTechniques; Dec. 2005; pp. 859-863; vol. 39; No. 6.

Snow et al., "Chemical Detection with a Single-Walled Carbon Nanotube Capacitor"; Science; Mar. 25, 2005; pp. 1942-1945; vol. 307; American Association for the Advancement of Science.

Spear et al.; "Isolation characterization, and recovery of small peptide phage display epitopes selected against viable malignant glioma cells"; Cancer Gene Therapy; Recieved Mar. 5, 2001; pp. 506-511; vol. 8, No. 7; Nature Publishing Group.

Sun et al.; "Broadband single cell impedance spetroscopy using maximum length sequences: theoretical analysis and practical considerations"; Measurement Science and Technology; 2007; pp. 2589-2868; vol. 18; IOP Publishing Ltd, UK.

Szeliski, Richard; "Image Alignment and Stitching: A Tutorial"; Computer Graphics and Vision; 2006; pp. 1-104; vol. 2; No. 1; R. Szeliski.

Tachon et al.; "Experimental conditions affect the site of tetrazolium violet reduction in the electron transport chain of Lactococcus lactis"; Microbiology; Accepted Jun. 7, 2009; pp. 2941-2948; vol. 155; SGM.

Terada et al.; "Bacterial adhesion to and viability on positively charged polymer surfaces"; Microbiology; Accepted on Aug. 22, 2006; pp. 3575-3583; vol. 152; SGM.

Ulicny, J.; "Lorenz-Mie Light Scattering in Cellular Biology"; Gen. Physiol. Biophys.; 1992; pp. 133-151; vol. 11.

Vashist, Sandeep Kumar; "A Review of Microcantilevers for Sensing Applications"; AZojono Journal of Nanotechnology Online; Jun. 2007; pp. 1-15; vol. 3; AZoM.com Pty Ltd.

Ye et al.; "Molecularly imprinted polymers as antibody and receptor mimics for assays, sensors and drug discovery"; Anal Bioanal Chem; Published online Jan. 22, 2004; pp. 1887-1897; vol. 378; Springer-Verlag.

Yusa et al.; "Controlled multiple quantum coherences of nuclear spins in a nanometre-scale device"; Nature; Apr. 21, 2005; pp. 1001-1005; vol. 434; Nature Publishing Group.

Zelada-Guillen et al.; "Immediate Detection of Living Bacteria at Ultralow Concentrations Using a Carbon Nanotube Based Potentiometric Aptasensor"; Angew. Chem. Int. Ed; 2009; pp. 1-4; vol. 48; Wiley-VCH Verlag GmbH & Co. KGaA; Weinheim.

Zharov et al.; "In vivo high-speed imaging of individual cells in fast blood flow"; Journal of Biomedical Optics; Sep./Oct. 2006; pp. 054034-1-054034-4; vol. 11; No. 5; SPIE.

Zharov et al.; "In vivo Photothermal Flow Cytometry: Imaging and Detection of Individual Cells in Blood and Lymph Flow"; Journal of Cellular Biochemistry; 2006; pp. 916-932; vol. 97; Wiley-Liss, Inc.

Zitova et al.; "Image registration methods: a survey"; Image and Vision Computing; accepted Jun. 2003; pp. 977-1000; vol. 21; Elsevier B. V.

\* cited by examiner

FIG. 28

2800 Dislodging at least one type of microbe from one or more regions of a skin surface of an individual with an epidermis-engaging component of a hand-held microbe profiling device, the hand-held microbe profiling device including
    a device head including the epidermis-engaging component and at least one access window; and
    a hand-held housing, at least a portion of the hand-held housing defining an opening aligned with the at least one access window, the hand held housing including
        a motor operably coupled to at least one motivatable component;
        a substrate disposed in relation to the at least one motivatable component and positioned in operable communication with the opening defined by the hand-held housing, a surface of the substrate including a microbe-capture region;
        a location-capture component including circuitry to determine a location of said one or more regions of the skin surface of the individual;
        at least one sensor component; and
        a computing component including a microprocessor, the computing component including circuitry 2810 Determining a location of said one or more regions of the skin surface of the individual with the location-capture component of the hand-held microbe profiling device as the epidermis-engaging component of the device head contacts said one or more regions of the skin surface of the individual and generating a location output, the location output including information associated with the location of said one or more regions of the skin surface of the individual 2820 Capturing the dislodged at least one type of microbe through the at least one access window of the device head and the aligned opening defined by the hand-held housing and onto a portion of the microbe-capture region of the substrate 2830 Actuating the at least one motivatable component with the motor to reposition the substrate relative to the opening defined by the hand-held housing 2840 Analyzing the microbe-capture region on the substrate with the at least one sensor component to detect one or more signals emitted or reflected from the at least one type of microbe captured on the microbe-capture region and transforming the detected one or more signals into a sensor output, the sensor output including at least one property of the detected one or more signals emitted or reflected from the at least one type of microbe captured on the microbe-capture region 2850 Receiving the sensor output with the computing component and comparing the at least one property of the detected one or more signals emitted or reflected from the at least one type of microbe captured on the microbe-capture region with a database of reference microbe signal properties 2860 Receiving the location output with the computing component and generating a digital alignment of the location of said one or more regions of the skin surface of the individual with the one or more signals emitted or reflected from the at least one type of microbe captured on the microbe-capture region from said one or more regions of the skin surface of the individual 2870 Generating a microbe profile from the digital alignment, the microbe profile including a spatial distribution of the at least one type of microbe on the skin surface of the individual

FIG. 29

2900 Dislodging at least one type of microbe from one or more regions of a skin surface of an individual with an epidermis-engaging component of a hand-held microbe profiling device, the hand-held microbe profiling device including
- a device head including the epidermis-engaging component and one or more fluid conduits; and
- a hand-held housing, at least a portion of the hand-held housing defining an opening aligned with the one or more fluid conduits, the hand-held housing including
    - a vacuum chamber connected to the device head through the opening defined by the hand-held housing;
    - a motor operably coupled to at least one motivatable component;
    - a substrate disposed in relation to the at least one motivatable component, a surface of the substrate including a microbe-capture region, the substrate including the microbe-capture region at least partially positioned in the vacuum chamber;
    - a location-capture component including circuitry to determine a location of said one or more regions of the skin surface of the individual;
    - at least one sensor component; and
    - a computing component including a microprocessor, the computing component including circuitry

2910 Determining a location of said one or more regions of the skin surface of the individual with the location-capture component of the hand-held microbe profiling device as the epidermis-engaging component of the device head contacts said one or more regions of the skin surface of the individual and generating a location output, the location output including information associated with the location of said one or more regions of the skin surface of the individual

2920 Pulling fluid and the dislodged at least one type of microbe through the one or more fluid conduits of the device head into the vacuum chamber and onto a portion of the microbe-capture region on the substrate at least partially positioned in the vacuum chamber

2930 Actuating the at least one motivatable component with the motor to reposition the substrate in the vacuum chamber

2940 Analyzing the microbe-capture region on the substrate with the at least one sensor component to detect one or more signals emitted or reflected from the at least one type of microbe captured on the microbe-capture region and transforming the detected one or more signals into a sensor output, the sensor output including at least one property of the detected one or more signals emitted or reflected from the at least one type of microbe captured on the microbe-capture region

2950 Receiving the sensor output with the computing component and comparing the at least one property of the detected one or more signals emitted or reflected from the at least one type of microbe captured on the microbe-capture region with a database of reference microbe signal properties

2960 Receiving the location output with the computing component and generating a digital alignment of the location of said one or more regions of the skin surface of the individual with the one or more signals emitted or reflected from the at least one type of microbe captured on the microbe-capture region from said one or more regions of the skin surface of the individual

2970 Generating a microbe profile from the digital alignment with the computing component, the microbe profile including a spatial distribution of the at least one type of microbe on the skin surface of the individual

FIG. 30

3000 Dislodging at least one type of microbe from one or more regions of a skin surface of an individual with an epidermis-engaging component of an hand-held microbe profiling device, the hand-held microbe profiling device including
    a device head including the epidermis-engaging component and at least one access window; and
    a hand-held housing, at least a portion of the hand-held housing defining an opening aligned with the at least one access window, the hand-held housing including
        a motor operably coupled to at least one motivatable component;
        a substrate disposed in relation to the at least one motivatable component and positioned in operable communication with the opening defined by the hand-held housing, a surface of the substrate including a plurality of signal-generating complexes;
    a location-capture component including circuitry to determine a location of said one or more regions of the skin surface of the individual;
    at least one sensor component; and
    a computing component including a microprocessor, the computing component including circuitry 3010 Determining a location of said one or more regions of the skin surface of the individual with the location-capture component of the hand-held microbe profiling device as the epidermis-engaging component of the device head contacts said one or more regions of the skin surface of the individual and generating a location output, the location output including information associated with the location of said one or more regions of the skin surface of the individual 3020 Capturing the dislodged at least one type of microbe through the at least one access window of the device head and the aligned opening defined by the hand-held housing and into contact with a portion of the substrate 3030 Actuating the at least one motivatable component with the motor to reposition the substrate relative to the opening defined by the hand-held housing 3040 Analyzing the substrate with the at least one sensor component to detect one or more signals emitted from at least one of the plurality of signal-generating complexes in response to contact with the dislodged at least one type of microbe and transforming the detected one or more signals into a sensor output, the sensor output including at least one property of the detected one or more signals emitted from the at least one of the plurality of signal-generating complexes 3050 Receiving the sensor output with the computing component and comparing the at least one property of the detected one or more signals emitted from the at least one of the plurality of signal-generating complexes in response to contact with the dislodged at least one type of microbe with a database of properties of reference signal-generating complexes 3060 Receiving the location output with the computing component and generating a digital alignment of the location of said one or more regions of the skin surface of the individual with the detected one or more signals emitted from the at least one of the plurality of signal-generating complexes in response to contact with the dislodged at least one type of microbe 3070 Generating a microbe profile from the digital alignment with the computing component, the microbe profile including a spatial distribution of the at least one type of microbe on the skin surface of the individual

FIG. 31

3100 Dislodging at least one type of microbe from one or more regions of a skin surface of an individual with an epidermis-engaging component of a hand-held microbe profiling device, the hand-held microbe profiling device including
    a device head including the epidermis-engaging component and one or more fluid conduits; and
    a hand-held housing, at least a portion of the hand-held housing defining an opening aligned with the one or more fluid conduits, the hand-held housing including
        a vacuum chamber connected to the device head through the opening defined by the hand-held housing;
        a motor operably coupled to at least one motivatable component;
        a substrate disposed in relation to the at least one motivatable component, a surface of the substrate including a plurality of signal-generating complexes, the substrate including the plurality of signal-generating complexes at least partially positioned in the vacuum chamber;
        a location capture component including circuitry to determine a location of said one or more regions of the skin surface of the individual;
        at least one sensor component; and
        a computing component including a microprocessor, the computing component including circuitry 3110 Determining a location of said one or more regions of the skin surface of the individual with the location-capture component of the hand-held microbe profiling device as the epidermis-engaging component of the device head contacts said one or more regions of the skin surface of the individual and generating a location output, the location output including information associated with the location of said one or more regions of the skin surface of the individual 3120 Pulling fluid and the dislodged at least one type of microbe through the one or more fluid conduits of the device head into the vacuum chamber and into contact with a portion of the plurality of signal-generating complexes on the substrate at least partially positioned in the vacuum chamber 3130 Actuating the at least one motivatable component with the motor to reposition the substrate in the vacuum chamber 3140 Analyzing the substrate with the at least one sensor component to detect one or more signals emitted from at least one of the plurality of signal-generating complexes in response to contact with the dislodged at least one type of microbe and transforming the detected one or more signals into a sensor output, the sensor output including at least one property of the detected one or more signals emitted from the at least one of the plurality of signal-generating complexes 3150 Receiving the sensor output with the computing component and comparing the at least one property of the detected one or more signals emitted from the at least one of the plurality of signal-generating complexes in response to contact with the dislodged at least one type of microbe with a database of properties of reference signal-generating complexes 3160 Receiving the location output with the computing component and generating a digital alignment of the location of said one or more regions of the skin surface of the individual with the detected one or more signals emitted from the at least one of the plurality of signal-generating complexes in response to contract with the dislodged at least one type of microbe from said one or more regions of the skin surface of the individual 3170 Generating a microbe profile from the digital alignment with the computing component, the microbe profile including a spatial distribution of the at least one type of microbe on the skin surface of the individual

FIG. 32

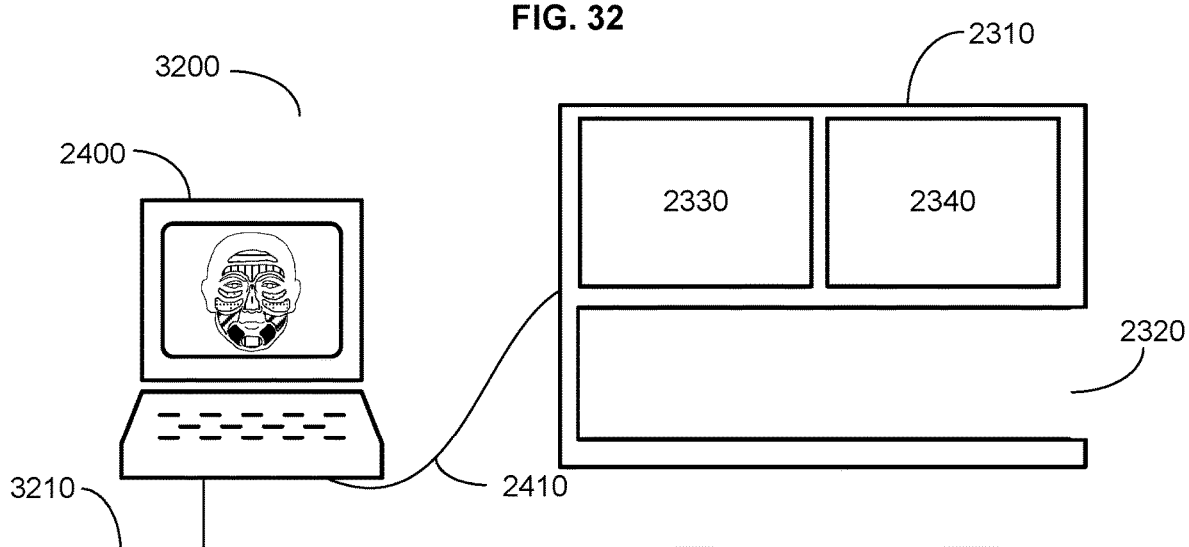

3220 one or more instructions for receiving the location output from the analyzer, the location output including information associated with the location of the one or more regions of the skin surface of the individual 3230 one or more instructions for receiving the sensor output from the analyzer, the sensor output including information associated with the at least one property of the one or more signals emitted or reflected from the microbe-capture region of the replaceable microbe sampling unit 3240 one or more instructions for comparing the at least one property of the one or more signals emitted or reflected from the microbe-capture region of the replaceable microbe sampling unit with a database of reference signal properties 3250 one or more instructions for identifying the at least one type of microbe captured on the microbe-capture region of the replaceable microbe sampling unit based on the comparison of the at least one property of the one or more signals emitted or reflected from the microbe-capture region of the replaceable microbe sampling unit with the database of reference signal properties 3260 one or more instructions for generating an alignment of the location of said one or more regions of the skin surface of the individual with the one or more signals emitted or reflected from the microbe-capture region 3270 one or more instructions for generating the microbe profile based on the alignment, the microbe profile including at least one of an identity or a spatial distribution of the at least one type of microbe on the skin surface of the individual 3280 one or more instructions for reporting the microbe profile to a user 3290 one or more instructions for generating a recommended treatment regimen based on a comparison of the microbe profile with a reference microbe profile; and one or more instructions for reporting the recommended treatment regimen to the user

3320
One or more instructions for receiving a location output, the location output including information associated with a location of one or more regions of a skin surface of an individual 3330
One or more instructions for receiving a sensor output, the sensor output including information associated with at least one property of one or more signals emitted or reflected from at least one type of microbe captured from said one or more regions of the skin surface of the indivdual 3340
One or more instructions for comparing the at least one property of the one or more signals emitted or reflected from the at least one type of microbe captured from said one or more regions of the skin surface of the individual with a database of reference signal properties 3350
One or more instructions for identifying the at least one type of microbe captured from said one or more regions of the skin surface of the individual based on the comparison with the database of reference signal properties 3360
One or more instructions for generating an alignment of the location of said one or more regions of the skin surface of the individual with the one or more signals emitted or reflected from the at least one type of microbe captured from said one or more regions of the skin surface of the individual 3370
One or more instructions for generating a microbe profile based on the alignment, the microbe profile including at least one of an identity or a spatial distribution of the at least one type of microbe on the skin surface of the individual 3380
One or more instructions for reporting the microbe profile to a user 3390
One or more instructions for generating a recommended treatment regimen based on a comparison of the microbe profile with a reference microbe profile; and
One or more instructions for reporting the recommended treatment regimen to the user

DEVICES AND METHODS FOR PROFILING MICROBIOTA OF SKIN

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation of U.S. patent application Ser. No. 14/091,762, entitled DEVICES AND METHODS FOR PROFILING MICROBIOTA OF SKIN, naming Michael H. Baym, Roderick A. Hyde, Jordin T. Kare, Eric C. Leuthardt, Gary L. Mcknight, Tony S. Pan, Elizabeth A. Sweeny, Clarence T. Tegreene, and Lowell L. Wood, Jr. as investors, filed 27 Nov. 2013 , which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a microbe profiling device includes, but is not limited to, a device head including an epidermal-engaging component and at least one access window, the device head configured to dislodge at least one type of microbe from a skin surface of an individual; and a hand-held housing, at least a portion of the hand-held housing defining an opening aligned with the at least one access window, the hand-held housing including a motor operably coupled to at least one motivatable component, the motor including circuitry to drive the at least one motivatable component, a substrate disposed in relation to the at least one motivatable component and configured to be in operable communication with the opening defined by the hand-held housing, a surface of the substrate including a microbe-capture region, the microbe-capture region positioned to capture the at least one type of microbe dislodged by the epidermis-engaging component of the device head, a location-capture component including circuitry to determine a location of one or more regions of the skin surface of the individual as the epidermis-engaging component of the device head contacts said one or more regions of the skin surface of the individual, at least one sensor component including circuitry to detect one or more signals emitted or reflected from the at least one type of microbe captured on the microbe-capture region of the substrate from said one or more regions of the skin surface of the individual and to transform the detected one or more signals into a sensor output, and a computing component including a microprocessor, the computing component including circuitry configured to receive information associated with the location of said one or more regions of the skin surface of the individual from the location-capture component, receive the sensor output from the at least one sensor component, associate the location of said one or more regions of the skin surface of the individual with the detected one or more signals; and output information regarding an association between the location of said one or more regions of the skin surface of the individual and the detected one of more signals. In addition to the foregoing, other device aspects are described in the claims, drawings, and text forming a part of the present disclosure.

In an aspect, a microbe profiling device includes, but is not limited to a device head including an epidermis-engaging component and one or more fluid conduits, the device head configured to dislodge at least one type of microbe from a skin surface of an individual; and a hand-held housing, at least a portion of the hand-held housing defining an opening aligned with the one or more fluid conduits of the device head and including a vacuum chamber connected to the device head through the opening defined by the hand-held housing, the vacuum chamber positioned to pull fluid and the at least one type of microbe dislodged from the skin surface of the individual through the one or more fluid conduits and into the vacuum chamber, a motor operably coupled to at least one motivatable component, the motor including circuitry to drive the at least one motivatable component, a substrate disposed in relation to the at least one motivatable component, a surface of the substrate including a microbe-capture region, the substrate including the microbe-capture region at least partially positioned in the vacuum chamber to come in contact with the fluid and the at least one type of microbe pulled into the vacuum chamber through the one or more fluid conduits, a location-capture component operably coupled to the at least one rotatable component and including circuitry to determine a location of one or more regions of the skin surface of the individual as the epidermis-engaging component of the device head contacts said one or more regions of the skin surface of the individual, at least one sensor component including circuitry to detect one or more signals emitted or reflected from the at least one type of microbe captured on the microbe-capture region of the substrate from said one or more regions of the skin surface of the individual and to transform the detected one or more signals into a sensor output, and a computing component including a microprocessor, the computing component including circuitry configured to receive information associated with the location of said one or more regions of the skin surface of the individual from the location-capture component, receive the sensor output from the at least one sensor component, associate the location of said one or more regions of the skin surface of the individual with the detected one or more signals, and output information regarding an association between the location of said one or more regions of the skin surface of the individual and the detected one or more signals. In addition to the foregoing, other device aspects are described in the claims, drawings, and text forming a part of the present disclosure.

In an aspect, a method of profiling microbiota of a skin surface includes, but is not limited to dislodging at least one type of microbe from one or more regions of a skin surface of an individual with an epidermis-engaging component of a hand-held microbe profiling device, the hand-held microbe profiling device including a device head including the epidermis-engaging component and at least one access window, and a hand-held housing, at least a portion of the hand-held housing defining an opening aligned with the at least one access window, the hand-held housing including a motor operably coupled to at least one motivatable component, a substrate disposed in relation to the at least one motivatable component and positioned in operably communication with the opening defined by the hand-held housing, a surface of the substrate including a microbe-capture region, a location-capture component including circuitry to determine a location of said one or more regions of the skin surface of the individual, at least one sensor component, and a computing component including a microprocessor, the computing component including circuitry; determining a location of said one or more regions of the skin surface of the individual with the location-capture component of the hand-held microbe profiling device as the epidermis-engaging component of the device head contacts said one or more regions of the skin surface of the individual and generating a location output, the location output including the location of said one or more regions of the skin surface of the individual; capturing the dislodged at least one type of microbe through the at least one access window of the device head and the aligned opening defined by the hand-held housing and onto a portion of the microbe-capture region of the substrate; actuating the at least one motivatable component with the motor to reposition the substrate relative to the opening defined by the hand-held housing; analyzing the microbe-capture region on the substrate with the at least one sensor component to detect one or more signals emitted or reflected from the at least one type of microbe captured on the microbe-capture region and transforming the detected one or more signals into a sensor output, the sensor output including at least one property of the detected one or more signals emitted or reflected from the at least one type of microbe captured on the microbe-capture region; receiving the sensor output with the computing component and comparing the at least one property of the detected one or more signals emitted or reflected from the at least one type of microbe captured on the microbe-capture region with a database of reference microbe signal properties; receiving the location output with the computing component and generating a digital alignment of the location of said one or more regions of the skin surface of the individual with the one or more signals emitted or reflected from the at least one type of microbe captured on the microbe-capture region from said one or more regions of the skin surface of the individual; and generating a microbe profile from the digital alignment with the computing component, the microbe profile including a spatial distribution of the at least one type of microbe on the skin surface of the individual. In addition to the foregoing, other method aspects are described in the claims, drawings, and text forming a part of the present disclosure.

In an aspect, a method of profiling microbiota of a skin surface includes, but is not limited to dislodging at least one type of microbe from one or more regions of a skin surface of an individual with an epidermis-engaging component of a hand-held microbe profiling device, the hand-held microbe profiling device including a device head including the epidermis-engaging component and one or more fluid conduits; and a hand-held housing, at least a portion of the hand-held housing defining an opening aligned with the one or more fluid conduits, the hand-held housing including a vacuum chamber connected to the device head through the opening defined by the hand-held housing, a motor operably coupled to at least one motivatable component, a substrate disposed in relation to the at least one motivatable component, a surface of the substrate including a microbe-capture region, the substrate including the microbe-capture region at least partially positioned in the vacuum chamber, a location-capture component including circuitry to determine a location of said one or more regions of the skin surface of the individual, at least one sensor component, and a computing component including a microprocessor, the computing component including circuitry; determining a location of said one or more regions of the skin surface of the individual with the location-capture component of the hand-held microbe profiling device as the epidermis-engaging component of the device head contacts said one or more regions of the skin surface of the individual and generating a location output, the location output including the location of said one or more regions of the skin surface of the individual; pulling the fluid and the dislodged at least one type of microbe through the one or more fluid conduits of the device head into the vacuum chamber and onto a portion of the microbe-capture region of the substrate at least partially positioned in the vacuum chamber; actuating the at least one motivatable component with the motor to reposition the substrate within the vacuum chamber; analyzing the microbe-capture region on the substrate with the at least one sensor component to detect one or more signals emitted or reflected from the at least one type of microbe captured on the microbe-capture region and transforming the detected one or more signals into a sensor output, the sensor output including at least one property of the detected one or more signals emitted or reflected from the at least one type of microbe captured on the microbe-capture region; receiving the sensor output with the computing component and comparing the at least one property of the detected one or more signals emitted or reflected from the at least one type of microbe captured on the microbe-capture region with a database of reference microbe signal properties; receiving the location output with the computing component and generating a digital alignment of the location of said one or more regions of the skin surface of the individual with the one or more signals emitted or reflected from the at least one type of microbe captured on the microbe-capture region from said one or more regions of the skin surface of the individual; and generating a microbe profile from the digital alignment with the computing component, the microbe profile including a spatial distribution of the at least one type of microbe on the skin surface of the individual. In addition to the foregoing, other method aspects are described in the claims, drawings, and text forming a part of the present disclosure.

In an aspect, a microbe profiling device includes, but is not limited to a device head including an epidermis-engaging component and at least one access window, the device head configured to dislodge at least one type of microbe from a skin surface of an individual; and a hand-held housing, at least a portion of the hand-held housing defining an opening aligned with the at least one access window, the hand-held housing including a motor operably coupled to at least one motivatable component, the motor including circuitry to drive the at least one motivatable component, a substrate disposed in relation to the at least one motivatable component and configured to be in operable communication with the opening defined by the hand-held housing, a surface of the substrate including a plurality of signal-generating complexes, at least one of the plurality of signal-generating complexes configured to emit one or more signals in response to contact with the at least one type of microbe dislodged from the skin surface of the individual by the epidermis-engaging component of the device head, a location-capture component including circuitry to determine a location of one or more regions of the skin surface of the individual as the epidermis-engaging component of the device head contacts said one or more regions of the skin surface of the individual, at least one sensor component including circuitry to detect one or more signals emitted from the at least one of the plurality of signal-generating complexes in response to contact with the at least one type of microbe dislodged from the skin surface of the individual and to transform the detected one or more signals into a sensor output, and a computing component including a microprocessor, the computing component including circuitry configured to receive information associated with the location of said one or more regions of the skin surface of the individual from the location-capture component, receive the sensor output from the at least one sensor component, associate the location of said one or more regions of the skin surface of the individual with the detected one or more signals, and generate an output including information regarding an association between the location of said one or more regions of the skin surface of the individual and the detected one or more signals. In addition to the foregoing, other device aspects are described in the claims, drawings, and text forming a part of the present disclosure.

In an aspect, a microbe profiling device includes, but is not limited to a device head including an epidermis-engaging component and one or more fluid conduits, the device head configured to dislodge at least one type of microbe from a skin surface of an individual; and a hand-held housing, at least a portion of the hand-held housing defining an opening aligned with the one or more fluid conduits of the device head and including a vacuum chamber connected to the device head through the opening defined by the hand-held housing, the vacuum chamber positioned to pull fluid and the at least one type of microbe dislodged from the skin surface of the individual through the one or more fluid conduits and into the vacuum chamber, a motor operably coupled to at least one motivatable component, the motor including circuitry to drive the at least one motivatable component, a substrate disposed in relation to the at least one motivatable component, a surface of the substrate including a plurality of signal-generating complexes, at least one of the plurality of signal-generating complexes configured to emit one or more signals in response to contact with the at least one type of microbe, the substrate including the plurality of signal-generating complexes at least partially positioned in the vacuum chamber to come in contact with the fluid and the at least one type of microbe pulled into the vacuum chamber through the one or more fluid conduits, a location-capture component including circuitry to determine a location of one or more regions of the skin surface of the individual as the epidermis-engaging component of the device head contacts said one or more regions of the skin surface of the individual, at least one sensor component including circuitry to detect one or more signals emitted from the at least one of the plurality of signal-generating complexes in response to contact with at least one type of microbe dislodged from the skin surface of the individual and to transform the detected one or more signals into a sensor output, and a computing component including a microprocessor, the computing component including circuitry configured to receive information associated with the location of said one or more regions of the skin surface of the individual from the location-capture component, receive the sensor output from the at least one sensor component, associate the location of said one or more regions of the skin surface of the individual with the detected one or more signals, and generate an output including information regarding an association between the location of said one or more regions of the skin surface of the individual and the detected one or more signals. In addition to the foregoing, other device aspects are described in the claims, drawings, and text forming a part of the present disclosure.

In an aspect, a method of profiling microbiota of a skin surface includes, but is not limited to dislodging at least one type of microbe from one or more regions of a skin surface of an individual with an epidermis-engaging component of a hand-held microbe profiling device, the hand-held microbe profiling device including a device head including the epidermis-engaging component and at least one access window; and a hand-held housing, at least a portion of the hand-held housing defining an opening aligned with the at least one access window, the hand-held housing including a motor operably coupled to at least one motivatable component; a substrate disposed in relation to the at least one motivatable component and positioned in operable communication with the opening defined by the hand-held housing, a surface of the substrate including a plurality of signal-generating complexes; a location-capture component including circuitry to determine a location of said one or more regions of the skin surface of the individual; at least one sensor component; and a computing component including a microprocessor, the computing component including circuitry; determining a location of said one or more regions of the skin surface of the individual with the location-capture component of the hand-held microbe profiling device as the epidermis-engaging component of the device head contacts said one or more regions of the skin surface of the individual and generating a location output, the location output including the location of said one or more regions of the skin surface of the individual; capturing the dislodged at least one type of microbe through the at least one access window of the device head and the aligned opening defined by the hand-held housing and onto a portion of the microbe-capture region of the substrate; actuating the at least one motivatable component with the motor to reposition the substrate relative to the opening defined by the hand-held housing; analyzing the substrate with the at least one sensor component to detect one or more signals emitted from at least one of the plurality of signal-generating complexes in response to contact with the at least one type of microbe dislodged from the skin surface of the individual and transforming the detected one or more signals into a sensor output, the sensor output including at least one property of the detected one or more signals emitted from the at least one of the plurality of signal-generating elements; receiving the sensor output with the computing component and comparing the at least one property of the detected one or more signals emitted from the at least one of the plurality of signal-generating complexes in response to contact with the at least one type of microbe with a database of properties of reference signal-generating complexes; receiving the location output with the computing component and generating a digital alignment of the location of said one or more regions of the skin surface of the individual with the one or more signals emitted from the at least one of the signal-generating complexes in response to contact with the at least one type of microbe from said one or more regions of the skin surface of the individual; and generating a microbe profile from the digital alignment with the computing component, the microbe profile including a spatial distribution of the at least one type of microbe on the skin surface of the individual. In addition to the foregoing, other method aspects are described in the claims, drawings, and text forming a part of the present disclosure.

In an aspect, a method of profiling microbiota of a skin surface includes, but is not limited to dislodging at least one type of microbe from one or more regions of a skin surface of an individual with an epidermis-engaging component of a hand-held microbe profiling device, the hand-held microbe profiling device including a device head including the epidermis-engaging component and one or more fluid conduits; and a hand-held housing, at least a portion of the hand-held housing defining an opening aligned with the one or more fluid conduits, the hand-held housing including a vacuum chamber connected to the device head through the opening defined by the hand-held housing; a motor operably coupled to at least one motivatable component; a substrate disposed in relation to the at least one motivatable component, a surface of the substrate a plurality of signal-generating complexes, the substrate including the plurality of signal-generating complexes positioned adjacent to at least a portion of the vacuum chamber; a location-capture component including circuitry to determine a location of said one or more regions of the skin surface of the individual; at least one sensor component; and a computing component including a microprocessor, the computing component including circuitry; determining a location of said one or more regions of the skin surface of the individual with the location-capture component of the hand-held microbe profiling device as the epidermis-engaging component of the device head contacts said one or more regions of the skin surface of the individual and generating a location output, the location output including the location of said one or more regions of the skin surface of the individual; pulling the fluid and the dislodged at least one type of microbe through the one or more fluid conduits of the device head into the vacuum chamber and into contact with a portion of the plurality signal-generating complexes on the substrate at least partially positioned in the vacuum chamber;

actuating the at least one motivatable component with the motor to reposition the substrate within the vacuum chamber; analyzing the substrate with the at least one sensor component to detect one or more signals emitted from at least one of the plurality of signal-generating complexes in response to contact with the at least one type of microbe dislodged from the skin surface of the individual and transforming the detected one or more signals into a sensor output, the sensor output including at least one property of the detected one or more signals emitted from the at least one of the plurality of signal-generating elements; receiving the sensor output with the computing component and comparing the at least one property of the detected one or more signals emitted from the at least one of the plurality of signal-generating complexes in response to contact with the at least one type of microbe with a database of properties of reference signal-generating complexes; receiving the location output with the computing component and generating a digital alignment of the location of said one or more regions of the skin surface of the individual with the one or more signals emitted from the at least one of the signal-generating complexes in response to contact with the at least one type of microbe from said one or more regions of the skin surface of the individual; and generating a microbe profile from the digital alignment with the computing component, the microbe profile including a spatial distribution of the at least one type of microbe on the skin surface of the individual. In addition to the foregoing, other method aspects are described in the claims, drawings, and text forming a part of the present disclosure.

In an aspect, a microbe profiling system includes, but is not limited to a replaceable microbe sampling unit including a substrate including a microbe-capture region, the microbe-capture region configured to capture at least one type of microbe from one or more regions of a skin surface of an individual, and a location information storage component configured to store information associated with the location of said one or more regions of the skin surface of the individual; and an analyzer including a receiving region sized to accept the replaceable microbe sampling unit, at least one sensor component including circuitry configured to detect one or more signal emitted or reflected from the microbe-capture region of the substrate of the replaceable microbe sampling unit and to transform the detected one or more signals into a sensor output including information associated with at least one property of the detected one or more signals, and at least one location information reader including circuitry to read the information associated with the location of said one or more regions of the skin surface of the individual from the replaceable microbe sampling unit and to transform the information into a location output. In addition to the foregoing, other system aspects are described in the claims, drawings, and text forming a part of the present disclosure.

In an aspect, a microbe profiling system includes, but is not limited to a replaceable microbe sampling unit, a microbe sampling device, an analyzer, and a computing device; the replaceable microbe sampling unit including a substrate including a microbe-capture region, and a location information storage component; the microbe sampling device including a device head including an epidermis-engaging component and at least one access window, the device head configured to dislodge at least one type of microbe from the skin surface of the individual, and a hand-held housing, at least a portion of the hand-held housing defining an opening aligned with the at least one access window of the device head, the hand-held housing including a region sized for receiving the replaceable microbe sampling unit, the region configured to position at least a portion of the substrate of the replaceable microbe sampling unit in operable communication with the opening defined by the hand-held housing, at least one motivatable component operably coupled to the substrate of the replaceable microbe sampling unit, a motor operably coupled to the at least one motivatable component, the motor including circuitry to drive the at least one motivatable component, and a location-capture component including circuitry to determine a location of one or more regions of the skin surface of the individual as the epidermis-engaging component contacts said one or more regions of the skin surface of the individual and to output information associated with the location of said one or more regions of the skin surface of the individual to the information storage component of the replaceable microbe sampling unit; the analyzer including a receiving region sized to accept the replaceable microbe sampling unit, at least one sensor component including circuitry configured to detect one or more signals emitted or reflected from the microbe-capture region of the substrate of the replaceable microbe sampling unit and to transform the detected one or more signals into a sensor output including information associated with at least one property of the detected one or more signals, and at least one location information reader including circuitry to read the information associated with the location of said one or more regions of the skin surface of the individual from the location information storage component of the replaceable microbe sampling unit and to transform the information into a location output; and the computing device including a processor and circuitry configured to receive the location output from the analyzer, the location output including information associated with the location of said one or more regions of the skin surface of the individual, receive the sensor output from the analyzer, the sensor output including the information associated with the at least one property of the detected one or more signals emitted or reflected from the microbe-capture region, compare the at least one property of the one or more signals emitted or reflected from the microbe-capture region with a database of reference signal properties, generate an alignment of the location of said one or more regions of the skin surface of the individual with the detected one or more signals emitted or reflected from the microbe-capture region, generate a microbe profile based on the alignment, the microbe profile including a spatial distribution of at least one type of microbe on the skin surface of the individual, and report the microbe profile to a user. In addition to the foregoing, other system aspects are described in the claims, drawings, and text forming a part of the present disclosure.

In an aspect, a microbe profiling system includes, but is not limited to a replaceable microbe sampling unit, a microbe sampling device, an analyzer, and a computing device; the replaceable microbe sampling unit including at least one motivatable component, a substrate disposed in relation to the at least one motivatable component, the substrate including a microbe-capture region, and a location information storage component; the microbe sampling device including a device head including an epidermis-engaging component and at least one access window, the device head configured to dislodge at least one type of microbe from the skin surface of the individual, and a hand-held housing, at least a portion of the hand-held housing defining an opening aligned with the at least one access window of the device head, the hand-held housing including a region sized for receiving the replaceable microbe sampling unit, the region configured to position at least a portion of the substrate of the replaceable microbe sampling unit in operable communication with the opening defined by the hand-held housing, a motor operably coupled to the at least one motivatable component of the replaceable microbe sampling unit, the motor including circuitry to drive the at least one motivatable component, and a location-capture component including circuitry to determine a location of one or more regions of the skin surface of the individual as the epidermis-engaging component contacts said one or more regions of the skin surface of the individual and to output information associated with the location of said one or more regions of the skin surface of the individual to the location information storage component of the replaceable microbe sampling unit; the analyzer including a receiving region sized to accept the replaceable microbe sampling unit, at least one sensor component including circuitry configured to detect one or more signals emitted or reflected from the microbe-capture region of the substrate of the replaceable microbe sampling unit and to transform the detected one or more signals into a sensor output including information associated with at least one property of the detected one or more signals, and at least one location information reader including circuitry to read the information associated with the location of said one or more regions of the skin surface of the individual from the location information storage component of the replaceable microbe sampling unit and to transform the information into a location output; and the computing device including a processor and including circuitry configured to receive the location output from the analyzer, the location output including information associated with the location of said one or more regions of the skin surface of the individual, receive the sensor output from the analyzer, the sensor output including the information associated with the at least one property of the detected one or more signals emitted or reflected from the microbe-capture region, compare the at least one property of the one or more signals emitted or reflected from the microbe-capture region with a database of reference signal properties, generate an alignment of the location of said one or more regions of the skin surface of the individual with the detected one or more signals emitted or reflected from the microbe-capture region, generate a microbe profile based on the alignment, the microbe profile including a spatial distribution of at least one type of microbe on the skin surface of the individual, and report the microbe profile to a user. In addition to the foregoing, other system aspects are described in the claims, drawings, and text forming a part of the present disclosure.

In an aspect, a microbe sampling unit includes, but is not limited to a substrate including a microbe-capture region, the microbe-capture region configured to capture at least one type of microbe from one or more regions of a skin surface of an individual; and a location information storage component configured to store information associated with the location of the one or more regions of the skin surface of the individual. In addition to the foregoing, other device aspects are described in the claims, drawings, and text forming a part of the present disclosure.

In an aspect, a microbe profiling system includes but is not limited to an analyzer, a computing device, and non-transitory machine readable media; the analyzer including a receiving region sized to accept a replaceable microbe sampling unit, the replaceable microbe sampling unit including a substrate with a microbe-capture region to capture at least one type of microbe from one or more regions of a skin surface of an individual and a location information storage component including information associated with a location of said one or more regions of the skin surface of the individual, at least one sensor component including circuitry configured to detect one or more signals emitted or reflected from the microbe-capture region of the substrate of the replaceable microbe sampling unit and to transform the detected one or more signals into a sensor output including information associated with at least one property of the detected one or more signals, and at least one location information reader including circuitry to read the information associated with the location of said one or more regions of the skin surface of the individual from the location information storage component of the replaceable microbe sampling unit and to transform the information into a location output; the computing device operably coupled to the analyzer and including a processor; the non-transitory machine readable media bearing one or more instructions for generating a microbe profile, the one or more instructions including one or more instructions for receiving the location output from the analyzer, the location output including information associated with the location of said one or more regions of the skin surface of the individual, one or more instructions for receiving a sensor output from an analyzer, the sensor output including information associated with the at least one property of the one or more signals emitted or reflected from the microbe-capture region of the replaceable microbe sampling unit, one or more instructions for comparing the at least one property of the one or more signals emitted or reflected from the microbe-capture region of the replaceable microbe sampling unit with a database of reference signal properties, one or more instructions for identifying the at least one type of microbe captured on the microbe-capture region of the replaceable microbe sampling unit based on the comparison of the at least one property of the one or more signals emitted or reflected from the microbe-capture region of the replaceable microbe sampling unit with the database of reference signal properties, one or more instructions for generating an alignment of the location of said one or more regions of the skin surface of the individual with the one or more signals emitted or reflected from the microbe-capture region, one or more instructions for generating the microbe profile based on the alignment, the microbe profile including at least one of an identity or a spatial distribution of the at least one type of microbe on the skin surface of the individual, and one or more instructions for reporting the microbe profile to a user. In addition to the foregoing, other system aspects are described in the claims, drawings, and text forming a part of the present disclosure.

In an aspect, an article of manufacture includes but is not limited to non-transitory machine readable media bearing one or more instructions for generating a profile of microbiota of skin, the one or more instructions including one or more instructions for receiving a location output, the location output including information associated with a location of one or more regions of a skin surface of an individual; one or more instructions for receiving a sensor output, the sensor output including information associated with at least one property of one or more signals emitted or reflected from at least one type of microbe captured from said one or more regions of the skin surface of the individual; one or more instructions for comparing the at least one property of the one or more signals emitted or reflected from the at least one type of microbe captured from said one or more regions of the skin surface of the individual with a database of reference signal properties; one or more instructions for identifying the at least one type of microbe captured from said one or more regions of the skin surface of the individual based on the comparison with the database of reference signal properties; one or more instructions for generating an alignment of the location of said one or more regions of the skin surface of the individual with the one or more signals emitted or reflected from the at least one type of microbe captured from said one or more regions of the skin surface of the individual; one or more instructions for generating a microbe profile based on the alignment, the microbe profile including at least one of an identity or a spatial distribution of the at least one type of microbe on the skin surface of the individual; and one or more instructions for reporting the microbe profile to a user.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 28 is a flowchart of a method for profiling microbiota of skin.
FIG. 29 is a flowchart of a method for profiling microbiota of skin.
FIG. 30 is a flowchart of a method for profiling microbiota of skin.
FIG. 31 is a flowchart of a method for profiling microbiota of skin.

FIG. 32 is a schematic of a system for generating a profile of microbiota of skin.

FIG. 33 is a schematic of an article of manufacture for generating a profile of microbiota of skin.

DETAILED DESCRIPTION

Figure 1:
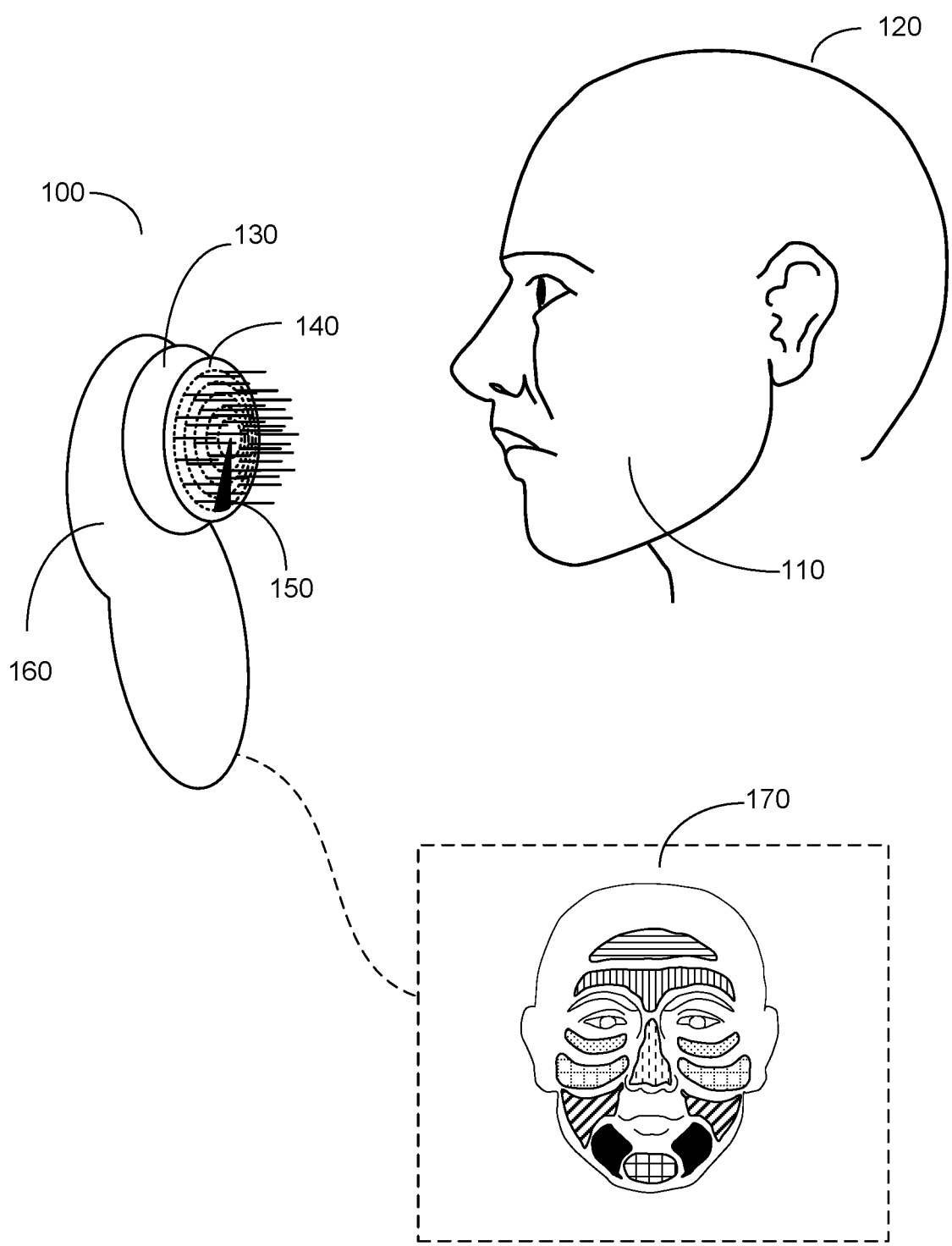
FIG. 1 is a schematic of a microbe profiling device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The skin, the largest organ of the mammalian body, is inhabited at any one time by a diverse array of microbes. Such microbes can include bacteria, fungi, viruses, parasites, archaea, or small arthropods (e.g., mites). Variations in regional properties of the skin, e.g., variations in pH, moisture, pores, texture, and the like, from one body location to another contribute to the spatial diversity of skin-associated microbes. Similarly, the type of microbes and/or spatial distribution of one or more microbes on the skin surface may change in response to cleaning of the skin surface, application of anti-microbial agents, application of irritating agents, e.g., make-up, lotion, or sun screen, or exposure to irritating conditions, e.g., diet, disease, wind, or sun exposure. In some instances, skin-resident microbes on the skin surface, e.g., commensal bacteria, provide a benefit to the individual. For example, Staphylococcus epidermidis has been demonstrated to modulate the host innate immune response, inhibiting the growth of other bacterial pathogens such as *Staphylococcus aureus* and Group A *Streptococcus*. See, e.g., Grice & Segre (2011) *Nat. Rev. Microbiol.* 9:244-53, which is incorporated herein by reference. In some instances, microbes have been linked to pathological conditions including acne, psoriasis, and atopic dermatitis. See, e.g., Cho & Blaser (2012) *Nat. Rev. Genet.* 13:260-270, which is incorporated herein by reference. In general, understanding the identity and spatial distribution of microbes on the skin under normal and/or pathological conditions can contribute to decisions regarding therapeutic, preventative, and/or cosmetic treatments. Described here are embodiments of systems, methods, and devices for assessing the microbiota of skin.

With reference to FIG. 1, shown is an example of a microbe profiling device 100 including components configured to sample and report to a user the identity and the spatial distribution of microbes on a skin surface of an individual, which can serve as a context for one or more devices, systems, and methods described herein. Microbe profiling device 100 is a hand-held device including components to sample at least one type of microbe from the skin surface 110 of individual 120. For example, microbe profiling device 100 can be the size of a common smart phone, or an electric razor. Microbe profiling device 100 includes device head 130 attached to hand-held housing 160. Device head 130 includes an epidermis-engaging component 140, e.g., a brush head, to dislodge at least one type of microbe from skin surface 110 of individual 120. At least a portion of device head 130 includes an access window 150. Access window 150 is an opening defined by device head 130 that aligns with an opening defined by hand-held housing 160, allowing one or more microbes dislodged from skin surface 110 of individual 120 to fall or be pushed through access window 150 and the opening defined by hand-held housing 160 into an interior space that includes at least one motivatable component, e.g., a rotatable component, and a substrate disposed thereto for capturing the one or more microbes. Microbe profiling device 100 includes a location-capture component for determining a location of one or more regions of skin surface 110 contacted by epidermis-engaging component 140. Microbe profiling device 100 further includes at least one sensor component configured to detect one or more signals emitted or reflected from one or more microbes captured on the substrate and to transform the one or more signals into a sensor output, the sensor output including information regarding at least one property and a spatial distribution of the one or more signals. Microbe profiling device 100 further includes a computing component including circuitry to associate the sensor output from the at least one sensor component and the location of the one or more regions of skin surface 110 of individual 120 determined by the location-capture component to generate a microbe profile 170. The microbe profile, including the identity and spatial distribution of at least one type of microbe on the skin surface of the individual can be reported to a user of the device, e.g., individual 120 or another individual, e.g., a service provider, and can be used in determining a recommended treatment regimen to maintain or alter the current types and spatial distribution of microbes on the skin surface of the individual.

Figure 2:
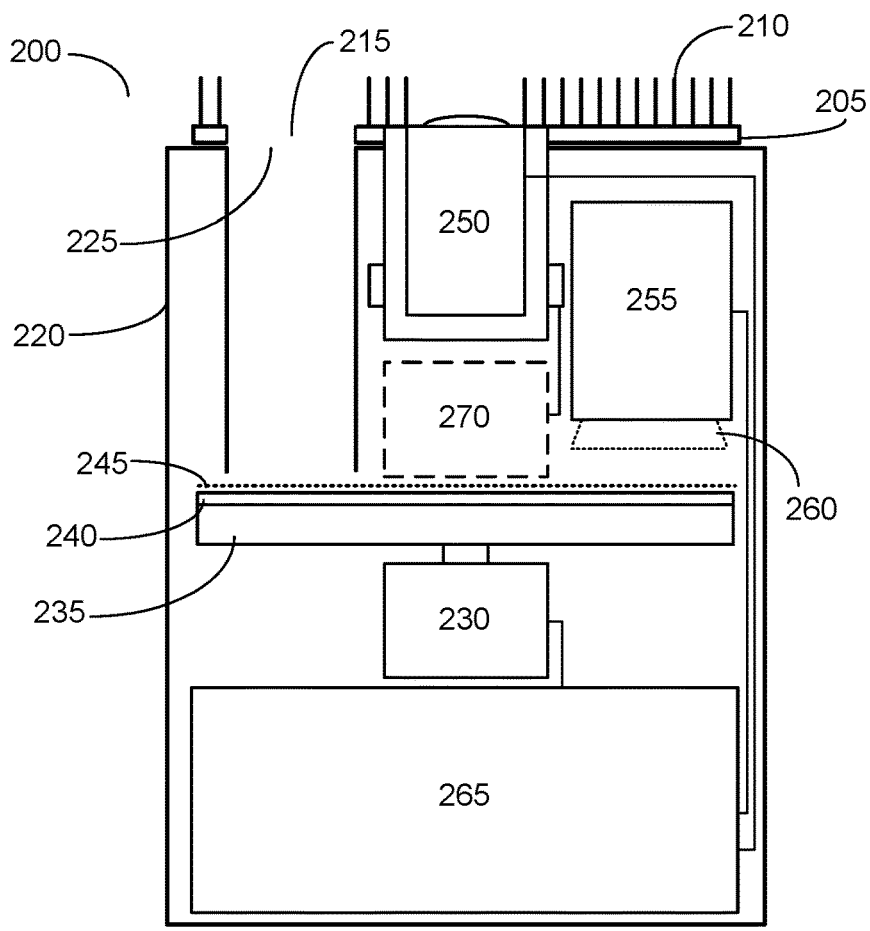
FIG. 2 is a schematic of a microbe profiling device.

FIG. 2 is a cross-sectional view of a schematic of an embodiment of a microbe profiling device. Microbe profiling device 200 includes device head 205 including epidermis-engaging component 210 and at least one access window 215. Device head 205 including epidermis-engaging component 210, e.g., a brush-head, a pad or abrasive surface, or a bladed surface, is configured to dislodge at least one type of microbe from a skin surface of an individual. Microbe profiling device 200 further includes hand-held housing 220 defining an opening 225 which is aligned with at least one access window 215 of device head 205. Hand-held housing 220 of microbe profiling device 200 includes motor 230 operably coupled to at least one motivatable component 235. Motor 230 includes circuitry to drive movement, e.g., rotation, of at least one motivatable component 235. Substrate 240 is disposed in relation to at least one motivatable component 235, e.g., disposed on an outer surface, and is configured to be in operably communication with opening 225 defined by hand-held housing 220. A surface of substrate 240 includes microbe-capture region 245. Microbe-capture region 245 is positioned to capture the at least one type of microbe dislodged by epidermis-engaging component 210 of device head 205. For example, the microbe-capture region 245 can include an adhesive that non-specifically captures microbes dislodged from the skin surface of an individual. For example, the microbe-capture region 245 can include a specific-microbe binding element that specifically captures at least one type of microbe dislodged from the skin surface of an individual.

Hand-held housing 220 further includes location-capture component 250. Location-capture component includes hardware and circuitry configured to determine a location of one or more regions of the skin surface of the individual as epidermis-engaging component 210 of device head 205 contacts said one or more regions of the skin surface of the individual. For example, location-capture device 250 can include an image-capture device, e.g., a small camera equipped with a charge coupled device (CCD). In some embodiments, location-capture component 250 can be operably coupled to at least one motivatable component 235 such that the timing of capturing location information is coordinated with the rotation of the substrate.

Hand-held housing 220 further includes at least one sensor component 255 including circuitry to detect one or more signals emitted or reflected from at least one type of microbe captured on microbe-capture region 245 of substrate 240 from said one or more regions of the skin surface of the individual and to transform the one or more detected signals into a sensor output. In some embodiments, at least one sensor component 255 includes a directed energy source, the directed energy source configured to emit directed energy 260 to elicit one or more signals from microbe-capture region 245. For example, the at least one sensor component 255 can include a sensor system configured to detect autofluorescence emitted from at least one type of microbe on the microbe-capture region in response to a directed energy 260, e.g., a wavelength of excitation electromagnetic energy.

Hand-held housing 220 of microbe profiling device 200 further includes computing component 265 including a microprocessor. Computing component 265 includes circuitry configured to (e.g., includes at least one of software or a processor programed to) control at least one of location-capture component 250 or at least one sensor 255. Computing component 265 may further include a communication link for transmitting and/or receiving data. For example, the communication link can include at least one of a wireless communication link, e.g., Bluetooth or other radio transmission link, or a wired communication link. In some embodiment, computing component 265 of microbe profiling device 200 can include a transmission unit including an antenna for receiving and/or transmitting information. Computing component 265 further includes circuitry configured to receive information associated with the location of said one or more regions of the skin surface of the individual from location-capture component 250, to receive the sensor output from the at least one sensor 255, to associate the location of said one or more regions of the skin surface of the individual with the detected one or more signals, and to generate an output including information regarding an association between the location of said one or more regions of the skin surface of the individual and the detected one or more signals, e.g., a microbe profile of the at least one type of microbe on the skin surface of the individual.

Device Head

Microbe profiling device 200 includes a device head including an epidermis-engaging component. The epidermis-engaging component is configured to dislodge one or more microbes from the skin surface of an individual for capture and analysis by the microbe profiling device. In an aspect, the epidermis-engaging component includes a brush head, e.g., a surface with one or more bristles or protuberances. In an aspect, the brush head is configured to dislodge the at least one type of microbe from the skin surface of the individual by brushing the skin surface and pushing the at least one type of microbe through the access window for capture on the internal substrate.

In an aspect, the epidermis-engaging component includes at least one bladed surface. In an aspect, the at least one bladed surface is a sharp-edged component configured to dislodge the at least one type of microbe from the skin surface of an individual by scraping the skin surface. In an aspect, the at least one bladed surface is made of a corrosive-resistant iron alloy, e.g., stainless steel. In an aspect, the at least one bladed surface includes a coating of at least one material, e.g., a coating of PTFE or carbon. In an aspect, the at least one bladed surface includes at least one stainless steel bladed surface akin to the straight bladed surfaces used in non-electric razors. For example, the device head can include two or more steel blades or may include a single-edged blade, a double-edged blade, a triple-edged blade, or the like.

In an aspect, the epidermis-engaging component includes a pad. In an aspect, the pad can include, in part or in whole, a fabric such as cotton, linen, or synthetic fabric. In an aspect, the epidermis-engaging component includes an abrasive pad. In an aspect, the abrasive pad is configured to dislodge the at least one type of microbe from the skin surface of the individual by rubbing the abrasive surface of the pad across the skin surface. In an aspect, the abrasive pad can include a synthetic or natural abrasive substance. For example, the abrasive pad can include a synthetic or natural sponge. For example, the abrasive pad can include a natural substance that is made from a plant, e.g., from a seed, a nut, cellulose, or fiber. In an aspect, the abrasive pad can include abrasive particulates, non-limiting examples of which include aluminum oxide, silicon carbide, sand, shells, or plant-based particles.

In an aspect, the device head including the epidermis-engaging component is replaceable. For example, a used device head may be replaced with a new device head. In an aspect, the device head including the epidermis-engaging component is interchangeable. For example, a device head including a brush head may be interchangeable with a device head including either at least one bladed surface or an abrasive pad. In an aspect, the entire device head is removable. For example, the device head may attach to the hand-held housing with a fitting, a luer, or a coupling. For example, the device head may snap on and off. For example, the device head may attach to the hand-held housing with a clickable connection. For example, the device head may twist on and off and may attach to the hand-held housing with a female-to-male screwed connection or a luer lock. For example, the device head may attach to the hand-held housing with a magnetic connection. In an aspect, only a part of the device head is removable, e.g., the epidermis-engaging component. For example, the device head can include an abrasive pad that is removed after a single use and replaced with a new abrasive pad. In an aspect, microbe profiling device 200 includes replaceable device heads with varying degrees of abrasiveness. For example a user may have a choice of replaceable device heads, varying in abrasiveness. In an aspect, a less abrasive device head is used on sensitive skin while a more abrasive device head is used on less sensitive skin. In an aspect, different device heads are configured for use on different parts of the body. For example, a more abrasive device head might be used on an extremity or the back of an individual while a less abrasive device head might be used on the face or neck of the individual.

In an aspect, microbe profiling device 200 optionally includes second motor 270 operably coupled to device head 205. Second motor 270 incudes circuitry to move device head 205, e.g., circuitry to rotate, reciprocate, oscillate, or vibrate device head 205. In an aspect, device head 205 is configured for rotary motion in which the entirety of the device head turns in a full circle, moving in one direction. In some embodiments, device head 205 is rotated in one direction over multiple revolutions. In some embodiments, device head 205 is rotated back and forth, changing rotational direction every so many degrees of rotation or every so many seconds or fractions of a second. In an aspect, device head 205 includes two or more separate device head units, each of the device head units rotating in different directions in a counter-rotational manner. In an aspect, the device head is configured for side-to-side motion. In an aspect, the device head is configured for oscillating/rotating motion in which the entire device head oscillates from a center point, but does not rotate in a full circle.

Hand-Held Housing

Microbe profiling device 200 includes a hand-held housing. In an aspect, the hand-held housing is sized for use with one hand. For example, the hand-held housing can be sized for allowing a user to hold the device with a single hand, e.g., the size of an electric razor, and to easily move the device across the skin surface of an individual. In an aspect, the hand-held housing is sized to accommodate the various components of the microbe profiling device, e.g., sized to accommodate at least one motivatable component, a substrate associated with the at least one motivatable component, a location-capture component, at least one sensor component, a computing device, and any additional components, e.g., a power source, a receiver, a transmitter, at least one motor, a user interface, and the like.

In an aspect, the hand-held housing is constructed of plastic. For example, the hand-held housing may be constructed of two or more pieces of molded plastic configured to enclose the various components of the microbe profiling device. In this instance, the two or more pieces of plastic may be held together around the various components of the device by one or more screws, adhesive or glue, laser or heat welding, interlocking pins or snaps, or the like. In an aspect, the hand-held housing is constructed of one or more of plastic, metal, ceramic, resin, rubber, or polymer. For example, the hand-held housing can be constructed of a polymer, e.g., polycarbonate. For example, the hand-held housing can be constructed of a ceramic material, e.g., zirconia and/or alumina (see, e.g., U.S. Patent Application 2013/0078298, which is incorporated herein by reference). In an aspect, the hand-held housing includes an ergonomic design, e.g., features that allow for ease of gripping the microbe profiling device with a single hand. For example, the hand-held housing may include molded exterior portions shaped to accommodate one or more fingers gripping the microbe profiling device.

In an aspect, hand-held housing defines an opening which is aligned with an access window defined by the device head. In an aspect, the opening defined by the hand-held housing is positioned along one edge of the hand-held housing. For example, the opening defined by the hand-held housing may be positioned along a top edge of the hand-held housing and adjacent to the device head.

Motor

In an aspect, the microbe profiling device includes at least one motor operably coupled to at least one motivatable component. In an aspect, the at least one motor is an electric motor. In an aspect, the motor is a rotary shaft motor, such as a conventional DC, pulse, or AC motor. In an aspect, the motor can include a brush DC motor. In an aspect, the motor can include a DC servo. In an aspect, the motor can include a rotary piezoelectric motor. Other non-limiting examples of motors for use in running the at least one motivatable component include a stepper control motor, a brushless DC commutated control motor, or a universal motor. In general, motors for use in small electronics or hand-held devices are known in the art and available from commercial sources.

Power Source

In an aspect, the at least one motor and other components of the microbe profiling device are powered by a power source incorporated into the microbe profiling device. In an aspect, at least one motor and other components of the microbe profiling device are powered by one or more batteries. In an aspect, the one or more batteries include one or more disposable batteries, e.g., cells, buttons, thin-film batteries, or microbatteries. For example, the at least one motor and other components of the microbe profiling device can be powered by a conventional battery, e.g., a disposable 9 volt battery. Non-limiting examples of disposable batteries include zinc-carbon, alkaline, lithium, zinc-chloride, zinc-air, or silver-oxide batteries. In an aspect, the one or more batteries include one or more rechargeable batteries. For example, the at least one motor and other components of the microbe profiling device can be powered by one or more rechargeable lithium-ion batteries. Non-limiting examples of rechargeable batteries include nickel-cadmium, nickel-zinc, nickel metal hydride, silver-zinc, or lithium ion. In an aspect, the at least one motor and other components of the microbe profiling device are powered through kinetic energy, which may include stored kinetic energy.

In an aspect, the at least one motor and other components of the microbe profiling device are powered through an electrical cord accessing power through a common electrical output/socket.

Motivatable Component

The microbe profiling device includes at least one motivatable component. In an aspect, the at least one motivatable component is configured to move a substrate so as to expose all or part of the substrate to at least one type of microbe dislodged from the skin surface with the epidermis-engaging component of the microbe profiling device. In an aspect, the motivatable component is configured to rotate. In an aspect, the motivatable component is configured to move up and down and/or side to side. In an aspect, the motivatable component moves horizontally or vertically in a pattern, e.g., in a grid pattern or other pattern. For example, the motivatable component can include a platform operably coupled to the motor and configured to move up and down and/or side to side.

In some aspects, a single piece of substrate is moved from one position to the next by the at least one motivatable component to capture at least one type of microbe from one or more regions of the skin surface of the individual. For example, a first portion of a single piece of substrate may be used to capture microbes from a first region of the skin surface, and a second portion of the single piece of substrate may be used to capture microbes from a second region of the skin surface, and the at least one motivatable component is used to move the substrate from the first position to the second position. In some aspects, multiple pieces of substrate are used to capture at least one type of microbe from one or more regions of the skin surface of the individual. In an aspect, multiple pieces of substrate are moved by the at least one motivatable component in and out of the path of the dislodged microbes. For example, a first piece of substrate may be used to capture microbes from a first skin region while a second piece of substrate is used to capture microbes from a second skin region. For example, a piece of substrate from a stack of substrates may be picked up by the motivatable component, e.g., a moving arm, moved into position to capture microbes from a first skin region, moved out of position, and released. The process is repeated with at least one second piece of substrate for capturing microbes from at least one second region of the skin surface.

In an aspect, the motivatable component includes at least one substrate transfer component configured to move at least a portion of the substrate. In an aspect, the at least one substrate transfer component facilitates transfer of all or part of the substrate to and from the path including the opening defined by the hand-held housing. In an aspect, the at least one motivatable component includes at least one of a piston, an arm, or a pneumatic component configured to move at least a portion of the substrate into operable communication with the opening defined by the hand-held housing. For example, a piston can be used to push at least a portion of the substrate into the path of the opening defined by the hand-held housing so as to capture at least one type of microbe dislodged from the skin surface of the individual. For example, an arm can be used to pivot or swing a substrate into the path of the opening defined by the hand-held housing so as to capture at least one type of microbe dislodged from the skin surface of the individual.

In an aspect, the at least one motivatable component includes an additional component to facilitate reversible and/or irreversible attachment of the substrate to the motivatable component. In an aspect, the at least one motivatable component includes at least one of a suction component or an adhesive component. For example, a slight vacuum may be used to keep a substrate associated with the at least one motivatable component. For example, a pivoting arm can include a suction component that allows the arm to pick up a piece of substrate, e.g., a piece of filter paper or nitrocellulose, from a stack of substrates, move the substrate in and out of position relative to dislodged microbes, and release the piece of substrate in proximity to at least one sensor component for analysis. For example, an adhesive may be used to adhere the substrate to the motivatable component. In an aspect, the at least one motivatable component includes sprockets, or the like, configured to engage perforations in the substrate.

In an aspect, the at least one motivatable component is a rotatable component. In an aspect, the motivatable component includes at least one rotatable disc. In an aspect, the flat surface of the disc is positioned at a 90 degree angle relative to the path of microbes falling into the microbe profiling device through the access window of the device head and the opening defined by the hand-held housing. In an aspect, the substrate is disposed on the flat surface of the disc. In an aspect, the flat surface of the disc is aligned with the opening defined by the hand-held housing. For example, the substrate can include a disc-shaped piece of filter paper that is disposed on the flat surface of the disc. As the disc is rotated, the substrate, e.g., the filter paper, is advanced from one position to a second position.

In an aspect, the edge of the rotatable disc is positioned in the path of the microbes falling into the microbe profiling device through the access window of the device head and the opening defined by the hand-held housing. In an aspect, the substrate in disposed on the outer edge of the disc. For example, the substrate can include an elongated flexible strip that is disposed, e.g., wound, on the outer edge of the disc. As the disc is rotated, the substrate is advanced from one position to a second position.

In an aspect, the motivatable component includes at least one rotatable reel. For example, the microbe profiling device can include a substrate, e.g., an elongated flexible strip, that is attached at at least one end to the at least one rotatable component. As the at least one rotatable component is rotated, the substrate is advanced from one position to a second position. In an aspect, the at least one rotatable component includes at least one supply rotatable component and/or at least one take-up rotatable component. In an aspect, a first portion of a substrate, e.g., an elongated flexible strip, is wound around an outer surface of a supply rotatable component and a second portion of the substrate is wound around an outer surface of the take-up rotatable component. In an aspect, the at least one rotatable component includes two or more rotatable components.

In an aspect, the at least one motivatable component periodically moves. For example, the at least one motivatable component can periodically rotate a portion of a turn. For example, the at least one motivatable component can rotate a fraction of a full rotation, revealing a fresh portion of the substrate and/or microbe-capture region for contact with microbes. For example, the at least one motivatable component can rotate a fraction of a full rotation every 5 seconds. For example, the at least one motivatable component can rotate a fraction of a full rotation every 1 second, 2 seconds, 5 seconds, 10 seconds, 15 seconds, 20 seconds, 30 seconds, or 60 seconds. In an aspect, the at least one motivatable component rotates a portion of a turn based on a user moving the microbe profiling device to a different region of the skin surface. For example, the at least one motivatable component rotates a portion of a turn as the microbe profiling device is moved across the surface of the skin. In an aspect, an accelerometer is used to detect movement. In an aspect, the location-capture component is used to detect movement based on a detected change in location. In an aspect, a user can control the movement of the at least one motivatable component using an user interface, e.g., a button or switch.

In an aspect, the at least one motivatable component includes at least one conduit including the opening defined by the hand-held housing, the motor including circuitry to drive movement of the motivatable component including the conduit across a surface of the substrate over time. In some embodiments, the motivatable component includes a portion of the hand-held device that moves the opening defined by the hand-held housing relative to an otherwise stationary substrate. For example, the motivatable component can include a rotatable portion on the surface of the hand-held housing adjacent to the device head, the rotatable portion defining an opening that aligns with the access window of the device head. In an aspect, both the rotatable component and the device head rotate in synchrony so as to keep the opening defined by the rotatable component aligned with the access window of the device head. For example, the microbe profiling device can include a vibrating brush head that slowly rotates in synchrony with a rotatable component of the hand-held housing. A conduit for flow of microbes to a stationary substrate positioned within the hand-held housing is formed between an access window of the vibrating brush head aligned with an opening defined by the hand-held housing.

Substrate

The microbe profiling device includes a substrate disposed in relation to the at least one motivatable component and configured to be in operable communication with the opening defined by the hand-held housing. The substrate is positioned so as to capture or to come in contact with one or more microbes dislodged from one or more regions of a skin surface of an individual, the one or more microbes falling, pushed, or pulled through the access window of the device head, through the opening defined by the hand-held housing, and onto the underlying substrate. In an aspect, the substrate is disposed on an outer surface of the at least one motivatable component, e.g., at least one rotatable component, and configured to pass the opening defined by the hand-held housing.

In an aspect, the substrate is disc shaped and configured for placement on a disc shaped motivatable component. In an aspect, the substrate is an elongated flexible strip and configured to be wound around and/or be guided around an outer surface or edge of at least one motivatable component, e.g., a disc or a reel. In an aspect, the substrate includes a sheet. For example, the substrate can include a sheet of material cut into any of a number of dimensions, e.g., square, rectangular, oval, circular, trapezoid, or multi-sided. In an aspect, the substrate is manufactured from cellulose, e.g., paper or nitrocellulose. In an aspect, the substrate is manufactured from plastic. In an aspect, the substrate is manufactured from one or more of plastic, polymer, fabric, cellulose, nitrocellulose, paper, metal, gel, or any other material capable of being manufactured in discs, elongated flexible strips, and/or sheets.

In an aspect, the substrate is about 1 millimeter to about 4 centimeters wide. For example, the substrate can include an elongated flexible strip that is about 1 millimeter to about 4 centimeters wide. For example, the substrate can include a disc that is about 1 millimeter to about 4 centimeters in diameter. For example, the substrate can be 1 millimeter, 2 millimeters, 3 millimeters, 4 millimeters, 5 millimeters, 6 millimeters, 7 millimeters, 8 millimeters, 9 millimeters, 1 centimeter, 1.1 centimeters, 1.2 centimeters, 1.3 centimeters, 1.4 centimeters, 1.5 centimeters, 1.6 centimeters, 1.7 centimeters, 1.8 centimeters, 1.9 centimeters, 2 centimeters, 2.1 centimeters, 2.2 centimeters, 2.3 centimeters, 2.4 centimeters, 2.5 centimeters, 2.6 centimeters, 2.7 centimeters, 2.8 centimeters, 2.9 centimeters, 3 centimeters, 3.1 centimeters, 3.2 centimeters, 3.3 centimeters, 3.4 centimeters, 3.5 centimeters, 3.6 centimeters, 3.7 centimeters, 3.8 centimeters, 3.9 centimeters, or 4 centimeters in width or diameter.

In an aspect, the substrate is about 1 centimeter long to about 10 meters long. For example, the substrate can include a substrate that is an elongated flexible strip that is about 1 centimeter long to about 10 meters long. For example, the substrate can be 1 centimeter, 5 centimeters, 10 centimeters, 20 centimeters, 30 centimeters, 40 centimeters, 50 centimeters, 60 centimeters, 70 centimeters, 80 centimeters, 90 centimeters, 1 meter, 1.5 meters, 2 meters, 2.5 meters, 3 meters, 3.5 meters, 4 meters, 4.5 meters, 5 meters, 5.5 meters, 6 meters, 6.5 meters, 7 meters, 7.5 meters, 8 meters, 8.5 meters, 9 meters, 9.5 meters, or 10 meters in length.

In an aspect, the microbe profiling device includes two or more substrates. For example, the microbe profiling device can include a stack of substrates from which the at least one motivatable component retrieves a substrate for positioning in communication with the opening defined by the hand-held housing. In an aspect, the microbe profiling device includes two or more substrates attached to at least one motivatable component. For example, the microbe profiling device can include a rotating disc or other moveable platform that includes two or more pieces of substrate.

In an aspect, the substrate includes a thin piece of material that is at least partially permeable to the flow of fluid, e.g., air or liquid. For example, the substrate can include a thin piece of material that is loosely woven, e.g., a mesh-like material, through which at least a portion of a fluid flow is able to pass. In an aspect, the substrate includes a thin piece of fluid-permeable material made from plastic, polymer, fabric, cellulose, paper, gel, metal, or a combination thereof through which at least a portion of a fluid flow is able to pass.

Microbe-Capture Region—Non-Specific

The microbe profiling device includes a substrate including a microbe-capture region configured to capture at least one type of microbe dislodged from one or more regions of a skin surface of an individual by the epidermis-engaging component. The at least one type of microbe includes at least one type of bacteria, fungus, virus, parasite, archaea, or small arthropod (e.g., mites). In an aspect, the at least one type of microbe includes at least one type of mutualistic microbe, commensal microbe, or pathogenic microbe. In an aspect, the at least one type of microbe includes at least one type of introduced microbe, e.g., a probiotic. In an aspect, the at least one type of microbe includes at least one type of skin-resident microbe. Non-limiting examples of skin-associated or skin-resident bacteria include proteobacteria, e.g., *Pseudomonas* sp., *Janthinobacterium* sp, *Alphaproteobacteria*, other gammaproteobacteria, and betaproteobacteria; *Actinobacteria*, e.g., *Kocuria* sp., *Propionibacteria* sp.; *Firmicutes*, e.g., *Staphylococcus epidermidis*; *Bacteroidetes*; and *Spirochaetes*. See, e.g., Grice et al. (2008) *Genome Res.* 18:1043-1050; Grice & Segre (2011) *Nat. Rev. Microbiol.* 9:244-253, which are incorporated herein by reference. Non-limiting examples of fungi, including skin-resident or associated types of fungi, include dermatophtyes, e.g., trichophyton, microsporum, epidermophyton, tinea capitis. Other skin-associated fungi include but are not limited to yeast, *Candida*, e.g., *Candida albicans*; and *Malassezia* spp (e.g., *M. dermatis, M. furfur, M. globosa*, and *M. restricta*). See, e.g., Gaitanis et al. (2012) *Clin. Microbiol. Rev.* 25:106-141, which is incorporated herein by reference. Non-limiting examples of skin-associated or skin-resident viruses include herpes simplex virus type I (HSV-1), *herpes zoster, Molluscum contagiosum*, human papillomavirus (HPV), Coxsackie virus A16, and herpes gladiatorum. Non-limiting examples of other parasites resident or associated with a skin surface include skin-associated parasitic arthropods including parasitic mites, e.g., *Demodex* spp including *D. folliculorum* and *D. brevis*, and *Sarcoptes scabiei*, a skin parasite associated with scabies.

Figure 3:
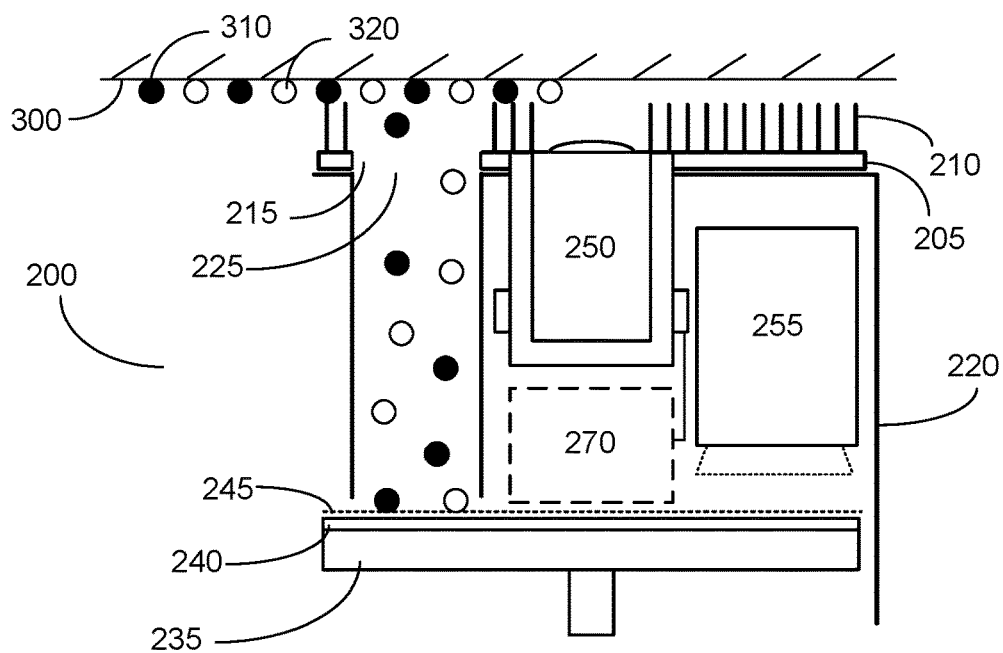
FIG. 3 is a schematic of a portion of a microbe profiling device in contact with a skin surface.

FIG. 3 illustrates a schematic of a microbe profiling device in contact with a skin surface of an individual. A portion of microbe profiling device 200 is shown in contact with skin surface 300. Skin surface 300 includes at least one first type of microbe 310 and at least one second type of microbe 320. FIG. 3 depicts epidermis-engaging component 210 of device head 205 in contact with skin surface 300, which includes at least one first type of microbe 310 and at least one second type of microbe 320. At least one first type of microbe 310 and at least one second type of microbe 320 are dislodged from skin surface 300 and are pushed or fall through access window 215 of device head 205 and through opening 225 defined by hand-held housing 220. Location-capture component 250 is configured to determine the location of said one or more regions of skin surface 300 as epidermis-engaging component 210 is contacting said one or more regions. At least one first type of microbe 310 and at least one second type of microbe 320 are captured on microbe-capture region 245 on substrate 240 disposed on at least one motivatable component 235. At least one motivatable component 235 is operably coupled to a motor and is periodically moved, e.g., rotated, to change the portion of microbe-capture region 245 available for capturing microbes. For example, a first portion of microbe-capture region 245 is positioned to capture at least one first type of microbe 310 and at least one second type of microbe 320. At least one motivatable component 235 is rotated so as to move the first portion of microbe-capture region 245 in range of at least one sensor component 255 and to move a second portion of microbe-capture region 245 in position to capture one or more microbes. In an aspect, microbe profiling device 200 further includes second motor 270 operably coupled to device head 205 and including circuitry to rotate, reciprocate, oscillate, or vibrate device head 205 to aid in dislodging at least one first type of microbe 310 and/or at least one second type of microbe 320 from skin surface 300.

In an aspect, the microbe-capture region includes one or more materials configured to non-selectively capture microbes from the skin surface of the individual. In an aspect, the microbe-capture region includes one or more materials configured to non-selectively capture a representative sample of the microbes, i.e., a representative sample of all microbes, on the skin surface of the individual. In an aspect, the microbe-capture region includes one or more materials configured to non-selectively capture a subtype of microbe, e.g., all of a type of microbe, for example, bacteria versus fungi. In general, the microbe-capture region can include one or more materials that interact with biomolecules on the outer surface of microbes, e.g., proteins, polysaccharides, carbohydrates, phospholipids, proteoglycans, and the like. In an aspect, the one or more materials take advantage of hydrogen bonding, electrostatic and/or hydrophobic interactions to capture microbes from the skin surface onto the microbe-capture region. Non-limiting examples of materials for use in a microbe-capture region include poly-ionic surfaces, e.g., poly-cationic surfaces such as polyamino acids (e.g., polylysine) and fibronectin for binding microbes that have an overall negative surface charge. Other non-limiting examples of materials for use in a microbe-capture region include nitrocellulose, cellulose nitrate, hydrophobic polymers, polyvinylidene fluoride coating, nylon coating, streptavidin or bioting, proteins, peptides, Concanavalin A, epoxy for binding proteins and peptides, aldehydes for immobilizing amino modified oligos and cDNAs, native proteins, tissues, and cells, and amines for immobilizing long oligos and cDNAs.

Figure 4:
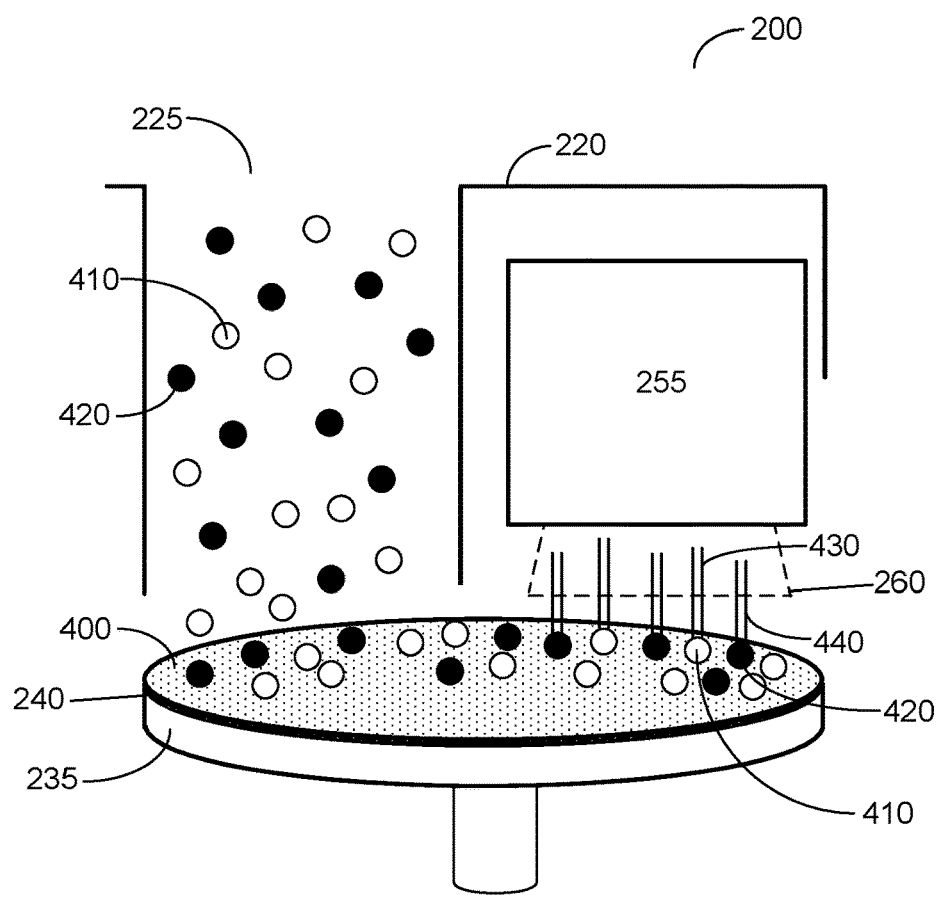
FIG. 4 is a schematic of a portion of a microbe profiling device including a non-specific microbe-capture region.

FIG. 4 is a schematic illustrating an embodiment of a microbe-profiling device including a non-specific microbe-capture region. FIG. 4 shows a schematic of a portion of a microbe profiling device such as that shown in FIG. 2 and includes a portion of hand-held housing 220 defining an opening 225. Shown is substrate 240 disposed on an outer surface of least one motivatable component 235. Substrate 240 includes non-specific microbe-capture region 400. In this example, substrate 240 including non-specific microbe-binding region 400 is positioned to contact at least one first type of microbe 410 and at least one second type of microbe 420 as said microbes fall or are pushed from the access window of the device head (see FIG. 2 or 3) through opening 225 defined by hand-held housing 220. At least one motivatable component 235 is operably coupled to a motor that periodically moves at least one motivatable component 235, advancing the associated non-specific microbe-capture region 400 from a first position in the path of the falling or pushed microbes to a second position in range of at least one sensor component 255. Substrate 240 advances past at least one sensor component 255 where at least one first type of microbe 410 and at least one second type of microbe 420 captured on non-specific microbe-capture region 245 are exposed to directed energy 260. In response to directed energy 260, at least one first type of microbe 410 emits or reflects one or more signals 430 and at least one second type of microbe 420 emits or reflects one or more signals 440. One or more signals 430 and 440 are detected by at least one sensor component 255 and transformed into a sensor output including properties of the one or more signals.

In an aspect, the microbe-capture region covers the entire outer surface of the substrate. In an aspect, the microbe-capture region covers at least a portion of the inner and the outer surfaces of the substrate. In an aspect, the microbe-capture region is an integral part of the substrate, e.g., the entirety of the substrate has microbe-capturing properties. For example, one or more materials used to form the substrate may include properties, e.g., "tackiness" or charge properties, which allow for non-selective capture of one or more types of microbes from a skin surface. For example, the substrate may include a gel-like material that non-selectively captures one or more types of microbes.

In an aspect, the microbe-capture region forms a separate layer on a surface of the substrate. For example, the microbe-capture region may include a material, e.g., a liquid, a gel, a coating, or a spray which is spread on a surface of the substrate to generate the microbe-capture region. For example, the microbe-capture region may include an adhesive material that is added to a surface of the substrate. For example, the microbe-capture region may include a biocompatible pressure-sensitive adhesive that is layered onto a moveable strip of plastic film.

In an aspect, the microbe-capture region is replaceable. In an aspect, the microbe-capture region includes at least one consumable. For example, the at least one consumable can include a consumable liquid, spread, or spray containing one or more materials for applying a microbe-capture region to a surface of the substrate. For example, the substrate may include a washable material, a surface of which is repeatedly coated with one or more material to form the microbe-capture region. For example, the microbe-capture region may include a material, e.g., an adhesive, which can be removed, e.g., washed off, from a surface of the substrate after a first use and replaced with a fresh coating of adhesive for one or more subsequent uses. For example, the microbe-capture region may include one or more strips of material that can be removed from a surface of the substrate and replaced with a new strip or sheet of material. For example, the microbe-capture region may include multiple sheets of material, and after each use, the used sheet is removed revealing a fresh, underlying sheet.

In an aspect, the substrate including the microbe-capture region is a consumable, capable of being replaced. In some embodiments, a used substrate can be replaced with a new substrate including an unused microbe-capture region. For example, a new substrate, e.g., a disc of filter paper or nitrocellulose including a microbe-capture region can be attached to the at least one motivatable component, e.g., a disc. For example, a new substrate, e.g., an elongated flexible strip, may be wound onto the at least one motivatable component, e.g., a rotatable component, of the microbe profiling device. For example, a new substrate, e.g., an elongated flexible strip, includes replaceable cylinders or reels including the new substrate that can be attached to the at least one motivatable component. In some embodiments, the substrate including the microbe-capture region is part of a replaceable cassette that can be inserted into the microbe profiling device.

In an aspect, the microbe-capture region includes a charged surface, e.g., a positively charged surface. In an aspect, the positive charge is provided by the one or more materials used to form the substrate. In an aspect, the positive charge is provided by a positively charged material used to coat at least the outer surface of the substrate to form the microbe-capture region. For example, polymers of secondary and tertiary amino groups can be used to create a positively charged surface capable of binding bacteria. See, e.g., Terada et al. (2006) *Microbiology* 152:3575-3583, which is incorporated herein by reference. For example, poly-L-lysine, a highly positively charged amino acid chain, can be used to bind microbes to a surface. See, e.g., Cowan et al. (2001) *Biotechnology Letters* 23:1235-1241, which is incorporated herein by reference. For example, the positively charged surface can include cationic polymer, e.g., Kymene® or a responsive polymer. See, e.g., U.S. Patent Application 2007/0134337 and WO2010094976, which are incorporated herein by reference.

In an aspect, the microbe-capture region includes at least one of an adhesive, an absorbent, or an adsorbent. For example, the microbe-capture region can include an adhesive or sticky substance that non-selectively captures microbes. In an aspect, the adhesive can include one or more pressure-sensitive adhesive, e.g., adhesive tape. Non-limiting examples of adhesives designed for healthcare use include any of a number of silicone-based pressure sensitive adhesives from, for example, Dow Corning, Midland, Mich. or 3M, St. Paul, Minn. In an aspect, the adhesive forms a separate layer on at least the outer surface of the substrate. For example, a biocompatible adhesive may be applied to the outer surface of a long and narrow piece of Mylar or comparable piece of plastic film.

In an aspect, the microbe-capture region includes a biomolecule-binding polymer. In an aspect, the biomolecule-binding polymer includes a form of cellulose, e.g., nitrocellulose. Binding of biomolecules, e.g., proteins, to nitrocellulose is by a combination of weak intermolecular forces, probably dominated by hydrophobic and van der Waals interactions. In an aspect, biomolecule-binding polymer includes agarose, starch, cellulose acetate, or polyacrylamide. In an aspect, the biomolecule-binding polymer includes one or more polyamino acids. Non-limiting examples of polyamino acids include poly-L-lysine, poly-D-lysine, poly-L-ornithine. For example, poly-L-lysine contains positively charged hydrophilic amino groups that electrostatically bind to the cell surface of bacteria and other cell types.

In an aspect, the microbe-capture region includes one or more biological materials associated with an extracellular matrix, non-limiting examples of which include collagen, laminin, fibronectin, mucopolysaccharides, heparin sulfate, hyaluronidate, and chondroitin sulfate. In an aspect, the microbe-capture region includes albumin. See, e.g., de Chateau et al. (1996) *J. Biol. Chem.* 271:26609-26615, which is incorporated herein by reference.

In an aspect, the microbe-capture region includes one or more microbe-binding lipids. For example, one or more glycosphingolipids and/or one or more phospholipids can be attached to at least the outer surface of a substrate, e.g., a strip of polyvinylidene fluoride (PVDF) membrane, to form the microbe-capture region.

In an aspect, the microbe-capture region includes a gel. Non-limiting examples of gels include at least one of a hydrogel, a colloid, agar, or gelatin. In an aspect, the outer surface of the substrate is coated with a gel. In an aspect, the entirety of the substrate is comprised of a semi-rigid gel. In an aspect, the microbe-capture region includes agar as a layer on the outer surface of the substrate. For example, the substrate may be coated on the outer surface with a thin layer of gel, e.g., agar, to form the microbe-capture region.

Microbe-Capture Region Specific

In an aspect, the microbe-capture region is configured to only capture a specific type or types of microbes. In an aspect, the microbe-capture region includes a plurality of specific microbe-binding elements that specifically recognize at least one type of microbe, e.g., at least one type of bacteria, fungus, virus, or parasite. In an aspect, each of the plurality of specific microbe-binding elements recognizes at least one type of mutualistic microbe, commensal microbe, or pathogenic microbe. In an aspect, each of the plurality of specific microbe-binding elements recognizes at least one type of microbe resident on the skin surface of the individual. In an aspect, the specific microbe-binding element is configured to specifically recognize and bind a particular microbe or class of microbes. In an aspect, the specific microbe-binding element may be specific for a particular type of microbe, e.g., bacteria versus fungus. In an aspect, the specific microbe-binding element may be specific for Gram-positive versus Gram-negative bacteria or for a particular genus of microbes, e.g., *Propionibacterium* versus *Staphylococcus*. In an aspect, the specific microbe-binding element may be specific for a particular species of bacteria within a genus, e.g., *S. aureus* versus *S. epidermidis*.

Figure 5:
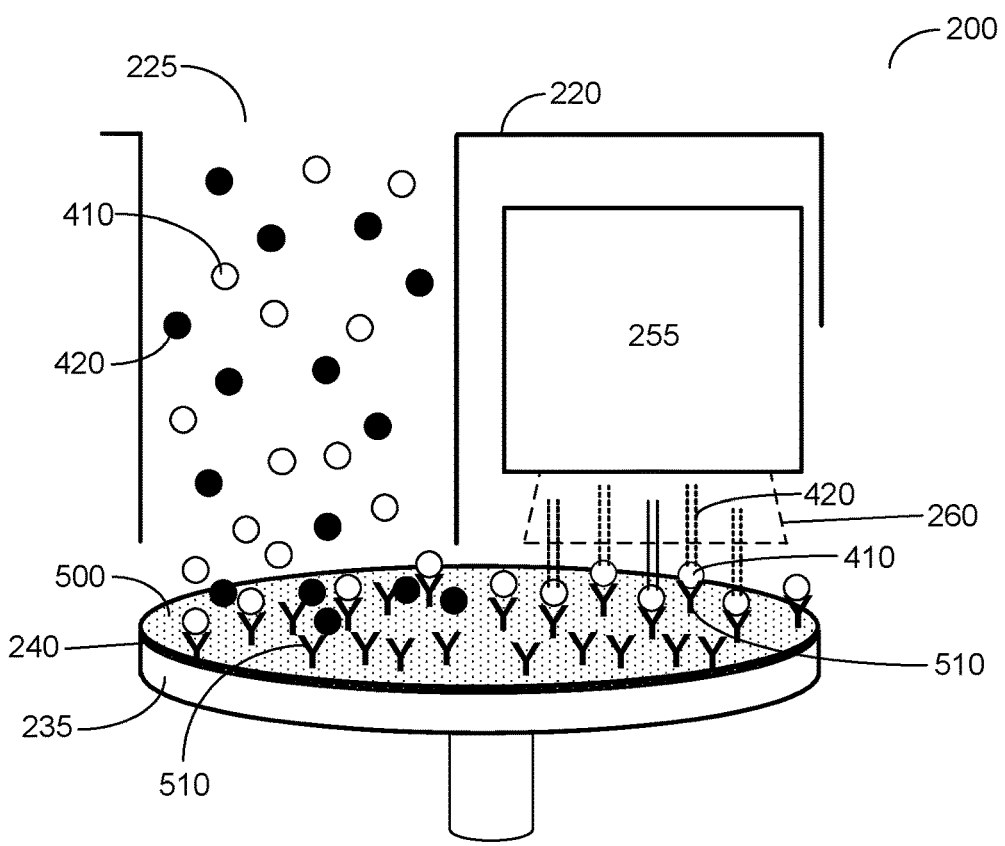
FIG. 5 is a schematic of a portion of a microbe profiling device including a plurality of specific microbe-binding elements.

FIG. 5 is a schematic illustrating an embodiment of a microbe-profiling device including a microbe-capture region including a plurality of specific microbe-binding elements. FIG. 5 shows a schematic of a portion of microbe profiling device 200 including a portion of hand-held housing 220 defining an opening 225. Microbe profiling device 200 includes at least one motivatable component 235 at least partially disposed in opening 225 defined by hand-held housing 220. Substrate 240 is disposed on the outer surface of at least one motivatable component 235. The outer surface of substrate 240 includes microbe-capture region 500 including a plurality of specific microbe-binding elements 510. In this example, substrate 235 including a plurality of specific microbe-binding elements 510 is positioned to come in contact with at least one first type of microbe 410 and at least one second type of microbe 420 that have fallen or been pushed through opening 225 defined by hand-held housing 220 from the access window of an associated device head (not shown). In this example, the plurality of specific microbe-binding elements specifically recognize and bind at least one first type of microbe 410 and do not recognize or bind at least one second type of microbe 420, allowing for specific profiling of just one type of microbe from the skin surface of an individual. In an aspect, a biocompatible fluid, e.g., buffered saline, is used to remove the unbound at least one second type of microbe 420. At least one motivatable component 235 is operably coupled to a motor (as shown in FIG. 2) that periodically moves at least one motivatable component 235, advancing plurality of specific microbe-binding elements 500 from a first position in the path of the falling or pushed microbes to a second position in range of at least one sensor component 255. Substrate 240 advances past at least one sensor component 255 where at least one first type of microbe 410 bound to at least one of plurality of specific microbe-binding elements 510 is exposed to directed energy 260. In response to directed energy 260, at least one first type of microbe 410 emits or reflects one or more signals 430. One or more signals 430 are detected by at least one sensor component 255 and transformed into a sensor output including properties of the one or more signals.

In some embodiments, the microbe-capture region includes a plurality of specific microbe-binding elements of at least one first type to recognize at least one first type of microbe and a plurality of specific microbe-binding elements of at least one second type to recognize at least one second type of microbe. In an aspect, the plurality of specific microbe-binding elements of the at least one first type differs from the plurality of specific microbe-binding elements of the at least one second type but the at least one first type of microbe does not differ from the at least one second type of microbe. For example, a specific antibody and a specific aptamer or a specific first antibody and a specific second antibody can be used to capture a single specific type of microbe, e.g., *Staphylococcus*. In an aspect, the plurality of specific microbe-binding elements of the at least one first type differ from the plurality of specific microbe-binding elements of the at least one second type and the at least one first type of microbe differs from the at least one second type of microbe. For example, the substrate may include a plurality of a first antibody against *Propionibacterium* that specifically recognizes *Propionibacterium* and a plurality of a second antibody against *Staphylococcus* that specifically recognizes *Staphylococcus*. In this example, other microbes dislodged from the skin surface are not recognized by the first or the second antibody and are not captured on the microbe-capture region. In this manner, two or more types of microbes can be specifically captured by the microbe-capture region and profiled.

Specific microbe-binding elements can include substances derived from natural or synthetic sources. Non-limiting examples of specific microbe-binding elements include antibodies, aptamers, oligonucelotides, or anti-16S rRNA ligands. Other non-limiting examples of specific microbe-binding elements include antibody fragments, peptides, peptide nucleic acids, proteins, viruses, lipid, glycolipids, sphingolipids, phospholipids, carbohydrates, enzymes, receptors, lectins, peptide aptamers, bacteria, cells, cell fragments, inorganic molecules, organic molecules, artificial binding substrates (e.g., those formed by molecular imprinting), or combinations thereof.

In an aspect, each specific microbe-binding element recognizes one or more components of at least one type of microbe. In an aspect, the specific microbe-binding element recognizes one or more biomolecules associated with the surface of a microbe, e.g., bacteria, a virus, or a fungus. In an aspect, the specific microbe-binding element recognizes components of microbe surface biomolecules including amino acid sequences, oligosaccharides, proteoglycans, proteins, peptides, and/or lipids. For example, the specific microbe-binding element can recognize and bind teichoic acids and/or peptidoglycans associated with Gram-positive bacteria. For example, the specific microbe-binding element can recognize and bind common lipopolysaccharide moieties, e.g., 2-keto-3-deoxyoctanate, associated with Gram-negative bacteria. For example, the specific microbe-binding element can recognize and bind chitin associated with fungi. In an aspect, the specific microbe-binding element recognizes nucleic acids. For example, the specific microbe-binding element may be configured to recognize and bind one or more DNA or RNA sequence associated with the at least one type of microbe.

In an aspect, the specific microbe-binding element recognizes one or more biomolecules associated with the bacterial outer membrane, cell wall, and/or cytoplasmic membrane. Non-limiting examples of biomolecules associated with the bacterial outer membrane of Gram-negative bacteria include, but are not limited to, lipopolysaccaride and OMP (outer membrane protein) porins, the latter of which are exemplified by OmpC, OmpF and PhoP of *E. coli*. Non-limiting examples of biomolecules associated with the bacterial cell wall of both Gram-positive and Gram-negative bacterial include, but are not limited to, peptidoglycans, i.e., polymers composed of an alternating sequence of N-acetyl-glucoamine and N-acetyl-muraminic acid and crosslinked by amino acids and amino acid derivatives. Non-limiting examples of biomolecules associated with the bacterial cytoplasmic membrane include, but are not limited to, the MPA1-C (also called polysaccharide copolymerase, PCP2a) family of proteins, the MPA2 family of proteins, and the ABC bacteriocin exporter accessory protein (BEA) family of proteins. Other examples of biomolecules associated with bacteria include, but are not limited to, transporters, e.g., sugar porter (major facilitator superfamily), amino-acid/polyamine/organocation (APC) superfamily, cation diffusion facilitator, resistance-nodulation-division type transporter, SecDF, calcium:cation antiporter, inorganic phosphate transporter, monovalent cation:proton antiporter-1, monovalent cation:proton antiporter-2, potassium transporter, nucleobase:cation symporter-2, formate-nitrite transporter, divalent anion:sodium symporter, ammonium transporter, and multi-antimicrobial extrusion; channels, e.g., major intrinsic protein, chloride channel, and metal ion transporter; and primary active transporters, e.g., P-type ATPase, arsenite-antimonite efflux, Type II secretory pathway (SecY), and sodium-transporting carboxylic acid decarboxylase. A number of other potential biomolecules associated with bacteria have been described in Chung, et al. (2001) *J. Bacteriology* 183:1012-1021, which is incorporated herein by reference.

In an aspect, the specific microbe-binding element recognizes one or more biomolecules associated with at least one type of fungus. Non-limiting examples of biomolecules associated with fungi, e.g., biomolecules associated with the outer surface of fungi, include chitins and glucans, e.g., alpha glucans (dextran, glycogen, pullulan, starch) and beta glucans (cellulose, curdlan, laminarin, chrysolaninarin, lentinan, lichenin, pleuran, zymosan).

In an aspect, the specific microbe-binding element recognizes one or more biomolecules associated with at least one type of virus. For example, the specific microbe-binding element may be configured to recognize one or more capsid proteins of a virus. For example, the specific microbe-binding element may be configured to recognize VP5, a major capsid protein of herpes viruses.

In an aspect, the specific microbe-binding element can include a specific microbe-binding antibody. For example, the specific microbe-binding element can include a specific microbe-binding antibody able to recognize and bind one or more bacterium, fungus, and/or virus. Antibodies or fragments thereof for use in generating the specific microbe-binding element can include, but are not limited to, monoclonal antibodies, polyclonal antibodies, Fab fragments of monoclonal antibodies, Fab fragments of polyclonal antibodies, $F(ab')_2$ fragments of monoclonal antibodies, $F(ab')_2$ fragments of polyclonal antibodies, chimeric antibodies, non-human antibodies, fully human antibodies, and synthetic antibodies among others. Single chain or multiple chain antigen-recognition sites can be used. Multiple chain antigen recognition sites can be fused or unfused. Antibody fragments can be produced by modification of whole antibodies or synthesized de novo using recombinant DNA technologies. Antibodies or fragments thereof may be generated using standard methods.

Alternatively, an antibody or fragment thereof directed against one or more microbe may be generated, for example, using phage display technology. See, e.g., Kupper et al. (2005) *BMC Biotechnology* 5:4, which is incorporated herein by reference. An antibody or a fragment thereof, or an artificial antibody, e.g., Affibody® artificial antibodies (Affibody AB, Bromma, Sweden), can be prepared using in silico design (Knappik et al. (2000) *J. Mol. Biol.* 296:57-86, which is incorporated herein by reference). In some embodiments, antibodies directed against specific microbes may be available from a commercial source (from e.g., Novus Biological, Littleton, Colo.; Sigma-Aldrich, St. Louis, Mo.; United States Biological, Swampscott, Mass.). Non-limiting sources of antibodies designed to bind specific microbes, e.g., specific bacteria, fungi, viruses, or parasites, can be found in Linscott's Directory of Immunological and Biological Reagents (accessible through the website address http://www.linscottsdirectory.com/).

In an aspect, the specific microbe-binding element includes a specific microbe-binding aptamer. The specific microbe-binding aptamer can be an oligonucleotide RNA- or DNA-based aptamer configured to recognize and bind one or more of a bacteria, fungus, virus, or parasite. Aptamers are artificial oligonucleotides (DNA or RNA) that can bind to a wide variety of entities (e.g., metal ions, small organic molecules, proteins, and cells) with high selectivity, specificity, and affinity. Aptamers may be isolated from a large library of $10^{14}$ to $10^{15}$ random oligonucleotide sequences using an iterative in vitro selection procedure termed "systemic evolution of ligands by exponential enrichment" (SELEX). See, e.g., Cao, et al (2005) *Current Proteomics* 2:31-40; Proske et al. (2005) *Appl. Microbiol. Biotechnol.* 69:367-374, which are incorporated herein by reference. In general, SELEX may be used to generate aptamers against any of a number of microbial targets, including but not limited to bacteria, fungi, viruses, and parasites. See, e.g., Chen et al. (2007) *Biochem. Biophys, Res. Commun.* 357:743-748, Nitsche et al. (2007) *BMC Biotechnol.* 7:48; Gopinath et al. (2012) *J. Virol.* 86:6732-6744; Low et al. (2009) *Biochem. Biophys, Res. Commun.* 386:544-548, which are incorporated herein by reference.

In an aspect, the specific microbe-binding element includes a novel peptide configured to specifically recognize and bind one or more microbes. Novel peptides that bind specific targets, e.g., a surface component of a bacteria, virus, or fungi, can be generated, for example, using phage display methodologies. See, e.g., Spear, et al. (2001) *Cancer Gene Ther.* 8:506-511, which is incorporated herein by reference.

In an aspect, the specific microbe-binding element can include a ligand that specifically recognizes one or more microbes. For example, the specific microbe-binding element can include CD14, which is a protein associated with monocyte/macrophages and known to bind lipopolysaccharide associated with Gram-negative bacteria as well as lipoteichoic acid associated with the Gram-positive bacteria *Bacillus subtilis* (see, e.g., Fan, et al. (1999) *Infect. Immun.* 67: 2964-2968). In an aspect, the specific microbe-binding element can include all or part of a pattern recognition receptor that recognizes microbe-specific molecules (e.g., bacterial carbohydrates, bacterial or viral DNA or RNA, bacterial peptides, peptidoglycans, lipoteichoic acids, N-formylmethionine, lipoproteins, and fungal glucans). Non-limiting examples of pattern recognition receptors with microbe-binding properties include toll-like receptors, C-type lectin receptors, NOD-like receptors, RIG-I-like receptors, RNA helicases, complement receptors, collectins, ficolins, pentraxins, C-reactive proteins, lipid transferases, and the like. See, e.g., Modlin (2012) *J. Invest. Dermatol.* 132:882-886; Gauglitz et al. (2012) *Acta Derm. Venereol.* 92:291-298, which are incorporated herein by reference.

In an aspect, the specific microbe-binding element includes plasminogen, which recognizes and binds to a fungus, e.g., *Candida albicans*. See, e.g., Crowe et al. (2003) *Mol. Microbiol.* 47:1637-1651, which is incorporated herein by reference.

In an aspect, the specific microbe-binding element includes a lectin. Lectins include carbohydrate-binding proteins that bind cell surface glycoproteins and/or glycolipids. Non-limiting examples of lectins include algal lectins, e.g., b-prism lectin; animal lectins, e.g., tachylectin-2, C-type lectins, C-type lectin-like proteins, calnexin-calreticulin, capsid protein, chitin-binding protein, ficolins, fucolectin, H-type lectins, I-type lectins, sialoadhesin, siglec-5, siglec-7, micronemal protein, P-type lectins, pentrxin, b-trefoil, galectins, congerins, selenocosmia huwena lectin-I, Hcgp-39, Ym1; bacterial lectins, e.g., Pseudomonas PA-IL, Burkholderia lectins, chromobacterium CV-IIL, Pseudomonas PA IIL, Ralsonia RS-ILL, ADP-ribosylating toxin, Ralstonia lectin, Clostridium hemagglutinin, botulinum toxin, tetanus toxin, cyanobacterial lectins, FimH, GafD, PapG, Staphylococcal enterotoxin B, toxin SSL11, toxin SSL5; fungal and yeast lectins, e.g., Aleuria aurantia lectin, integrin-like lectin, Agaricus lectin, Sclerotium lectin, Xerocomus lectin, Laetiporus lectin, Marasmius oreades agglutinin, agrocybe galectin, coprinus galectin-2, Ig-like lectins, L-type lectins; plant lectins, e.g., alpha-D-mannose-specific plant lectins, amaranthus antimicrobial peptide, hevein, pokeweed lectin, Urtica dioica UD, wheat germ WGA-1, WGA-2, WGA-3, artocarpin, artocarpus hirsute AHL, banana lectin, Calsepa, heltuba, jacalin, Maclura pomifera MPA, MornigaM, Parkia lectins, abrin-a, abrus agglutinin, amaranthin, castor bean ricin B, ebulin, mistletoe lectin, TKL-1, cyanovirin-N homolog, and various legume lectins; and viral lectins, e.g., capsid protein, coat protein, fiber knob, hemagglutinin, and tailspike protein. See, e.g., Kumar & Mittal (2011) *Bioinformation* 6:134-136, which is incorporated herein by reference.

In an aspect, the specific microbe-binding element includes an artificial binding substrate formed by the process of molecular imprinting. For example, an artificial binding substrate can be formed by combining a template, e.g., a microbe or part thereof, with functional monomers, e.g., acrylamide and ethylene glycol dimethacrylate, and cross-linking the monomers to form a polymer matrix that surrounds the template. Removal of the template leaves a stable cavity in the polymer matrix that is complementary in size and shape to the template. See, e.g., Alexander, et al. (2006) *J. Mol. Recognit.* 19:106-180, which is incorporated herein by reference. Additional non-limiting examples of functional monomers, cross-linkers and initiators that can be used to generate an artificial binding substrate are provided. See, e.g., U.S. Pat. No. 7,319,038; Alexander, et al. (2006) *J. Mol. Recognit.* 19:106-180, each of which is incorporated herein by reference. In an aspect, hydrogels can be used for molecular imprinting. Other examples of synthetic binders are provided. See, e.g., U.S. Pat. Nos. 6,255,461; and 6,797,522; and Ye and Haupt (2004) *Anal Bioanal Chem.* 378: 1887-1897; Peppas and Huang (2002) *Pharm Res.* 19: 578-587, each of which is incorporated herein by reference.

In an aspect, the specific microbe-binding element recognizes and binds DNA and/or RNA sequences associated with the at least one type of microbe. For example, cytoplasmic components of the microbes, e.g., RNA and/or DNA, can be made accessible to a specific microbe-binding element by lysing the microbes with a lysing agent, e.g., a detergent. For example, the specific microbe-binding element may be a cDNA element engaged in DNA-DNA hybridization with microbe DNA sequence. In an aspect, the specific microbe-binding element may include oligonucleotides capable of binding to unique 16S small subunit ribosomal (rRNA) genes. In an aspect, various phylogenetic markers may be targeted including ribosomal RNA, elongation and initiation factors, RNA polymerase subunits, DNA gyrases, heat shock proteins, and recA proteins.

In an aspect, the plurality of specific microbe-binding elements includes a plurality of specific microbe-binding elements of a single type. In an aspect, "a single type" refers to a type of specific microbe-binding elements, e.g., an antibody versus an aptamer. In an aspect, "a single type" refers to a specific antibody, e.g., a monoclonal antibody with a specific protein sequence or an aptamer with a specific nucleotide sequence. In an aspect, the plurality of specific microbe-binding elements includes a plurality of specific microbe-binding elements of one or more types. In an aspect, the "one or more types" refers to an antibody versus an aptamer. In an aspect, the "one or more types" refers to one or more distinct antibodies with distinct protein sequences and/or recognition specificities or one or more distinct aptamer with distinct nucleotides sequences and/or recognition specificities.

In an aspect, the plurality of specific microbe-binding elements are incorporated into the substrate. In an aspect, the plurality of specific microbe-binding elements are substantially uniformly distributed throughout the substrate. For example, the plurality of specific microbe-binding elements may be uniformly dispersed in a liquid or gelled form during manufacture of the substrate.

In an aspect, the plurality of specific microbe-binding elements are substantially distributed along at least one surface of the substrate. In an aspect, the plurality of specific microbe-binding elements are functionally attached to at least one surface of the substrate. In an aspect, the plurality of specific microbe-binding elements are covalently attached to at least one surface of the substrate through amine groups, carbohydrate groups, sulfhydryl groups, or combinations thereof using a homobifunctional, heterobifunctional, and/or photoreactive crosslinking reagent. For example, the at least one surface of the substrate may include a layer of silane to which is bound one arm of the heterobifunctional crosslinking reagent. The other arm of the heterobifunctional crosslinking reagent is covalently bound at least one type of specific microbe-binding element. See, e.g., U.S. Pat. No. 5,077,210, which is incorporated herein by reference.

In an aspect, the plurality of specific microbe-binding elements are non-covalently attached to at least one surface of the substrate. Non-limiting examples of non-covalent interactions include hydrogen bonds, ionic bonds, van der Waals forces, and hydrophobic interactions. For example, a specific microbe-binding element that is an oligonucleotide could be non-covalently attached through hybridization to at least one surface of the substrate that includes a complementary oligonucleotide sequence. In an aspect, the plurality of specific microbe-binding elements are non-covalently covalently attached to at least one surface of the substrate through protein-protein interactions. For example, a type of specific microbe-binding element that includes biotin can be non-covalently attached to at least one surface of the substrate including streptavidin or avidin. For example, a single chain antibody may incorporate streptavidin as part of a fusion protein to facilitate attachment of the antibody to a solid substrate via a biotin-streptavidin linkage. See, e.g., Koo et al. (1999) *Appl. Environ. Microbiol.* 64:2497-2502, which is incorporated herein by reference. Other non-limiting examples non-covalent interactions include interactions between protein A or protein G and immunoglobulins, ligands with receptors, and secondary antibodies with primary antibodies.

Signal-Generating Element in Reservoir

Figure 6:
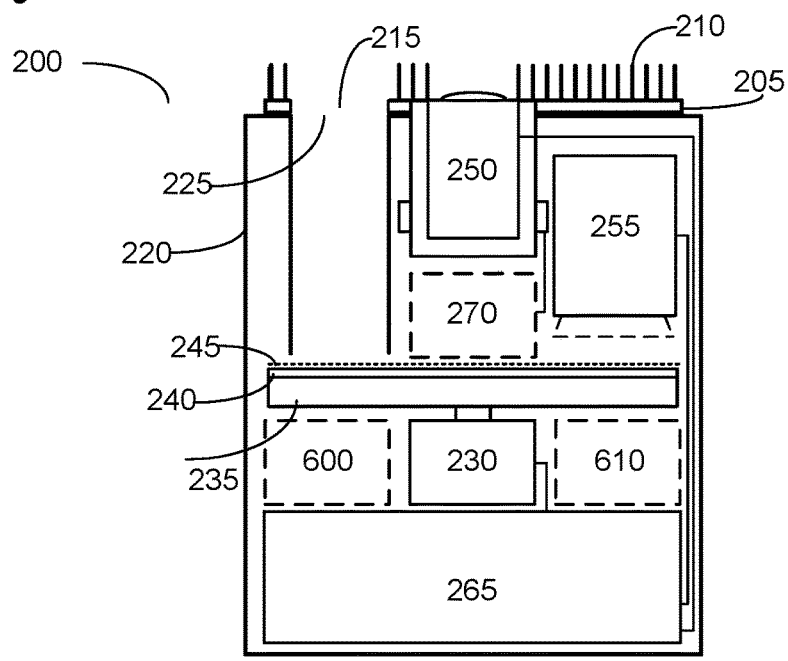
FIG. 6 is a schematic of a microbe profiling device.
Figure 7:
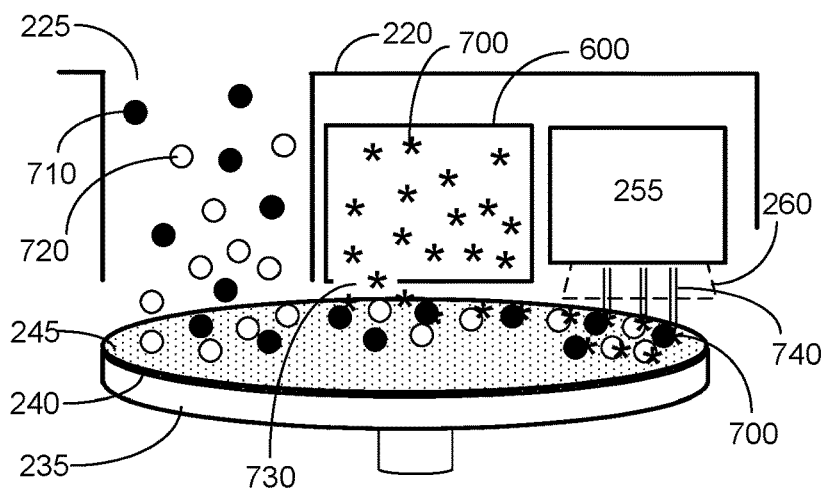
FIG. 7 is a schematic of a portion of a microbe profiling device including a reservoir including a plurality of signal-generating elements.
Figure 8:
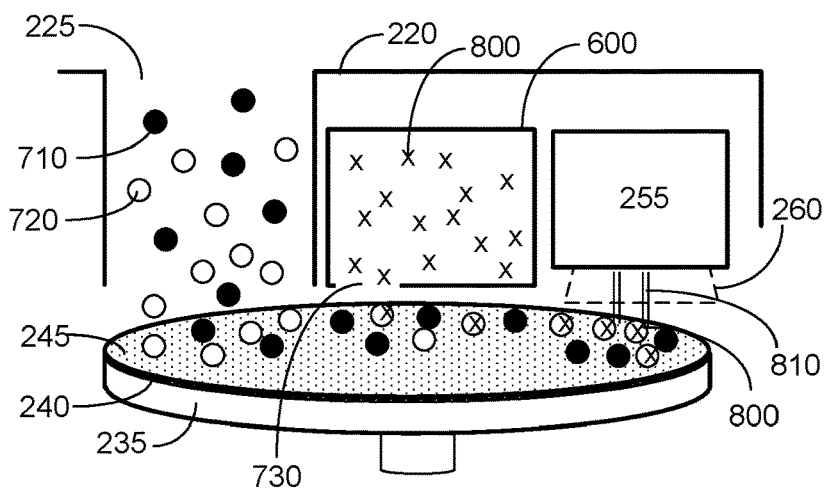
FIG. 8 is a schematic of a portion of a microbe profiling device including a reservoir including a plurality of signal-generating elements.

FIGS. 6, 7, and 8 illustrate further aspects of a microbe profiling device. FIG. 6 shows a cross-section through a schematic of an embodiment of a microbe profiling device. Microbe profiling device 200 includes device head 205 including epidermis-engaging component 210 and at least one access window 215. Device head 205 including epidermis-engaging component 210 is configured to dislodge at least one type of microbe from a skin surface of an individual. Microbe profiling device 200 further includes hand-held housing 220 defining an opening 225 which is aligned with at least one access window 215 of device head 205. Hand-held housing 220 of microbe profiling device 200 includes motor 230 operably coupled to at least one rotatable component 235. Motor 230 includes circuitry to drive at least one motivatable component 235. Hand-held housing 220 of microbe profiling device 200 further includes substrate 240 disposed in relation to at least one motivatable component 235. Substrate 240 is configured to pass opening 225 defined by hand-held housing 220. A surface of substrate 240 includes microbe-capture region 245. Microbe-capture region 245 is positioned to capture the at least one type of microbe dislodged by epidermis-engaging component 210 of device head 205. Hand-held housing 220 further includes location-capture component 250. Location-capture component includes circuitry to determine a location of one or more regions of the skin surface of the individual as epidermis-engaging component 210 of device head 205 contacts said one or more regions of the skin surface of the individual.

Hand-held housing 220 further includes reservoir 600 configured to hold a plurality of at least one type of signal-generating element. The at least one type of signal-generating element is capable of binding or otherwise interacting with at least one type of microbe captured on microbe-capture region 245 and of emitting or reflecting one or more signals that are detectable by at least one sensor component 255. Reservoir 600 further includes at least one opening, the opening adjacent to at least a portion of substrate 235. In some embodiments, substrate 235 is positioned to traverse the at least one opening defined by reservoir 600 to make contact with at least one of the plurality of at least one type of signal-generating element. Hand-held housing 220 further includes at least one sensor component 255 including circuitry to detect one or more signals emitted or reflected from at least one of the at least one type of signal-generating element bound or otherwise interacting with at least one type of microbe captured on the microbe-capture region and to transform the one or more detected signals into a sensor output. Hand-held housing 220 of microbe profiling device 200 further includes computing device 265 including a microprocessor. In some embodiments, hand-held housing 220 of microbe profiling device 200 further includes second motor 270 operably coupled to device head 205 and including circuitry to move, e.g., rotate, reciprocate, oscillate, and/or vibrate, device head 205.

In some embodiments, the microbe-profiling device includes at least one type of signal-generating element. Non-limiting examples of signal-generating elements include optical signal-generating elements, chromogenic signal-generating elements, fluorogenic signal-generating elements, magnetic signal-generating element, electrical signal-generating element, electromagnetic signal-generating element, radioactive signal-generating element, or radio signal-generating element, or acoustic signal-generating element. In an aspect, the at least one signal-generating element can emit or reflect one or more of a chromogenic signal, a fluorescent signal, an electromagnetic signal, an electrical signal, an radio signal, a magnetic signal, or an acoustic signal. Non-limiting examples of signal-generating elements include, but are not limited to, at least one of a fluorescent element, an electromagnetic-emitting element, a quantum dot, a gold label, dye, or chemiluminescent dye, or a combination thereof. Non-limiting examples of additional signal-generating elements include at least one of a radioactive element; radiopaque dye; radiofrequency identification tag; chromogenic element; a contrast element, visible dye, or volatile label; mass label; luminescent label, e.g., bioluminescent or chemiluminescent; metallic label, e.g., gold particles, magnetic beads, or paramagnetic beads; dye, e.g., direct, indirect, or releasable dye; or a combination thereof.

In an aspect, the at least one type of signal-generating element is configured to bind to all types of microbes captured on the microbe-capture region of the substrate. FIG. 7 is a schematic illustrating an embodiment of a microbe profiling device including a plurality of non-specific signal-generating elements. Shown in FIG. 7 is a schematic of an embodiment of microbe profiling device 200 including a portion of hand-held housing 220 defining opening 225. Microbe profiling device 200 includes at least one motivatable component 235 at least partially disposed in opening 225 defined by hand-held housing 220. Substrate 240 is disposed on the outer surface of at least one motivatable component 234 and includes microbe-capture region 245. In this example, substrate 235 including microbe-capture region 245 is positioned to come in contact and capture at least one first type of microbe 710 and at least one second type of microbe 720 that have fallen or been pushed through opening 225 defined by hand-held housing 220 from the access window of an associated device head (as shown in FIG. 2). At least one motivatable component 235 is operably coupled to a motor (as shown in FIG. 2) that periodically moves at least one motivatable component 235, advancing microbe-capture region 245 from a first position in the path of the falling or pushed microbes to a second position adjacent to reservoir 600. Reservoir 600 includes a plurality of non-specific signal-generating elements 700 that will interact with at least one first type of microbe 710 and at least one second type of microbe 720 captured on microbe-capture region 245. Reservoir 600 defines at least one opening 730; substrate 240 including microbe-capture region 245 traverses said at least one opening 730 defined by reservoir 600 to be exposed to plurality of non-specific signal-generating elements 700. Substrate 240 advances past at least one sensor component 255. Sensor component 255 detects one or more signals emitted or reflected from at least one of the plurality of non-specific signal-generating elements 700 associated with at least one first type of microbe 710 and/or at least one second type of microbe 720 and transforms the one or more signals 740 into a sensor output. In some embodiments, at least one sensor component 255 includes a directed energy source, the directed energy source configured to emit directed energy 260 to elicit one or more signals from at least one of the plurality of non-specific signal-generating elements 700 associated with at least one first type of microbe 710 and/or at least one second type of microbe 720.

In an aspect, reservoir 600 includes a replaceable module. For example, the reservoir containing the plurality of signal-generating elements can include a cartridge that is inserted into at least a portion of the hand-held housing. In an aspect, the reservoir includes a module connected to a portion of the hand-held housing through a conduit, e.g., tubing.

In an aspect, the at least one type of signal-generating element is an optical signal-generating element. In an aspect, the optical signal-generating element can be a chemical entity that changes color in response to binding a microbe. In an aspect, the optical signal-generating element can change color in response to metabolism of at least one type of microbe captured on the microbe-capture region. For example, the optical signal-generating element can by linked to metabolism of certain classes of biochemicals including sugars, hexo-phoshates, amino acids, hexose sugars, carboxylic acids, esters, and fatty acids. For example, tetrazolium salts form violet colored formazans in response to microbe metabolism. See, e.g., Tachon et al. (2009) *Microbiology* 155:2941-2948, which is incorporated herein by reference.

In an aspect, the at least one type of signal-generating element can include an ink, stain, or dye that emits or reflects ultraviolet, visible, near infrared, or infrared electromagnetic energy. In an aspect, signal-generating element can include one or more histological stain, non-limiting examples of which include crystal violet, safranin, fuschin, methylene blue, or Giemsa stain. In an aspect, signal-generating element can include a differential stain, e.g., a Gram's stain, which uses crystal violet with the mordant Gram's iodine and a counterstain, or an acid-fast stain. In an aspect, signal-generating element can include a non-selective vital dye, e.g., a redox stain, e.g., 5-cyano-2,3-ditolyl tetrazoliumchloride (CTC). In an aspect, signal-generating element includes a vital dye that intercalates into nucleic acids of microbes, non-limiting examples of which include DAPI (4',6-diamidino-2-phenylindole), acridine orange, or Hoechst stain. Other non-limiting examples of vital dyes include calcein AM, carboxyfluorescein diacetate, DiOC (3,3'-dihexyloxacarbocyanine iodide), rhodamine 123, and Nile red. In an aspect, signal-generating element can include a stain that will react with a polysaccharide, non-limiting examples of which include Schiff's reagent or a diamino stilbene, e.g., Calcofluor (from, e.g., Polysciences, Inc., Warrington, Pa.). In an aspect, the signal-generating element can include a negative stain, e.g., India ink or nigrosin, which stains the area surrounding the captured microbes, but not the microbes.

In an aspect, the at least one type of signal-generating element can include a chromogenic, fluorogenic, or luminescent substrate. Chromogenic substrates can include peptides that react with microbe-derived proteolytic enzymes under the formation of color. For example, the chromogenic substrate may include a chemical group which when released after enzyme cleavage gives rise to color. The color change can be followed spectrophotometrically and may be proportional to the proteolytic activity. For example, the fluorogenic substrate may include a chemical group including a fluorophore, which, when released after enzymatic cleavage or chemical reaction, is fluorescent. For example, a chemiluminescent substrate may include a chemical group which when released after enzyme cleavage or chemical reaction produces light.

In an aspect, the at least one type of signal-generating element is a fluorogenic signal-generating element. In an aspect, fluorogenic signal-emitting elements can include chemical dyes that emit light, i.e., fluoresce, at various wavelengths in response to excitation energy. In an aspect, the fluorogenic signal-generating element can include a quantum dot or semiconductor nanocrystals that fluoresce at various wavelengths in response to excitation energy. See, e.g., Jaiswal et al. (2003) *Nature Biotech.* 21:47-51, which is incorporated herein by reference. Non-limiting examples of fluorescing dyes include fluorescein (FITC), indocyanine green (ICG) and rhodamine B, red and near infrared emitting fluorophores (600-1200 nm) including cyanine dyes such as Cy5, Cy5.5, and Cy7 (Amersham Biosciences, Piscataway, N.J., U.S.A.) and/or a variety of Alexa Fluor dyes such as Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., U.S.A.). Additional fluorophores include IRDye800, IRDye700, and IRDye680 (LI-COR, Lincoln, Neb., U.S.A.), NIR-1 and IC5-OSu (Dejindo, Kumamotot, Japan), LaJolla Blue (Diatron, Miami, Fla., U.S.A.), FAR-Blue, FAR-Green One, and FAR-Green Two (Innosense, Giacosa, Italy), ADS 790-NS and ADS 821-NS (American Dye Source, Montreal, CA), NIAD-4 (ICx Technologies, Arlington, Va.). Other fluorescing dyes include BODIPY-FL, europium, green, yellow and red fluorescent proteins, luciferase.

In an aspect, the signal-generating element can include a magnetic marker, e.g., magnetic beads, magnetic particles or carbon nanotubes. Magnetic beads and magnetic particles of various sub-millimeter size are available from commercial sources (e.g., from Seradyn-Thermo Scientific, Indianapolis, Ind.; Dynal-Invitrogen, Carlsbad, Calif.). Carbon nanotubes with various functionalities can be synthesized de novo (see, e.g., Didenko & Baskin (2006) BioTechniques 40:295-302, which is incorporated herein by reference) or may be available from commercial sources (e.g., from Nanolab, Newton, Mass.; Swan Chemical Inc., Lyndhurst, N.J.). In an aspect, the signal-generating element includes paramagnetic and supramagnetic elements with one or more unpaired electrons, e.g., manganese, iron, or gadolinium, for use in magnetic imaging.

In an aspect, the signal-generating element can include a radiofrequency identification (RFID) tag, sub-millimeter versions of which have been described. See, e.g., Hornyak *Scientific American Magazine,* pp 68-71, February 2008, which is incorporated herein by reference. Alternatively, the signal-generating element can include one or more bokodes, millimeter sized visual tags that can be captured with a camera. See, e.g., Mohan et al. *ACM Transactions on Graphics* Proceedings of SIGGRAPH 2009, Aug. 3-7, 2009, New Orleans, which is incorporated herein by reference.

In an aspect, the microbe profiling device includes at least one type of signal-generating element conjugated to a specific microbe-binding element to enable signaling from specific microbes captured from the skin surface of the individual. For example, the microbe profiling device can include a fluorescing antibody that binds to a specific type of microbe. In an aspect, at least one type of signal-generating element can be conjugated to an antibody, aptamer, or other specific microbe-binding element that recognizes at least one type of microbe captured on the microbe-capture region. In an aspect, the binding component of the signal-generating element can be configured to recognize components of microbe surface biomolecules including amino acid sequences and oligosaccharides. For example, the antibody, aptamer, or other specific microbe-binding element conjugated to the at least one type of signal-generating element can bind to one or more biomolecules exposed on the outer surface of a microbe, e.g., a protein, carbohydrate or lipid biomolecule exposed on the outer surface of the microbe. The at least one type of signal-generating element associated with the antibody, aptamer, or other binding element can include a fluorescent element, a colored element, or a chemiluminescent element For example, the antibody, aptamer, or other binding element configured to bind to at least one type of microbe may further include fluorescein for direct fluorescence detection or horseradish peroxidase (HRP) for indirect detection using colorimetric or chemiluminesence following addition of peroxidase substrate. In some embodiments, the antibody, aptamer, or other binding element configured to bind the at least one type of microbe may further include biotin conjugates available for binding with avidin or streptavidin. In an aspect, signal-generating element includes at least one fluorescence-generating element. In an aspect, signal-generating element includes at least one chemiluminescence-generating element. In an aspect, the at least one type of signal-generating element, e.g., a chromophore or fluorophore, is conjugated to an anti-16S rRNA ligand. In an aspect, the at least one signal generating element is conjugated to universal primers of the type used for amplification of microbial 16S gene sequencing the 1.4 kb amplicon and comparing with known sequences in a database. See, e.g., references regarding Ribosomal Database Project (Cole et al. (2009) *Nucl. Acids Res.* 37(D1):D141-D145); SILVA (Quast et al. (2013) *Nucl. Acids Res.* 41(D1):D590-D596); CORE ("core human oral microbiome;" Griffen et al. (2011), *PLoS ONE* 6(4): e19051), which are incorporated herein by reference. Other non-limiting examples of signal-generating elements include radioactive elements, magnetic elements, radiofrequency identification tags, or contrast elements. In an aspect, the at least one type of signal-generating element can be conjugated to antibodies, aptamers, oligonucelotides, anti-16S rRNA ligands, antibody fragments, peptides, protein nucleic acids, proteins, viruses, lipids, phospholipids, carbohydrates, enzymes, receptors, lectin, peptide aptamer, bacteria, cells, cell fragments, inorganic molecules, organic molecules, synthetic ligands, artificial binding substrates, mimetic binding elements (e.g., formed by molecular imprinting), combinations thereof, or any other molecule capable carrying a label and interacting with one or more components of the at least one type of microbe captured on the microbe-capture region of the substrate.

FIG. 8 is a schematic illustrating an embodiment of a microbe profiling device including a signal-generating element conjugated to a specific microbe-binding element, e.g., a fluorescent signal-generating element conjugated to an antibody. Shown in FIG. 8 is a schematic of an embodiment of microbe profiling device 200 including a portion of hand-held housing 220 defining opening 225. Microbe profiling device 200 includes at least one motivatable component 235 at least partially disposed in opening 225 defined by hand-held housing 220. Substrate 240 is disposed on the outer surface of at least one motivatable component 235 and includes microbe-capture region 245. In this example, substrate 240 including microbe-capture region 245 is positioned to come in contact and capture at least one first type of microbe 710 and at least one second type of microbe 720 that have fallen or been pushed through opening 225 defined by hand-held housing 220 from the access window of an associated device head (not shown). At least one motivatable component 235 is operably coupled to a motor (not shown) that periodically moves at least one motivatable component 235, advancing microbe-capture region 245 from a first position in the path of the falling or pushed microbes to a second position adjacent to reservoir 600. Reservoir 600 includes signal-generating elements conjugated to specific microbe-binding elements 800. In this example, signal-generating elements conjugated to specific microbe-binding elements 800 specifically recognize and bind to at least one first type of microbe 710. Reservoir 600 defines at least one opening 730, substrate 240 including microbe-capture region 245 traversing said at least one opening 730 defined by reservoir 600 to be exposed to signal-generating elements conjugated to specific microbe-binding elements 800. Substrate 240 advances past at least one sensor component 255. Sensor component 255 detects one or more signals 810 emitted or reflected from at least one of the plurality of signal-generating elements conjugated to a specific microbe-binding element 800 associated with at least one first type of microbe 710 and transforms the one or more signals 810 into a sensor output. In some embodiments, directed energy 260, e.g., electromagnetic energy of a specific wavelength is used to elicit a response, e.g., to elicit a fluorescence response.

Other Agents

Returning to FIG. 6, in some embodiments, microbe profiling device includes at least one second reservoir 610. The at least one second reservoir is configured to hold and controllably release at least one agent. In an aspect, the at least one second reservoir is configured to hold and controllably release at least one agent onto the microbe-capture region and/or the substrate. In an aspect, the at least one second reservoir is configured to hold and controllably release at least one agent onto the skin surface of the individual. For example, the at least one second reservoir can include a controllable gate, port, valve, or switch that is operably coupled to and controlled by the computing component. For example, the at least one second reservoir can include a controllable gate, port, valve, or switch that is manually and/or electronically controlled by the user through a switch, button, or the like. In an aspect, the at least one second reservoir includes a replaceable module at least partially positioned in the hand-held housing of the microbe profiling device.

In some embodiments, at least one second reservoir 610 is configured to hold and controllably release a plurality of signal-generating elements. For example, at least one second reservoir 610 of a microbe profiling device can be configured to release to the skin surface a plurality of signal-generating elements, e.g., a fluorescing vital dye such as acridine orange, that interacts and stains one or more microbes prior to being captured by the microbe profiling device. Non-limiting examples of signal-generating elements have been described above herein.

In some embodiments, at least one second reservoir 610 is configured to hold and controllably release an aqueous solution, e.g., water, saline, or buffered saline. In an aspect, at least one second reservoir 610 is configured to hold and controllably release an aqueous solution onto the microbe-capture region. In an aspect, at least one second reservoir 610 is configured to hold and controllably release an aqueous solution onto the skin surface of the individual prior to or concurrent with contacting the skin surface with the epidermis-engaging component. In an aspect, an aqueous environment promotes dislodging of microbes from the skin surface. In an aspect, an aqueous environment promotes interaction of microbes with the microbe-capture region. In an aspect, an aqueous environment promotes flow of the dislodged microbes into the microbe profiling device. In an aspect, an aqueous environment, e.g., buffered saline, is used to remove microbes and/or other agents, e.g., signal-generating elements, that have not bound to the microbe-capture region and/or to associated specific microbe-binding elements.

In some embodiments, at least one second reservoir 610 is configured to hold and controllably release at least one enhancing agent. In an aspect, at least one second reservoir 610 is configured to hold and controllably release at least one enhancing agent to enhance dislodging of the at least one type of microbe from the skin surface of the individual. In an aspect, at least one second reservoir 610 is configured to hold and controllably release at least one enhancing agent to enhance interaction of the at least one type of microbe or parts thereof with the substrate and/or microbe-capture region. Non-limiting examples of enhancing agents include at least one of a skin-softener, a detergent, or a lysing compound. For example, the enhancing agent can be applied to the skin surface prior to using the microbe profiling device. In an aspect, the enhancing agent is included in the at least one second reservoir and released onto a region of the skin surface prior to or concurrent with making contact with the epidermis-engaging component of the microbe profiling device. In general, the enhancing agent either enhances capture of microbes from the skin surface, e.g., enhancing accessibility, or enhances detection of one or more biomolecules associated with the microbes. In an aspect, the enhancing agent includes at least one skin-softener, non-limiting examples of which include emollients, moisturizers, lubricants, and/or oils. In an aspect, the enhancing agent includes a lysing compound to lyse the one or more microbes either directly on the skin surface or on the microbe-capture region. The lysing compound allows biomolecules, e.g., proteins or nucleic acids, in the interior of the microbe to be more accessible for detection. Non-limiting examples of lysing compounds includes urea, enzymes for lysing bacterial cell walls (e.g., lysozyme, labiase, lysostaphin, mutanolysis, achromopeptidase), and enzymes for lysing fungal, e.g., yeast, cell walls (e.g., kitalase, lyticase, chitinase, glucanase). One or more detergents or surfactants may also be used for lysing cells, non-limiting examples of which include nonionic detergents, e.g., Triton X-100, Nonidet P-40, Tween 20; zwitterionic detergents, e.g., CHAPS; and ionic detergents, e.g., sodium dodecyl sulfate.

In some embodiments, at least one second reservoir 610 is configured to hold and controllably release at least one medicament. In an aspect, the at least one medicament is part of a recommended treatment regimen. Non-limiting examples of medicaments include antimicrobial agents, e.g., antibiotics, antiviral, or antifungal agents, antiseptics, vitamins (e.g., Vitamin A or Vitamin D) or derivatives thereof, peroxide, salicylic acid or other acids, hormone or retinoid creams, or probiotics and/or prebiotics.

In some embodiments, at least one second reservoir 610 is configured to hold and to controllably release at least one agent that includes one or more fiducial markers. For example the at least one second reservoir can be configured to controllably release one or more fiducial markers while the location-capture component is recording placement.

In an aspect, other means may be used to enhance dislodging of the at least one type of microbe from the skin surface or to enhance capture on the microbe-capture region of substrate of the microbe profiling device. In an aspect, one or more of a thermal means, a vacuum means, or a humidity means may be used to enhance dislodging or capture of the at least one type of microbe. For example, a thermal means, e.g., heat at a temperature compatible with skin, may be used to open skin pores to allow access for sampling by the microbe profiling device. For example, a vacuum means associated with the microbe profiling device may be used to pull the at least one type of microbe from the skin surface and onto the microbe-capture region of the substrate. For example, a humidity means, e.g., pre-wetting the skin surface, may be used to create an aqueous environment for binding.

Location-Capture Component

A microbe profiling device as described herein further includes a location-capture component including circuitry configured to determine a location of one or more regions of a skin surface of an individual as the epidermis-engaging component of the device head contacts said one or more regions of the skin surface of the individual. In an aspect, the location-capture component is operably coupled to the at least one motivatable component. In an aspect, each time the at least one motivatable component moves the substrate from a first position to a second position or replaces a first substrate with a second substrate, the location-capture component determines a corresponding location of the region of the skin surface from which microbes are being dislodged and captured on the microbe-capture region of the substrate. In an aspect, each time the at least one motivatable component, e.g., a rotatable component, rotates a fraction of a turn to move the exposed substrate and/or microbe-capture region, the location-capture component determines a corresponding location of said first and second regions of the skin surface. In an aspect, the location-capture component includes circuitry to sequentially determine a location of one or more regions of the skin surface of an individual as the epidermis-engaging component of the microbe profiling device contacts a first region of the skin surface followed by a second region of the skin surface. The location of the one or more regions of the skin surface of the individual is used to define a position at which a microbe sample has been dislodged from the skin surface and captured on the microbe-capture region of the substrate.

In an aspect, the location-capture component includes an image-capture device configured to capture images of one or more regions of the skin surface of the individual as the epidermis-engaging component contacts said one or more regions of the skin surface of the individual. In some embodiments, the image-capture device is operably coupled to the motivatable component of the microbe profiling device. In an aspect, each time the motivatable component moves or replaces the substrate, the image-capture device captures a corresponding image of the region. In an aspect, the at least one image of a region of a skin surface of an individual is registered with a specific portion of the microbe-capture region that has sampled at least one type of microbe from the same region of the skin surface of the individual. In an aspect, at least one image and a specific portion of the microbe-capture region or substrate are simultaneously time-stamped, marked, or otherwise coded to register the at least one image with the specific portion of the microbe-capture region and/or substrate. In an aspect, the at least one image provides information regarding the location from which at least one type of microbe was captured from a skin surface. In an aspect, the image-capture device can include one or more passive or active scanners, digital cameras, charge-coupled device (CCD), complementary metal oxide semiconductor (CMOS), infrared sensor, or any other device suited to capturing an image of a skin surface. Other non-limiting examples of an image-capture device include an ultrasound device, a photoacoustic device, a thermal imaging device, a capacitance measuring device, an electomyographic device, or other biomedical imaging devices.

In an aspect, the image-capture device includes at least one camera, e.g., a digital camera, configured to capture one or more images of one or more regions of a skin surface of an individual. In an aspect, the at least one camera may capture one or more images in the visible spectrum. In an aspect, the at least one camera may capture one or more images in other portions of the electromagnetic spectrum, e.g., infrared or ultraviolet. The image-capture device can include one or more electronic image sensors, e.g., photodiodes, photoresistors, charge-coupled devices (CCD), and/or complementary metal oxide semiconductor (CMOS) devices. In an aspect, the image-capture device includes a single-shot capture device with one CCD with a Bayer filter mosaic or three separate image sensors, which are exposed to the same image via a beam splitter. In an aspect, the image-capture device includes a multi-shot capture device. For example, a single CCD sensor may obtain additive color information by capturing an image three times, each with a different filter (e.g., red, green, and blue). For example, the CCD sensor may capture images as it is moved to various locations on the focal plane and a high resolution composite image "stitched" together. In an aspect, the image-capture device includes a scanning device in which the sensor moves across the focal plane.

In an aspect, the location-capture component includes an active scanner. An active scanner emits some form of radiation or light which when beamed onto a skin surface creates a measureable reflection. The emitted radiation or light can include electromagnetic radiation, ultrasound, or x-ray. Non-limiting examples of active non-contact scanners include hand-held laser scanners as well as a number of three-dimensional scanners (3D scanners) including time-of-flight scanners, triangulation laser scanners, structured-light scanners, and modulated light scanners. In some embodiments, the one or more active scanners can include one or more time-of-flight laser scanners in which a laser rangefinder is used to determine the distance between a surface, e.g., the one or more regions of an individual, and the laser emitter by timing the round-trip time of a pulse of light. The time-of-flight laser scanner scans the entire field of view one point at a time by changing the rangefinders view. Scanners for scanning head, face and/or whole body are commercially available (from, e.g., Cyberware, Monterery Calif.; Accurex Measurement Inc., Swathmore, Pa.; 3dMD Atlanta, Ga.; Konica/Minolta, Ramsey, N.J.)

In an aspect, images of one or more regions of the skin surface can be aligned with a larger image, map, or reference of the skin surface to determine the location of said one or more regions. For example, a wide-angle reference view of the skin surface can be captured with a camera prior to treatment with the microbe profiling device and the one or more images of specific regions of the skin surface captured with the location-capture component can be aligned with the wide-angle reference view of the skin surface to register the location of the specific regions.

In an aspect, the location-capture component includes a fiducial reader. In an aspect, the location-capture component includes a fiducial reader that reads one or more fiducials on the skin surface of the individual. In an aspect, the one or more fiducials are inherent properties of the skin surface, e.g., physical landmarks on the skin surface of the individual. Non-limiting examples of physical landmarks include pigmentation, pigmented areas, tattoos, skin texture pattern, blemishes, scars, anatomical features, or subsurface blood vessels associated with the skin surface. In an aspect, the location-capture component uses the physical landmarks on the skin surface of the individual to register the position of the skin surface relative to the microbes captured in that vicinity. For example, the microbe profiling device can include location-capture component that is a digital camera periodically imaging the skin surface as the device is moved along the skin surface to sample microbes. The imaged landmarks can be registered with a reference image to determine a location of each region contacted by the microbe profiling device.

In an aspect, the fiducial reader reads one or more fiducial markers, e.g., spots or templates, placed on the skin surface of the individual prior to microbe profiling. For example, the fiducial reader, e.g., a camera, can image one or more washable ink spots placed on the skin surface of the individual prior to microbe profiling. In an aspect, the one or more fiducial markers include one or more of radiofrequency identification (RFID) tags, electronic nodes, or audio nodes. In an aspect, the one or more fiducial markers include one or more RFID tags placed at various locations on a skin surface of an individual. In an aspect, the location-capture component includes a fiducial reader that includes a radiofrequency antenna including circuitry to receive a radiofrequency signal. In an aspect, the radiofrequency antenna receives one or more signals from one or more RFID tags placed on the skin surface of the individual. For example, three tags can be placed on a skin surface in a triangular pattern in the area to be profiled and the three tags used to triangulate the location of the microbe profiling device at any given time while it is being moved along the skin surface. In an aspect, the location-capture component includes a fiducial reader that includes a receiver for signals sent from one or more fiducial markers that are electronic nodes. In an aspect, the location-capture component includes a fiducial reader that includes an audio receiver, e.g., a microphone, for signals sent from one or more fiducial markers that are audio nodes.

In an aspect, the location-capture component includes one or more receivers/transmitters for use with a local position system. For example, the location-capture capture component may include receivers/transmitters to receive/transmit ultrasonic or radiofrequency signals from one or more beacons to allow triangulation of the position of the microbe profiling device on the skin surface of the individual.

In an aspect, the location-capture component includes circuitry to determine the location of the one or more regions on the skin surface of the individual using triangulation, trilateration, multilateration, or a combination thereof. In an aspect, the location can be defined as coordinates. In an aspect, the coordinates for each location are further mapped to a reference image of the skin surface of the individual.

At Least One Sensor Component

In an aspect, the microbe profiling device includes at least one sensor component including circuitry to detect one or more signals emitted or reflected from one or more microbes captured on the microbe-capture region of the substrate and to transform the detected one or more signals into a sensor output. In an aspect, the one or more signals from the at least one type of microbe captured on the microbe-capture region are representative of one or more properties of the at least one type of microbe. The one or more properties can include one or more inherent properties or characteristics of the at least one type of microbe that are measureable by the at least one sensor component. In an aspect, the one or more properties of the at least one type of microbe can include at least one of an optical property, autofluorescence property, an infrared spectral property, a reflective property, a light scattering property, or an opacity property of the at least one type of microbe. In an aspect, the one or more properties of the at least one type of microbe include at least one of metabolic properties, lipid properties, carbohydrate properties, protein properties, or genomic properties of the at least one type of microbe.

In an aspect, the microbe profiling device includes at least one sensor component including circuitry to detect one or more signals emitted or reflected from at least one type of signal-generating element associated with at least one type of microbe on the microbe-capture region and/or substrate and to transform the detected one or more signals into a sensor output. In an aspect, the one or more signals from the at least one type of signal-generating element includes optical signals, fluorescent signals, electrical signals, electromagnetic signals, acoustic signals, radioactive signals, magnetic signals, or radio signals.

In an aspect, the one or more signals emitted or reflected from the at least one type of microbe captured on the microbe-capture region of the outer surface of the substrate are indicative of the identity and/or spatial distribution of microbes dislodged from one or more regions of the skin surface of the individual.

In an aspect, the at least one sensor component includes an energy-emitting mechanism and circuitry to scan the outer surface of the substrate to detect one or more signals emitted or reflected from one or more microbes captured on the microbe-capture region of the substrate. For example, the at least one sensor component can include an electromagnetic energy source, e.g., a laser, that emits a wavelength of light that causes autofluorescence of the one or more microbes captured on the microbe-capture region. In an aspect, the at least one sensor component includes an energy emitting mechanism and circuitry to scan the outer surface of the substrate to detect one or more signals emitted or reflected from at least one type of signal-generating element associated with at least one type of microbe on the microbe-capture region and/or substrate. For example, the at least one sensor component can include an electromagnetic energy source, e.g., a laser, that emits a wavelength of light that causes a fluorescence-generating element associated with the at least one type of microbe to fluoresce.

In an aspect, the at least one sensor component can be configured to measure the light absorption, light emission, fluorescence, luminescence, chemiluminescence, or phosphorescence associated with the at least one type of microbe or signal-generating element associated with the at least one type of microbe. Such electromagnetic properties can be inherent properties of all or a portion of the at least one type of microbe (e.g. auto-fluorescence), or can be associated with one or more signal-generating elements incorporated into or added to the microbe-capture region on the substrate or the at least one type of microbe.

In an aspect, the at least one sensor component includes at least one optical sensor. In an aspect, the at least one sensor component includes at least one optical sensor that is an image-capture device, e.g., a camera such as a digital camera, configured to capture one or more images of the substrate and associated microbe-capture region. In an aspect, the at least one camera may capture one or more images of the substrate in the visible spectrum. In an aspect, the at least one camera may capture one or more images of the substrate in other portions of the electromagnetic spectrum, e.g., infrared or ultraviolet. In an aspect, the at least one camera may capture emitted and/or reflected light. In an aspect, the at least one sensor component includes one or more electronic image sensors, e.g., photodiodes, photoresistors, charge-coupled devices (CCD), and/or complementary metal oxide semiconductor (CMOS) devices. In an aspect, the at least one sensor component includes a single-shot capture device with one CCD with a Bayer filter mosaic or three separate image sensors, which are exposed to the same image via a beam splitter. In an aspect, the at least one sensor component includes a multi-shot capture device. For example, a single CCD sensor may obtain additive color information by capturing an image three times, each with a different filter (e.g., red, green, and blue). In an aspect, the at least one sensor component includes components for micro-scanning in which a single CCD sensor with a Bayer filter is moved over the focus plane of the lens to "stitch" together a higher resolution image than the CCD would allow otherwise. In an aspect, the micro-scanning device includes a micro laser scanning device. See, e.g., Seidl et al. (2006) *International Society for Photogrammetry and Remote Sensing*. Volume XXXVI Part 5. Sep. 25-27, 2006, Dresden Germany. In an aspect, the image sensor can include an area array of CCD or CMOS sensors. In an aspect, the image sensor can include a linear array of CCD (monochrome) or 3-strip CCD with color filters. In an aspect, the at least one sensor component includes a lens-free imaging system. See, e.g., Kim et al. (2012) *J. Lab. Automation* 17:43-49, which is incorporated herein by reference.

In an aspect, the at least one sensor component includes at least one scanning device. Non-limiting examples of scanners include optical scanners, fluorescence scanners, acoustic scanners, electrical scanners, electromagnetic scanners, or magnetic scanners. In an aspect, the scanner includes an energy-emitting mechanism, e.g., a light source or a laser, and circuitry to scan the surface of the substrate with directed energy, e.g., light of a specified wavelength, to detect one or more signals emitted or reflected from the surface of the substrate and to transform the one or more detected signals into a sensor output.

In an aspect, the at least one sensor component includes a colorimetric scanner configured to detect a reflective property, e.g., color, of the at least one type of microbe or a colored reagent in proximity to the at least one type of microbe. For example, the color may arise from addition of one or more developing reagents, e.g., a chromogenic antibody or chemically modified antibody, e.g., alkaline phosphatase- or horseradish peroxidase-modified antibody, capable of undergoing a colorimetric change, or a stain or dye able to directly apply color to a microbe or to the substrate. In an aspect, the colorimetric scanner includes a camera or other image-capture device.

In an aspect, the at least one sensor component measures changes in refractive index on the outer surface of the substrate. For example, the surface of the substrate can be illuminated with a light source at various angles and resonance occurring at specific angles measured to detect the presence of the microbes on the surface. See, e.g., Barlen, et al. (2007) *Sensors*, 7:1427-1446; and Kashyap & Nemova (2009) *J. Sensors*: Article ID 645162, each of which is incorporated herein by reference.

In an aspect, the at least one sensor component includes a darkfield scanner capable of scanning an optical pattern of microbes, e.g., bacteria on a solid surface. See, e.g., Adak et al. (2010) *Bioconjug. Chem.* 21:2065-2075, which is incorporated herein by reference.

In an aspect, the at least one sensor component includes a fluorescence scanning device. In an aspect, the fluorescence scanning device can include a light source that delivers light of fixed excitation/emission wavelengths based on the use of standard commercially available fluorescent dyes in the green, red, and near infrared wavelengths. For example, the fluorescence scanning device can include a two color scanner for scanning at least two distinct wavelengths or wavelength bands. In an aspect, the fluorescence scanning device can include a light source that delivers light of adjustable excitation/emission wavelengths, e.g., with one or more excitation sources and filters to adjust the excitation/emission wavelengths.

In an aspect, the at least one sensor component includes circuitry to detect one or more signals associated with autofluorescence emitted from the at least one type of microbe captured on the outer surface of the substrate in response to a directed energy, e.g., light of a specific wavelength, applied to the microbe-capture region of the substrate. For example, naturally occurring autofluorescence emitted by microbes may be derived from fluorophore-containing biomolecules associated with the microbes, e.g., porphyrins, certain amino acids, flavins, and coenzymes NADP and NADPH (see, e.g., Koenig et al. (1994) *J. Fluoresc.* 4:17-40, which is incorporated herein by reference). In an aspect, a fluorescence scanning device can include directed energy that includes one or more excitation wavelengths for exciting autofluorescence emission from captured microbes. For example, the excitation maxima of endogenous fluorophores, e.g., porphyrins, lie in the range of 250-450 nm (spanning the ultraviolet/visible (UV/VIS) spectral range), whereas their emission maxima lie in the range of 280-540 nm (see, e.g., Ammor (2007) *J. Fluoresc.* 17:455-459, which is incorporated herein by reference). See, e.g., U.S. Patent Application 2011/0117025, which is incorporated herein by reference.

In an aspect, autofluorescence associated with naturally occurring, endogenous prophyrins can be used to detect bacteria. For example, a number of skin-associated bacteria produce protophorphyrins, including *Propinibacterium acnes, Staphylococcus aureus, Clostridium, Bifidobacterium,* and *Actinomyces* (see, e.g., Koenig et al. (1994) *J. Fluoresc.* 4:17-40, which is incorporated herein by reference). In an aspect, bacteria may be detected using fluorescence lifetimes measured at 430, 487, and 514 nm after selective excitation at 340, 405, and 430 as described by Bouchard et al. (2006) in *J. Biomed. Opt.* 11:014011, 1-7, which is incorporated herein by reference. In another example, autofluorescence may be used to detect *Staphylococcus* sp. and/or *Pseudomonas aeruginosa* using a scanning device emitting electromagnetic energy at a wavelength of 488 nm as described by Hilton (1998) *SPIE* 3491:1174-1178, which is incorporated herein by reference. For example, *Staphylococcus aureus* may be distinguished from *Escherichia coli* based on emission spectra induced by excitations at 410-430 nm (see, e.g., Giana et al. (2002) *J. Fluoresc.* 13:489-493, which is incorporated herein by reference).

In an aspect, autofluorescence may be used to detect fungi. For example, *Candida albicans* irradiated with electromagnetic energy at wavelengths of 465-495 nm autofluoresces at an emission wavelength of 515-555 mm (see, e.g., Mateus et al. (2004) *Antimicrob. Agents Chemother.* 48:3358-3336, which is incorporated herein by reference). For example, *Aspergillus* may be detected using autofluorescence in response to excitation at 450-490 nm and emission at 560 (see, e.g., Graham (1983) *Am. J. Clin. Pathol.* 79:231-234, which is incorporated herein by reference).

In an aspect, autofluorescence may be used to distinguish between different types of microbes, e.g., bacteria versus fungi. For example, bacteria, e.g., *Lactobacillus,* and fungi, e.g., *Saccharomyces,* can be differentiated using fluorescence spectroscopy, each having its own spectral fingerprint. See, e.g., Bhatta et al. (2006) *Appl. Microbiol. Biotechnol.* 71:121-126, which is incorporated herein by reference. For example, a number of skin associated fungi, e.g., dermatophytosis and tinea, exhibit autofluorescence. See, e.g., Elston (2001) *BMC Microbiology* 1:21, which is incorporated herein by reference.

In an aspect, autofluorescence emitted by one or more microbes is detected by a photosensor such as, for example, a charge coupled device (CCD) and/or a complementary metal oxide semiconductor (CMOS) sensor. In an aspect, the autofluorescence signals are transformed into a sensor output including information associated with at least one property of the autofluorescence signals. The at least one property of the autofluoresence signals, e.g., the emitted wavelength, is compared with preset algorithms defining, for example, the autofluorescence properties of reference microbes.

In an aspect, the at least one sensor component is able to detect chemiluminescence, e.g., light, emitted from at least one type of microbe or signal-generating element on the surface of the substrate as a result of a chemical reaction. For example, a chemiluminscent response, i.e., emitted light, may be generated using horseradish peroxidase associated with a specific microbe-binding element, e.g., an antibody or aptamer, in the presence of luminol, hydrogen peroxide, and iron or copper. Chemiluminescence on a solid substrate can be detected using a CCD camera system (e.g., GeneGnome5, Syngene U.S.A., Fredrick Md.).

In an aspect, the at least one sensor component includes one or more imaging sensors including, but not limited to, one or more piezo transducers, one or more MEMS device, one or more cavity resonators, one or more magneto-resistive sensors, one or more magnetic field sensors, and/or one or more thermal sensors.

In an aspect, the at least one sensor component includes a confocal laser scanner. In an aspect, the confocal laser scanner includes a MEMS confocal laser scanner. See, e.g., Murakami et al. (2003) *The 12$^{th}$ International Conference on Solid State Sensors, Actuators and Microsystems,* Boston, Jun. 8-12, 2003, pp. 587-590, which is incorporated herein by reference.

In an aspect, the at least one sensor component includes a spectrometer or spectrophotometer. In an aspect, the spectrophotometer includes a fiber optic spectrophotometer (from, e.g., Ocean Optics, Dunedin Fla.). In an aspect, the sensor component includes a means of vibrational spectroscopy. Examples of vibrational spectroscopy include, but are not limited to, Fourier transform infrared (FTIR) spectroscopy and micro-Raman spectroscopy. Raman spectroscopy can further include UV-resonance Raman spectroscopy, surface enhanced Raman scattering, or tip-enhanced Raman scattering. See, e.g., Harz et al. (2009) *Cytometry A* 75:104-113, which is incorporated herein by reference.

In an aspect, the at least one sensor component includes an acoustic scanning device capable of using focused sound to image the at least one type of microbe captured on the outer surface of the skin-covering material. See, e.g., Hildebrand et al. (1981) *Proc. Natl. Acad. Sci., U.S.A.* 78:1656-1660, which is incorporated herein by reference.

In an aspect, the at least one sensor can include an optical scanning device. In an aspect, the at least one sensor includes light scattering, electrical impedance, infrared spectroscopy, acoustic imaging, thermal imaging, photothermal imaging, or visible light absorption or refraction. See, e.g., Doornbos et al. (1993) *Cytometry* 14:589-594; Gao et al. (2003) *Proceedings of the 25th Annual International Conference of the IEEE EMS,* Cancun, Mexico, Sep. 17-21, 2003; Oberreuter et al. (2002) *Int. J. Syst. Evol. Microbiol.* 52:91-100; Baddour et al. (2002) *Ultrasonics Symposium IEEE* 2:1639-1644; Zharov et al. (2006) *J. Biochem.* 97:916-932; Zharov et al. (2006) *J. Biomed. Opt.* 11:054034-1-4; Koenig et al. (1994) *J. Fluoresc.* 4:17-40; which are each incorporated herein by reference. In an aspect, the at least one sensor can include a scanning laser beam and a charge-coupled device camera to acquire light scatter-image signatures. See, e.g., Huff et al. (2012) *Microbial Biotechnology* 5:607-620, which is incorporated herein by reference.

In an aspect, the at least one sensor component detects one or more infrared spectral properties of the at least one type of microbe on the microbe-capture region. In general, cells including microbes contain various chemical components with characteristic infrared spectra, including proteins, nucleic acids, carbohydrates and lipids. The spectra are created when a molecule converts infrared radiation into molecular vibrations. These vibrations create bands in a spectrum that occur at specific wavelengths. Differences in the chemical composition of a microbe can be distinguished by changes in spectra. For example, Fourier Transfer Infrared (FTIR) Spectroscopy can be used to distinguish *Streptococcus* from a virus using a spectral range of wavenumbers from 4000 to 800 cm1 (U.S. Pat. No. 6,379,920, which is incorporated herein by reference). Alternatively, FTIR data may be obtained at various frequency ranges, such as for example, 3000-2800 cm$^{-1}$, 1800-1500 cm$^{-1}$, 1500-1200 cm$^-$, and 1200-900 cm$^-$, and 900-700 cm$^-$ and spectra obtained in these various ranges compared with known spectra of various bacteria. See, e.g., Oberreuter et al. (2002) *Int. J Syst. Evol. Microbiol.* 52:91-100 and Helm et al. (1991) *J. General Microbiology* 137:69-79, which are incorporated herein by reference.

In an aspect, the at least one sensor component can include a thermal sensor, e.g., an infrared sensor. For example, the at least one sensor component can include at least one infrared photosensor, e.g., an indium gallium arsenide and/or mercury cadmium telluride based photosensor.

In an aspect, the at least one sensor component can detect one or more signals indicative of a size, a morphological property, and/or a physical feature of the at least one type of microbe captured on the microbe-capture region. For example, the at least one sensor component, e.g., an image-capture device, can be configured to detect by optical or other means the shape, outline, and/or periphery of the at least one type of microbe on the microbe-capture region. The shape, outline, and/or periphery can be further used to determine a size, a morphological property, or a physical feature of the at least one type of microbe. For example, bacteria typically range in size from 0.5 to 5.0 micrometers. Common morphologies of bacteria include spherical, e.g., cocci, or rod shaped, e.g., bacilli. Additional morphologies include corkscrew, filamentous, helical, enlarged rod, and spirochete. Physical features include hypha or stock of budding or appendaged bacteria, or flagella. In contrast, fungi can be multicellular or unicellular. Multicellular fungi are composed of filamentous hyphae. Unicellular fungi include a wide variety of budding yeast. Some fungi, such as *Candida,* are dimorphic with yeast phases and filamentous phases. Viruses range in size from 20 to 300 nanometers. The use of contrast agents, e.g., a tungsten heavy electron dense stain, can increase contrast to aid in visualizing viruses and other microbes. In an aspect, physical features may also include intracellular shapes, outlines, and/or peripheries, e.g., of organelles and the like, associated with a type of microbe. In an aspect, the size of the microbe is correlated with its light scattering properties. See, e.g., Ulicny (1992) *Gen. Physiol. Biophys.* 11:133-151, which is incorporated herein by reference.

In an aspect, the at least one type of microbe can be identified based on pattern and image recognition or signal recognition analysis. Various methods have been described for image and shape analysis of cells and subcellular components of cells. See, e.g., Fei-Fei et al. (2006) *IEEE Transactions on Pattern Analysis and Machine Intelligence* 28:594-611; and Martin et al. (2004) *IEEE Transactions on Pattern Analysis and Machine Intelligence* 26:530-549, which are incorporated herein by reference.

In an aspect, the at least one sensor component includes at least one chemical sensor. In an aspect, the at least one sensor component includes at least one electrochemical sensor, sensor chips, enose, biosensor, or cantilevers. In an aspect, the at least one sensor component includes at least one chemical sensor that is a gas sensor, such as an acoustic wave, chemiresistant, or piezoelectric sensors, or an electronic nose. One or more sensors are optionally small in size, for example a sensor or array that is a chemical sensor (see, e.g., Snow (2005) *Science* 307:1942-1945, which is incorporated herein by reference), a gas sensor (see, e.g., Hagleitner, et al. (2001) *Nature* 414:293-296, which is incorporated herein by reference), an electronic nose, and/or a nuclear magnetic resonance imager (see, e.g., Yusa (2005), *Nature* 434:1001-1005, which is incorporated herein by reference). Further examples of sensors are provided in The Biomedical Engineering Handbook, Second Edition, Volume I, J. D. Bronzino, Ed., Copyright 2000, CRC Press LLC, pp. V-1-51-9, and U.S. Pat. No. 6,802,811) and/or known in the art.

A sensor component capable of micro electrical impedance spectroscopy may be generated using MEMS and/or Lab-on-a-chip technology and incorporated into the device described herein (see, e.g., Sun et al. (2007) *Meas. Sci. Technol.* 18:2859-2868; Mohanty et al., *Microtechnologies in Medicine and Biology* 485-488, which are incorporated herein by reference).

Computing Component

The microbe profiling device includes a computing component including a microprocessor. The computing component further includes circuitry configured to receive information associated with the location of one or more regions of the skin surface of the individual from the location-capture component, receive the sensor output from the at least one sensor component, associate the location of said one or more regions of the skin surface of the individual with the detected one or more signals, and output information regarding an association between the location of said one or more regions of the skin surface of the individual with the detected one or more signals.

The computing component includes circuitry to execute one or more instructions for operating the motor operably coupled to the at least one rotatable component, the location-capture component and the at least one sensor component. The computing component includes circuitry to execute one or more instructions for operating any or all other components incorporated into the microbe profiling device, e.g., a second motor, a user interface, a transmission unit, and/or one or more reservoirs. The computing component includes circuitry to execute one or more instructions for receiving information from the location-capture component and the at least one sensor component, associating the information received from the location-capture component and the at least one sensor component, and output information regarding the association. In some embodiments, the computing component further executes one or more instructions for identifying the at least one type of microbe detected by the at least one sensor, generating a microbe profile including the spatial distribution and/or identity of the at least one type of microbe, generating a recommended treatment regimen, and reporting the microbe profile and/or the recommended treatment regimen to a user.

In an aspect, the computing component includes a microprocessor, e.g., a central processing unit, for controlling one or more functions of the microbe profiling device. The computing component further includes a system memory and a system bus that couples various system components including the system memory to the microprocessor. The microprocessor can include a processing unit, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof In an aspect, the computing component includes one or more ASICs having a plurality of pre-defined logic components. In an aspect, the component includes one or more FPGA having a plurality of programmable logic commands.

In some embodiments, the computing component is connected to a user interface, e.g., one or more input components and/or output components for use by a user to interface with the microbe profiling device. The one or more input components can be used to enter information into the microbe profiling device, e.g., patient information, operating instructions, or treatment regimen, and may be integrated into the microbe profiling device or may be one or more peripheral devices operably connected through a wired or wireless connection to the microbe profiling device. Non-limiting examples of input components include a graphical user interface, a display, a keyboard, a keypad, a touch-screen, a microphone, a stylus pen, a switch, a dial, or the like. In some embodiments, the user interface is user driven. For example, the user inputs data or operating conditions into the microbe sampling device using the user interface, e.g., a touch-screen. In some embodiments, the user interface, e.g., a switch, is circuitry driven. For example, an on/off switch may be toggled based on proximity of a portion of the microbe profiling device, e.g., the device head, to the skin surface of an individual.

The user interface includes one or more output components over which processed information is viewed as output results and may be integrated into the microbe profiling device or may be one or more peripheral devices operably connected through a wired or wireless connection to the microbe profiling device. For example, the user interface may be used to report to a user a microbe profile of an individual including a spatial distribution and/or an identity of at least one type of microbe on the skin surface of the individual and/or a recommended treatment regimen based on the microbe profile. Non-limiting examples of output components include but are not limited to television screens, computer monitors, liquid crystal displays, audio speakers, audio headphones, and printers.

In an aspect, the one or more input/output components are connected to the microprocessor of the computing component through one or more user input interfaces that are coupled to the system bus, but may be connected by other interfaces and bus structures, such as a parallel port, game port, or a universal serial bus (USB). For example, external input components or output components may be connected to the microprocessor through a USB port. The computing component may further include or be capable of connecting to a flash card memory. The computing component may further include or be capable of connecting with a network through a network port and network interface, and through wireless port and corresponding wireless interface may be provided to facilitate communication with other peripheral devices, for example, a smart phone, a computer, a display monitor, and/or a printer.

In an aspect, the computing component is operably coupled to a transmission unit. A "transmission unit," as used herein, can be one or more of a variety of units that are configured to send and/or receive signals, such as signals carried as electromagnetic waves. A transmission unit generally includes at least one antenna and associated circuitry.

A transmission unit can include a transmitter and a receiver. A transmission unit can include volatile or non-volatile memory. A transmission unit can include a processor and/or be operably connected to a processor. A transmission unit can be operably connected to an energy source, such as a battery. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification,* Klaus Finkenzeller, John Wiley & Sons, (2003), which is incorporated herein by reference. A transmission unit can include an oscillator and encoder configured to generate a programmable pulse position-modulated signal in the radio frequency range (see, e.g., U.S. Pat. No. 4,384,288, which is incorporated herein by reference). A transmission unit can include a radio frequency identification device (RFID), which can be a passive RFID device, a semi-passive RFID device, or an active RFID device, depending on the embodiment (see, e.g., Chawla & Ha, "An Overview of Passive RFID," *IEEE Applications and Practice,* 11-17 (September 2007), which is incorporated herein by reference). A transmission unit including an RFID device can be configured to transmit signals in the UHF standard range. A transmission unit can include a battery-assisted passive RFID device, such as sold by Alien Technology®, Morgan Hill, Calif. A transmission unit can include an optical transmission unit. A transmission unit can include a hybrid backscatter system configured to function in an RFID, IEEE 802.11x standard and Bluetooth system (see, e.g., U.S. Pat. No. 7,215,976, which is incorporated herein by reference). A transmission unit can include a near field communication (NFC) device. A transmission unit can include a Wireless Identification and Sensing Platform (WISP) device.

In an aspect, image-based applications such as viewers and/or toolkits (e.g., Insight Segmentation and Registration Toolkit (ITK)), are incorporated for further intake of information. In an aspect, CAD implementations, image segmentation, or other image analysis algorithms may allow processing of images received from the location-capture component and/or the at least one sensor component.

The computing component can further include memory chips, e.g., ROM or flash memory chips, for providing storage of operating systems, look-up tables, database information regarding reference signals, e.g., microbe signal properties, and algorithms for comparing input data with reference data. The system memory of the computing component may include read-only memory (ROM) and random access memory (RAM). A number of program modules may be stored in the ROM or RAM, including an operating system, one or more application programs, other program modules and program data.

The computing component includes computer-readable media products and may include any media that can be accessed by the computing component including both volatile and nonvolatile media, removable and non-removable media. By way of example, and not of limitation, computer-readable media may include non-transitory signal-bearing media. Non-limiting examples of non-transitory signal-bearing media include a recordable type medium such as magnetic tape, a hard disk drive, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, flash memory, magnetic tape, MINIDISC, non-volatile memory card, EEPROM, optical disk, optical storage, RAM, ROM, system memory, web server, cloud, or the like. By way of example, and not of limitation, computer-readable media may include computer storage media, e.g., magnetic tape, magnetic disk storage, optical disk storage, memory cards, flash memory cards, electrically erasable programmable read-only memory (EEPROM), solid state RAM, and solid state ROM or any other medium which can be used to store the desired information and which can be accessed by the computing component. By way of further example, and not of limitation, computer-readable media may include a communication media, e.g., wired media, such as a wired network and a direct-wired connection, and wireless media such as acoustic, RF, optical, and infrared media.

In an aspect, the computing component includes circuitry to receive the information associated with the location of said one or more regions of the skin surface of the individual from the location-capture component. In an aspect, the computing component includes circuitry to receive one or more images of said one or more regions of the skin surface of the individual. In an aspect, the computing component includes circuitry to receive one or more coordinates provided by the location-capture component. In an aspect, the location-capture component determines the location of the one or more regions of the skin surface of the individual based on comparison with a reference map and transmits the location information as a location output. In an aspect, the location-capture component transmits data, e.g., images or coordinates, which the computing component compares with a reference map to determine the location information.

In an aspect, the computing component includes circuitry configured to align the location information, e.g., one or more images of one or more regions of the skin surface of the individual or one or more fiducials captured from the one or more images of skin surface of the individual, with a larger reference map of the skin surface. In an aspect, a reference map of the skin surface of the individual, e.g., the entirety of the face, can be captured with a digital camera. In an aspect, a reference map of the skin surface of the individual can include a grid or coordinate system of fiducial markers. In an aspect, the computing component may include circuitry to align the one or more images of the one or more regions of the skin surface of the individual with the reference map of the skin surface based on aligning one or more physical landmarks, e.g., one or more of pigmentation, pigmented areas, tattoos, skin texture patterns, blemishes, scars, anatomical features, or subsurface blood vessels. The one or more images of the one or more regions of the skin region can be aligned with the reference map of the skin surface to map the location of the one or more regions using any of a number of image registration algorithms, programs, or software.

In an aspect, the computing component includes circuitry configured to detect one or more features depicted in the one or more images, e.g., the physical landmarks, and match these features with features in the reference image. Features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. The computing component is further operable to match the features detected in the one or more images of skin surface of the individual with features in the reference image using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods. The following references are incorporated by reference and include descriptions of computational methods for image registration: Szeliski *Foundations and Trends in Computer Graphics and Vision,* Vol. 2, No. 1 (2006) 1-104, Zitova & Flusser *Image Vision Computing* (2003) 21:977-1000.

In an aspect, the computing component includes circuitry configured to receive the sensor output from the at least one sensor component. In an aspect, the sensor output includes at least one property of the detected one or more signals emitted or reflected from the at least one type of microbe captured on the microbe-capture region. In an aspect, the sensor output includes at least one property of the detected one or more signals emitted or reflected from one or more signal-generating elements in contact with the at least one type of microbe.

In an aspect, the computing component includes circuitry configured to associate the location of said one or more regions of the skin surface of the individual with the detected one or more signals. For example, the computing component can include circuitry to associate a time-stamp or other code linked to an image or coordinates with a time-stamp or other code linked to a portion of the microbe-capture region to register the image with one or more signals emitted or reflected from the corresponding portion of the microbe-capture region. In an aspect, the computing component includes circuitry to align the location information from a given region of the skin surface with the detected one or more signals emitted or reflected from the at least one type of microbe captured from said region. For example, the computing component includes circuitry to associate one or more signals emitted or reflected from the substrate with a region of an individual's face previously contacted with the epidermis-engaging component to dislodge one or more microbes.

In an aspect, the computing component further includes circuitry configured to receive the sensor output from the at least one sensor component, the sensor output including information associated with at least one property of the detected one or more signals emitted or reflected from the at least one type of microbe captured on the microbe-capture region from said one or more regions of the skin surface of the individual; compare the at least one property of the detected one or more signals from the at least one type of microbe with a database of reference microbe signal properties; generate a digital alignment of the location of said one or more regions of the skin surface of the individual with the detected one or more signals emitted or reflected from the at least one type of microbe captured on the microbe-capture region from said one or more regions of the skin surface of the individual; and report to a user a microbe profile based on the digital alignment, the microbe profile including a spatial distribution of the at least one type of microbe on the skin surface of the individual.

In an aspect, the computing component includes circuitry configured to identify the at least one type of microbe captured on the microbe-capture region from said one or more regions of the skin surface of the individual based on the comparison of the at least one property of the detected one or more signals emitted or reflected from the at least one type of microbe with the database of reference microbe signal properties. For example, the computing component can include a database containing a reference library of microbes and associated autofluorescence properties at given excitation wavelengths. For example, the computing component can include a database containing a reference library of microbes and associated optical, fluorescence, reflective, light scattering, opacity, magnetic, acoustic, infrared spectral, electromagnetic, or electrical properties. For example, the computing component can include a database containing a reference library of microbes and size, morphological properties, and physical features. For example, the computing component can include a database containing a reference library of microbes and their protein properties, carbohydrate properties, metabolic properties, lipid properties, or genomic properties. In an aspect, the computing component includes one or more algorithms to process the sensor output provided the at least one sensor component. For example, the one or more algorithms can include an algorithm for assessing the number of microbes in an image field. See, e.g., Selinummi et al., (2005) *BioTechniques* 29:859-863, which is incorporated herein by reference.

In an aspect, the computing component includes circuitry configured to identify the at least one type of microbe captured on the microbe-capture region from said one or more regions of the skin surface of the individual based on the comparison of the at least one property of the detected one or more signals emitted or reflected from a signal-generating element associated with the at least one type of microbe. For example, the computing component can include stored data including signal properties associated with signal-generating elements linked to specific types of microbes. For example, the computing component can include stored data regarding signal properties associated with specific pairings of signal-generating elements and specific microbe-binding elements.

In an aspect, the computing component further includes circuitry configured to report to a user a microbe profile, the microbe profile including an identity of the at least one type of microbe and a spatial distribution of the identified at least one type of microbe on the skin surface of an individual. The microbe profile may be generated from the digital alignment of the location of one or more regions of the skin surface of the individual with the detected one or more signals emitted or reflected from the at least one type of microbe captured on the microbe-capture region from said one or more regions of the skin surface of the individual. In an aspect, the user includes the individual, e.g., the individual for whom the microbe profile is generated. In an aspect, the user includes a service-provider, e.g., a medical professional or cosmetologist who performs the steps to generate the microbe profile for an individual. In an aspect, the user includes a third party individual, e.g., a manufacturer, an insurance company and/or a research group.

In an aspect, the computing component includes circuitry configured to provide a visual representation of the microbe profile on a display. In an aspect, the display is operably coupled to the computing component. For example, a visual representation of an individual's microbe profile may be shown on a display of the microbe profiling device, e.g., a small liquid crystal display. For example, a visual representation of an individual's microbe profile may be sent through a wired or wireless communication link to another display, e.g., a computer monitor, in the individual's home, in a medical professional a cosmetologist office, a cosmetic counter, or in a kiosk. For example, the microbe profile may be available on a display associated with a second hand-held device, e.g., a smartphone device.

In an aspect, the computing component includes circuitry configured to transmit the microbe profile to a printer to provide a printout to a user. The printout can include textual description and/or visual representation of the microbe profile. For example, the printout may provide the microbe profile as a textual description, e.g., identification of the at least one type of microbe on the skin surface of the individual and generally where the microbes are distributed, e.g., the nose area, the "T-zone," the forehead, and the like. For example, the printout may provide the microbe profile as a hardcopy version of the visual representation shown on a display.

In an aspect, the computing component includes circuitry configured to export information regarding the microbe profile to a computing device. For example, the microbe profile may be generated with the microbe profiling device in an individual's home and subsequently downloaded to one or more other computing devices, e.g., the individual's home computer or smartphone device. For example, the microbe profile may be generated with the microbe profiling device in a service-provider's office, and subsequently downloaded to one or more computing devices accessible by the service provider, e.g., an office computer, or by the individual, e.g., a home computer or a smartphone device. In an aspect, the other computing device is associated with a retailer capable of providing a recommended treatment regimen, e.g., a pharmacy, a cosmetic counter, or other retailer. In an aspect, the other computing device is associated with a manufacturer, e.g., the manufacturer of the microbe profiling device and/or a component of a treatment regimen. In an aspect, the other computing device is associated with a third party payer, e.g., an insurance company. In an aspect, the other computing device is associated with a research group.

In an aspect, the computing component includes circuitry configured to generate a recommended treatment regimen based on an identity and a spatial distribution of the at least one type of microbe on the skin surface of the individual. For example, the circuitry can be configured to generate a recommended treatment regimen including an antimicrobial treatment based on the types of microbes present, e.g., antibiotics for bacteria, fungicide for fungus, or antiviral for a virus. For example, the circuitry can be configured to generate a recommended treatment regimen including a type of skin cleaning process, e.g., a type of soap or antiseptic rinse, based on the identity and the distribution of the at least one type of microbe. For example, the circuitry can be configured to generate a recommended treatment regimen including one or more probiotics or prebiotics to alter the microbe profile on the skin surface, e.g., to balance beneficial microbes against harmful microbes. For example, the circuitry can be configured to generate a recommended treatment regimen including a certain type of cosmetic product that is compatible with the microbes present, e.g., helps to maintain beneficial microbes but discourages harmful microbes and can include probiotics and/or prebiotics. For example, the circuitry can be configured to generate a recommended treatment regimen including one or more medicaments, e.g., hormone creams, oral hormones, or retinoid creams. Non-limiting examples of components of a recommended treatment regimen include antimicrobial agents, cleansing products, cosmetic products, probiotics, prebiotics, medicaments, procedures (e.g., shaving or not in sensitive areas, applying warm compresses to open pores, use of a pore-opening or cleaning device, abrasion, and the like), and changes in diet. In an aspect, the circuitry can be configured to alert the individual as to whether the identity and the spatial distribution of the at least one type of microbe warrants discussion with a medical professional. In an aspect, the computing component includes circuitry configured to report to the user the recommended treatment regimen including via a display, a printout, or exportation of data to another device, e.g., a personal handheld device.

In an aspect, the computing component includes circuitry configured to compare the microbe profile with a reference microbe profile, generate a recommended treatment regimen for the individual based on the comparison, and report the recommended treatment regimen to a user. In an aspect, the reference microbe profile is a microbe profile generated for the individual at at least one previous point in time. For example, the reference microbe profile may include a microbe profile generated for an individual prior to treatment for a skin condition. For example, the reference microbe profile may include a microbe profile generated when the individual was younger. In an aspect, the reference microbe profile is a microbe profile generated for one or more other individuals. For example, the reference microbe profile can represent an optimal microbe profile generated by averaging microbe profile information gathered from a number of other individuals. For example, the reference microbe profile can represent an optimal microbe profile generated from one or more other individuals with a complexion preferred by the individual. For example, the reference microbe profile can represent an optimal microbe profile from a celebrity with a complexion or skin properties preferred by the individual.

In an aspect, the microbe profiling device includes additional features. In an aspect, the microbe profiling device includes a timer. In an aspect, the time is set by the manufacturer, e.g., the motor operably coupled to the at least one motivatable component and/or the second motor operably coupled to the device head once turned one are operational for a set period of time. In an aspect, the time is variable and set by the user. In an aspect, the motor operably coupled to the at least one motivatable component and/or the second motor operably coupled to the device head includes variable speed control for different modes of sampling and comfort for the individual. In an aspect, the microbe profiling device includes a pressure indicator to monitor how much pressure is being applied to the skin surface with the device head. For example, more or less pressure may be need to dislodge the at least one type of microbe from the skin surface of the individual with the epidermis-engaging component of the device head.

Device With Signal-Generating Complexes

In some embodiments, the microbe-profiling device includes a plurality of signal-generating complexes, each of the signal-generating complexes including at least one signal-generating element operably coupled to at least one specific microbe-binding element and configured to emit one or more signals in response to interaction with at least one type of microbe.

In an aspect, the signal-generating element is incorporated into a surface of the substrate. In an aspect, the signal-generating element can include a responsive material attached to a surface of the substrate. For example, the surface of the substrate can include a polymer which changes color in response to binding a target, e.g., bacteria. See, e.g., WO2008/059274, which is incorporated herein by reference. In an aspect, the surface of the substrate can include a negative chromogen which loses color in response to binding a microbe.

Figure 9:
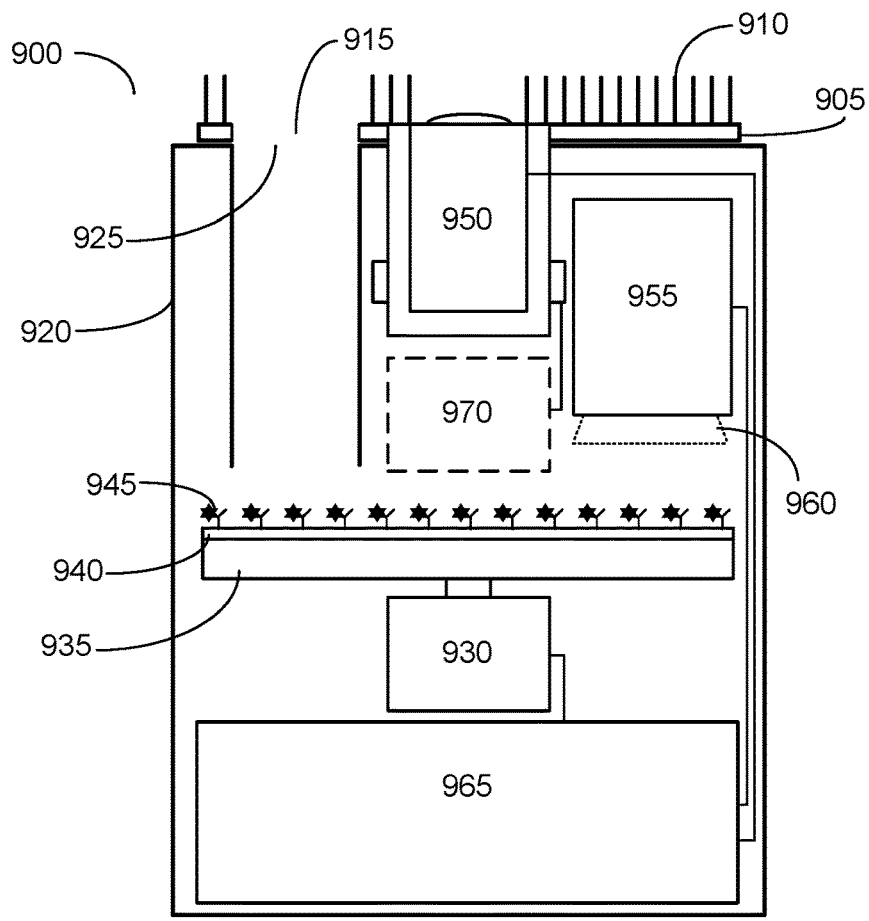
FIG. 9 is a schematic of a microbe profiling device including a plurality of signal-generating complexes.

FIG. 9 is a cross-sectional view of a schematic of an embodiment of a microbe profiling device. Microbe profiling device 900 includes device head 905 including epidermis-engaging component 910 and at least one access window 915. Device head 905 including epidermis-engaging component 910, e.g., a brush-head, pad or abrasive surface, or bladed surface, is configured to dislodge at least one type of microbe from a skin surface of an individual. Microbe profiling device 900 further includes hand-held housing 920 defining an opening 925 which is aligned with at least one access window 915 of device head 905. Hand-held housing 920 of microbe profiling device 900 includes motor 930 operably coupled to at least one motivatable component 935. Motor 930 includes circuitry to drive the at least one motivatable component 935. Hand-held housing 920 of microbe profiling device 900 further includes substrate 940 disposed in relation to at least one motivatable component 935. Substrate 940 is configured to be in operable communication, e.g., at least partially positioned in, opening 925 defined by hand-held housing 920. Substrate 940 includes a plurality of signal-generating complexes 945. At least one of the plurality of signal-generating complexes 945 is configured to emit one or more signals in response to contact with at least one type of microbe dislodged from the skin surface of the individual by epidermis-engaging component 910 of device head 905.

Hand-held housing 920 further includes location-capture component 950. Location-capture component includes circuitry to determine a location of said one or more regions of the skin surface of the individual as epidermis-engaging component 910 of device head 905 contacts said one or more regions of the skin surface of the individual.

Hand-held housing 920 further includes at least one sensor component 955 including circuitry to detect one or more signals emitted from the at least one of the plurality of signal-generating complexes 945 in response to contact with at least one type of microbe dislodged from the skin surface of the individual and to transform the detected one or more signals into a sensor output. In some embodiments, at least one sensor component 955 includes a directed energy source, the directed energy source configured to emit directed energy 960 to elicit one or more signals from the plurality of signal-generating complexes 945. For example, the at least one sensor component 955 can include a sensor system configured to detect fluorescence emitted from at least one of the plurality of signal-generating complexes 945 in response to a directed energy 960, e.g., a wavelength of excitation electromagnetic energy.

Hand-held housing 920 of microbe profiling device 900 further includes computing component 965 including a microprocessor. Computing component 965 includes circuitry configured to control at least one of location-capture component 950 or at least one sensor 955. Computing component 965 may further include a communication link for transmitting and/or receiving data. For example, the communication link can include at least one of a wireless communication link, e.g., Bluetooth or other radio transmission link, or a wired communication link, e.g., an electrical link. In some embodiment, computing component 965 of microbe profiling device 900 can include a transmission unit including an antenna for receiving and/or transmitting information. Computing component 965 further includes circuitry configured to receive information associated with the location of said one or more regions of the skin surface of the individual from location-capture component 950, to receive the sensor output from the at least one sensor 955, to associate the location of said one or more regions of the skin surface of the individual with the detected one or more signals, and to generate an output including information regarding an association between the location of said one or more regions of the skin surface of the individual and the detected one or more signals, e.g., a microbe profile of the at least one type of microbe on the skin surface of the individual.

In an aspect, microbe profiling device 900 further includes second motor 970 operably coupled to device head 905 and including circuitry to rotate, reciprocate, oscillate, or vibrate device head 905

In an aspect, at least one of the plurality of signal-generating complexes is configured to emit one or more signals upon interaction with at least one type of microbe dislodged from the skin surface of an individual. In an aspect, the interaction with the at least one type of microbe is a binding interaction, in which the at least one type of microbe binds to a portion of the signal-generating complex and induces emission of a signal. In an aspect, the microbe may be physically attached to the signal-generating complex. In an aspect, a brief interaction between a microbe and the signal-generating complex may be sufficient to induce a signal. In an aspect, the interaction of the signal-generating complex with the at least one type of microbe is a chemical interaction, in which some component of the microbe, e.g., an excreted component or metabolite, interacts with the signal-generating complex to induce emission of a signal.

Figure 10:
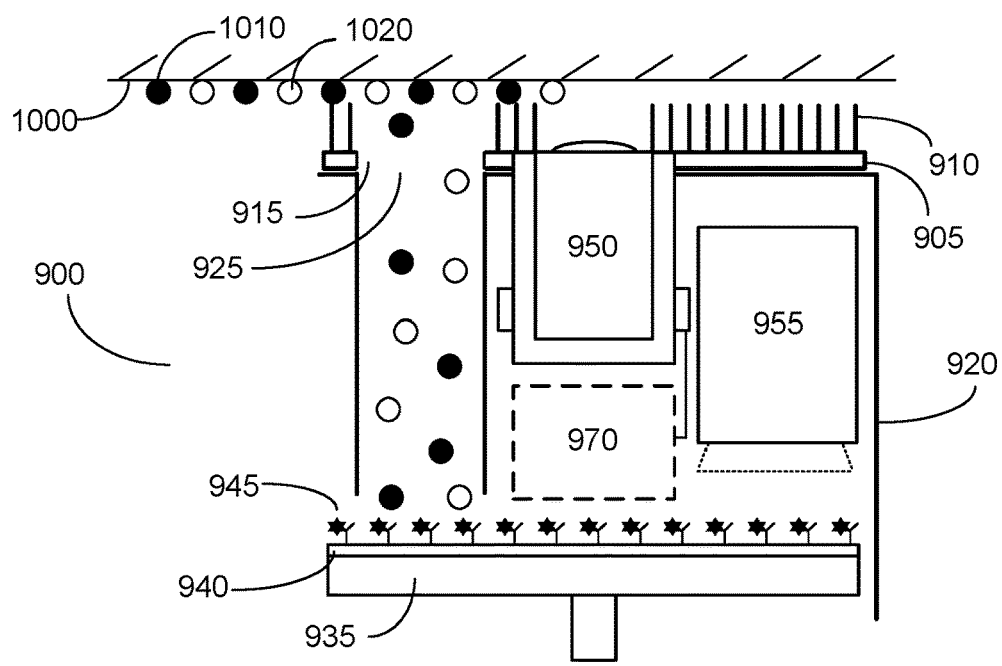
FIG. 10 is a schematic of a portion of a microbe profiling device in contact with a skin surface.

FIG. 10 illustrates a schematic of a microbe profiling device such as illustrated in FIG. 9 in contact with a skin surface of an individual. FIG. 10 depicts epidermis-engaging component 910 of device head 905 of microbe profiling device 900 in contact with skin surface 1000, the latter of which includes at least one first type of microbe 1010 and at least one second type of microbe 1020. At least one first type of microbe 1010 and at least one second type of microbe 1020 are dislodged from skin surface 1000 and are pushed or fall through access window 915 of device head 905 and through opening 925 defined by hand-held housing 920. Location-capture component 950 is configured to determine the location of said one or more regions of skin surface 1000 as epidermis-engaging component 910 is contacting contacts said one or more regions. At least one first type of microbe 1010 and at least one second type of microbe 1020 come in contact with the plurality of signal-generating complexes 945 on substrate 940. At least one motivatable component 935 is operably coupled to a motor and is periodically moved to change the portion of the plurality of signal-generating complexes 945 available for contacting microbes. For example, a first portion of the plurality of signal-generating complexes 945 is available for contacting at least one first type of microbe 1010 and at least one second type of microbe 1020. At least one motivatable component 935 is actuated so as to move the first portion of the plurality of signal-generating complexes 945 in range of at least one sensor component 955 and to move a second portion of the plurality of signal-generating complexes 945 in position to contact one or more microbes. In an aspect, microbe profiling device 900 further includes second motor 970 operably coupled to device head 905 and including circuitry to rotate, reciprocate, oscillate, or vibrate device head 905 to aid in dislodging at least one first type of microbe 1010 and/or at least one second type of microbe 1020 from skin surface 1000.

In an aspect, the plurality of signal-generating complexes are incorporated into the substrate. In an aspect, the plurality of signal-generating complexes are substantially uniformly distributed throughout the substrate. For example, the plurality of signal-generating complexes may be uniformly dispersed in a liquid or gelled form during manufacture of the substrate. In an aspect, at least a portion of the plurality of signal-generating complexes are distributed along at least a portion of the outer surface of the substrate. In an aspect, the plurality of signal-generating complexes are substantially uniformly distributed over at least a portion of the outer surface of the substrate. In an aspect, at least a portion of the plurality of signal-generating complexes are functionally attached to the outer surface of the substrate. In an aspect, at least one of the plurality of signal-generating complexes are covalently attached to the outer surface of the substrate. In an aspect, at least one of the plurality of signal-generating complexes is non-covalently attached to the outer surface of the substrate.

In an aspect, one or more of the plurality of signal-generating complexes are covalently attached to at least an outer surface of the substrate using a crosslinking reagent, e.g., a homobifunctional, heterobifunctional, and/or photoreactive crosslinking reagent. The signal-generating complexes can be cross-linked to the outer surface of the substrate through amine groups, carbohydrate groups, sulfhydryl groups, or combinations thereof associated with a component of the signal-generating complex. A variety of crosslinking reagents are known and available from commercial sources (from, e.g., Pierce-Thermo Fisher Scientific, Inc., Rockford, Ill.).

In an aspect, one or more of the plurality of signal-generating complexes are non-covalently attached to a surface of the substrate. Non-limiting examples of non-covalent interactions include hydrogen bonds, ionic bonds, van der Waals forces, and hydrophobic interactions. For example, a signal-generating complex that includes an oligonucleotide could be non-covalently bound to a complementary oligonucleotide attached to a surface of the substrate. In an aspect, the one or more of the plurality of signal-generating complexes are non-covalently attached to the substrate through protein-protein interactions. For example, a signal-generating complex that includes biotin could be non-covalently attached to a surface that includes streptavidin or avidin. Other non-limiting examples non-covalent interactions include interactions between protein A or protein G and immunoglobulins, ligands with receptors, and secondary antibodies with primary antibodies.

In an aspect, the plurality of signal-generating complexes associated with a surface of the substrate are configured to emit one or more signals in response to two or more types of microbes, each type of microbe associated with a unique signal emitted from one or more of the plurality of signal-generating complexes. In an aspect, the plurality of signal generating complexes includes a plurality of signal-generating complexes of at least one first type and a plurality of signal-generating complexes of at least one second type. In an aspect, the plurality of signal-generating complexes of the at least one first type differ from the plurality of signal-generating complexes of the at least one second type. In an aspect, the plurality of the signal-generating complexes of the at least one first type emit one or more signals of a first type in response to at least one first type of microbe and the plurality of signal-generating complexes of the at least one second type emit one or more signals of a second type in response to at least one second type of microbe. In an aspect, the at least one first type of microbe differs from the at least one second type of microbe. For example, the at least one first type of microbe can include a different phylum from the at least one second type of microbe, e.g., bacteria versus fungi. For example, the at least one first type of microbe can include a different genus from the at least one second type of microbe, e.g., *Staphylococcus* versus *Propionibacterium*. For example, the at least one first type of microbe can includes a different species from the at least one second type of microbe, e.g., *Staphylococcus aureus* versus *Staphylococcus epidermidis*. In an aspect, the one or more signals of the first type differ from the one or more signals of the second type. For example, the one or more signals of the first type can differ in wavelength, e.g., color, from the one or more signals for the second type. In an aspect, a specific color can be associated with a response to a specific microbe, e.g., a red signal associated with *Staphylococcus* and a green signal associated with *Propionibacterium*.

In an aspect, each of the plurality of signal-generating complexes includes at least one signal-generating element, e.g., a chromogenic or fluorogenic signal-generating element, and at least one specific microbe-binding element, e.g., an antibody, aptamer, or oligonucleotide. Non-limiting examples of signal-generating elements and specific microbe-binding elements for use in forming a signal-generating complex have been described above herein. In an aspect, the at least one signal-generating element is operably coupled to the at least one specific microbe-binding element, the at least one signal-generating element configured to emit one or more signals in response to at least one microbe bound to the at least one operably coupled specific microbe-binding element. In an aspect, the signal-generating element emits one or more signals in response to a structural change in the signal-generating complex in the presence of a microbe. In an aspect, the signal-generating element emits one or more signals only when a microbe is bound, e.g., an on/off detection system. Alternatively, the signal-generating element emits a first signal type in the absence of a bound microbe and a second signal type in the presence of a bound microbe, e.g., a change in the color or other property of emitted light. In an aspect, a given type of signal-generating element is operably coupled to a given type of specific microbe-binding element to provide a microbe-specific signal. For example, a first signal-generating element emitting light at a first wavelength band, e.g., red fluorescence, may be operably coupled to a first type of specific microbe-binding element that binds a first type of microbe while a second signal-generating element emitting light at a second wavelength band, e.g., green fluorescence, may be operably coupled to a second type of specific microbe-binding element that binds a second type of microbe, allowing for distinct detection of the first type of microbe versus the second type of microbe.

In an aspect, the substrate includes a plurality of signal-generating complexes of at least one first type including at least one signal-generating element of a first type operably coupled to at least one specific microbe-binding element of a first type, the at least one signal-generating element of the first type to emit one or more signals of a first type in response to at least one first type of microbe bound to the operably coupled at least one specific microbe-binding element of the first type and a plurality of signal-generating complexes of at least one second type including at least one signal-generating element of a second type operably coupled to at least one specific microbe-binding element of a second type, the at least one signal-generating element of the second type to emit one or more signals for a second type in response to at least one second type of microbe bound to the operably coupled at least one specific microbe-binding element of the second type. In an aspect, the at least one first type of microbe differs from the at least one second type of microbe. In an aspect, the one or more signals of the first type differ from the one or more signals of the second type.

Figure 11:
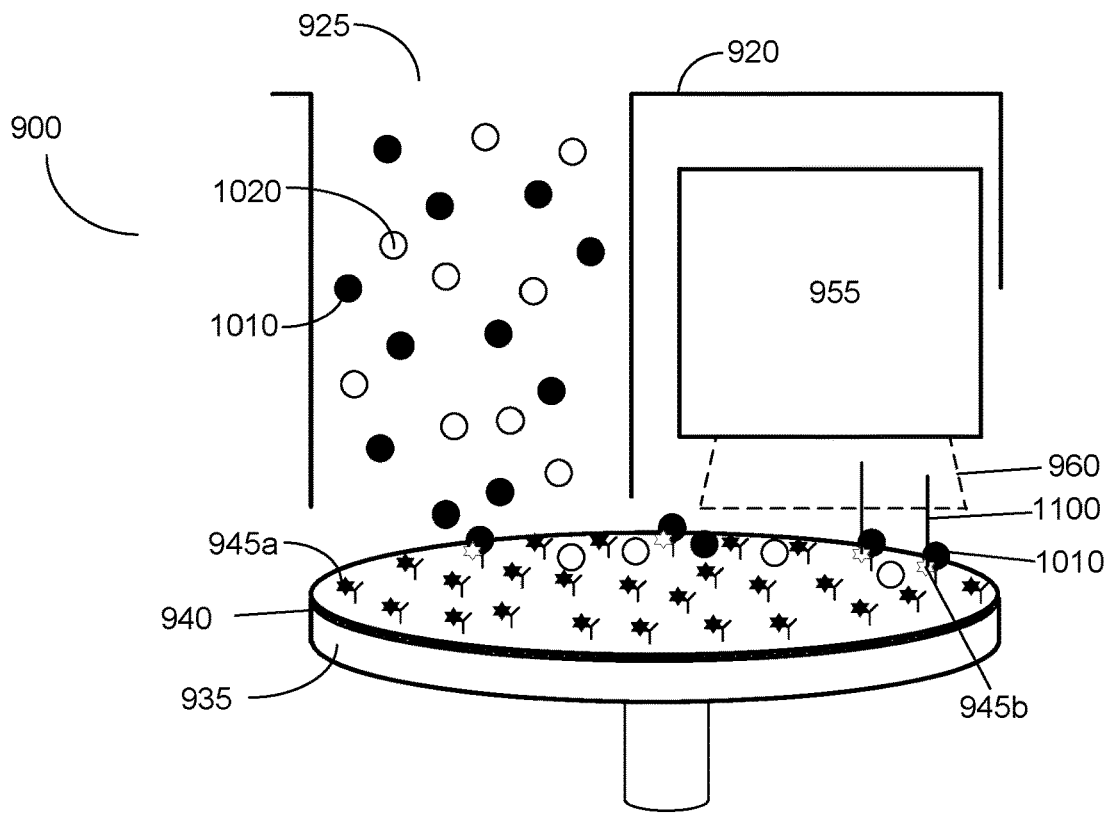
FIG. 11 is a schematic of a portion of a microbe profiling device including a plurality of signal-generating complexes.

FIG. 11 is a schematic of an embodiment of a microbe-profiling device including a plurality of signal-generating complexes of a first type. FIG. 11 shows a schematic of a portion of microbe profiling device such as that shown in FIG. 9 and includes a portion of hand-held housing 920 defining an opening 925. Shown is substrate 940 disposed on a surface of at least one motivatable component 935. Substrate 940 includes a plurality of signal-generating complexes in a first state 945a. Substrate 940 including a plurality of signal-generating complexes in a first state 945a is positioned to contact at least one first type of microbe 1010 and at least one second type of microbe 1020 as said microbes fall or are pushed from the access window of the device head (not shown) through opening 925 defined by hand-held housing 920. At least one of the plurality of signal-generating complexes in a first state 945a is configured to convert to a signal-generating complex in a second state 945b to emit one or more signals 1100 in response to contact with at least one first type of microbe 1010. The plurality of signal-generating complexes in a first state 945a are non-responsive to contact with at least one second type of microbe 1020. Substrate 940 is advanced into at least one sensor component 955. At least one sensor component 955 is configured to detect one or more signals 1100 emitted from a plurality of signal-generating complexes in a second state 945b and to transform the detected one or more signals 1100 into a sensor output. In some embodiments, directed energy 960, e.g., electromagnetic energy, is used to elicit a signal response, e.g., fluorescence, from signal-generating complex 945b. In some embodiments, the signal-generating complexes are configured to emit one or more signals when in contact with the intended at least one type of microbe. In some embodiments, the signal-generating complexes are configured to emit one or more signals of varying quality, e.g., wavelength or intensity, in response to contact with the intended at least one type of microbe. For example, the signal-generating complex can be configured to emit blue fluorescence in the absence of the microbe and to emit green fluorescence in response to interacting with the microbe.

Figure 12:
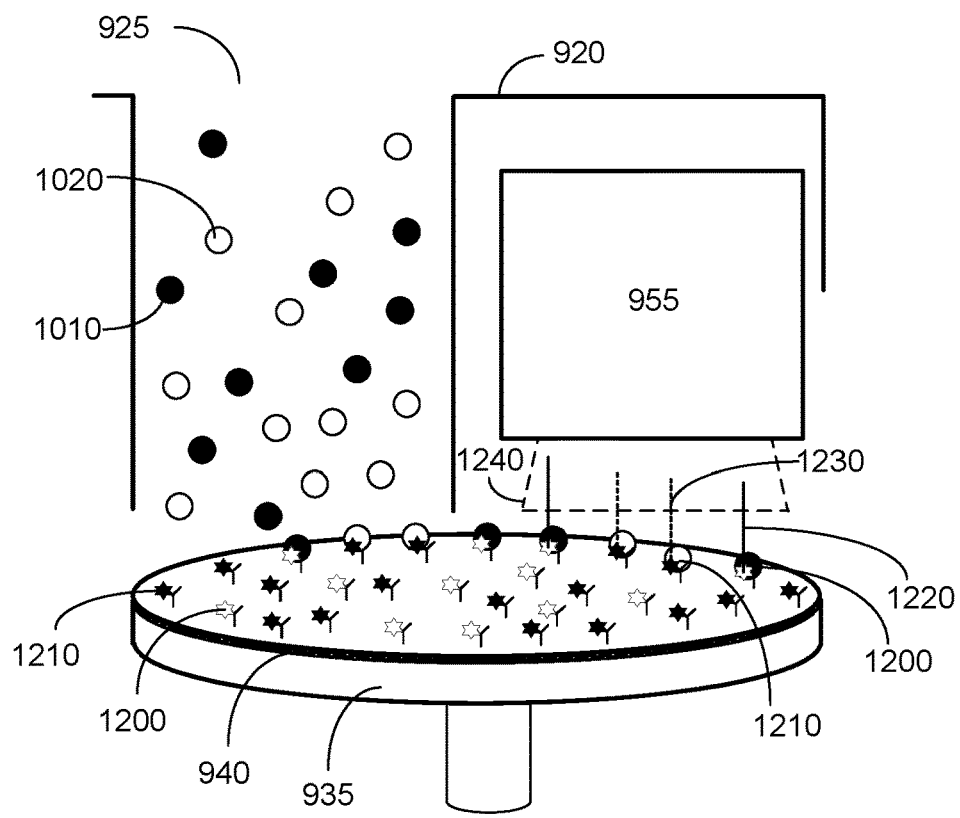
FIG. 12 is a schematic of a portion of a microbe profiling device including a plurality of signal-generating complexes.

FIG. 12 is a schematic of an embodiment of a microbe-profiling device including a plurality of signal-generating complexes of a first type and a plurality of signal-generating complexes of a second type. FIG. 12 shows a schematic of a portion of microbe profiling device 900 including a portion of hand-held housing 920 defining an opening 925. Substrate 940 is disposed relative to at least one motivatable component 935 and includes a plurality of signal-generating complexes of a first type 1200 and a plurality of signal-generating complexes of a second type 1210. Substrate 940 is positioned to contact at least one first type of microbe 1010 and at least one second type of microbe 1020 as said microbes fall or are pushed from the access window of the device head (not shown) through opening 925 defined by hand-held housing 920. As substrate 940 is positioned into opening 925 defined by hand-held housing 920, at least a portion of the plurality of signal-generating complexes of a first type 1200 come into contact with at least one first type of microbe 1010 and at least a portion of the plurality of signal-generating complexes of a second type 1210 come in contact with at least one second type of microbe 1020. At least one motivatable component 935 is configured to move substrate 940 into proximity of at least one sensor component 955. At least one sensor component 955 is configured to detect one or more signals 1220 emitted from a plurality of signal-generating complexes of a first type 1200 and one or more signals 1230 emitted from a plurality of signal-generating complexes of a second type 1210 and to transform the detected signals into a sensor output. In some embodiments, directed energy 1240, e.g., electromagnetic energy, is used to elicit a signal response, e.g., fluorescence, from signal-generating complex 1200 and/or signal-generating complex 1210.

In an aspect, the signal-generating complex includes a chromogenic or fluorogenic signal-generating element. In an aspect, the chromogenic or fluorogenic signal-generating element can be a chemical entity operably coupled to the specific microbe-binding element, so that the chemical entity changes color in response to an interaction with a microbe, e.g., binding the microbe. In an aspect, the chromogenic or fluorogenic signal-generating element can change color in response to metabolism of a microbe bound to and/or in proximity to the outer surface of the skin-covering material. In an aspect, the chromogenic or fluorogenic signal-generating element can change color in response to one or more components excreted from a microbe in proximity to the signal-generating complex. For example, the chromogenic or fluorogenic signal-generating element can by linked to metabolic activity of certain classes of biochemicals including sugars, hexo-phoshates, amino acids, hexose sugars, carboxylic acids, esters, and fatty acids. In an aspect, the chromogenic or fluorogenic signal-generating element can change color in response to an interaction with a microbe independent of the specific microbe-binding element. For example, the chromogenic or fluorogenic signal-generating element can include tetrazolium salts, which form violet-colored formazans in response to microbe metabolism. See, e.g., Tachon et al. (2009) *Microbiology* 155:2941-2948, which is incorporated herein by reference.

In an aspect, the signal-generating complex includes a chromogenic substrate. Chromogenic substrates can include peptides that generate color in response to interaction with microbe-derived proteolytic enzymes. For example, the chromogenic substrate may include in part a chemical group, e.g., para-nitroaniline, which generates a color change when released by enzymatic cleavage. For example, a chromogenic substrate associated with the outer surface of the substrate may interact with an enzyme located on the exterior of the microbe, e.g., located in a bacterial cell wall, to generate a color signal. As an example, L-alanine-4-nitroanilide can be used as a chromogenic substrate for L-alanine-aminopeptidase, commonly associated with Gram-negative bacteria. The substrate L-alanine-4-nitroanilide is split by L-alanine aminopeptidases into L-alanine and 4-nitroaniline, the latter producing a yellow color. The color change can be followed spectrophotometrically and may be proportional to the proteolytic activity.

In an aspect, the signal-generating complex includes a fluorogenic signal-generating complex. In an aspect, fluorogenic signal-generating complex can include chemical dyes or fluorophores that emit light, i.e., fluoresce, at various wavelengths in response to excitation energy. In an aspect, the fluorogenic signal-generating complex can include a quantum dot or semiconductor nanocrystals that fluoresce at various wavelengths in response to excitation energy. In an aspect, the fluorogenic signal-generating complex includes at least one fluorogenic signal-generating element, e.g., a fluorescing dyes, non-limiting examples of which have been described above herein.

In an aspect, the signal-generating complex includes a magnetic signal-generating complex including magnetic beads or particles. In an aspect, the signal-generating complex can include magnetic beads or particles conjugated to the complex via an enzymatically cleavable linkage which in the presence of a microbe is cleaved, releasing the magnetic bead or particle. In an aspect, magnetic beads and magnetic particles of various sub-millimeter size are available from commercial sources (e.g., from Seradyn-Thermo Scientific, Indianapolis, Ind.; Dynal-Invitrogen, Carlsbad, Calif.).

In an aspect, the signal-generating complex includes a radiofrequency identification tag. In an aspect, the signal-generating complex can include a radiofrequency identification tag conjugated to the complex via an enzymatically cleavable linkage, which in the presence of a microbe is cleaved, releasing the radiofrequency identification tag. In an aspect, the signal-generating complex can include a sub-millimeter radiofrequency identification tag. See, e.g., Hornyak (2008) *Scientific American Magazine,* pp 68-71, February 2008, which is incorporated herein by reference. Alternatively, the signal-generating complex can include one or more bokodes, millimeter sized visual tags that can be captured with a camera. See, e.g., Mohan et al. *ACM Transactions on Graphics* Proceedings of SIGGRAPH 2009, Aug. 3-7, 2009, New Orleans, which is incorporated herein by reference.

In an aspect, the signal-generating complex can be configured such that binding of one or more microbes to the specific microbe-binding element operably coupled to the signal-generating element results in a conformational change that induces a fluorescence resonance energy transfer (FRET). FRET is a distance-dependent interaction between the electronic excited states of two dye molecules in which excitation is transferred from a donor molecule to an acceptor molecule without emission of a photon. In an aspect, interaction of a donor molecule with an acceptor molecule can lead to a shift in the emission wavelength associated with excitation of the acceptor molecule. In an aspect, interaction of a donor molecule with an acceptor molecule can lead to quenching of the donor emission. In an aspect, the signal-generating complex can include at least one signal-generating element that includes at least one donor molecule and at least one acceptor molecule attached to a specific microbe-binding element, e.g., an antibody or aptamer. In this configuration, interaction of at least one type of microbe with the specific microbe-binding element, e.g., the antibody or aptamer, causes a conformational change in the specific microbe-binding element and results in a change in the distance between the donor and acceptor molecules components of the signal-generating element and a change in measurable signal, e.g., fluorescence.

A variety of donor and acceptor fluorophore pairs can be considered for FRET including, but not limited to, fluorescein and tetramethylrhodamine; IAEDANS and fluorescein; fluorescein and fluorescein; and BODIPY FL and BODIPY FL. A number of Alexa Fluor (AF) fluorophores (Molecular Probes-Invitrogen, Carlsbad, Calif., U.S.A.) can be paired with other AF fluorophores for use in FRET. Some examples include, but are not limited to, AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

Other non-limiting examples of fluorophores for FRET-based signaling include cyanine dyes Cy3, Cy5, Cy5.5 and Cy7, which emit in the red and far red wavelength range (>550 nm). For example, Cy3, which emits maximally at 570 nm and Cy5, which emits at 670 nm, can be used as a donor-acceptor pair. When Cy3 and Cy5 are not proximal to one another, excitation at 540 nm results only in the emission from of light from Cy3 at 590 nm. In contrast, when Cy3 and Cy5 are brought into proximity by a conformation change, e.g., by binding of a microbe to a specific microbe-binding element, excitation at 540 nm results in an emission at 680 nm.

In an aspect, the signal-generating complex includes a quenching dye to quench the fluorescence of visible light-excited fluorophores. Non-limiting examples of quenching dyes include DABCYL, the non-fluorescing diarylrhodamine derivative dyes QSY 7, QSY 9 and QSY 21 (Molecular Probes, Carlsbad, Calif., U.S.A.), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., U.S.A.). Non-limiting examples of donor fluorophore and quencher pairs include fluorescein with DABCYL; EDANS with DABCYL; or fluorescein with QSY 7 and QSY 9. For example, QSY 7 and QSY 9 dyes can be used to quench the fluorescence emission of donor dyes including blue-fluorescent coumarins, green- or orange-fluorescent dyes, and conjugates of the Texas Red and Alexa Fluor 594 dyes. Non-limiting examples of fluorophores and quenching molecules are known and commercially available (from, e.g., Molecular Probes-Invitrogen, Carlsbad, Calif., U.S.A.).

In an aspect, the signal-generating complex for FRET-based signaling includes a specific microbe-binding element that is an RNA or DNA oligonucleotide-based aptamer and a signal-generating element that includes one or more donor fluorophore and one or more acceptor fluorophore or quencher. See, e.g., Cao et al. (2005) *Current Proteomics* 2:31-40 and U.S. Patent Application 2009/0186342, which are incorporated herein by reference. For example, the aptamer including a donor fluorophore and an acceptor fluorophore or quencher can be configured to undergo a conformational change upon binding a target, e.g., a microbe, causing the distance between the donor fluorophore and the acceptor fluorophore or quencher to shift and leading to a change in measurable fluorescence. See, e.g., Ikanovic et al. (2007) *J. Fluorescence* 17:193-199; Jhaveri, et al. (2000) *Nature Biotech.* 18:1293-1297, which are incorporated herein by reference. The fluorophores can be attached to various linkers that allow for attachment at various sites within the aptamer. For example, 3-prime-DABCYL CPG can be used to place the fluorophore DABCYL at the 3-prime terminus of an aptamer whereas 5-prime-DABCYL phosphoramidite can be used to place DABCYL at the 5-prime terminus of an aptamer (see, e.g., product information at Glen Research, Sterling, Va.). DABCYL deoxythymidine (dT) can be used to place DABCYL within the body of an aptamer sequence. Modifying aptamers with appropriate commercially available fluorophores can be achieved following instructions provided by the respective manufacturer. Alternatively, custom made aptamer-based signaling complexes are available from commercial sources (from, e.g., Biosearch Technologies, Inc., Novato, Calif., U.S.A.).

In an aspect, an aptamer-based signal-generating complex includes a semiconductor quantum dot (QDs). Various methods are available for attaching quantum dots to the DNA backbone of an aptamer such as, for example, covalent linkage of amine-modified DNA to carboxylated quantum dots and linkage of biotinylated DNA to streptavidin modified quantum dots. See, e.g., Cady, et al. (2007) *J. Mol. Cell. Probes* 21:116-124, which is incorporated herein by reference. For example, carboxy quantum dots (from, e.g., Quantum Dot Corporation, Hayward, Calif., U.S.A.) can be attached to an aptamer through a C6 amino modifier placed on either the 5-prime or 3-prime end of the aptamer sequence. For example, streptavidin quantum dots (from, e.g., Quantum Dot Corporation, Hayward, Calif., U.S.A.) can be attached to an aptamer through a biotin attached to the 5-prime end of the aptamer sequence.

In an aspect, the signal-generating complex for FRET-based signaling includes a specific microbe-binding element that is an antibody configured to bind at least one type of microbe and a signal-generating element that includes one or more donor fluorophore and one or more acceptor fluorophore or quencher. For example, the antibody including a donor fluorophore and an acceptor fluorophore or quencher can be configured to undergo a conformational change upon binding a target, e.g., a microbe, causing the distance between the donor fluorophore and the acceptor fluorophore or quencher to shift, the shift leading to a change in measurable fluorescence. See, e.g., Dwarakanath et al. (2004) *Biochem. Biophys. Res. Commun.* 323:739-743; Brennan (1999) *J. Fluor.* 9:295-312, which are incorporated herein by reference. In an aspect, the antibody is modified with a fluorescence signal-generating element such that binding of the target microbe to the antibody shields a solvent sensitive fluorescence signal-generating element near the active binding site from a solvent, e.g., water, resulting in a 3-5 fold increase in fluorescence intensity. See, e.g., Bright, et al. (1990) *Anal. Chem.* 62:1065-1069, which is incorporated herein by reference.

In an aspect, the signal-generating complex for FRET-based signaling includes an antibody with a flexible arm. For example, the antibody can include a donor fluorophore near the binding site of a target, e.g., a microbe, as well as a flexible arm containing an analog of the target or part thereof that is labeled with a quencher and recognized by the antibody. A measurable change in the FRET signal is detected when the analog is competitively displaced by the actual target. See, e.g. U.S. Patent Application 2006/0172318, which is incorporated herein by reference.

In an aspect, the signal-generating complex can be configured such that binding of one or more microbes to the specific microbe-binding element operably coupled to the signal-generating element results in a conformational change that can be measured using chemiluminescence resonance energy transfer (CRET). In an aspect, the image-capture device is able to detect luminescence. For example, the interaction of luminol with hydrogen peroxide in the presence of iron or copper and enhanced by horseradish peroxidase results in emitted light. See, e.g., Freeman et al. (2011) *J. Am. Chem. Soc.* 133:11597-11604; Lee et al. (2012) *ACS Nano* 6:2978-2983, which are incorporated herein by reference.

In an aspect, the at least one specific microbe-binding element of the signal-generating complex is chemically coupled to the at least one signal-generating element. In an aspect, the specific microbe-binding element and the signal-generating element are directly associated with one another through chemical cross-linking, non-covalent linking, or synthesis as a single molecule. For example, the signal-generating element may be operably coupled to the specific microbe-binding element through one or more of a chemical cross-link, a streptavidin/biotin interaction, a fusion protein construct, a common substrate, or a combination thereof.

In an aspect, the signal-generating element is conjugated to the specific microbe-binding element using one or more of a cross-linking agent, non-limiting examples of which have been describe above herein. In general, any of a number of cross-linking agents can be used to conjugate an appropriately derivatized signal-generating element to an appropriately derivatized or functionalized specific microbe-binding element. For example, a fluorescent dye, e.g., rhodamine, derivatized with succinimidyl ester (from, e.g., Invitrogen, Carlsbad, Calif.) will react efficiently with primary amines of proteins, e.g., antibodies, to generate a stable fluorescent dye-protein conjugate. As another example, amine-derivatized, poly-ethylene glycol coated quantum dots can be cross-linked to an antibody via an amine-thiol crosslinker SMCC using a commercially available kit (Qdot® Antibody Conjugation Kit, Invitrogen, Carlsbad, Calif.). Similarly, various methods are available for attaching quantum dots to a DNA backbone of an aptamer such as, for example, covalent linkage of amine-modified DNA to carboxylated quantum dots. For example, carboxy quantum dots (from, e.g., Quantum Dot Corporation, Hayward, Calif., U.S.A.) can be attached to an aptamer through a C6 amino modifier placed on either the 5-prime or 3-prime end of the aptamer sequence. Magnetic beads derivatized with carboxylic acid, amine groups or tosylactivated for cross-linking to proteins and appropriately derivatized oligonucleotides are also commercially available (from, e.g., Dynal Biotech, Brown Deer, Wis.). Quantum dots, fluorescent dyes, and magnetic particles derivatized for cross-linking to antibodies, aptamers or other biomolecules are available from a number of commercial sources (from, e.g., Invitrogen, Carlsbad, Calif.; Seradyn-Thermo Scientific, Indianapolis, Ind.; Sigma-Aldrich, St. Louis, Mo.).

In an aspect, the at least one specific microbe-binding element is non-covalently linked to the signal-generating element. For example, the signal-generating element can be non-covalently linked to the specific microbe-binding element using one or more interactions between biotin and avidin, streptavidin or derivatives thereof. In an aspect, a biotinylated signal-generating element can be reacted with a biotinylated specific microbe-binding element in the presence of streptavidin to form the signal-generating complex. An antibody or other protein-based binding component can be biotinylated using an amine reactive biotinylation reagent such as, for example, EZ-Link Sulfo-NHS-SS-Biotin (sulfosuccinimidyl 2-(biotinamido)-ethyl-1,3-dithiopropionate; from, e.g., Pierce-Thermo Scientific, Rockford, Ill.). An aptamer or other nucleotide-based binding component can be biotinylated by introducing a biotinylated nucleotide, e.g., biotin-5-deoxycytidine-5-triphosphate (from, e.g., ChemCyte, Inc., San Diego, Calif.) into the aptamer sequence during in vitro transcription.

In an aspect, the signal-generating element or the specific microbe-binding element of can be modified with streptavidin, avidin, or derivative thereof and directly bound to a biotinylated signal-generating element or a specific microbe-binding element. In an aspect, the signal-generating element is modified with streptavidin and combined with a biotinylated specific microbe-binding element. For example, streptavidin-modified quantum dots (available from, e.g., Quantum Dot Corporation, Hayward, Calif., U.S.A.) can be attached to an aptamer through a biotin modification to the 5-prime end of the aptamer sequence. See, e.g., Cady et al. (2007) *Mol. Cell. Probes* 21:116-124, which is incorporated herein by reference. Examples of other streptavidin modified fluorescent dyes are available (from, e.g., PerkinElmer, Waltham, Mass.; Alpha Diagnostic Intl. Inc., San Antonio, Tex.). Streptavidin modified magnetic beads are also commercially available (e.g., Dynabeads® MyOne™ Streptavidin, Dynal Biotech, Brown Deer, Wis.). In another aspect, the specific microbe-binding element can contain all or part of the streptavidin protein for use in binding to a biotin modified signal-generating element. For example, cDNA sequence encoding all or part of an antibody or other protein/peptide can be genetically modified to contain all or part of the streptavidin gene using standard cloning procedures, resulting in a streptavidin-antibody fusion protein. See, e.g., Koo, et al. (1998) *Appl. Environ. Microbiol.* 64:2497-2502, which is incorporated herein by reference.

In an aspect, the signal-generating element can be incorporated into the specific microbe-binding element at the time of synthesis. In an aspect, the signal-generating complex can include a fusion protein with a specific microbe-binding element, e.g., antibody, peptide ligand, or receptor, and a signal-generating element including all or part of green fluorescent protein (GFP) derived from *Aequorea victoria* jellyfish or yellow, red and blue fluorescing derivatives thereof. A number of expression constructs for generating recombinant GFP fusion proteins are available from commercial sources (from, e.g., Invitrogen, Carlsbad, Calif.).

In an aspect, the plurality of signal-generating complexes associated with the outer surface of the substrate are incorporated into a field effect transistor (FET) based biosensor, in which a change in electrical signal is used to detect interaction of one or more microbes with one or more of the plurality of signal-generating complexes. See, e.g., U.S. Pat. No. 7,303,875, which is incorporated herein by reference. In an aspect, the one or more electrical signals are processed to generate one or more optical signals using light-emitting diodes or semiconductor optical amplifier, the one or more optical signals detectable by the at least one sensor component. In an aspect, the signal-generating complex can include carbon nanotubes functionalized with a specific microbe-binding element. See, e.g., Zelada-Guillen, et al., (2009) *Angew. Chem. Int. Ed.,* 48:7334-7337, which is incorporated herein by reference. Single walled carbon nanotubes can act as efficient ion-to-electron transducers in potentiometric analysis. The carbon nanotubes can be functionalized with a specific microbe-binding element, e.g., an oligonucleotide aptamer. Upon microbe binding to the aptamer, the aptamers change conformation, separating the phosphate groups of the aptamer from the side-walls of the carbon nanotubes and inducing a charge change to the carbon nanotube and recorded potential.

In an aspect, the signal-generating complex can include one or more microcantilevers configured to detect changes in cantilever bending or vibrational frequency in response to binding of one or more microbes to the surface of the microcantilever. In an aspect, the outer surface of the substrate can include a plurality of biochips including microcantilever bi-material formed from gold and silicon, as sensing elements. See, e.g. Vashist (2007) *J. Nanotech Online* 3:DO:10.2240/azojono0115, which is incorporated herein by reference. The gold component of the microcantilever can be functionalized with one or more specific microbe-binding elements, e.g., aptamer, antibodies, or other microbe binding element. A number of microcantilever deflection detection methods can be used to measure microbe binding including, among other things, optical deflection detection, interferometry deflection detection, optical diffraction grating deflection detection, and charge coupled device detection. In some aspects, the one or more microcantilever can be a nanocantilever with nanoscale components. The one or more microcantilevers and/or nanocantilevers can be arranged into arrays for detection of one or more target cells. Both microcantilevers and nanocantilevers can find utility in microelectromechnical systems (MEMS) and/or nanoelectromechanical systems (NEMS).

In an aspect, the signal-generating complex includes label-free optical biosensors that incorporate other optical methodologies, e.g., interferometers, waveguides, fiber gratings, ring resonators, and photonic crystals. See, e.g., Fan et al., *Anal. Chim. Acta* 620:8-26, 2008, which is incorporated herein by reference.

Microbe Profiling Device With Bladed Structure and Elongated Flexible Strip

Figure 13A:
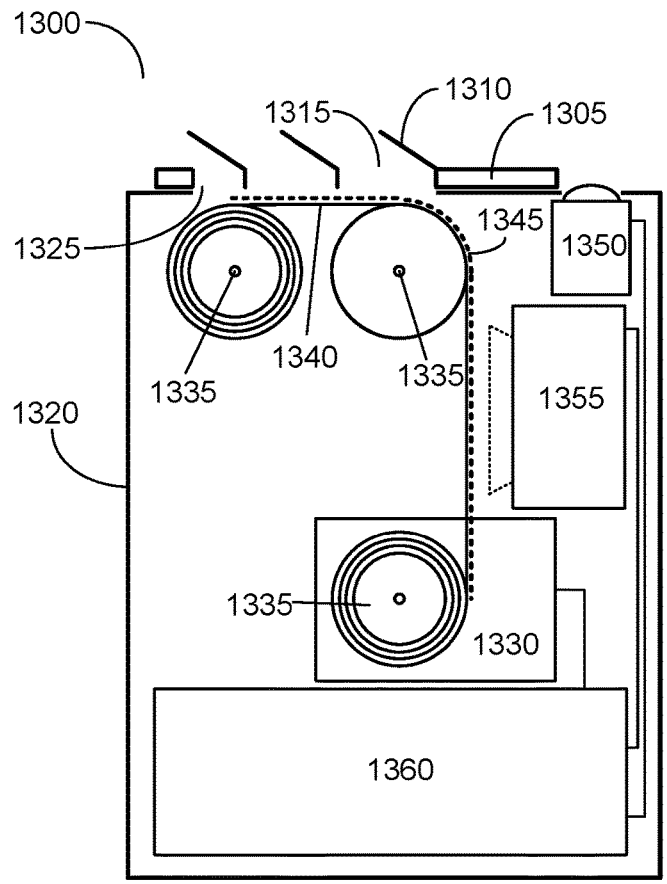
FIG. 13A is a schematic of a microbe profiling device.

FIGS. 13A-D illustrate embodiments of a microbe profiling device. In FIG. 13A, microbe profiling device 1300 includes device head 1305 including epidermis-engaging component 1310 and at least one access window 1315. In this embodiment, epidermis-engaging component 1310 includes at least one bladed surface, e.g., at least one stainless steel blade. Device head 1305 including epidermis-engaging component 1310, e.g., at least one bladed surface, is configured to dislodge, e.g., scrape, at least one type of microbe from a skin surface of an individual. Microbe profiling device 1300 further includes hand-held housing 1320 defining an opening 1325 which is aligned with at least one access window 1315 of device head 1305. Hand-held housing 1320 of microbe profiling device 1300 includes motor 1330 operably coupled to at least one motivatable component 1335, e.g., at least one rotatable reel. Motor 1330 includes circuitry to drive rotation of at least one motivatable component 1335. Hand-held housing 1320 of microbe profiling device 1300 further includes substrate 1340, e.g., an elongated flexible strip, disposed on an outer surface of at least one motivatable component 1335. Substrate 1340 is configured to pass opening 1325 defined by hand-held housing 1320. A surface of substrate 1340 includes microbe-capture region 1345. Microbe-capture region 1345 is positioned to capture or contact the at least one type of microbe dislodged by epidermis-engaging component 1310 of device head 1305. For example, the microbe-capture region 1345 can include an adhesive that non-specifically captures microbes from the skin surface of an individual. For example, the microbe-capture region 1345 can include a specific microbe-binding element that specifically captures at least one type of microbe from the skin surface of an individual. In some embodiments, substrate 1340 includes a plurality of signal-generating complexes.

Hand-held housing 1320 further includes location-capture component 1350. Location-capture component includes circuitry to determine a location of said one or more regions of the skin surface of the individual as epidermis-engaging component 1310 of device head 1305 contacts said one or more regions of the skin surface of the individual. For example, location-capture component 1350 can include an image-capture device, e.g., a small camera equipped with a charge coupled device (CCD). In some embodiments, location-capture component 1350 can be operably coupled to at least one rotating component 1335 such that the timing of capturing location information is coordinated with the rotation of substrate 1340.

Hand-held housing 1320 further includes at least one sensor component 1355 including circuitry to detect one or more signals emitted or reflected from at least one type of microbe captured on microbe-capture region 1345 of substrate 1340 from said one or more regions of the skin surface of the individual and to transform the one or more detected signals into a sensor output.

Hand-held housing 1320 of microbe profiling device 1300 further includes computing component 1360 including a microprocessor. Computing component 1360 includes circuitry configured to control at least one of location-capture component 1350 or at least one sensor 1355. Computing component 1360 may further include a communication link for transmitting and/or receiving data. For example, the communication link can include at least one of a wireless communication link, e.g., Bluetooth or other radio transmission link, or a wired communication link, e.g., an electrical link. In some embodiment, computing component 1360 of microbe profiling device 1300 can include a transmission unit including an antenna for receiving and/or transmitting information. Computing component 1360 further includes circuitry configured to receive information associated with the location of said one or more regions of the skin surface of the individual from location-capture component 1350, to receive the sensor output from the at least one sensor 1355, to associate the location of said one or more regions of the skin surface of the individual with the detected one or more signals, and to generate an output including information regarding an association between the location of said one or more regions of the skin surface of the individual and the detected one or more signals, e.g., a microbe profile of the at least one type of microbe on the skin surface of the individual.

Figure 13B:
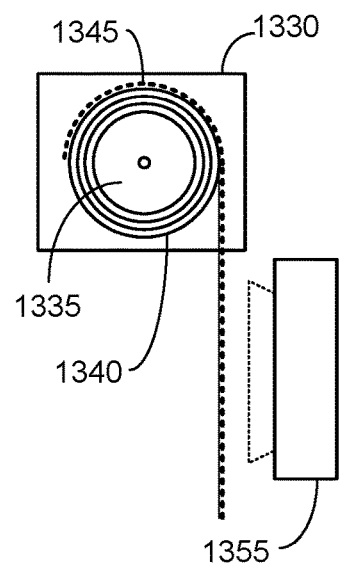
FIG. 13B is a schematic of another embodiment of a microbe profiling device such as shown in FIG. 13A.

In some embodiments, microbe profiling device 1300 includes a single rotatable component. FIG. 13B is a schematic showing a portion of a microbe profiling device such as that shown in FIG. 13A with a single rotatable component 1335 including substrate 1340. Substrate 1340 further includes microbe-capture region 1345. Motor 1330 is configured to drive rotation of single rotatable component 1335. As motor 1330 rotates, single rotatable component 1335 moves substrate 1340, e.g., an elongated flexible strip, past at least one sensor component 1355.

Figure 13C:
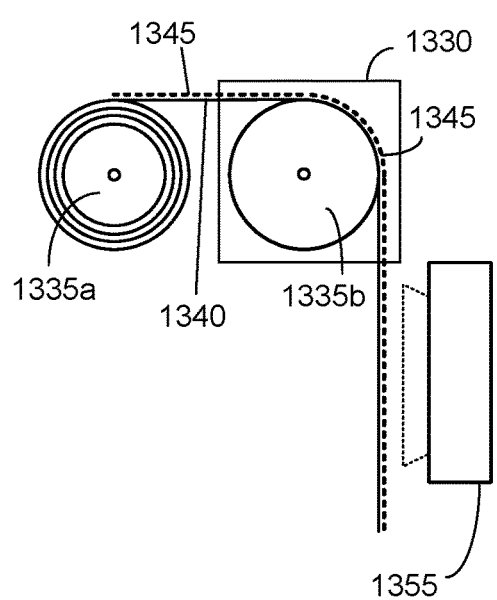
FIG. 13C is a schematic of another embodiment of a microbe profiling device such as shown in FIG. 13A.
Figure 13D:
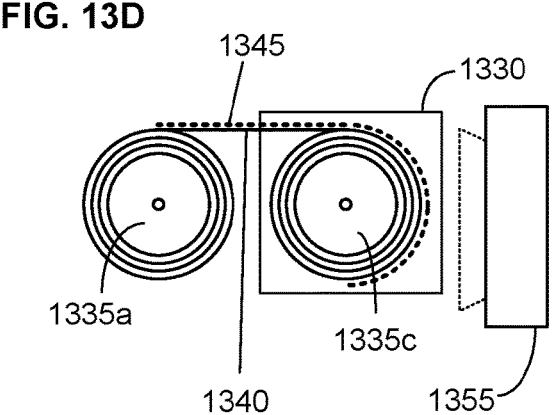
FIG. 13D is a schematic of another embodiment of a microbe profiling device such as shown in FIG. 13A.

In some embodiments, microbe profiling device 1300 includes two rotatable components 1335. FIG. 13C is a schematic showing a portion of a microbe profiling device such as shown in FIG. 13A with supply rotatable component 1335a and rotatable component 1335b. One end of substrate 1340 winds around supply rotatable component 1335a, while the other end is looped over rotatable component 1335b. Substrate 1340 includes microbe-capture region 1345. Motor 1330 is configured to drive rotation of rotatable component 1335b and drive substrate 1340 including microbe-capture region 1350 past at least one sensor component 1355. FIG. 13D is a schematic showing a portion of a microbe profiling device such as that shown in FIG. 13A with supply rotatable component 1335a and take-up rotatable component 1335c. A first end of substrate 1340, e.g., an elongated flexible strip, including microbe-capture region 1345, is wound around supply rotatable component 1335a, and a second end of substrate 1340 is wound around take-up rotatable component 1335c. Substrate 1340 includes microbe-capture region 1345. Motor 1330 is configured to drive rotation of take-up rotatable component 1335c, driving substrate 1340 from supply rotatable component 1335a, past at last one sensor component 1355, and onto take-up rotatable component 1335c.

Microbe Profiling Device With Vacuum

Figure 14:
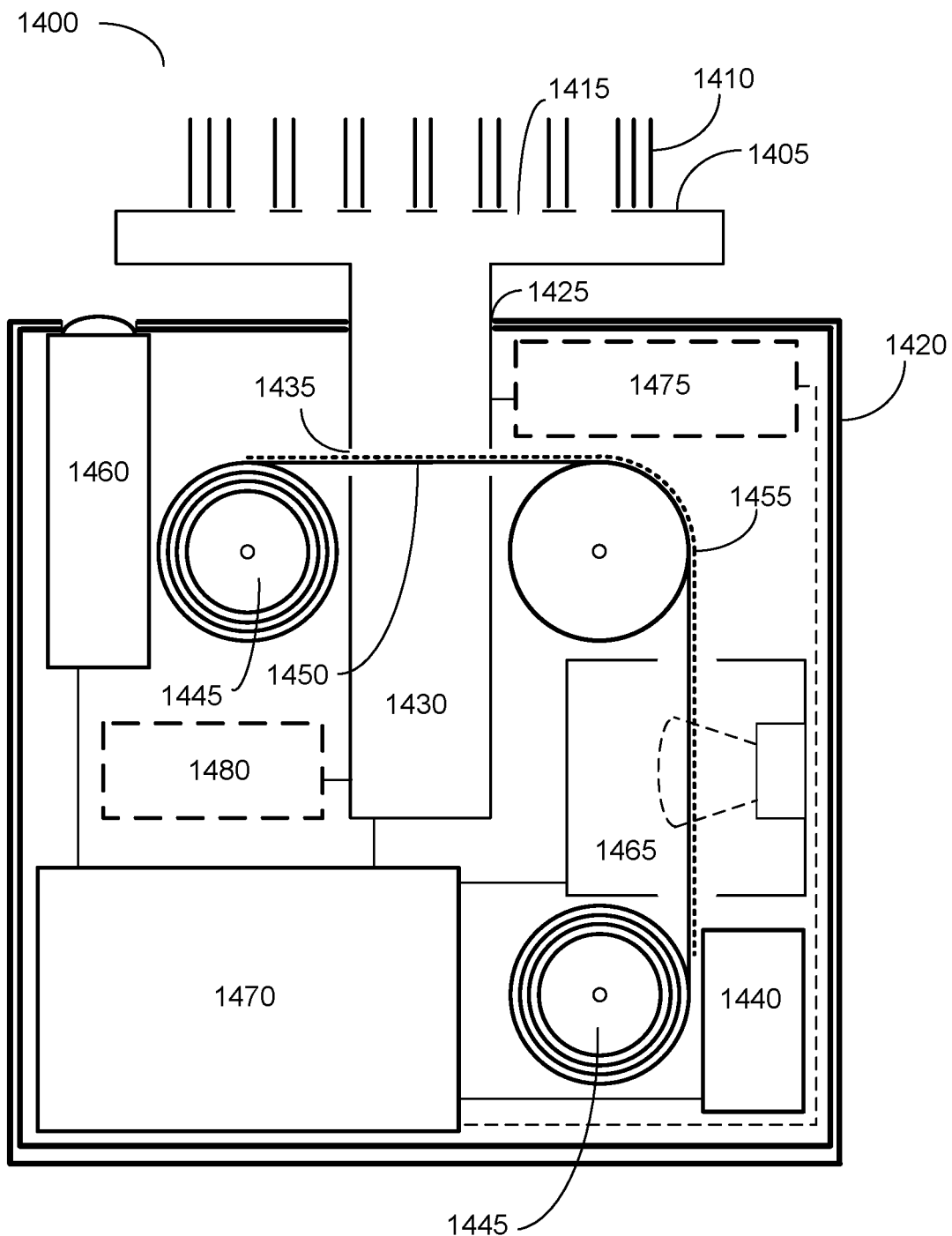
FIG. 14 is a schematic of a microbe profiling device including a vacuum chamber.

A microbe profiling device is described that includes a vacuum component for pulling at least one type of microbe from the skin surface of an individual and into the microbe profiling device. FIG. 14 illustrates a schematic of an embodiment of a microbe profiling device including a device head, e.g., a brush head, and a vacuum chamber. Microbe profiling device 1400 includes a device head 1405 including an epidermis-engaging component 1410 and one or more fluid conduits 1415, wherein device head 1405 is configured to dislodge at least one type of microbe from a skin surface of an individual. Microbe profiling device 1400 further includes hand-held housing 1420 defining an opening 1425. Hand-held housing 1420 includes vacuum chamber 1430 connected to device head 1405 through opening 1425 defined by hand-held housing 1420. Vacuum chamber 1430 is positioned to pull fluid and the at least one type of microbe through one or more fluid conduits 1415 of device head 1405, vacuum chamber 1430. In an aspect, vacuum chamber 1430 defines at least one opening 1435. Hand-held housing 1420 further includes motor 1440 operably coupled to at least one motivatable component 1445, motor 1440 including circuitry to drive at least one motivatable component 1445. Hand-held housing 1420 further includes substrate 1450, e.g., an elongated flexible strip, disposed on an outer surface of at least one motivatable component 1445 and configured to pass through the at least one opening 1435 defined by vacuum chamber 1430. A surface of substrate 1450 includes a microbe-capture region 1455. The microbe-capture region 1455 is positioned to capture the at least one type of microbe from the fluid pulled into vacuum chamber 1430 through one or more fluid conduits 1415 of device head 1405. Hand-held housing 1420 further includes location-capture component 1460 including circuitry to determine a location of one or more regions of the skin surface of the individual as epidermis-engaging component 1410 of device head 1405 contacts said one or more regions of the skin surface of the individual. Hand-held housing 1420 further includes at least one sensor component 1465 including circuitry to detect one or more signals emitted or reflected from the at least one type of microbe captured on microbe-capture region 1455 of substrate 1450 from said one or more regions of the skin surface of the individual and to transform the detected one or more signals into a sensor output. Hand-held housing 1420 further includes computing component 1470 including a microprocessor, computing component 1470 including circuitry configured to receive information associated with the location of said one or more regions of the skin surface of the individual from location-capture component 1460, receive the sensor output from the at least one sensor component 1465, associate the location of said one or more regions of the skin surface of the individual with the detected one or more signals, and output information regarding an association between the location of said one or more regions of the skin surface of the individual and the detected one or more signals. In some embodiments, microbe profiling device 1400 further includes second motor 1475 operably coupled to device head 1405 and including circuitry to move device head 1475, e.g., to rotate, reciprocate, oscillate, and/or vibrate device head 1405. In an aspect, microbe profiling device 1400 further includes at least one of a user interface, a transmission unit including an antenna, and/or one or more reservoirs including at least one agent.

Device Head and Fluid Conduits

In an aspect, device head 1405 of microbe profiling device 1440 includes an epidermis-engaging component 1410, e.g., a brush head, at least one bladed surface, or an abrasive pad, and one or more fluid conduits. In an aspect, the one or more fluid conduits are configured to flow a gas, e.g., air. In an aspect, the one or more fluid conduits are configured to flow a liquid. In an aspect, a liquid is applied to the skin surface of the individual to generate an aqueous environment for microbe profiling. For example, a liquid may be held and controllably released onto the skin surface from one or more reservoirs incorporated into microbe profiling device 1440. For example, a liquid may be applied onto the skin surface from an exogenous source. In an aspect, the fluid conduits are located in the base of the device head 1405. In an aspect, the fluid conduits are incorporated into epidermis-engaging component 1410. In an aspect, one or more fluid conduits are incorporated into bristles or protuberances of an epidermis-engaging component. For example, the bristles of a brush head can be hollow, tubular structures attached at one end to the device head and including one or more fluid conduits, e.g., holes, through which fluid, e.g., air or liquid, can be pulled. In an aspect, a fluid conduit of a bristle, e.g., a hollow center portion, is contiguous with a fluid conduit of the device head, allowing fluid to be pulled through the bristles and into vacuum chamber 1430.

In an aspect, epidermis-engaging component 1410 includes a pad, non-limiting examples of which have been described above herein. In an aspect, epidermis-engaging component 1410 includes an abrasive surface or pad. Non-limiting examples of pads and abrasive surfaces have been described above herein. In an aspect, the pad is attached to device head 1405 and is configured to dislodge at least one type of microbe from a skin surface of an individual. For example, the pad can include an abrasive surface that dislodges the at least one type of microbe. In an aspect, the pad includes one or more fluid conduits. For example, the pad can include one or more fluid conduits that are one or more openings defined by the pad. In an aspect, the one or more fluid conduits of the pad are contiguous with fluid conduits 1415 of device head 1405. In an aspect, the pad is sufficiently porous, e.g., a fibrous mesh, to allow fluid, e.g., air, to be pulled through the pad and into the fluid conduits of device 1405.

In an aspect, device head 1405 and/or components thereof are replaceable. In an aspect, the entirety of device head 1405 is replaceable. For example, a first device head, e.g., a used device head, can be disconnected from the vacuum chamber and replaced with a second device head, e.g., a new device head. For example, the device head may attach to the hand-held housing with a leak-proof connection. For example, the device head may be attached to the hand-held housing with a fitting, a luer lock, or a coupling. In an aspect, only part of device head 1405 is replaceable. For example, a first epidermis-engaging component may be removed from a device head and replaced with a second epidermis-engaging component. For example, a first pad may be removed from a device head and replaced with a second pad.

Vacuum Chamber

Microbe profiling device 1400 includes vacuum chamber 1430 connected to device head 1405 through opening 1425 defined by hand-held housing 1420 and positioned to pull fluid and at least one type of microbe through the one or more fluid conduits 1415 of device head 1405. In an aspect, the vacuum chamber forms a continuous space with an internal portion of the device head through which the one or more fluid conduits connect. In an aspect, the vacuum chamber comprises an enclosure as part of the hand-held housing. In an aspect, the vacuum chamber comprises the entirety of the hand-held housing. In an aspect, vacuum chamber 1430 is operably coupled to vacuum source 1480. In an aspect, vacuum source 1480 is at least partially contained within hand-held housing 1420 of microbe profiling device 1400. For example, vacuum source 1480 can include any of a number of small, commercially available vacuum pumps sized for use in small appliances (from, e.g., Hargraves Technology Corp, Mooresville, N.C.). In an aspect, vacuum source 1480 is external to microbe profiling device 1400 but connected, e.g., by a fitting, luer, or connection, to an outlet of vacuum chamber 1430 with a vacuum conduit, e.g., a hose or tubing.

Figure 15:
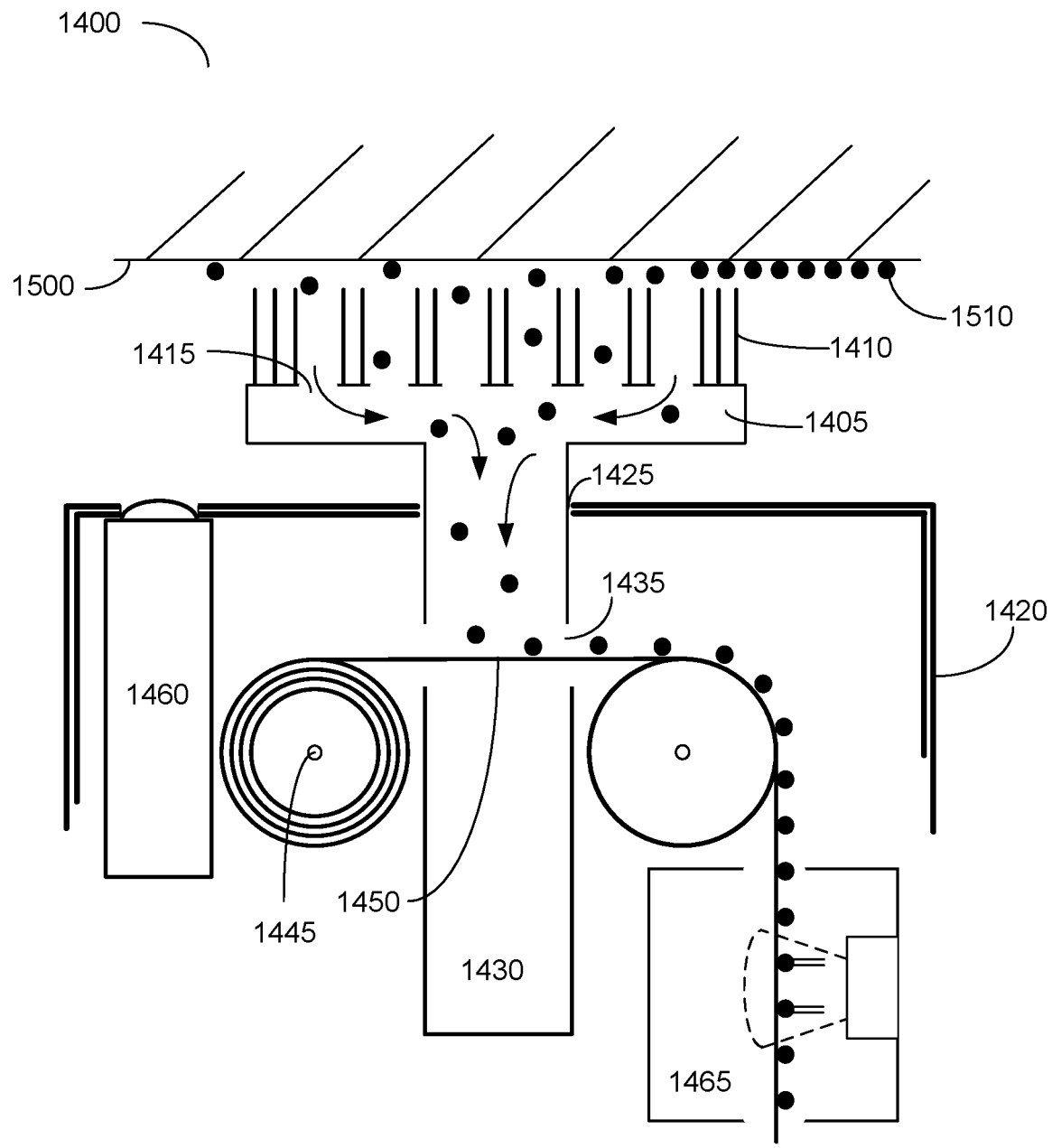
FIG. 15 is a schematic of a microbe profiling device including a vacuum chamber in contact with a skin surface.

FIG. 15 illustrates further aspects of a microbe profiling device such as shown in FIG. 14 in contact with a skin surface. FIG. 15 shows a schematic of a portion of a microbe profiling device including device head 1405 including epidermis-engaging component 1410 and one or more fluid conduits 1415. Device head 1405 is configured to dislodge at least one type of microbe 1510 from skin surface 1500 of an individual. Microbe profiling device 1400 further includes hand-held housing 1420 defining an opening 1425. Hand-held housing 1420 includes vacuum chamber 1430 connected to device head 1405 through opening 1425 defined by hand-held housing 1420. Vacuum chamber 1430 is position to pull fluid and the at least one type of microbe 1510 from skin surface 1500 through one or more fluid conduits 1415 of device head 1405 and onto substrate 1450 disposed on at least one rotatable component 1445. Substrate 1450 passes through opening 1435 defined by vacuum chamber 1430, carrying the at least one type of microbe 1510 to at least one sensor component 1465 for signal detection. Hand-held housing 1420 further includes location-capture component 1460 including circuitry to determine a location of one or more regions of the skin surface of the individual as epidermis-engaging component 1410 of device head 1405 contacts said one or more regions of the skin surface of the individual. At least one sensor component 1465 includes circuitry to detect one or more signals emitted or reflected from at least one type of microbe 1510 captured on the microbe-capture region of substrate 1450 from said one or more regions of the skin surface of the individual and to transform the detected one or more signals into a sensor output.

Microbe Sampling Device and Replaceable Microbe Sampling Unit

Figure 16:
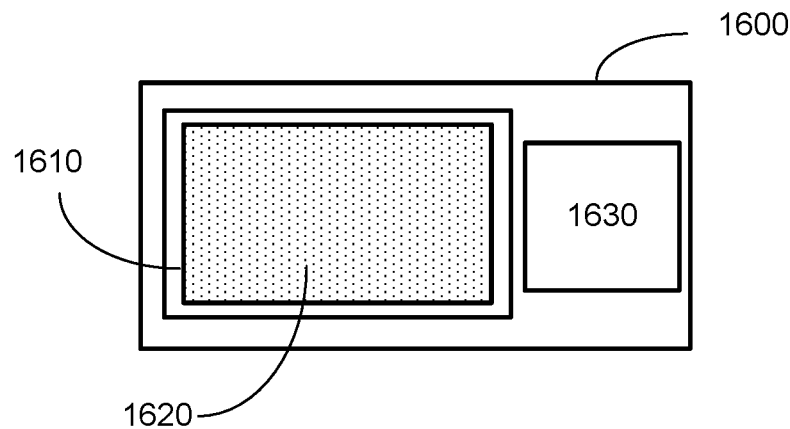
FIG. 16 is a schematic of a replaceable microbe sampling unit.
Figure 17:
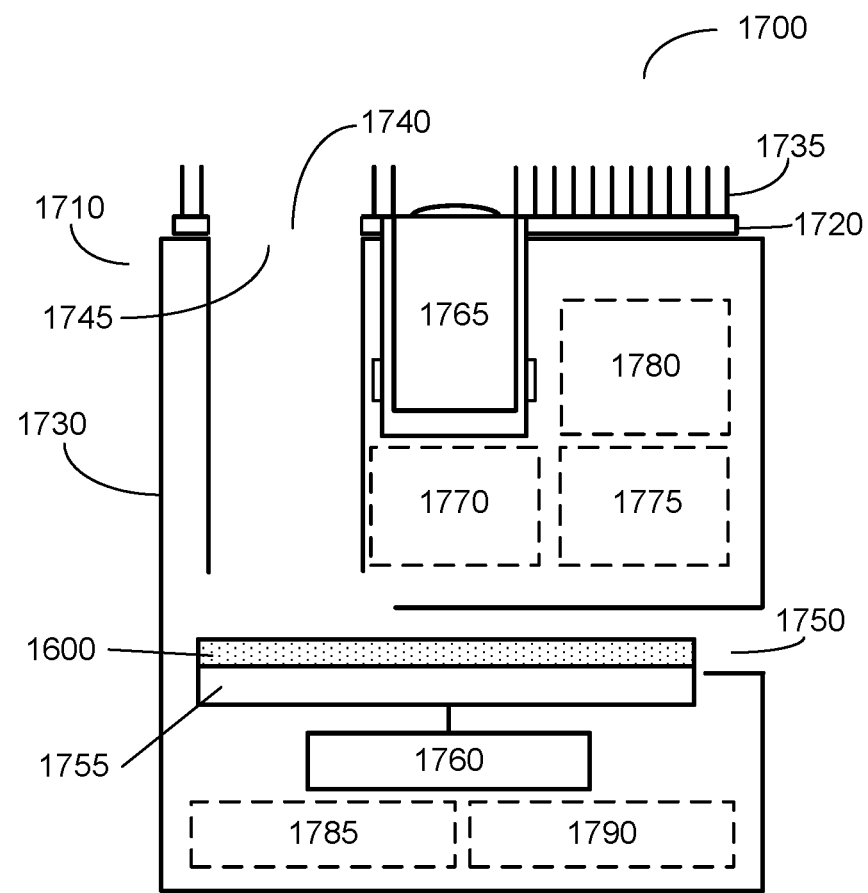
FIG. 17 is a schematic of system including a microbe sampling device and a replaceable microbe sampling unit.

Systems and devices for sampling microbiota of a skin surface are described herein. In an embodiment, a system for sampling microbiota of a skin surface includes a replaceable microbe sampling unit and a microbe sampling device. FIG. 16 illustrates aspects of a replaceable microbe sampling unit and FIG. 17 illustrates aspects of a system including a replaceable microbe sampling unit such as shown in FIG. 16.

FIG. 16 illustrates a schematic of an embodiment of a replaceable microbe sampling unit. Replaceable microbe sampling unit 1600 includes substrate 1610 including microbe-capture region 1620. Microbe-capture region 1620 is configured to capture at least one type of microbe from one or more regions of a skin surface of an individual. Replaceable microbe sampling unit 1600 further includes location information storage component 1630 for storing information associated with the location of said one or more regions of the skin surface of the individual.

Replaceable microbe sampling unit 1600 includes substrate 1610. In some embodiments, the substrate is a separate layer on a surface of the replaceable microbe sampling unit. In some embodiments, the substrate forms the main body of the replaceable microbe sampling unit. For example, the replaceable microbe sampling unit can include a piece of substrate, e.g., plastic, paper, or nitrocellulose, including a microbe-capture region. In an aspect, the substrate includes at least one of a disc shape, an elongated flexible strip, or a sheet. In an aspect, the substrate includes one or more of plastic, cellulose, fabric, paper, polymer, gel, or metal. In an aspect, the substrate is about 1 millimeter wide to about 40 millimeters wide. In an aspect, the substrate is about 1 centimeter to about 10 meters long. Other non-limiting examples of widths and/or lengths for a substrate have been described above herein.

Substrate 1610 further includes microbe-capture region 1620. In an aspect, the microbe-capture region is a property of the substrate. In an aspect, the microbe-capture region forms a separate layer on at least one surface of the substrate. In an aspect, the microbe-capture region covers at least a portion of at least one surface of the substrate. In an aspect, the microbe-capture region includes at least one of a charged surface, an adhesive, an absorbent, an adsorbent, a biomolecule-binding polymer, or a gel, non-limiting examples of which have been described above herein. In an aspect, the microbe-capture region includes a plurality of specific microbe-binding elements. In an aspect, the specific microbe-binding element includes an antibody, an oligonucleotide, a protein, a peptide, a lectin, a carbohydrate, an anti-16S rRNA ligand, an aptamer, a synthetic ligand, or a mimetic binding element, non-limiting examples of which have been described above herein. In some embodiments, the substrate includes a plurality of signal-generating complexes. Non-limiting examples of signal-generating complexes have been described above herein.

Replaceable microbe sampling unit 1600 further includes location information storage component 1630. In an aspect, the location information storage component includes an electronic location information storage component. For example, the location information storage component may include a computer-writeable medium to which information associated with a location of one or more regions of a skin surface of an individual can be written. In an aspect, the location information storage component includes a computer-readable medium. In an aspect, the location information storage component includes a receiver, the receiver including circuitry configured to receive location output from an external source, e.g., a location-capture component of a microbe sampling device. In an aspect, location information storage component includes a transmitter with circuitry configured to transmit information associated with a location of one or more regions of a skin surface of an individual.

In an aspect, the location information storage component is part of the substrate. For example, the location information storage component may be directly written onto a surface of the substrate. In an aspect, the location information storage component is positioned on a surface of the substrate. In an aspect, the location information storage component includes at least one mark on the substrate, the at least one mark including information associated with the location of said one or more regions of the skin surface of the individual. In an aspect, the at least one mark includes at least one of a chromophore, e.g., an ink or dye, a fluorophore, e.g., a fluorescent ink or dye, a bar code, an electrical charge, a magnetic substance, e.g., a magnetic dye, a quantum dot, a radiofrequency identification tag, or other means of adding or writing information to a surface.

FIG. 17 illustrates aspects of a microbe sampling system 1700 including replaceable microbe sampling unit 1600 and microbe sampling device 1710. Microbe sampling device 1710 includes device head 1720 and hand-held housing 1730. In an aspect, hand-held housing is sized for use with one hand, e.g., approximately the size of an electric razor. Device head 1720 includes epidermis-engaging component 1735 and at least one access window 1740 and is configured to dislodge at least one type of microbe from a skin surface of an individual. In an aspect, epidermis-engaging component 1735 can include at least one of brush head, a bladed structure, a pad, or an abrasive surface. In an aspect, at least a portion of device head 1720 is replaceable. In an aspect, epidermis-engaging component 1735 is replaceable. Hand-held housing 1730 defines opening 1745. Opening 1745 defined by hand-held housing 1730 is aligned with at least one access window 1740 of device head 1720.

Hand-held housing 1730 further includes region 1750 sized for accepting replaceable microbe sampling unit 1600. Region 1750 is further configured to position at least a portion of the substrate of replaceable microbe sampling unit 1600 in operable communication with opening 1745 of hand-held housing 1730. Replaceable microbe sampling unit 1600 is disposed in relation to at least one motivatable component 1755 of microbe sampling device 1710. In an aspect, at least one motivatable component 1755 can include at least one of an arm, a piston, or a pneumatic component. In an aspect, at least one motivatable component 1755 can include a rotatable component. In an aspect, at least one motivatable component 1755 can include a suction component or an adhesive component. Hand-held housing 1730 further includes motor 1760 coupled to at least one motivatable component 1755, motor 1760 including circuitry to drive at least one motivatable component 1755. In an aspect, at least one motivatable component 1755 is configured to move replaceable microbe sampling unit 1600 in and/or out of microbe sampling device 1710 through region 1750. In an aspect, at least one motivatable component 1755 is configured to move substrate 1610 of replaceable microbe sampling unit 1600 in and/or out of communication with opening 1745 and at least one type of microbe dislodged from the skin surface with epidermis-engaging component 1735.

Hand-held housing 1730 further includes location-capture component 1765 including circuitry to determine a location of one or more regions of a skin surface of an individual as epidermis-engaging component 1735 contacts said one or more regions of the skin surface of the individual and to output information associated with the location of said one or more regions of the skin surface of the individual to location information storage component 1630 of replaceable microbe sampling unit 1600. The information associated with the location is transmitted to and stored by the location information storage component 1630 of replaceable microbe sampling unit 1600. In an aspect, location-capture component 1765 of microbe sampling device 1710 includes an image capture device, e.g., a digital camera. In an aspect, location-capture component 1765 includes a fiducial reader. In an aspect, the fiducial reader includes at least one of an image capture device, a radiofrequency identification (RFID) reader, an electronic reader, or an audio reader. In an aspect, the fiducial reader is configured to read endogenous fiducials, e.g., physical landmarks on a skin surface. In an aspect, the fiducial reader is configured to read fiducial markers placed on the skin surface, e.g., colored or fluorescent dots or RFID tags.

In an aspect, microbe sampling device 1710 further includes marking means 1770. Marking means 1770 includes circuitry configured to receive information associated with a location of one or more regions of a skin surface of an individual from location-capture component 1765 and to deposit at least one mark on a surface of replaceable microbe sampling unit 1600. In an aspect, the at least one mark is representative of the information associated with the location of the one or more regions of the skin surface of the individual. In an aspect, the at least one mark can include a visual ink mark, e.g., a chromogenic or fluorogenic ink mark. In an aspect, the marking means includes a form of printing, e.g., dot matrix or inkjet type printing, for depositing at least one mark on the replaceable microbe sampling unit. In an aspect, the at least one mark includes a bar code. In an aspect, the marking means can include a form of lithography. In an aspect, the at least one mark includes an electrical charge. In an aspect, the at least one mark includes a magnetic charge. In an aspect, the marking means can include a form of xerography or electrophotography for adding the at least one mark to the replaceable microbe sampling unit. In an aspect, an electrostatic charge can be placed on the substrate of the replaceable microbe sampling unit. For example, the substrate may include a photosensitive or photoconductive area (e.g., selenium, zinc oxide, cadmium sulfide, or silicon). In an aspect, the microbe sampling device includes a photosensitive or photoconductive area, and the charged particles are transferred to the substrate of the replaceable microbe sampling unit. In an aspect, the at least one mark includes a radiofrequency identification tag (RFID tag). In an aspect, the marking means includes a placement matrix for depositing RFID tags on the replaceable microbe sampling unit. In an aspect, the marking means includes a perforating means, e.g., a sharp structure or a laser component, for perforating a portion of the replaceable microbe sampling unit in a representative pattern, the pattern including information associated with a location of one or more regions of a skin surface of an individual. For example, the marking means can include a laser component that burns a pattern onto a surface of the replaceable microbe sampling unit in representative pattern.

In an aspect, microbe sampling device 1710 of system 1700 optionally includes second motor 1775 operably linked to device head 1720, second motor 1775 including circuitry to move device head 1720. Second motor 1775 includes circuitry to rotate, reciprocate, vibrate, or oscillate device head 1720.

In an aspect, microbe sampling device 1710 of system 1700 optionally includes at least one reservoir 1780. In an aspect, reservoir 1780 is configured to hold and controllably release at least one agent. The at least one agent can include at least one of a signal-generating agent, a medicament, or an enhancing agent, non-limiting examples of which have been described above herein. In an aspect, reservoir 1780 is configured to controllably release the at least one agent into the microbe sampling device. For example, reservoir 1780 can be configured to hold and controllably release a plurality of signal-generating elements onto substrate 1610 of replaceable microbe sampling unit 1600. In an aspect, reservoir 1780 defines an opening, the opening defined by the reservoir 1780 adjacent to at least a portion of substrate 1610, reservoir 1780 configured to hold a plurality of at least one type of signal-generating element. In an aspect, reservoir 1780 is configured to controllably release the at least one agent onto the skin surface of the individual. For example, reservoir 1780 can be configured to hold and controllably release a medicament, e.g., an antibacterial agent, onto the skin surface of the individual.

In an aspect, microbe sampling device 1710 optionally includes user interface 1785. Non-limiting examples of user interfaces include buttons, switches, touchpads, microphones, speaker, displays, keypad, or keyboards. In an aspect, microbe sampling device 1710 optionally includes transmission unit 1790 including an antenna for receiving and transmitting information.

Figure 18:
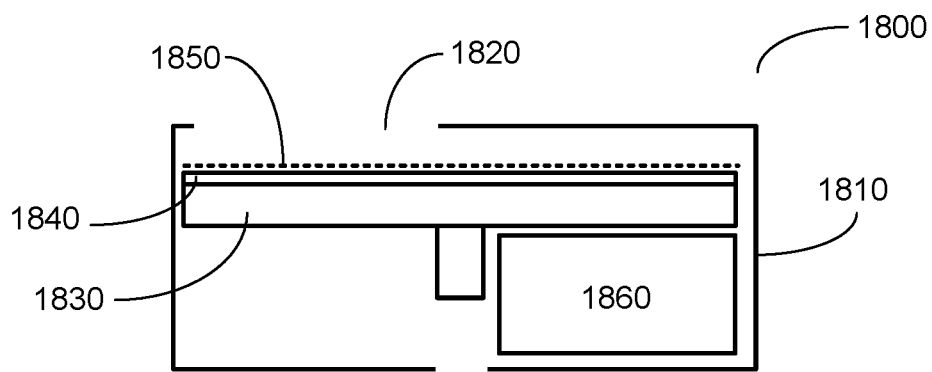
FIG. 18 is a schematic of a replaceable microbe sampling unit.

In some embodiments, at least one motivatable component is incorporated into the replaceable microbe sampling unit and a motor within the microbe sampling device is used to drive the at least one motivatable component. FIG. 18 is a schematic of an embodiment of a replaceable microbe sampling unit including at least one motivatable component. Replaceable microbe sampling unit 1800 includes housing 1810 defining an opening 1820. In an aspect, housing 1810 is appropriately sized for inserting into a hand-held microbe sampling device. For example, housing 1810 can be the size of a magnetic tape cassette. For example, housing 1810 can be the size of a flash drive. In an aspect, housing 1810 is constructed of at least one of plastic, metal, ceramic, rubber, polymer, or resin. Housing 1810 includes at least one motivatable component 1830 at least partially disposed in opening 1820 defined by housing 1810. In an aspect, at least one motivatable component 1830 includes at least one of an arm, a piston, or pneumatic component. In an aspect, at least one motivatable component 1830 includes at least one rotatable component, e.g., a rotatable reel or disc. In an aspect, at least one motivatable component 1830 of replaceable microbe sampling unit 1800 includes at least one of a supply motivatable component or a take-up motivatable component. In an aspect, a first portion of substrate 1840 is wound around an outer surface of the supply motivatable component and a second portion of substrate 1840 is wound around an outer surface of the take-up motivatable component. Substrate 1840 is disposed in relation to at least one motivatable component 1830. In some embodiments, the substrate is disposed on a surface of the at least one motivatable component. A surface of substrate 1840 further includes microbe-capture region 1850 configured to capture at least one type of microbe from one or more skin regions of an individual.

Replaceable microbe sampling unit 1800 further includes location information storage component 1860. Location information storage component 1860 includes circuitry configured to receive, store, and transmit information associated with the location of said one or more regions of the skin surface of an individual. In an aspect, location information storage component 1860 includes an electronic location information storage component. For example, location information storage component 1860 may include a machine- or computer-writeable medium to which information associated with a location of one or more regions of a skin surface of an individual can be written. In an aspect, location information storage component 1860 includes a computer readable media. In an aspect, location information storage component 1860 includes a memory chip. In an aspect, location information storage component 1860 includes random access memory (RAM). In an aspect, location information storage component 1860 includes a receiver, the receiver including circuitry configured to receive location output from an external source, e.g., a location-capture component of a microbe sampling device. In an aspect, location information storage component includes a transmitter with circuitry configured to transmit information associated with a location of one or more regions of a skin surface of an individual.

In an aspect, location information storage component 1860 is part of the substrate. For example, location information storage component 1860 may be directly written onto a surface of the substrate. In an aspect, location information storage component 1860 is positioned on a surface of the substrate. In an aspect, location information storage component 1860 includes at least one mark on the substrate, the at least one mark including information associated with the location of said one or more regions of the skin surface of the individual. In an aspect, the at least one mark includes at least one of a chromophore, a fluorophore, a bar code, an electrical charge, a magnetic substance, a quantum dot, a radiofrequency identification tag, or other means of adding or writing information to a surface.

Figure 19:
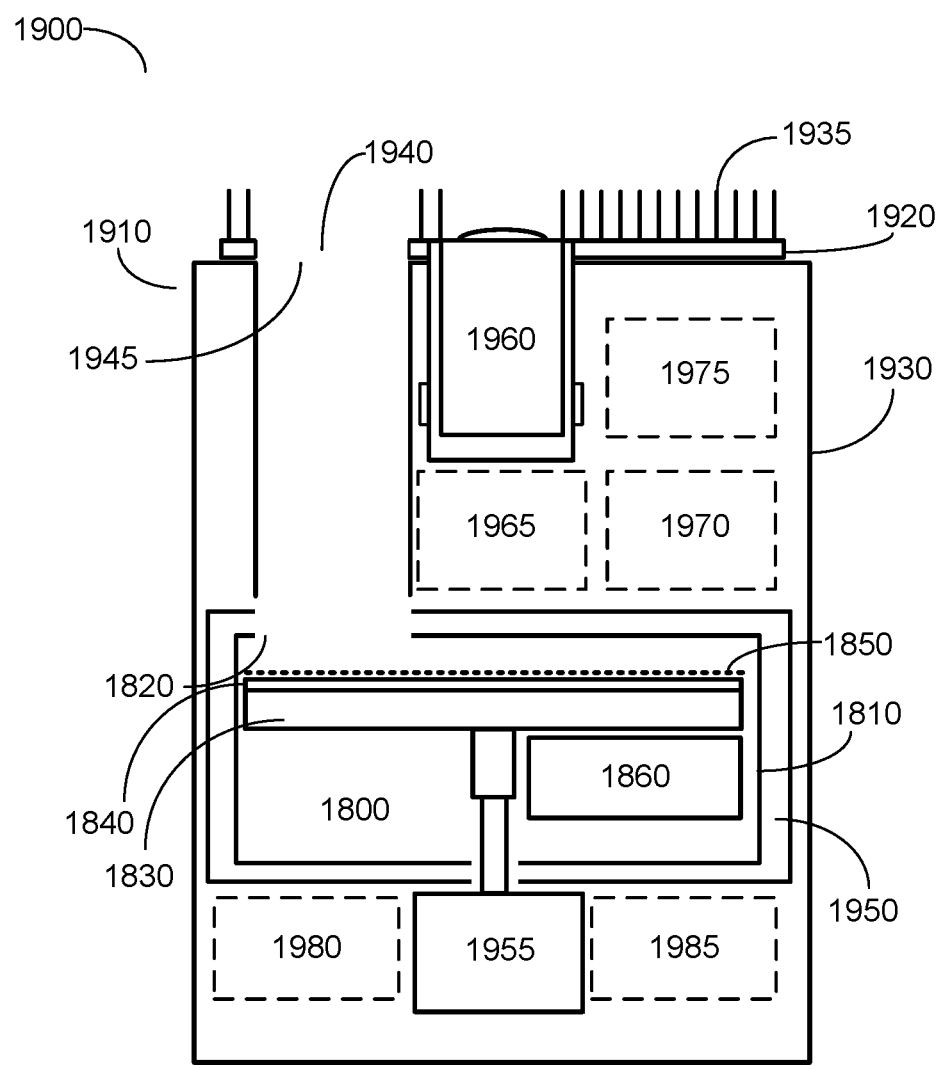
FIG. 19 is a schematic of system including a microbe sampling device and a replaceable microbe sampling unit.

FIG. 19 illustrates aspects of a microbe sampling system 1900 including replaceable microbe sampling unit 1800 and microbe sampling device 1910. Microbe sampling device 1910 includes device head 1920 and hand-held housing 1930. Device head 1920 includes epidermis-engaging component 1935 and at least one access window 1940 and is configured to dislodge at least one type of microbe from a skin surface of an individual. Hand-held housing 1930 defines opening 1945. Opening 1945 defined by hand-held housing 1930 is aligned with at least one access window 1940 of device head 1920. Hand-held housing 1930 includes region 1950 sized for accepting replaceable microbe sampling unit 1800, opening 1820 defined by housing 1810 of replaceable microbe sampling unit 1800 aligned with opening 1945 of hand-held housing 1930 of microbe sampling device 1910. Region 1950 is configured to position at least a portion of the substrate of replaceable microbe sampling unit 1800 in operable communication with opening 1945 defined by hand-held housing 1930. Hand-held housing 1930 further includes motor 1955 coupled to at least one motivatable component 1830 of replaceable microbe sampling unit 1800, motor 1955 including circuitry to drive at least one motivatable component 1830. Substrate 1840 is disposed in relation to at least one motivatable component 1830 and includes microbe-capture region 1850 positioned within region 1950 to capture at least one type of microbe dislodged from the skin surface of an individual by epidermis-engaging component of 1935 of microbe sampling device 1910. Hand-held housing 1930 further includes location-capture component 1960 including circuitry to determine a location of one or more regions of a skin surface of an individual as epidermis-engaging component 1935 contacts said one or more regions of the skin surface of the individual and to transform the determined location into a location output. The location output including information associated with the location of said one or more regions of the skin surface of the individual is transmitted to and stored by location information storage component 1860 of replaceable microbe sampling unit 1800.

In an aspect, microbe sampling device 1910 further includes marking means 1965. Marking means 1965 includes circuitry configured to receive information associated with a location of one or more regions of a skin surface of an individual from location-capture component 1960 and to deposit at least one mark on a surface of replaceable microbe sampling unit 1800. In an aspect, the at least one mark is representative of the information associated with the location of the one or more regions of the skin surface of the individual. Non-limiting examples of marks and marking means have been described above herein.

In an aspect, microbe sampling device 1910 optionally includes second motor 1970 operably linked to device head 1920, second motor 1970 including circuitry to move device head 1920. Second motor 1970 includes circuitry to rotate, reciprocate, vibrate, or oscillate device head 1720.

In an aspect, microbe sampling device 1910 optionally includes at least one reservoir 1975. In an aspect, reservoir 1975 is configured to hold and controllably release at least one agent. The at least one agent can include at least one of a signal-generating agent, a medicament, or an enhancing agent, non-limiting examples of which have been described above herein.

In an aspect, microbe sampling device 1910 optionally includes user interface 1980. Non-limiting examples of user interfaces include buttons, switches, touchpads, microphones, speaker, displays, keypad, or keyboards. In an aspect, microbe sampling device 1910 optionally includes transmission unit 1985 including an antenna for receiving and transmitting information.

Figure 20:
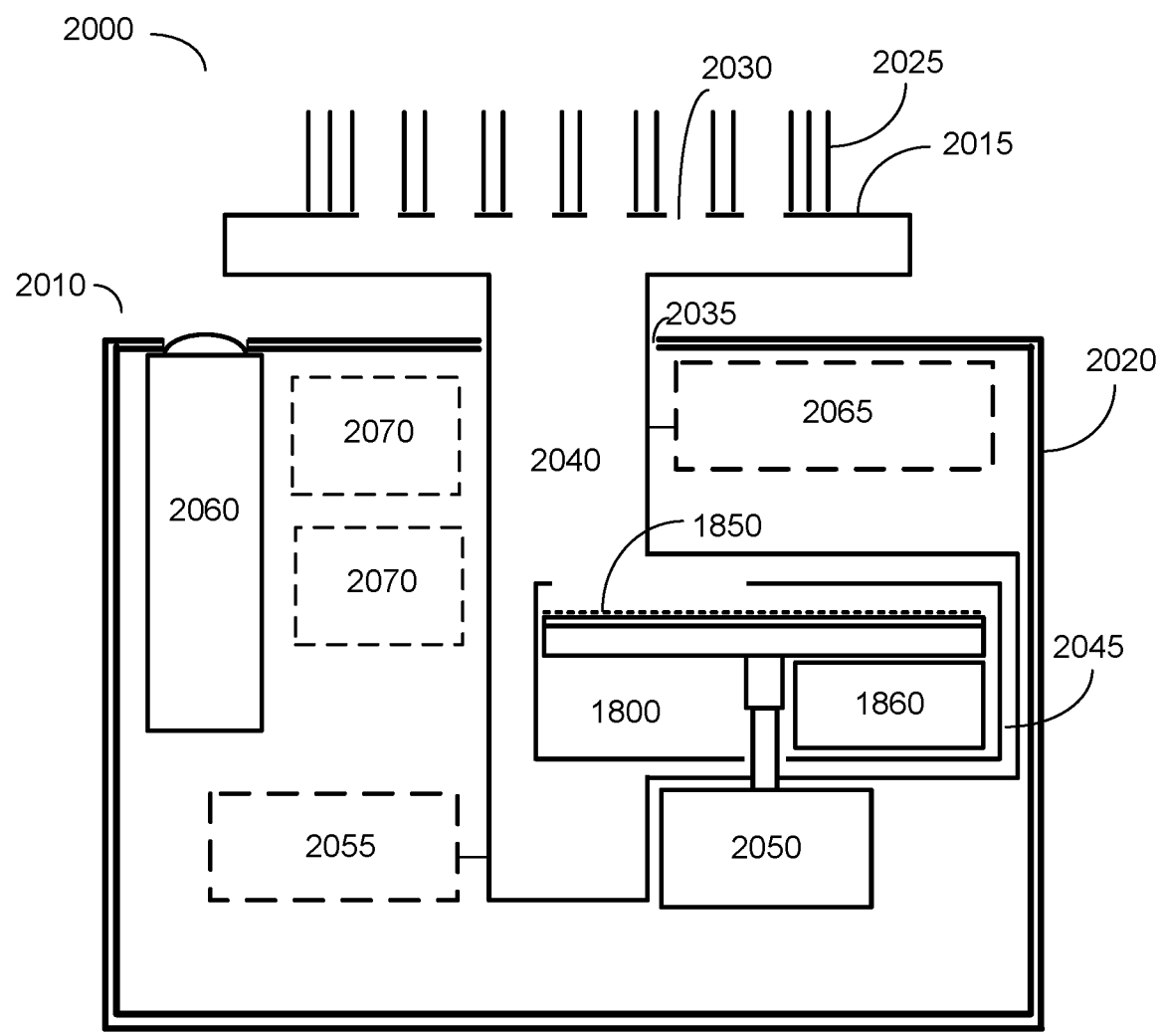
FIG. 20 is a schematic of system including a replaceable microbe sampling unit and a microbe sampling device with a vacuum chamber.

In some embodiments, the microbe sampling device of the system includes a vacuum chamber, the vacuum chamber configured to pull dislodged microbes from the skin surface and onto the microbe-capture region of the replaceable microbe sampling unit. FIG. 20 illustrates aspects of a system 2000 including a replaceable microbe sampling unit 1800 and a microbe sampling device 2010 including a vacuum chamber. Microbe sampling unit 2010 includes device head 2015 and hand-held housing 2020. Device head 2015 includes epidermis-engaging component 2025, e.g., a brush head, and at least one access window forming one or more fluid conduits 2030. Hand-held housing 2020 includes vacuum chamber 2040. Vacuum chamber 2040 is connected to device head 2015 through opening 2035 defined by hand-held housing 2020. Hand-held housing 2020 includes region 2045 at least partially disposed in vacuum chamber 2040 and sized to accommodate replaceable microbe sampling unit 1800. Vacuum chamber 2040 is positioned to pull fluid and at least one type of microbe through one or more fluid conduits 2030 of device head 2015 and into contact with microbe-capture region 1850 of replaceable microbe sampling unit 1800. In an aspect, vacuum chamber 2040 is operably coupled to vacuum source 2055. Vacuum source 2055 is at least partially contained within hand-held housing 2020. In some embodiments, vacuum source 2055 may be entirely exterior to hand-held housing 2020 but connected to vacuum chamber 2040 through a vacuum conduit, e.g., a vacuum tube or hose. Hand-held housing 2020 further includes motor 2050 operably coupled to at least one motivatable component of replaceable microbe sampling unit 1800. Hand-held housing further includes location-capture component 2060 including circuitry to determine a location of one or more regions of the skins surface of the individual as epidermis-engaging component 2025 contacts said one or more regions of the skin surface of the individual. Location-capture component 2060 further includes circuitry to output information associated with the location of said one or more regions of the skin surface of the individual to the location information storage component of replaceable microbe sampling unit 1800. Hand-held housing optionally includes at least one second motor 2065 for moving device head 2015. Hand-held housing 2020 optionally includes at least one reservoir 2070 for holding and releasing signal-generating elements, medicaments, and/or enhancing agents. In some embodiments, hand-held housing 2020 of microbe sampling device 2010 further includes a marking means, a user interface, and/or a transmission unit.

Figure 21:
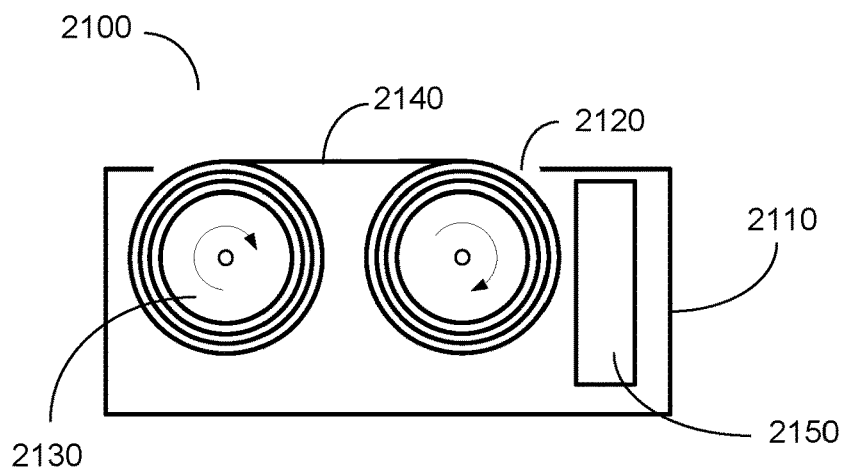
FIG. 21 is a schematic of a replaceable microbe sampling unit.
Figure 22:
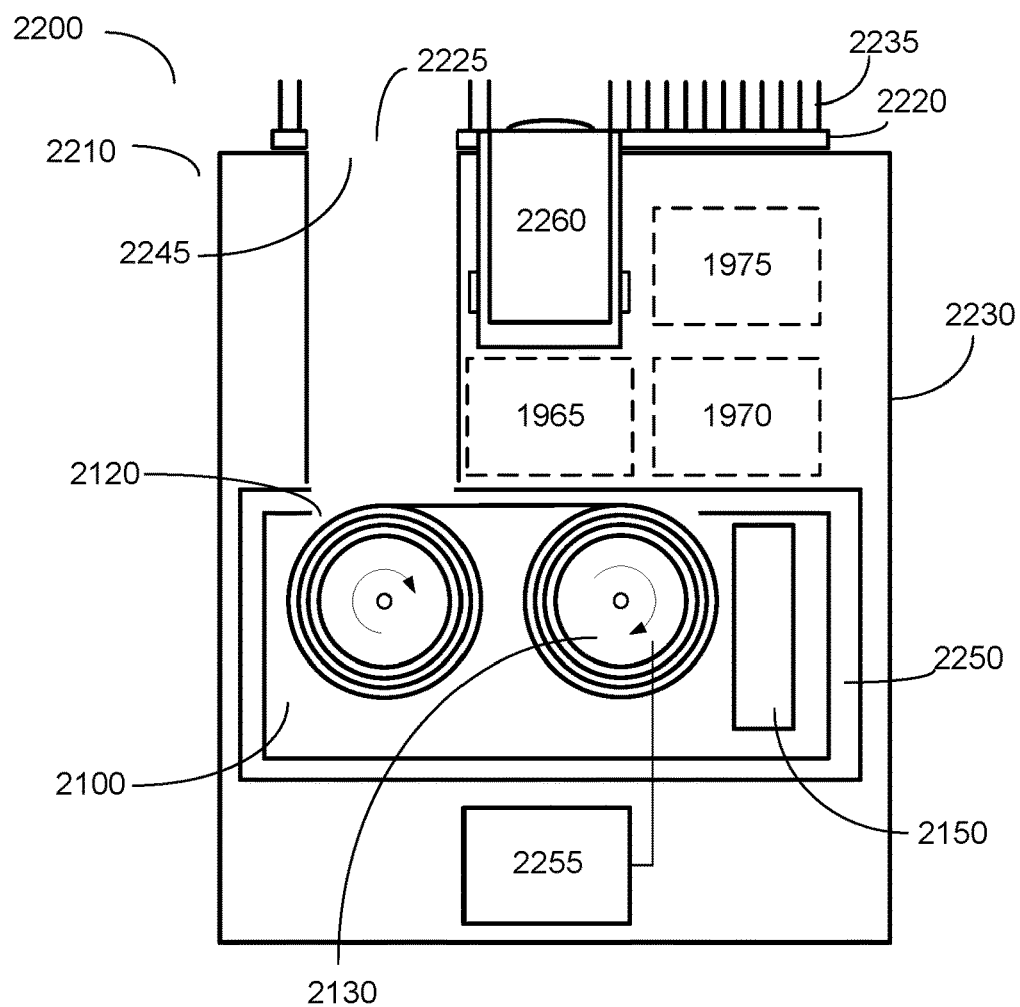
FIG. 22 is a schematic of a system including a microbe sampling device and a replaceable microbe sampling unit.

FIGS. 21 and 22 illustrate further embodiments of a replaceable microbe sampling unit and a system including said replaceable microbe sampling unit. FIG. 21 is a schematic of an embodiment of a replaceable microbe sampling unit. Replaceable microbe sampling unit 2100 includes housing 2110 defining an opening 2120. Housing 2110 includes at least one rotatable component 2130 at least partially disposed in opening 2120 defined by housing 2110. Substrate 2140 is disposed on an outer surface of at least one rotatable component 2130. In an aspect, an outer surface of substrate 2140 further includes a microbe-capture region configured to capture at least one type of microbe from one or more regions of a skin surface of an individual. In an aspect, an outer surface of substrate 2140 includes a microbe-capture region including a plurality of specific microbe-binding elements. In an aspect, an outer surface of substrate 2140 includes a plurality of signal-generating elements. Replaceable microbe sampling unit 2100 further includes location information storage component 2150. Location information storage component 2150 includes circuitry configured to receive, store, and transmit information associated with a location of said one or more regions of the skin surface of an individual.

FIG. 22 illustrates a system 2200 including replaceable microbe sampling unit 2100 and microbe sampling unit 2210. Microbe sampling unit 2210 includes device head 2220 and hand-held housing 2230. Device head 2220 includes at least one access window 2225. In an embodiment, hand-held housing 2230 includes region 2250 sized for accepting replaceable microbe sampling unit 2100. Region 2250 is configured to position opening 2120 defined by replaceable sampling unit 2100 with opening 2245 defined by hand-held housing 2230 of microbe sampling device 2210 to allow at least one type of microbe dislodged with epidermis-engaging component 2235 of device head 2220 to interact with the substrate of replaceable microbe sampling unit 2100. Motor 2255 is operably coupled to at least one rotatable component 2130 of replaceable microbe sampling unit 2100 and includes circuitry to rotate said at least one rotatable component. Hand-held housing 2230 further includes location-capture component 2260 including circuitry to determine a location of one or more regions of the skin surface of the individual as epidermis-engaging component 2235 contacts said one or more regions of the skin surface of the individual. Location-capture component 2260 further includes circuitry to output information associated with the location of said one or more regions of the skin surface of the individual to the location information storage component of replaceable microbe sampling unit 2100.

Figure 23:
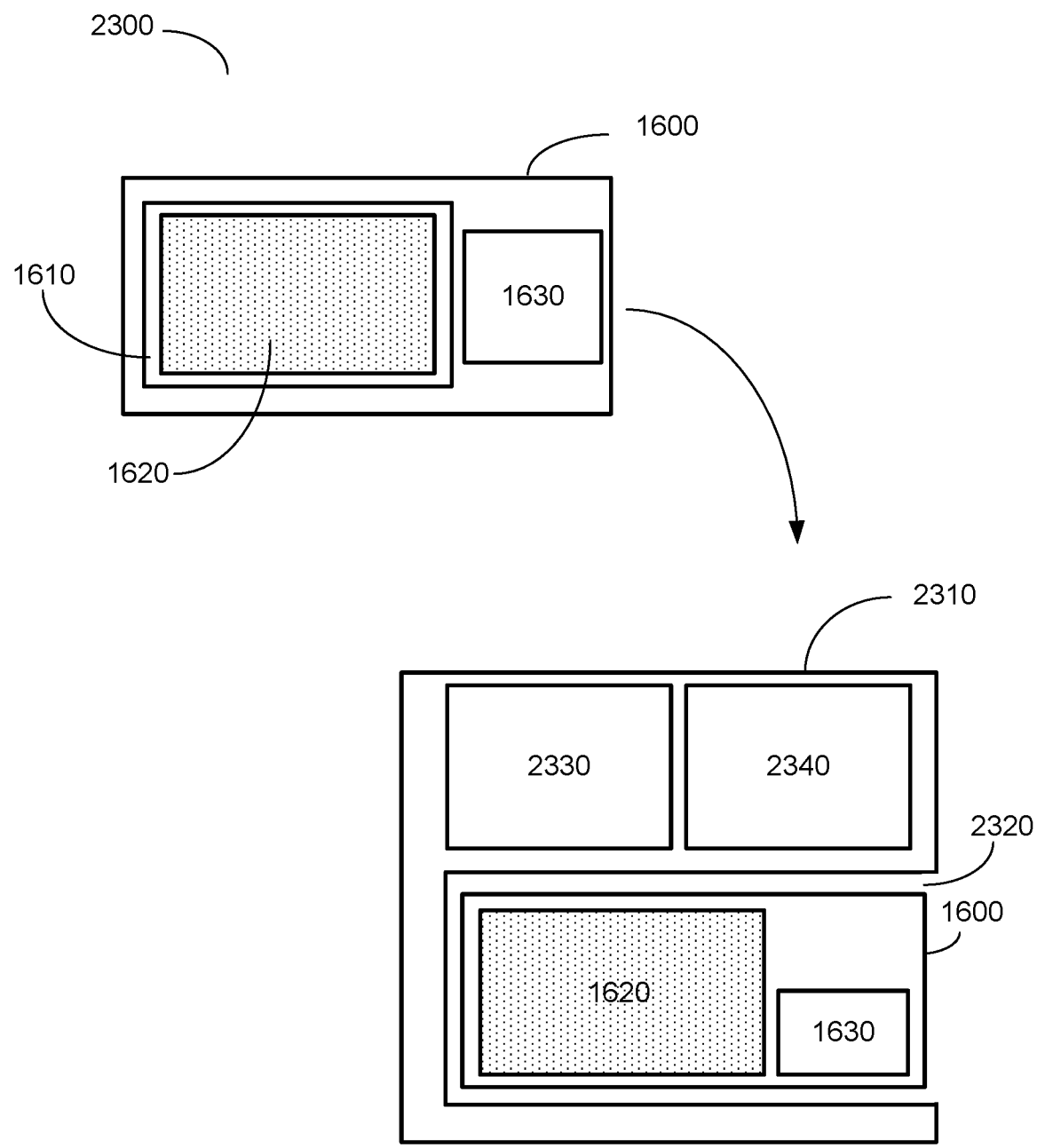
FIG. 23 is a schematic of a system for profiling microbiota of skin including an analyzer.

In an aspect, a system for profiling microbiota of a skin surface of an individual includes a replaceable microbe sampling unit and an analyzer configured to retrieve data from the replaceable microbe sampling unit. FIG. 23 is a schematic of a system for profiling microbiota of a skin surface. System 2300 includes replaceable microbe sampling unit 1600 and analyzer 2310. Replaceable microbe sampling unit 1600 includes substrate 1610 including microbe-capture region 1620, microbe-capture region 1620 configured to capture at least one type of microbe from one or more regions of a skin surface of an individual. Replaceable microbe sampling unit further includes location information storage component 1630 configured to store information associated with the location of said one or more regions of the skin surface of the individual. Non-limiting aspects of a replaceable microbe sampling unit have been described above herein and in FIGS. 16 and 18.

System 2300 further includes analyzer 2310. Analyzer 2310 includes receiving region 2320 sized to accept replaceable microbe sampling unit 1600. In an aspect, at least a portion of replaceable microbe sampling unit 1600 is sized for association with receiving region 2320. Analyzer 2310 further includes at least one sensor component 2330. At least one sensor component 2330 includes circuitry to detect one or more signals emitted or reflected from microbe-capture region 1620 of substrate 1610 of replaceable microbe sampling unit 1600. At least one sensor component 2330 further includes circuitry to transform the detected one or more signals into a sensor output including information associated with at least one property of the detected one or more signals.

In an aspect, the at least one sensor component can include at least one optical sensor. For example, the at least one sensor can include at least one image capture device or scanning device. In an aspect, the at least one sensor component can include at least one fluorescence sensor. For example, the at least one sensor can include at least one fluorescence scanning device. In an aspect, the at least one sensor component includes at least one of an electromagnetic sensor component, an electrical current sensor component, a piezoelectric sensor component, a magnetic sensor component, an acoustic sensor component, a radiofrequency sensor component, a chemical sensor component, or a radioactivity sensor component. Non-limiting examples of sensor components have been described above herein.

In an aspect, the at least one sensor component 2330 of analyzer 2310 includes circuitry configured to detect one or more signals emitted or reflected from at least one type of microbe captured on microbe-capture region 1620 of replaceable microbe sampling unit 1600. For example, at least one sensor component 2330 can include circuitry to detect one or more autofluorescence signals emitted from at least one type of microbe captured on microbe-capture region 1620. In an aspect, the at least one sensor component 2330 of analyzer 2310 includes circuitry to detect one or more optical signal, fluorescence signal, magnetic signal, electromagnetic signal, acoustic signal, light scattering signal, reflective signal, electrical signal, or radioactive signal emitted or reflected from the at least one type of microbe captured on microbe-capture region 1620 of replaceable microbe sampling unit 1600.

In an aspect, the at least one sensor component 2330 of analyzer 2310 includes circuitry configured to detect one or more signals emitted or reflected from at least one of a plurality of signal-generating elements associated with at least one type of microbe captured on microbe-capture region 1620 of replaceable microbe sampling unit 1600. For example, the at least one sensor component can include circuitry to detect one or more chromogenic or fluorogenic signals emitted or reflected from signal-generating elements bound to at least one type of microbeIn an aspect, the at least one sensor component 2330 of analyzer 2310 includes circuitry to detect one or more of an optical signal, a fluorescent signal, an electrical signal, an electromagnetic signal, an audio signal, a magnetic signal, a radioactive signal, a radiofrequency signal, or a chemical signal emitted or reflected from at least one of a plurality of signal-generating elements associated with the at least one type of microbe captured on microbe-capture region 1620 of replaceable microbe sampling unit 1600. In an aspect, the plurality of signal-generating elements are added directly to the skin surface of the individual prior to sampling. In an aspect, the plurality of signal-generating elements are held and controllably released onto the microbe-capture region of the replaceable microbe sampling unit from a reservoir associated with a microbe sampling device. In an aspect, the plurality of signal-generating elements are held in and controllably released from a reservoir associated with analyzer 2310.

In an aspect, the at least one sensor component 2330 of analyzer 2310 includes circuitry configured to detect one or more signals emitted from at least one of a plurality of signal-generating complexes associated with substrate 1610 of replaceable microbe sampling unit 1600 in response to contact with at least one type of microbe. In an aspect, the at least one sensor component 2330 of analyzer 2310 includes circuitry to detect one or more of an optical signal, a fluorescent signal, an electrical signal, an electromagnetic signal, an audio signal, a magnetic signal, a radioactive signal, a radiofrequency signal, or a chemical signal emitted from at least one of a plurality of signal-generating complexes associated with substrate 1610 of replaceable microbe sampling unit 1600 in response to contact with at least one type of microbe.

Analyzer 2310 further includes location information reader 2340. Location information reader 2340 includes circuitry to read the information associated with the location of the one or more regions of the skin surface of the individual from the location information storage component 1630 of replaceable microbe sampling unit 1600 and to transform the information into a location output. In an aspect, the location information reader is configured to read electronic or computer readable location information stored in the location information storage component. In an aspect, the location information reader is configured to read at least one mark on a surface of the replaceable microbe sampling unit, e.g., on a surface of the substrate. In an aspect, the location information reader includes an optical reader including circuitry to read one or more optical marks, e.g., ink or dye markings or bar codes. In an aspect, the location information reader includes a fluorescence reader. In an aspect, the location information reader includes a bar code reader. In an aspect, the location information reader includes an RFID tag reader including circuitry to read one or more RFID tags associated with the replaceable microbe sampling unit. In an aspect, the location information reader includes an electronic reader including circuitry to read electronic markings from the replaceable microbe sampling unit. In an aspect, the location information reader includes a magnetic reader, e.g., a magneto-optical scanner, including circuitry to read magnetic markings from the replaceable microbe sampling unit.

Figure 24:
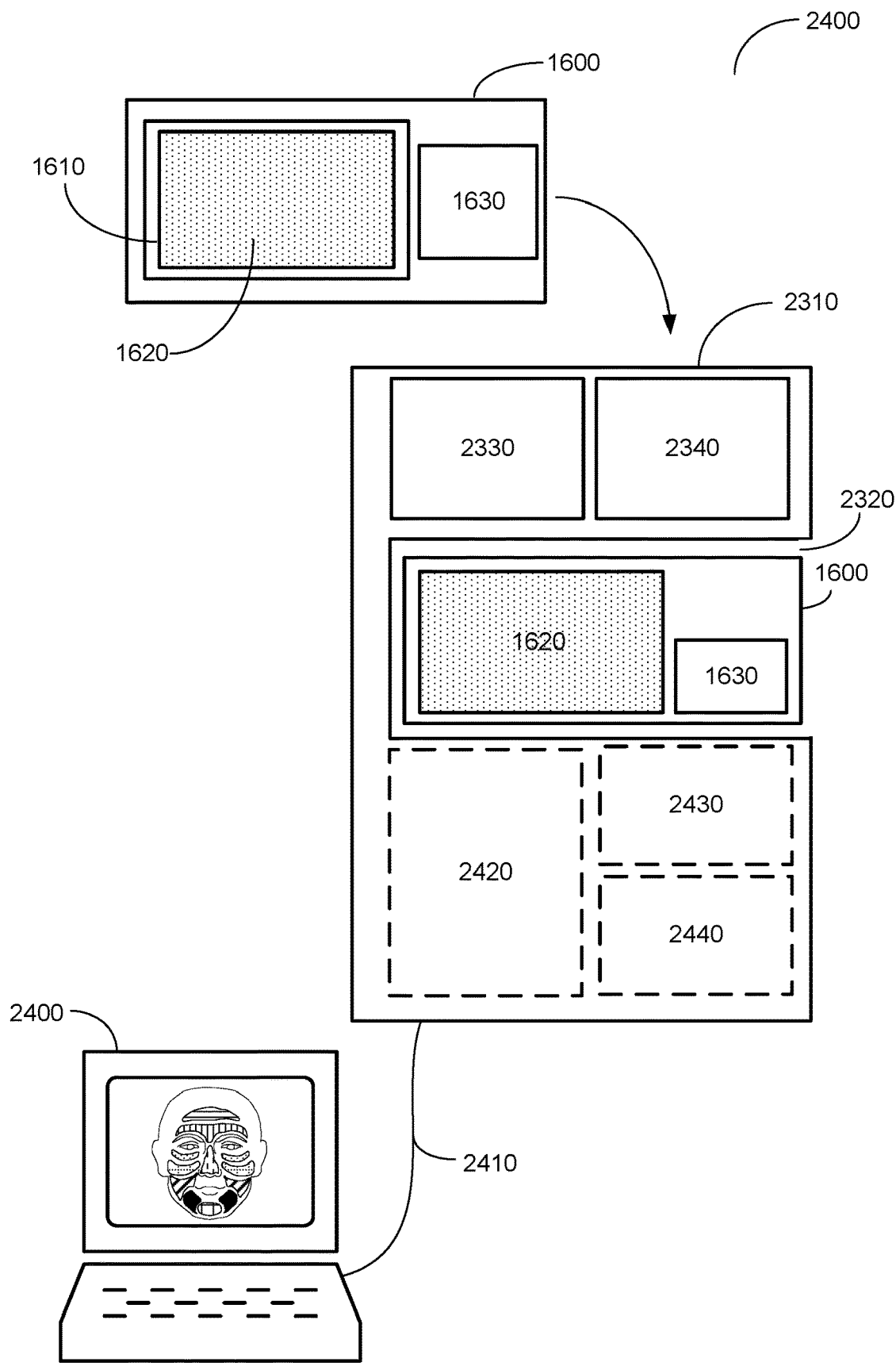
FIG. 24 illustrates further aspect of a system such as shown in FIG. 23.

FIG. 24 illustrates further aspects of a system for profiling microbiota of skin such as shown in FIG. 23. System 2300 can further include computing device 2400 including a processor. Computing device 2400 is operably coupled to analyzer 2310 through communication link 2410. Communication link 2410 can include at least one of a wireless communication link, e.g., Bluetooth or other radio transmission link, or a wired communication link. In an aspect analyzer 2310 and computing device 2400 including the processor are incorporated into a single unit. In an aspect, analyzer 2310 and computing device 2400 including the processor are incorporated into an interactive kiosk.

Computing device 2400 can take various forms or be part of an object, and can include, but is not limited to, a computer, a laptop computer, a personal electronic device, a dedicated computing device, a limited resource computing device, a wireless communication device, a mobile wireless communication device, a handheld electronic writing device, a tablet, a digital camera, a scanner, a cell phone, a PDA, an electronic tablet device, a printer, or any other like device that takes information as an input and gives it back to the end-users. Computing device 2400 can include a digital single processor, ASIC, microprocessor, or other type of processor operating on a system such as a personal computer, server, a router, of other device capable of processing data including network interconnection device. Computing device 2400 shares many aspects of a computing component, e.g., computing component 265 shown in FIG. 2, non-limiting aspects of which have been described above herein.

Computing device 2400 includes circuitry to receive the location output from analyzer 2310 through location information reader 2340, the location output including information associated with the location of said one or more regions of the skin surface of the individual, receive the sensor output from analyzer 2310, the sensor output including information associated with the at least one property of the detected one or more signals emitted or reflected from microbe-capture region 1620, compare the at least one property of the one or more signals emitted or reflected from microbe-capture region 1620 with a database of reference signal properties, generate an alignment of the location of said one or more regions of the skin surface of the individual with the detected one or more signals emitted or reflected from microbe-capture region 1620, generate a microbe profile based on the alignment, the microbe profile including a spatial distribution of the at least one type of microbe on the skin surface of the individual, and report the microbe profile to a user.

In an aspect, computing device 2400 includes circuitry to execute one or more instructions, the one or more instructions including one or more instructions for receiving the location output from analyzer 2310, the location output including information associated with the location of said one or more regions of the skin surface of the individual, one or more instructions for receiving the sensor output from analyzer 2310, the sensor output including information associated with the at least one property of the detected one or more signals emitted or reflected from microbe-capture region 1620, one or more instructions for comparing the at least one property of the one or more signals emitted or reflected from microbe-capture region 1620 with a database of reference signal properties, one or more instructions for generating an alignment of the location of said one or more regions of the skin surface of the individual with the detected one or more signals emitted or reflected from microbe-capture region 1620, one or more instructions for generating a microbe profile based on the alignment, the microbe profile including a spatial distribution of the at least one type of microbe on the skin surface of the individual, and one or more instructions for reporting the microbe profile to a user. In some embodiments, the computing device further executes one or more instructions for identifying the at least one type of microbe detected by the at least one sensor, generating a microbe profile including the spatial distribution and/or identity of the at least one type of microbe, generating a recommended treatment regimen, and reporting the microbe profile and/or the recommended treatment regimen to a user.

In an aspect, computing device 2400 includes circuitry to receive the location output from the analyzer, the location output including information associated with the location of one or more regions of the skin surface of an individual. In an aspect, the computing device includes circuitry to receive one or more images of said one or more regions of the skin surface of the individual. In an aspect, the computing device includes circuitry to receive one or more coordinates of said one or more regions of the skin surface of the individual. In an aspect, the computing device includes circuitry configured to align the location output, e.g., one or more images, fiducials, or coordinates of one or more regions of the skin surface of the individual with a larger reference map of the skin surface. In an aspect, a reference map of the skin surface of the individual, e.g., the entirety of the face, can be captured with a digital camera. In an aspect, a reference map of the skin surface of the individual can include a grid or coordinate system of fiducial markers. In an aspect, the computing device may include circuitry to align the one or more images of the one or more regions of the skin surface of the individual with the reference map of the skin surface based on aligning one or more physical landmarks on the skin surface. The one or more images of the one or more regions of the skin region can be aligned with the reference map of the skin surface to map the location of the one or more regions using any of a number of image registration algorithms, programs, or software. In an aspect, the computing device includes circuitry configured to detect one or more features depicted in the one or more images, e.g., the physical landmarks, and match these features with features in the reference image.

In an aspect, computing device 2400 includes circuitry configured to receive the sensor output from the at least one sensor component. In an aspect, the sensor output includes at least one property of the detected one or more signals emitted or reflected from the at least one type of microbe captured on the microbe-capture region. In an aspect, the sensor output includes at least one property of the detected one or more signals emitted or reflected from one or more signal-generating elements or one or more signal-generating complexes in contact with the at least one type of microbe.

In an aspect, computing device 2400 includes circuitry configured to compare the at least one property of the detected one or more signals with a database of reference signal properties. In an aspect, computing device 2400 includes circuitry to identify at least one type of microbe bound to the microbe capture region of the replaceable microbe sampling unit based on comparison of the at least one property of the detected one or more signals from the at least one type of microbe with the database of reference microbe signal properties. For example, the computing device can include a database containing a reference library of microbes and associated autofluorescence properties at given excitation wavelengths. For example, the computing device can include a database containing a reference library of microbes and associated optical, fluorescence, reflective, light scattering, opacity, magnetic, acoustic, infrared spectral, electromagnetic, or electrical properties. For example, the computing device can include a database containing a reference library of microbes and size, morphological properties, and physical features. For example, the computing device can include a database containing a reference library of microbes and their protein properties, carbohydrate properties, metabolic properties, lipid properties, or genomic properties. In an aspect, the computing device includes one or more algorithms to process the sensor output provided the at least one sensor component. For example, the one or more algorithms can include an algorithm for assessing the number of microbes in an image field. See, e.g., Selinummi et al., (2005) *BioTechniques* 29:859-863, which is incorporated herein by reference.

In an aspect, computing device 2400 includes circuitry to identify at least one type of microbe based on comparison of the at least one property of the detected one or more signals emitted or reflected from at least one of a plurality of signal-generating elements associated with the at least one type of microbe captured on the microbe-capture region with a database of signal properties of reference signal-generating elements. In an aspect, computing device 2400 includes circuitry to identify at least one type of microbe associated with the substrate of a replaceable microbe sampling unit based on comparison of at least one property of one or more signals emitted from at least one of a plurality of signal-generating complexes in response to contact with the at least one type of microbe with a database of signal properties of reference signal-generating complexes. For example, the computing device can include stored data including signal properties associated with signal-generating elements linked to specific types of microbes. For example, the computing device can include stored data regarding signal properties associated with specific pairings of signal-generating elements and specific microbe-binding elements. Non-limiting examples of signal properties of signal-generating elements and/or signal-generating complexes include fluorescence properties, chromogenic properties, optical properties, electrical properties, magnetic properties, audio properties, chemical properties, electromagnetic properties, radio frequency properties, and the like. In an aspect, the databases including signal properties are incorporated into the computing device. In an aspect, the databases including signal properties are accessed from a secondary computing device through a wireless communication link, e.g., through the Internet.

In an aspect, the computing device includes circuitry to report the microbe profile to a user. The microbe profile includes an identity of the at least one type of microbe and/or a spatial distribution of the identified at least one type of microbe on the skin surface of an individual. The microbe profile may be generated from the digital alignment of the location of one or more regions of the skin surface of the individual with the detected one or more signals emitted or reflected from the at least one type of microbe captured on the microbe-capture region from said one or more regions of the skin surface of the individual. In an aspect, the computing device includes circuitry to report the microbe profile to the user through the user interface device operably coupled to the computing device, e.g., a display or a printer. In an aspect, the computing device includes circuitry to report the microbe profile to the user by transmitting the microbe profile to a second computing device, e.g., a smartphone or a remote computing device. In an aspect, the user includes the individual, e.g., the individual for whom the microbe profile is generated. In an aspect, the user includes a service-provider, e.g., a medical professional or cosmetologist who performs the steps to generate the microbe profile for an individual. In an aspect, the user includes a third party individual, e.g., a manufacturer, an insurance company and/or a research group.

In an aspect, the computing device includes circuitry configured to report the microbe profile to the user through a user interface. In an aspect, the computing device includes circuitry configured to provide a visual representation of the microbe profile on a display and/or a printer. In an aspect, the display and/or printer is operably coupled to the computing device. In an aspect, a visual representation of an individual's microbe profile may be sent through a wired or wireless communication link to another display and/or printer in the individual's home, in a medical professional or cosmetologist office, or in a kiosk. For example, the microbe profile may be available on a display associated with a hand-held device, e.g., a smartphone device.

In an aspect, the computing device includes circuitry configured to transmit the microbe profile as a printout to a user. The printout can include textual description and/or visual representation of the microbe profile. For example, the printout may provide the microbe profile as a textual description, e.g., identification of the at least one type of microbe on the skin surface of the individual and generally where the microbes are distributed, e.g., the nose area, the "T-zone," the forehead, and the like. For example, the printout may provide the microbe profile as a hardcopy version of the visual representation shown on a display.

In an aspect, the computing device includes circuitry configured to export information regarding the microbe profile to a second computing device. For example, the microbe profile may be generated with the microbe profiling system in a medical professional's office and subsequently downloaded to one or more other computing devices, e.g., the individual's home computer or smartphone device. In an aspect, the second computing device is associated with a retailer capable of providing a recommended treatment regimen, e.g., a pharmacy, a cosmetic counter, or other retailer. In an aspect, the second computing device is associated with a manufacturer, e.g., the manufacturer of the skin-covering material and/or a component of a treatment regimen. In an aspect, the second computing device is associated with a third party payer, e.g., an insurance company. In an aspect, the second computing device is associated with a research group.

In an aspect, the computing device is connected to at least one user interface, e.g., one or more input components and/or output components for use by a user to interface with the computing device. Non-limiting examples of user interfaces include input components such as a graphical user interface, a display, a keyboard, a keypad, a trackball, a joystick, a touch-screen, a mouse, a microphone, an image scanner, a digital camera, a webcam, a light pen, a bar code reader, a fingerprint scanner, a retinal scanner, a game pad, a stylus pen a switch, a dial, or the like and output components such as television screens, computer monitors, liquid crystal displays, audio speakers, audio headphones, and printers. In an aspect, the user interface may be integrated into the computing device or may be one or more peripheral devices operably connected through a wired or wireless connection to the computing device. The user interface can be used to enter information into the computing device, e.g., patient information, operating instructions, or treatment regimen. The user interface can be used to view output results, e.g., the microbe profile of an individual.

The computing device may further include or be capable of connecting with a network through a network port and network interface or through a wireless port and corresponding wireless interface to facilitate communication with other peripheral devices, for example, a smart phone, a computer, a display monitor, and/or a printer. The network may include a LAN network environment, or a WAN network environment, such as the Internet.

The computing device can further include memory chips, e.g., ROM or flash memory chips, for providing storage of operating systems, look-up tables, database information regarding reference signals, e.g., microbe signal properties, and algorithms for comparing input data with reference data. The system memory of the computing device may include read-only memory (ROM) and random access memory (RAM). A number of program modules may be stored in the ROM or RAM, including an operating system, one or more application programs, other program modules and program data.

The computing device includes computer-readable media products and may include any media that can be accessed by the computing device including both volatile and nonvolatile media, removable and non-removable media. Computer-readable media may include non-transitory signal-bearing media, non-limiting examples of which include a recordable type medium such as magnetic tape, a hard disk drive, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, flash memory, magnetic tape, MINIDISC, non-volatile memory card, EEPROM, optical disk, optical storage, RAM, ROM, system memory, web server, cloud, or the like. Computer-readable media may include computer storage media, e.g., magnetic tape, magnetic disk storage, optical disk storage, memory cards, flash memory cards, electrically erasable programmable read-only memory (EEPROM), solid state RAM, and solid state ROM or any other medium which can be used to store the desired information and which can be accessed by the computing device. Computer-readable media may include a communication media, e.g., wired media, such as a wired network and a direct-wired connection, and wireless media such as acoustic, RF, optical, and infrared media.

In an aspect, computing device 2400 includes circuitry configured to generate a recommended treatment regimen based on an identity and/or a spatial distribution of the at least one type of microbe on the skin surface of the individual. For example, the circuitry can be configured to generate a recommended treatment regimen including an antimicrobial treatment based on the types of microbes present, e.g., antibiotics for bacteria, fungicide for fungus, or antiviral for a virus. For example, the circuitry can be configured to generate a recommended treatment regimen including a type of skin cleaning process, e.g., a type of soap or antiseptic rinse, based on the identity and the distribution of the at least one type of microbe. For example, the circuitry can be configured to generate a recommended treatment regimen including one or more probiotics or prebiotics to alter the microbe profile on the skin surface, e.g., to balance beneficial microbes against harmful microbes. For example, the circuitry can be configured to generate a recommended treatment regimen including a certain type of cosmetic product that is compatible with the microbes present, e.g., helps to maintain beneficial microbes but discourages harmful microbes and can include probiotics and/or prebiotics. For example, the circuitry can be configured to generate a recommended treatment regimen including one or more medicaments, e.g., hormone creams, oral hormones, or retinoid creams. Non-limiting examples of components of a recommended treatment regimen include antimicrobial agents, cleansing products, cosmetic products, probiotics, prebiotics, medicaments, procedures (e.g., shaving or not in sensitive areas, applying warm compresses to open pores, use of a pore-opening or cleaning device, abrasion, and the like), and changes in diet. In an aspect, the circuitry can be configured to alert the individual as to whether the identity and the spatial distribution of the at least one type of microbe warrants discussion with a medical professional. In an aspect, the computing device includes circuitry configured to report to the user the recommended treatment regimen including via a display, a printout, or exportation of data to another device, e.g., a personal handheld device.

In an aspect, the computing device includes circuitry configured to compare the microbe profile with a reference microbe profile, generate a recommended treatment regimen for the individual based on the comparison, and report the recommended treatment regimen to a user. In an aspect, the reference microbe profile is a microbe profile generated for the individual at at least one previous point in time. For example, the reference microbe profile may include a microbe profile generated for an individual prior to treatment for a skin condition. For example, the reference microbe profile may include a microbe profile generated when the individual was younger. In an aspect, the reference microbe profile is a microbe profile generated for one or more other individuals. For example, the reference microbe profile can represent an optimal microbe profile generated by averaging microbe profile information gathered from a number of other individuals. For example, the reference microbe profile can represent an optimal microbe profile generated from one or more other individuals with a complexion preferred by the individual. For example, the reference microbe profile can represent an optimal microbe profile from a celebrity with a complexion or skin properties preferred by the individual.

In an aspect, analyzer 2310 optionally includes motor 2420 operably coupled to at least one motivatable component 2430. At least one motivatable component 2430 is configured to move substrate 1610 of replaceable microbe sampling unit 1600 from one position to another. In some embodiments, such as shown in FIG. 24, at least one motivatable component 2430 is part of analyzer 2310. In an aspect, at least one motivatable component 2430 includes at least one substrate transfer component, the at least one substrate transfer component configure to move at least a portion of the substrate. In an aspect, at least one motivatable component 2430 includes at least one of an arm, a piston, or a pneumatic component. In an aspect, at least one motivatable component 2430 includes an adhesive component or a suction component. In an aspect, at least one motivatable component 2430 includes a rotatable component, e.g., a disk or a reel.

In an aspect analyzer 2310 includes a plurality of at least one type of signal-generating element, wherein the signal-generating elements associate with at least one microbe captured on microbe-capture region 1620 of replaceable microbe sampling unit 1600 and is detected by at least one sensor component 2330 of the analyzer 2310. Non-limiting examples of signal-generating elements have been described above herein. In an aspect, analyzer 2310 optionally includes reservoir 2440. In some embodiments, reservoir 2440 includes the plurality of at least one type of signal-generating element. In some embodiments, reservoir 2440 includes other agents, e.g., medicaments and/or enhancing agents. In an aspect, reservoir 2440 includes at least one opening defined by reservoir 2440, the opening adjacent to at least a portion of substrate 1610 of replaceable microbe sampling unit 1600.

Figure 25:
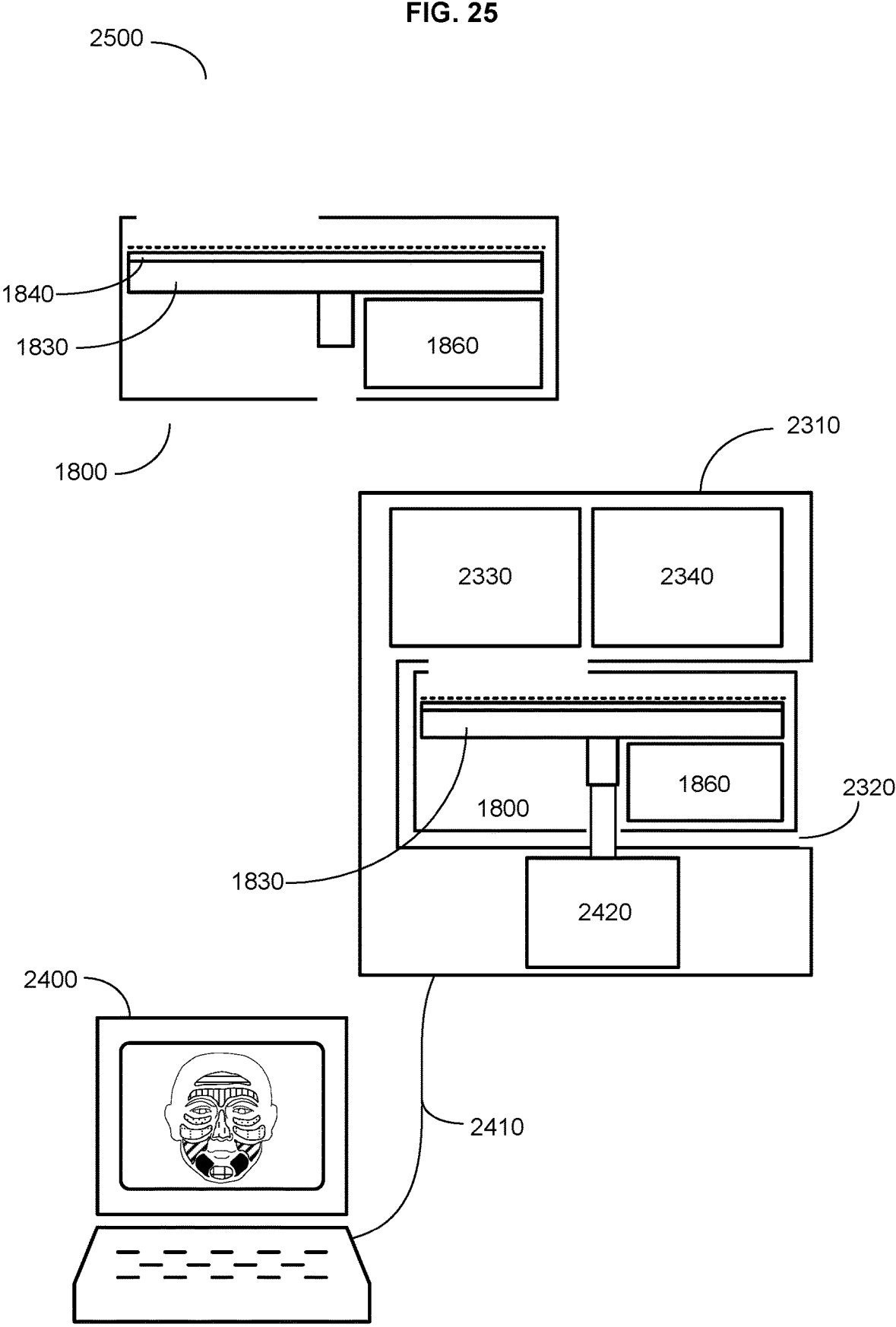
FIG. 25 is a schematic of a system for profiling microbiota of skin including an analyzer and a computing device.

In an aspect, a system for profiling microbiota of a skin surface includes an analyzer and a replaceable microbe sampling unit including at least one motivatable component. FIG. 25 illustrates aspects of a system 2500 including replaceable microbe sampling unit 1800, analyzer 2310, and computing device 2400 operably coupled to analyzer 2310 through communications link 2410. Replaceable microbe sampling unit 1800 includes at least one motivatable component 1830 including substrate 1840 as well as location information storage component 1860. Non-limiting aspects of a replaceable microbe sampling unit 1800 have been described above herein. Analyzer 2310 includes a receiving region 2320 sized to accept replaceable microbe sampling unit 1800. Analyzer 2310 further includes at least one sensor component 2330 and location information reader 2340. In an aspect, analyzer 2310 further includes motor 2420 operably coupled to at least one motivatable component 1830 of replaceable microbe sampling unit 1800 and configured to move substrate 1840 from one position to another within analyzer 2310.

Figure 26:
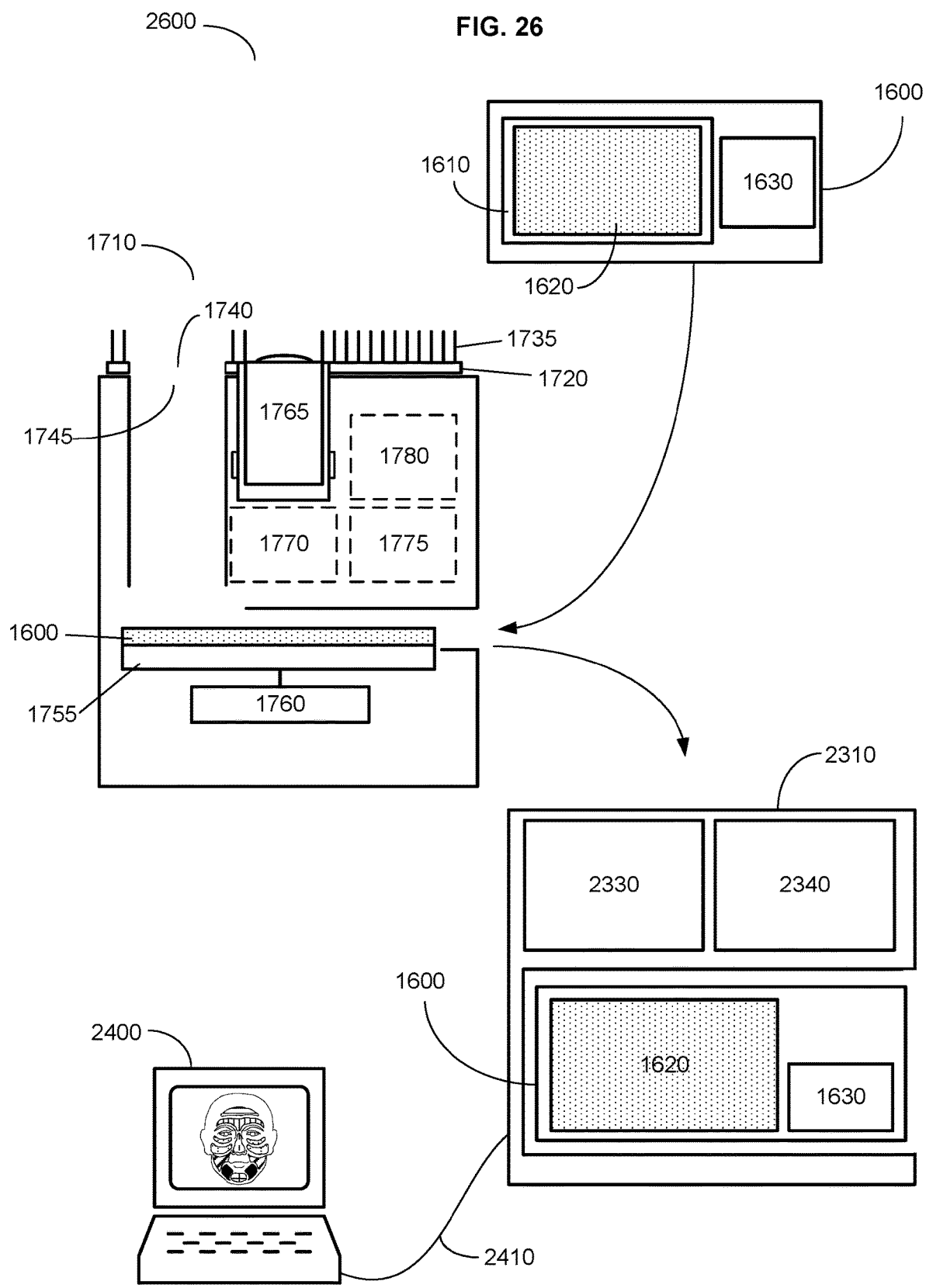
FIG. 26 is a schematic of a system for profiling microbiota of skin.

In an aspect, a system for profiling microbiota of a skin surface further includes a microbe sampling device. FIG. 26 illustrates aspects of a system 2600 including replaceable microbe sampling unit 1600, microbe sampling device 1710, analyzer 2310, and computing device 2400 operably linked to analyzer 2310 through communication link 2410. In an aspect, the components of system 2600 can be used to sample, analyze, and generate a microbe profile. Replaceable microbe sampling unit 1600 and microbe sampling device 1710 are configured to sample at least one type of microbe from a skin surface of an individual. Analyzer 2310 is configured to analyze data stored on replaceable microbe sampling unit 1600, e.g., the at least one type of microbe sampled from one or more regions of the skin surface of the individual and the location of said one or more regions of the skin surface. Computing device 2400 is configured to receive sensor and location output from analyze 2310 and to generate a microbe profile for the individual.

Figure 27:
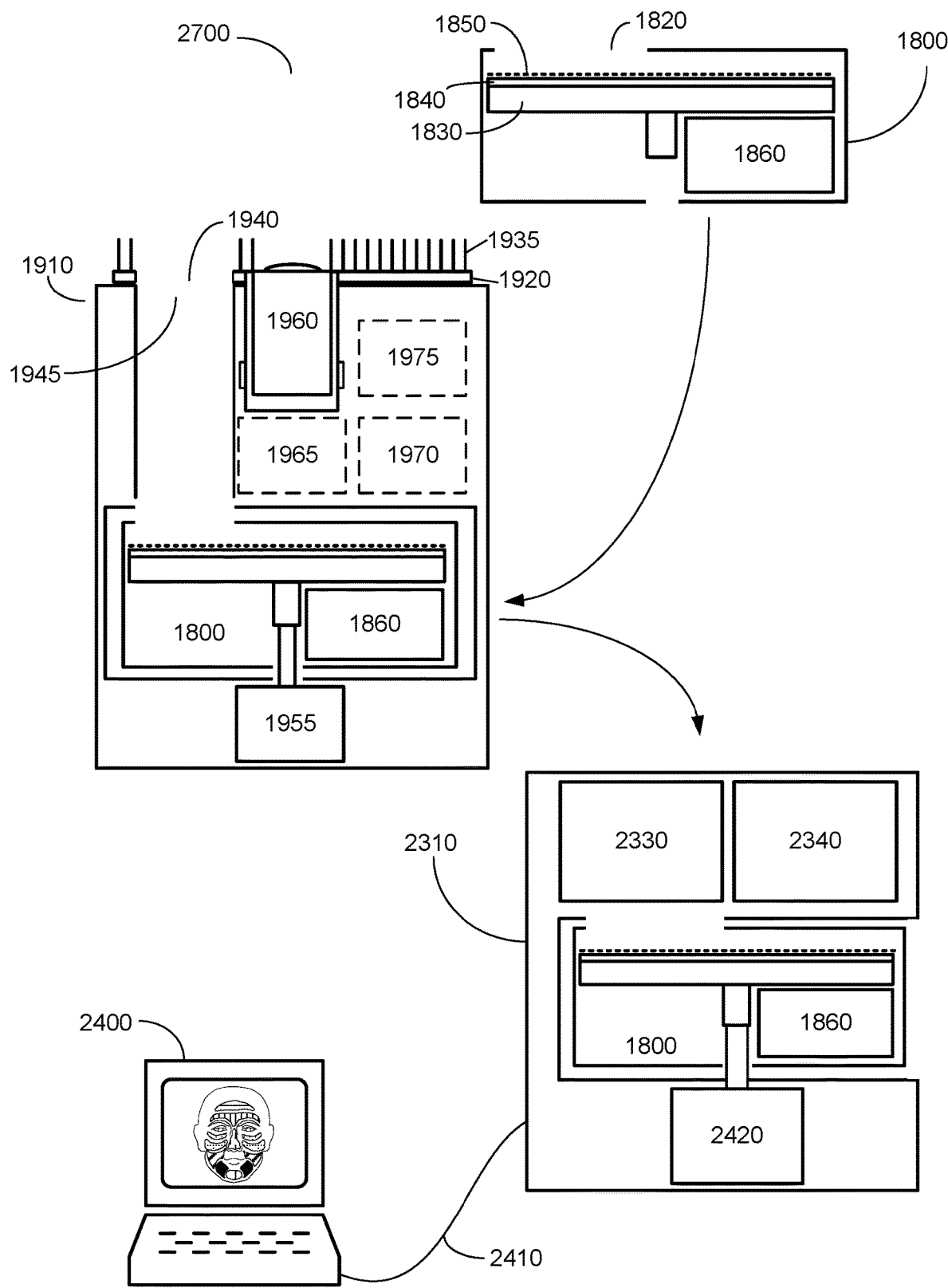
FIG. 27 is a schematic of a system for profiling microbiota of skin.

FIG. 27 is a schematic of an embodiment of a system for profiling microbiota of a skin surface of an individual. System 2700 includes replaceable microbe sampling unit 1800, microbe sampling device 1910, analyzer 2310, and computing device 2400 operably connected to analyzer 2310 through communication link 2410. In an aspect, the components of system 2700 can be used to sample, analyze, and generate a microbe profile. Replaceable microbe sampling unit 1800 and microbe sampling device 1910 are configured to sample at least one type of microbe from a skin surface of an individual. In this embodiment, at least one motivatable component, e.g., a disk or reel, is incorporated into replaceable microbe sampling unit 1800. The substrate of replaceable microbe sampling unit 1800 is disposed in relation to the at least one motivatable component, e.g., disposed on an outer surface of the at least one motivatable component. The motivatable component of replaceable microbe sampling unit 1800 is actuated during microbe sampling by motor 1955 associated with microbe sampling unit 1910 and actuated during signal analysis by motor 2420 associated with analyzer 2310. Analyzer 2310 is configured to analyze data stored on replaceable microbe sampling unit 1800, e.g., the at least one type of microbe sampled from one or more regions of the skin surface of the individual and the location of said one or more regions of the skin surface. Computing device 2400 is configured to receive sensor and location output from analyze 2310 and to generate a microbe profile for the individual.

Methods

FIGS. 28 and 29 show flowcharts of methods for profiling microbiota of a skin surface of an individual. The method of FIG. 28 includes in block 2800, dislodging at least one type of microbe from one or more regions of a skin surface of an individual with an epidermis-engaging component of a hand-held microbe profiling device, the hand-held microbe profiling device including a device head including the epidermis-engaging component and at least one access window, and a hand-held housing, at least a portion of the hand-held housing defining an opening aligned with the at least one access window and including a motor operably coupled to at least one motivatable component, a substrate disposed in relation to the at least one motivatable component and positioned in operable communication with the opening defined by the hand-held housing, a surface of the substrate including a microbe-capture region, a location-capture component including circuitry to determine a location of said one or more regions of the skin surface of the individual, at least one sensor component, and a computing component including a microprocessor, the computing component including circuitry; in block 2810, determining a location of said one or more regions of the skin surface of the individual with the location-capture component of the hand-held microbe profiling device as the epidermis-engaging component of the device head contacts said one or more regions of the skin surface of the individual and generating a location output, the location output including information associated with the location of said one or more regions of the skin surface of the individual; in block 2820, capturing the dislodged at least one type of microbe through the at least one access window of the device and the aligned opening defined by the hand-held housing and onto a portion of the microbe-capture region of the substrate; in block 2830, actuating the at last one motivatable component with the motor to reposition the substrate relative to the opening defined by the hand-held housing; in block 2840, analyzing the microbe-capture region on the substrate with the at least one sensor component to detect one or more signals emitted or reflected from the at least one type of microbe captured on the microbe-capture region and transforming the detected one or more signals into a sensor output, the sensor output including at least one property of the detected one or more signals emitted or reflected from the at least one type of microbe captured on the microbe-capture region; in block 2850, receiving the sensor output with the computing component and comparing the at least one property of the detected one or more signals emitted or reflected from the at least one type of microbe captured on the microbe-capture region with a database of reference microbe signal properties; in block 2860, receiving the location output with the computing component and generating a digital alignment of the location of said one or more regions of the skin surface of the individual with the one or more signals emitted or reflected from the at least one type of microbe captured on the microbe-capture region from said one or more regions of the skin surface of the individual; and in block 2870, generating a microbe profile from the digital alignment, the microbe profile including a spatial distribution of the at least one type of microbe on the skin surface of the individual.

The method of FIG. 29 includes in block 2900, dislodging at least one type of microbe from one or more regions of a skin surface of an individual with an epidermis-engaging component of a hand-held microbe profiling device, the hand-held microbe profiling device including a device head including the epidermis-engaging component and one or more fluid conduits, and a hand-held housing, at least a portion of the hand-held housing defining an opening aligned with the one or more fluid conduits and including a vacuum chamber connected to the device head through the opening defined by the hand-held housing, a motor operably coupled to at least one motivatable component, a substrate disposed in relative to the least one motivatable component, a surface of the substrate including a microbe-capture region, the substrate including the microbe-capture region at least partially positioned in the vacuum chamber, a location-capture component including circuitry to determine a location of said one or more regions of the skin surface of the individual, least one sensor component, and a computing component including a microprocessor, the computing component including circuitry; in block 2910, determining a location of said one or more regions of the skin surface of the individual with the location-capture component of the hand-held microbe profiling device as the epidermis-engaging component of the device head contacts said one or more regions of the skin surface of the individual and generating a location output, the location output including the location of said one or more regions of the skin surface of the individual; in block 2920, pulling fluid and the dislodged at least one type of microbe through the one or more fluid conduits of the device head into the vacuum chamber and onto a portion of the microbe-capture region on the substrate at least partially positioned in the vacuum chamber; in block 2930, actuating the at least one motivatable component with the motor to reposition the substrate in the vacuum chamber; in block 2940, analyzing the microbe-capture region on the substrate with the at least one sensor component to detect one or more signals emitted or reflected from the at least one type of microbe captured on the microbe-capture region and transforming the detected one or more signals into a sensor output, the sensor output including at least one property of the detected one or more signals emitted or reflected from the at least one type of microbe captured on the microbe-capture region; in block 2950, receiving the sensor output with the computing component and comparing the at least one property of the detected one or more signals emitted or reflected from the at least one type of microbe captured on the microbe-capture region with a database of reference microbe signal properties; in block 2960, receiving the location output with the computing component and generating a digital alignment of the location of said one or more regions of the skin surface of the individual with the one or more signals emitted or reflected from the at least one type of microbe captured on the microbe-capture region from said one or more regions of the skin surface of the individual; and in block 2970, generating a microbe profile from the digital alignment, the microbe profile including a spatial distribution of the at least one type of microbe one the skin surface of the individual.

A method of profiling microbiota of a skin surface of an individual such as illustrated in FIGS. 28 and 29 includes dislodging at least one type of microbe from one or more regions of the skin surface of an individual with an epidermis-engaging component of the hand-held microbe profiling device. In an aspect, the method includes dislodging the at least one type of microbe from one or more regions of the skin associated with the face, neck, head, upper extremities, lower extremities, abdomen, and/or back of an individual. In an aspect, the method includes dislodging the at least one type of microbe from the one or more regions of the skin surface of the individual with at least one of a brush head, a bladed surface, a pad, or an abrasive surface.

In an aspect, the method includes dislodging the at least one type of microbe from the one or more regions of the skin surface of the individual with the epidermis-engaging component in the presence of at least one agent, wherein the at least one agent includes at least one of a signal-generating element, a medicament, or an enhancing agent. For example, the method can include applying one or more of a signal-generating element, a medicament, and/or an enhancing agent to the skin surface prior to contacting the one or more regions of the skin surface of the individual with the microbe profiling device. In an aspect, the method includes releasing an agent from a reservoir included in the hand-held microbe profiling device to the skin surface of the individual. For example, the method can include releasing one or more of a signal-generating element, a medicament, and/or an enhancing agent from the microbe profiling device while contacting the one or more regions of the skin surface of the individual.

A method of profiling microbiota of a skin surface of an individual such as illustrated in FIGS. 28 and 29 includes determining a location of said one or more regions of the skin surface of the individual with a location-capture component. In an aspect, the method includes determining the location of said one or more regions of the skin surface of the individual with an image capture device, e.g., a digital camera. In an aspect, the method includes capturing one or more images of said one or more regions of the skin surface of the individual with an image capture device as the epidermis-engaging component contacts said one or more regions of the skin surface and aligning the one or more images of said one or more regions of the skin surface of the individual with a reference image of the skin surface of the individual.

In an aspect, the method includes determining the location of said one or more regions of the skin surface of the individual with a fiducial reader. In an aspect, the method includes determining the location of said one or more regions of the skin surface of the individual with a fiducial reader that is at least one of an image capture device, a radiofrequency identification reader, or an electronic reader. In an aspect, the method includes placing one or more fiducial markers, e.g., colored ink spots or RFID tags, on the skin surface of the individual, and reading the one or more fiducial markers on the skin surface of the individual with the location-capture component, e.g., a digital camera or a RFID tag reader, to determine a location of the one or more regions of the skin surface of the individual. In an aspect, placing the one or more fiducial markers is accomplished using the hand-held microbe profiling device. For example, one or more fiducial markers can be placed on the skin surface of the individual from at least one reservoir of the hand-held microbe profiling device.

A method of profiling microbiota of a skin surface of an individual such as illustrated in FIGS. 28 and 29 includes comparing the at least one property of the detected one or more signal emitted or reflected from the at least one type of microbe captured on the microbe-capture region with a database of reference microbe signal properties. In an aspect, the method includes comparing at least one optical property of the detected one or more signals emitted or reflected from the at least one type of microbe captured on the microbe-capture region with the database of reference microbe signal properties. In an aspect, the method includes comparing at least one of a fluorescence property, a magnetic property, an electromagnetic property, an acoustic property, a light scattering property, a reflective property, a radioactive property, or an electrical property of the detected one or more signals emitted or reflected from the at least one type of microbe captured on the microbe-capture region with the database of reference microbe signal properties. In an aspect, the database of reference microbe signal properties is stored in a data storage component of the computing component of the microbe profiling device. In an aspect, the computing component includes one or more comparison algorithms for comparing the at least one property of the detected one or more signals emitted or reflected from the at least one type of microbe captured on the microbe-capture device with the database of reference microbe signal properties.

In an aspect, comparing at least one property includes comparing at least one of a metabolic property, e.g., utilization of a carbon source. In an aspect, comparing the at least one property includes comparing at least one of a lipid property, e.g., association of one or more lipid types on a surface of at least one type of microbe. In an aspect, comparing the at least one property includes comparing at least one of a carbohydrate property, e.g., association and/or binding properties of at least one carbohydrate on a surface of at least one type of microbe. In an aspect, comparing the at least one property includes comparing at least one of a protein property, e.g., enzymatic and/or binding property of a protein. In an aspect, comparing the at least one property includes comparing at least one of a genomic property.

A method of profiling microbiota of a skin surface of an individual such as illustrated in FIGS. 28 and 29 includes generating a microbe profile from a digital alignment. In an aspect, the method further includes reporting the microbe profile to a user. In an aspect, the method includes reporting the microbe profile to the user on at least one of a display, a printout, or a computing device. In an aspect, the display is associated with the microbe profiling device. In an aspect, the display is associated with another device, e.g., a smartphone device, a computing device, or a kiosk. In an aspect, reporting the microbe profile to a user includes reporting the microbe profile to the user as a printout. In an aspect, the computing component of the microbe profiling device includes circuitry, e.g., as part of a transmission unit, to transmit the microbe profile either directly or indirectly to a printing device. A printout of the microbe profile can include a text only description of the identity and spatial profile of the identified at least one type of microbe on the skin surface of the individual. For example, the printout of the microbe profile can include a color-coded diagram illustrating the identity and the spatial profile of the identified at least one type of microbe on the skin surface of the individual. The color-coded information can be overlaid on an image of the skin surface of the individual. For example, the color-coded diagram can be overlaid over an image of the individual's face, illustrating the distribution of one or more types of microbes on the individual's face.

In an aspect, the method includes exporting the microbe profile to a computing device. For example, the microbe profile may be generated using a microbe profiling device in a service provider's office, and subsequently exported to a second computing device, e.g., an individual's home computer, a hand-held device, personal electronic device, or the like. For example, the microbe profile may be generated using a microbe profiling device in the individual's residence and subsequently exported, e.g., via the Internet, to a computing device associated with a service provider, e.g., a medical practitioner's office, a pharmacy, or cosmetic counter. For example, the microbe profile may be exported to a computing device associated with a manufacturer, e.g., the manufacturer of the skin-covering material and/or the system including the skin-covering material. For example, the microbe profile may be exported to a computing device associated with an insurance company. For example, the microbe profile may be exported to a computing device associated with a research group. In an aspect, the service provider may provide a recommended treatment regimen in response to receipt of an individual's microbe profile.

In an aspect, a method of profiling microbiota of a skin surface of an individual such as illustrated in FIGS. 28 and 29 includes identifying the at least one type of microbe captured on the microbe-capture region from said one or more regions of the skin surface of the individual based on the comparison of the at least one property of the detected one or more signals emitted or reflected from the at least one type of microbe captured on the microbe-capture region from said one or more regions of the skin surface of the individual with the database of reference microbe signal properties, adding the identification of the at least one type of microbe to the microbe profile, and reporting the microbe profile to the user, the microbe profile including at least one of the identification or the spatial distribution of the at least one type of microbe on the skin surface of the individual.

In an aspect, a method of profiling microbiota of a skin surface of an individual such as illustrated in FIGS. 28 and 29 includes comparing the microbe profile with a reference microbe profile, generating a recommended treatment regimen for the individual based on the comparison, and reporting the recommended treatment regimen to the user. In an aspect, the recommended treatment regimen can be generated based on comparing the identification and the spatial profile of the at least one type of microbe captured from an individual with a reference microbe profile, wherein the reference microbe profile can include identification and/or a spatial profile of at least one type of microbe captured from the same individual in the same location at a previous point in time. The previous point in time can be one or more days, one or more weeks, and/or one or more years previous to a current time point. The previous point in time may represent a point in time before onset of a condition and/or before onset of a treatment. In an aspect, the recommended treatment regimen can be generated based on comparing the identification and the spatial profile of the at least one type of microbe captured from an individual with a reference microbe profile that includes identification and/or a spatial profile of at least one type of microbe captured from one or more other individuals. For example, the reference microbe profile from the one or more other individuals may include an "average" or a "normal" distribution of microbes. For example, the reference microbe profile from the one or more other individuals may include an identification and/or spatial distribution of at least one type of microbe on a skin surface of an admired individual, e.g., a celebrity with healthy skin. In an aspect, the method can include alerting the individual as to whether the identity and the spatial distribution of the at least one type of microbe warrants discussion with a medical professional. In an aspect, reporting the recommended treatment regimen to the user includes reporting the recommended treatment regimen via a display, a printout, or exportation of data to another device, e.g., a personal handheld device.

In an aspect, the method can include generating a microbe profile for an individual at a first time point and at least one second microbe profile for the individual at at least one second time point. In an aspect, the first time point is at a first age of an individual and the second time point is at a second age of an individual. For example, the first time point and the at least one second time point may be separated by days, months, or years depending upon how frequently the skin microbiota of an individual is assessed or monitored. In an aspect, the first time point is at a time before therapeutic treatment and the at least one second time point is at a time after therapeutic treatment. In an aspect, the first time point is at a time point before a pathological condition, e.g., a normal baseline, and the at least one second time point is at a time point after a pathological condition has arisen. In an aspect, a comparison of the microbiota at a first time point versus an at least one second time point is used to generate a recommended treatment regimen, e.g., a cleansing protocol, preferred cosmetics, moisturizers, or antimicrobial treatment.

In an aspect, the method includes generating a recommended treatment regimen. For example, the method can include generating a recommended treatment regimen that includes an antimicrobial treatment based on the types of microbes present, e.g., antibiotics for bacteria, fungicide for fungus, or antiviral for a virus. For example, the method can include generating a recommended treatment regimen that includes a skin cleaning process, e.g., a type of soap or antiseptic rinse, based on the identity and the distribution of the at least one type of microbe. For example, the method can include generating a recommended treatment regimen that includes probiotics and/or prebiotics to modulate the microbe profile, e.g., to maintain and/or increase beneficial microbes and/or reduce harmful and/or pathogenic microbes. For example, the method can include generating a recommended treatment regimen that includes a certain type of cosmetic product that is compatible with the microbes present, e.g., helps to maintain good microbes but not encourage harmful microbes and can include probiotics and/or prebiotics. Non-limiting examples of treatment recommendations include antimicrobial agents, cleansing products, medicament, probiotics, prebiotics, cosmetic products, procedures (e.g., shaving or not in sensitive areas, applying warm compresses to open pores, use of a pore-opening or cleaning device, abrasion, and the like).

FIGS. 30 and 31 show flowcharts of methods for profiling microbiota of a skin surface of an individual. The method of FIG. 31 includes in block 3000, dislodging at least one type of microbe from one or more regions of a skin surface of an individual with an epidermis-engaging component of a hand-held microbe profiling device, the hand-held microbe profiling device including a device head including the epidermis-engaging component and at least one access window, and a hand-held housing, at least a portion of the hand-held housing defining an opening aligned with the at least one access window, the hand-held housing including a motor operably coupled to at least one motivatable component, a substrate disposed in relation to the at least one motivatable component and positioned in operable communication with the opening defined by the hand-held housing, a surface of the substrate including a plurality of signal-generating complexes, a location-capture component including circuitry to determine a location of said one or more regions of the skin surface of the individual, at least one sensor component, and a computing component including a microprocessor, the computing component including circuitry; in block 3010, determining a location of said one or more regions of the skin surface of the individual with the location-capture component of the hand-held microbe profiling device as the epidermis-engaging component of the device head contacts said one or more regions of the skin surface of the individual and generating a location output, the location output including the location of said one or more regions of the skin surface of the individual; in block 3020, capturing the dislodged at least one type of microbe through the at least one access window of the device head and the aligned opening defined by the hand-held housing and into contact with a portion of the substrate; in block 3030, actuating the at least one motivatable component with the motor to reposition the substrate relative to the opening defined by the hand-held housing; in block 3040, analyzing the substrate with the at least one sensor component to detect one or more signals emitted from at least one of the plurality of signal-generating complexes in response to contact with the dislodged at least one type of microbe and transforming the detected one or more signals into a sensor output, the sensor output including at least one property of the detected one or more signals emitted from the at least one of the plurality of signal-generating complexes; in block 3050, receiving the sensor output with the computing component and comparing the at least one property of the detected one or more signals emitted from the at least one of the plurality of signal-generating complexes in response to contact with the dislodged at least one type of microbe with a database of properties of reference signal-generating complexes; in block 3060, receiving the location output with the computing component and generating a digital alignment of the location of said one or more regions of the skin surface of the individual with the detected one or more signals emitted from the at least one of the plurality of signal-generating complexes in response to contact with the dislodged at least one type of microbe; and in block 3070, generating a microbe profile from the digital alignment, the microbe profile including a spatial distribution of the at least one type of microbe on the skin surface of the individual.

The method of FIG. 31 includes in block 3100, dislodging at least one type of microbe from one or more regions of a skin surface of an individual with an epidermis-engaging component of a hand-held microbe profiling device, the hand-held microbe profiling device including a device head including the epidermis-engaging component and one or more fluid conduits, and a hand-held housing, at least a portion of the hand-held housing defining an opening aligned with the one or more fluid conduits, the hand-held housing including a vacuum chamber connected to the device head through the opening defined by the hand-held housing, a motor operably coupled to at least one motivatable component, a substrate disposed in relation to the at least one motivatable component, a surface of the substrate including a plurality of signal-generating complexes, the substrate including the plurality of signal-generating complexes at least partially positioned in the vacuum chamber, a location-capture component including circuitry to determine a location of said one or more regions of the skin surface of the individual, at least one sensor component, and a computing component including a microprocessor, the computing component including circuitry; in block 3110, determining a location of said one or more regions of the skin surface of the individual with the location-capture component of the hand-held microbe profiling device as the epidermis-engaging component of the device head contacts said one or more regions of the skin surface of the individual and generating a location output, the location output including the location of said one or more regions of the skin surface of the individual; in block 3120, pulling fluid and the dislodged at least one type of microbe through one or more fluid conduits of the device head into the vacuum chamber and into contact with a portion of the plurality of signal-generating complexes on the substrate at least partially positioned in the vacuum chamber; in block 3130, actuating the at least one motivatable component with the motor to reposition the substrate in the vacuum chamber; in block 3140, analyzing the substrate with the at least one sensor component to detect one or more signals emitted from at least one of the plurality of signal-generating complexes in response to contact with the dislodged at least one type of microbe and transforming the detected one or more signals into a sensor output, the sensor output including at least one property of the detected one or more signals emitted from the at least one of the plurality of signal-generating complexes; in block 3150, receiving the sensor output with the computing component and comparing the at least one property of the detected one or more signals emitted from the at least one of the plurality of signal-generating complexes in response to contact with the dislodged at least one type of microbe with a database of properties of reference signal-generating complexes; in block 3160, receiving the location output with the computing component and generating a digital alignment of the location of said one or more regions of the skin surface of the individual with one or more signals emitted from the at least one of the plurality of signal-generating complexes in response to contact with the dislodged at least one type of microbe from said one or more regions of the skin surface of the individual; and in block 3170, generating a microbe profile from the digital alignment, the microbe profile including a spatial distribution of the at least one type of microbe on the skin surface of the individual.

A method of profiling microbiota of a skin surface of an individual such as illustrated in FIGS. 30 and 31 includes dislodging at least one type of microbe from one or more regions of the skin surface of an individual with an epidermis-engaging component of the hand-held microbe profiling device. In an aspect, the method includes dislodging the at least one type of microbe from one or more regions of the skin associated with the face, neck, head, upper extremities, lower extremities, abdomen, and/or back of an individual. In an aspect, the method includes dislodging the at least one type of microbe from said one or more regions of the skin surface of the individual with at least one of a brush head, a bladed surface, or an abrasive pad.

In an aspect, the method includes dislodging the at least one type of microbe from one or more regions of the skin surface of the individual with the epidermis-engaging component in the presence of at least one agent, wherein the at least one agent includes at least one or a signal-generating agent, a medicament, or an enhancing agent. In an aspect, the method includes releasing the agent directly from the hand-held microbe profiling device, e.g., from at least one reservoir incorporated into the device. For example, the method can include releasing at least one of a signal-generating element, a medicament, and/or an enhancing agent while contacting the one or more regions of the skin surface of the individual. In an aspect, the method includes applying the agent to the skin surface of the individual prior to contacting the skin surface of the individual with the epidermis-engaging component of the hand-held microbe profiling device.

A method of profiling microbiota of a skin surface of an individual such as illustrated in FIGS. 30 and 31 includes comparing the at least one property of the detected one or more signal emitted from at least one of the plurality of signal-generating complexes in response to contact with at least one type of microbe. In an aspect, the method includes comparing at least one of an optical property a fluorescence property, a magnetic property, an electromagnetic property, an acoustic property, a light scattering property, a reflective property, a radioactive property, or an electrical property of the detected one or more signals emitted from the at least one of the plurality of signal-generating complexes with the database of properties of reference signal-generating complexes. In an aspect, the database of properties of reference signal-generating complexes is stored in a data storage component of the computing component of the microbe profiling device. In an aspect, the computing component includes one or more comparison algorithms for comparing the at least one property of the detected one or more signals emitted from the at least one of the plurality of signal-generating complexes in response to contact with the at least one type of microbe with the database of properties of reference signal-generating complexes.

In an aspect, a method of profiling microbiota of a skin surface of an individual such as illustrated in FIGS. 30 and 31 further includes identifying the at least one type of microbe dislodged from the one or more regions of the skin surface of the individual from a comparison of the at least one property of the detected one or more signals emitted from the at least one of the plurality of signal-generating complexes in response to contact with the at least one type of microbe with the database of properties of reference signal-generating complexes; adding the identification of the at least one type of microbe to the microbe profile; and reporting the microbe profile to a user, the microbe profile including at least one of the identification or spatial distribution of the at least one type of microbe on the skin surface of the individual.

In an aspect, a method of profiling microbiota of a skin surface such as shown in FIGS. 30 and 31 further includes comparing the microbe profile with a reference microbe profile, generating a recommended treatment regimen for the individual based on the comparison, and reporting the recommended treatment regimen to the user. In an aspect, the method includes applying an agent to the skin surface of the individual prior to contacting the skin surface of the individual with the epidermis-engaging component of the hand-held microbe profiling device. In an aspect, the method includes releasing the agent directly from the hand-held microbe profiling device, e.g., from at least one reservoir incorporated into the device. In an aspect, the method includes using the hand-held microbe profiling device to identify endogenous microbiota, to change the endogenous microbiota as part of a treatment regimen, to identify, treat, and monitor an infection, or a combination thereof.

FIG. 32 illustrates aspects of a system including an analyzer, a computing device, and non-transitory machine readable media. System 3200 includes analyzer 2310 including receiving region 2320, at least one sensor component 2330, and location information reader 2340. Receiving region 2320 is configured to accept a replaceable microbe sampling unit, the replaceable microbe sampling unit including a substrate including a microbe-capture region and a location information storage component. Analyzer 2310 is operably coupled to computing device 2400 through communications link 2410. Non-limiting aspects of analyzers and computing devices have been described above herein.

System 3200 further includes non-transitory machine-readable media 3210. The non-transitory machine-readable media stores instructions and/or data for use in profiling microbiota of skin. In an embodiment, non-transitory machine-readable media 3210 can be computer readable media. In an embodiment, non-transitory machine-readable media 3210 can be recordable-type media. Computer readable media may also be recordable-type media, and the qualities of being "computer readable" and "recordable-type" should not be construed as being mutually exclusive, though in some cases a computer readable media may not be a recordable-type media, and vice versa. Machine-readable media include volatile and nonvolatile, removable and non-removable media implemented in any method or technology for storage of information such as machine readable instructions, data structures, program modules, or other data. Non-transitory machine-readable media include, but are not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other media which can be used to store the desired information. In a further embodiment, computer storage media may include a group of computer storage media devices. In an embodiment, machine readable media may include an information store. In an embodiment, an information store may include a quantum memory, a photonic quantum memory, or atomic quantum memory. Combinations of any of the above may also be included within the scope of non-transitory machine readable media.

Non-transitory machine readable media 3210 bears one or more instructions for generating a microbe profile, the one or more instructions including in block 3220 one or more instructions for receiving the location output from the analyzer, the location output including information associated with the location of the one or more regions of the skin surface of the individual; in block 3230, one or more instructions for receiving the sensor output from the analyzer, the sensor output including information associated with the at least one property of the one or more signals emitted or reflected from the microbe-capture region of the replaceable microbe sampling unit; in block 3240, one or more instructions for comparing the at least one property of the one or more signals emitted or reflected from the microbe-capture region of the replaceable microbe sampling unit with a database of reference signal properties; in block 3250, one or more instructions for identifying the at least one type of microbe captured on the microbe-capture region of the replaceable microbe sampling unit based on the comparison of the at least one property of the one or more signals emitted or reflected from the microbe-capture region of the replaceable microbe sampling unit with the database of reference signal properties; in block 3260, one or more instructions for generating an alignment of the location of the one or more regions of the skin surface of the individual with the one or more signals emitted or reflected from the microbe-capture region; in block 3270, one or more instructions for generating the microbe profile based on the alignment, the microbe profile including at least one of an identity or a spatial distribution of the at least one type of microbe on the skin surface of the individual; and in block 3280, one or more instructions for reporting the microbe profile to a user. In an aspect, non-transitory signal-bearing media 3210 further includes in block 3290 one or more instructions for generating a recommended treatment regimen based on a comparison of the microbe profile with a reference microbe profile and one or more instructions for reporting the recommended treatment regimen to the user.

In an aspect, system 3200 further includes a replaceable microbe sampling unit for sampling microbes. In an aspect, system 3200 further includes a microbe sampling device for use in combination with a replaceable microbe sampling unit to sample at least one type of microbe from one or more regions of a skin surface of an individual in conjunction with determining and storing information associated with a location of said one or more regions of the skin surface of the individual.

FIG. 33 illustrates aspects of an embodiment of an article of manufacture. Article of manufacture 3300 includes non-transitory machine readable media 3310 bearing one or more instructions for generating a profile of microbiota of skin, the one or more instructions including in block 3320 one or more instructions for receiving a location output, the location output including information associated with a location of one or more regions of a skin surface of an individual; in block 3330, one or more instructions for receiving a sensor output, the sensor output including information associated with at least one property of one or more signals emitted or reflected from at least one type of microbe captured from said one or more regions of the skin surface of the individual; in block 3340, one or more instructions for comparing the at least one property of the one or more signals emitted or reflected from the at least one type of microbe captured from said one or more regions of the skin surface of the individual with a database of reference signal properties; in block 3350, one or more instructions for identifying the at least one type of microbe captured from said one or more regions of the skin surface of the individual based on the comparison with the database of reference signal properties; in block 3360, one or more instructions from generating an alignment of the location of said one or more regions of the skin surface of the individual with the one or more signals emitted or reflected from the at least one type of microbe captured from said one or more regions of the skin surface of the individual; in block 3370, one or more instructions for generating a microbe profile based on the alignment, the microbe profile including at least one of an identity or a spatial distribution of the at last one type of microbe on the skin surface of the individual; and in block 3380, one or more instructions for reporting the microbe profile to a user. In an aspect, the article of manufacture further includes in block 3390 one or more instructions for generating a recommended treatment regimen based on a comparison of the microbe profile with a reference microbe profile; and one or more instructions for reporting the recommended treatment regimen to the user.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g.,"a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g.,"a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

PROPHETIC EXAMPLE 1

A Microbe Profiling Device Including a Microbe-Capture Region and Uses Thereof

Construction and use of a microbe profiling device are described. The microbe profiling device includes a brush head with nylon bristles. The brush head is attached to the main housing of the microbe profiling device and operably connected to a small vibration motor, e.g., a Pico Vibe™ motor from Precision Microdrives, London, UK. When actuated, the small vibration motor vibrates the brush head to aid in dislodging microbes from a skin surface. The plastic base of the brush head includes at least one access window, i.e., at least one opening.

The housing of the microbe profiling device includes an opening defined by a surface of the housing. The opening in the housing is aligned with the at least one access window at the base of the brush head, forming a conduit into an interior portion of the housing. The housing of the microbe profiling device further includes a second motor, e.g., a DC brush motor. The second motor is operably coupled to a motivatable component, e.g., a disc, and when actuated, rotates the disc. At least a portion of the disc is positioned adjacent to the conduit formed from the opening in the housing and the at least one access window.

A replaceable substrate, e.g., a disc shaped piece of nitrocellulose, is disposed on a surface of the disc. The nitrocellulose is positioned to capture at least one type of microbe dislodged from the skin surface. As the user moves the brush head over the surface of the skin, microbes are dislodged from the skin surface, fall through the conduit formed by the access window of the brush head and the opening defined by the housing, and captured on the nitrocellulose.

In some configurations, the microbe profiling device includes a miniature vacuum source, e.g., one of the series 100 Eccentric Diaphragm air pumps from Schwarzer Precision U.S.A., Madison, Conn. The vacuum source is positioned in the housing of the microbe profiling device to pull microbes into the device through air flow conduits formed from the access window of the brush head and the opening defined by the housing.

The microbe profiling device includes a location-capture component, e.g., a digital camera. The digital camera captures multiple images of the skin surface as the brush head moves over the surface of the skin. The images of the skin surface are correlated with a specific portion of the nitrocellulose disc using an event marker, e.g., a time stamp on a given image and a correlating portion of nitrocellulose.

The microbe profiling device further includes a reservoir including a single-generating element, e.g., acridine orange. Acridine orange is a cell-permeant nucleic acid fluorescent cationic dye that will stain DNA and RNA of microbes. When bound to DNA, acridine orange exhibits an excitation maximum of 502 nm and an emission maximum at 525 nm (green). When bound to RNA, acridine orange exhibits excitation maximum of 460 nm (blue) and an emission maximum of 650 nm (orange/red). In this instance, the acridine orange (Catalog #A1301 from Invitrogen, Carlsbad, Calif.) is stored in a 20 microgram/milliliter solution (w:v in phosphate buffered saline). The acridine orange solution is released from the reservoir onto the nitrocellulose substrate and is incorporated into the microbes captured on the substrate. The surface of the nitrocellulose substrate may be briefly rinsed with buffered saline released from a second reservoir to remove unincorporated acridine orange.

The surface of the nitrocellulose is illuminated with electromagnetic energy at about 502 nm with an electromagnetic energy source, e.g., a laser diode, and green fluorescence at 525 nm is captured using a charge-coupled device. The information regarding the intensity and spatial distribution of the green fluorescence is transformed into a sensor output and sent to a computing component of the microbe profiling device for further processing.

The computing component of the microbe profiling device includes circuitry to receive sensor output, e.g., acridine orange fluorescence intensity, and location output, e.g., one or more images of the skin surface. The computing component associates the fluorescence on any given portion of the nitrocellulose with the images of the skin surface by aligning the corresponding time stamps. The computing component includes circuitry to overlay the aligned fluorescence and images with a larger reference image of the skin surface to generate a microbe profile for an individual. The microbe profile includes a spatial distribution of the microbes on the skin surface of the individual. The computing component compares the microbe profile for the individual with that of another individual, for example, an average gender- and age-matched "control," and generates a recommended treatment regimen. The microbe profile is transmitted to the individual's personal computing device, e.g., a smartphone, for future access and viewing, and includes recommended cleansers, e.g., antibacterial soap, and non-comedogenic cosmetics based on the spatial distribution and relative abundance of the microbes detected on the skin surface.

PROPHETIC EXAMPLE 2

A Microbe Profiling Device Including a Plurality of Signal-Generating Complexes and Uses Thereof Construction and use of a microbe profiling device are described. The microbe profiling device includes a device head with three stainless steel blades aligned parallel to one another and positioned to scrape a skin surface. The base of the device head includes at least one access window, i.e., at least one opening. The device head is attached to the main housing of the microbe profiling device.

The housing of the microbe profiling device includes an opening defined by a surface of the housing. The opening in the housing is aligned with the at least one access window at the base of the device head, forming a conduit into an interior portion of the housing. The housing of the microbe profiling device further includes a motor, e.g., a DC brush motor. The motor is operably coupled to a motivatable component, e.g., a disc, and when actuated, rotates the disc. At least a portion of the disc is positioned adjacent to the conduit formed from the opening in the housing and the at least one access window.

Disposed on a surface of the disc is a disc-shaped substrate, e.g., a plastic disc-shaped sheet. At least one surface of the plastic sheet is modified with poly(dimethylsiloxane) and cross-linkers to facilitate attachment of oligonucleotides to a substrate as described in Blank et al. (2003) *Proc. Natl. Acad. Sci., U.S.A.* 100:11356-11360, which is incorporated herein by reference. Briefly, the plastic sheet is coated with a thin layer of PDMS (poly(dimethylsiloxane); Sylgard 184, Dow Corning, Midland, Mich.). The PDMS is derivatized with 3-aminopropyl-dimethylethoxysilane to generate free amino groups to which a heterobifunctional cross-linking agent, e.g., NHS-PEG-COOH (from, e.g., Pierce, Rockford, Ill.), is attached.

One or more fluorescently labeled aptamers specific for binding at least one type of microbe, e.g., *Staphylococcus aureus,* are generated as described by Chen et al. (2007) *Biochem. Biophys. Res. Commun.* 357:743-748 and Jhaveri, et al. (2000) *Nature Biotech.* 18:1293-1897, which are incorporated herein by reference. The aptamers are designed such that binding of a microbe leads to an increase in fluorescence intensity. Briefly, a library of fluorescently labeled oligonucleotides (45-60 residues in length) is generated using fluorescein-12-ATP during synthesis. The fluorescein-labeled library of oligonucelotides is screened against whole bacteria, e.g., whole *Staphylococcus aureus,* in which the whole *Staphylococcus aureus* are incubated with the fluorescein-labeled oligonucleotides, washed, and bound oligonucleotides are isolated. Those oligonucleotides that bind with high affinity during the screening process are further screened for fluorescence signaling properties in response to binding the target bacteria, e.g., a detectable increase in fluorescein signaling in response to binding *Staphylococcus aureus.* The resulting aptamers are further end-modified with an amine group during final synthesis.

The amino-modified, fluorescently labeled aptamer is mixed with a cross-linker, e.g., ethylene diaminecarbodiimide (EDC), and applied to the carboxy-modifed plastic sheet.

The device head including the stainless steel blades are moved across the skin surface of an individual to dislodge at least one type of microbe. A miniature vacuum source (e.g., one of the series 100 Eccentric Diaphragm air pumps from Schwarzer Precision U.S.A., Madison, Conn.) associated with the microbe profiling device pulls the dislodged microbes into an interior portion of the housing and in contact with the plastic sheet including the plurality of signal-generating aptamers.

The microbe profiling device includes a location-capture component, e.g., a digital camera. The digital camera captures multiple images of the skin surface as the device head moves over the surface of the skin. The images of the skin surface are correlated with a specific portion of the plastic sheet using an event marker, e.g., a time stamp on a given image and a correlating portion of the plastic sheet.

The surface of the disc-shaped sheet is illuminated with electromagnetic energy at about 502 nm with an electromagnetic energy source, e.g., a laser diode, and green fluorescence at 525 nm is captured using a charge-coupled device. The information regarding the intensity and spatial distribution of the green fluorescence is transformed into a sensor output and sent to a computing component of the microbe profiling device for further processing.

The computing component of the microbe profiling device includes circuitry to receive sensor output, e.g., fluorescein fluorescence intensity, and location output, e.g., one or more images of the skin surface. The computing component associates the fluorescence on any given portion of the plastic sheet with the images of the skin surface by aligning the corresponding time stamps. The computing component includes circuitry to overlay the aligned fluorescence and images with a larger reference image of the skin surface to generate a microbe profile for an individual. The microbe profile includes a spatial distribution of *Staphylococcus aureus* on the skin surface of the individual. The computing component generates a recommended treatment regimen that includes use of antibacterial soap and a non-prescription triple-antibiotic mixture. The microbe profile and the recommended treatment regimen are transmitted to the individual's personal computing device for future access and viewing.

PROPHETIC EXAMPLE 3

A Replaceable Microbe Sampling Unit Including a Plurality of Specific Microbe-Binding Elements and a Microbe Sampling Device The sampling microbiota from a skin surface is described using a microbe sampling device with a replaceable microbe sampling unit including a plurality of specific microbe-binding elements.

A microbe sampling device includes a device head including a pad with an abrasive surface and a plastic housing including a region sized to accept a replaceable microbe sampling unit, a motivatable component operably coupled to a motor, and a location-capture component. The device head includes at least one access window. The at least one access window aligns with an opening defined by the housing. The abrasive pad is constructed of an abrasive mesh constructed of plastic fibers. The mesh of the abrasive pad is sufficiently loose to allow microbes dislodged from the skin surface to fall through the at least one access window and the opening defined by the housing and into an interior portion of the housing including the region sized to accept the replaceable microbe sampling unit.

The motivatable component includes a platform configured to accept the replaceable microbe sampling unit and is operably connected to a motor through a moveable arm. Actuation of the motor causes the platform and the replaceable microbe sampling unit to move from one position to the next as microbes are sampled from the skin surface.

The location-capture component includes a fiducial reader that reads one or more fiducial markers, e.g., a template, placed on a skin surface in a grid pattern. The fiducial reader includes circuitry to generate coordinates for each of the detected fiducial markers and to "write" the coordinates to the replaceable microbe sampling unit.

In this example, the replaceable microbe sampling unit includes a thin substrate formed from poly(methyl methacrylate). The substrate is subjected to reactive ion etching (RIE) using an inductively coupled oxygen plasma to generate a textured surface conducive to antibody binding. See, e.g., Rucker et al. (2005) *Langmuir* 21:7621-7625, which is incorporated herein by reference.

The textured surface of the substrate is incubated with antibodies against *Propionibacterium acnes* and antibodies against *Staphylococcus epidermidis*. Antibodies to *Propionibacterium acnes* can be generated from heat inactivated bacteria as described in Nakatsuji et al. (2008) *J. Invest. Dermatol.* 127:2451-2457, which is incorporated herein by reference. Antibodies against *Staphylococcus epidermidis* are obtained from a commercial source (e.g., Thermo Scientific Pierce Antibodies, Rockford, Ill.). The antibodies are prepared in an aqueous solution, e.g., phosphate buffered saline, and applied in sufficient volume to cover the entirety of the substrate and allowed to dry for 1 hour. The substrate is rinsed with phosphate buffered saline supplemented with 0.1% Tween 20 to remove non-adhered antibody.

The substrate of the replaceable microbe sampling unit is further configured to accept location information from the fiducial reader of the microbe sampling device. The location information is "written" onto the surface of the substrate with an ink and can take the form of coordinates corresponding to one or more regions of a skin surface of an individual.

PROPHETIC EXAMPLE 4

A Replaceable Microbe Sampling Unit Including an Adhesive Microbe-Capture Region and at Least One Motivatable Component A replaceable microbe sampling unit is described. The replaceable microbe sampling unit includes at least two motivatable components, e.g., at least two rotatable reels. The replaceable microbe sampling unit further includes an elongated flexible strip, e.g., a thin plastic tape. An outer surface of the thin plastic tape is coated with an adhesive, e.g., Dow Corning 7-9700 Soft Skin Adhesive (from, e.g., Dow Corning, Midland, Mich.) to form a microbe-capture region on the thin plastic strip. A first end of the thin plastic strip is wound around a supply rotatable reel and the second end of the thin plastic strip is wound around a take-up rotatable reel such that the adhesive portion of the thin plastic strip is facing out and accessible for capturing at least one type of microbe from a skin surface of an individual.

The replaceable microbe sampling unit further includes a location information storage component. The location information storage component includes a memory card. The memory chip is configured to receive and store information associated with one or more regions of a skin surface of an individual from which the at least one type of microbe is captured.

The components of the replaceable microbe sampling unit are held in a plastic case. The plastic case includes at least one opening adjacent to at least a portion of the thin plastic strip so that the adhesive microbe-capture region is accessible for capturing microbes and for analysis with a sensor component.

PROPHETIC EXAMPLE 5

A System Including an Analyzer and a Computing Device for Generating a Microbe Profile A system is described that includes an analyzer and a computing device. The analyzer includes a receiving region sized to accept a replaceable microbe sampling unit such as the one described in Prophetic Example 3. The replaceable microbe sampling unit includes a substrate with a plurality of specific microbe-binding antibodies. A microbe sample is collected onto the substrate including the plurality of specific microbe-binding antibodies using a microbe sampling device such as described in Prophetic Example 3. The location-capture component of the microbe sampling device "writes" the information associated with one or more regions of a skin surface of an individual to the substrate of the replaceable microbe sampling unit in ink. The location information is in the form of one or more coordinates corresponding to the one or more regions of the skin surface. The one or more coordinates are based on one or more reference coordinates associated with a specific area of skin, e.g., an area of skin including the face. The replaceable microbe sampling unit including the microbe sample and the location information is inserted into the receiving region of the analyzer.

The analyzer includes a motivatable component, e.g., a platform, and a motor, e.g., a DC brush motor, configured to drive movement of the platform. The replaceable microbe sampling unit is disposed on the surface of the platform and the motor is used to move the substrate including any attached microbes from one position to the next during the analysis process.

The analyzer includes a sensor component configured to detect autofluorescence emitted from *Propionibacterium acnes* or *Staphylococcus epidermidis* captured on the plurality of specific microbe-binding elements associated with the replaceable microbe sampling unit. To detect autofluorescence associated with *Propionibacterium acnes*, the inner surface of the skin-covering material is imaged using a fluorescence spectrometer including a krypton ion laser, a color CCD camera, and a long-pass filter (cutoff wavelength, 550 nm) as described by Koenig & Schneckenburg (in *J. Fluorescence* (1994) 4:17-40, which is incorporated herein by reference). The excitation wavelength from the krypton laser is 407 nm. Fluorescent spots or regions of yellow and red corresponding to autofluorescence peak emissions of about 580-600, 620, and about 640 nm are imaged using the CCD camera. To detect autofluorescence associated with *Staphylococcus epidermidis*, the inner surface of the skin-covering material is subjected to directed energy at 488-nm line from an Argon laser the resulting autofluorescence captured with a CCD camera through 530/430-nm bandpass.

The location information, e.g., sets of coordinates for one or more regions of the skin surface of an individual, is retrieved from the replaceable microbe sampling unit with a location information reader, e.g., an optical reader, associated with the analyzer. The location information reader generates a digital location output.

The computing device receives the sensor output as well as the location output. The computing device is equipped with software such as that described by Selinummi et al. to assess both the intensity of the fluorescence as well as the quantity of spots. See, e.g., Selinummi et al. (2005) *BioTechniques* 39:859-863, which is incorporated herein by reference. The computing device associates the sensor output with the location output to generate a microbe profile for an individual. The spatial distribution of the fluorescent spots or regions is digitally overlaid with the corresponding coordinates of one or more regions of the skin surface, e.g., an individual's face, to create a microbe profile for the individual. The microbe profile includes the spatial distribution of the captured autofluorescence from *Propionibacterium acnes* and the spatial distribution of the captured autofluorescence from *Staphylococcus epidermidis* and is provided to a user as a two color spatial profile, for example, red for *Propionibacterium acnes* and green for *Staphylococcus epidermidis*. A color scale, e.g., degrees of red and/or green, may be used to highlight the abundance of each bacteria detected on the skin surface.

The computing device compares the microbe profile of the individual with a reference microbe profile of an "average" individual of matched gender, ethnicity, and age. The comparison reveals an above "normal" distribution of bacteria in the "T-zone" (forehead, nose, and chin), and the computing device generates a recommended treatment regimen including cleansing twice daily with a mild soap and use of a topical antibiotic cream, e.g., 1% Clindamycin lotion. A printout including the microbe profile and the recommended treatment regimen is provided to the individual.

PROPHETIC EXAMPLE 6

A System Including an Analyzer and a Computing Device for Generating a Microbe Profile A system is described that includes an analyzer and a computing device. The analyzer includes a receiving region sized to accept a replaceable microbe sampling unit such as the one described in Prophetic Example 4.

The replaceable microbe sampling unit includes a thin plastic strip including an adhesive. The thin plastic strip is wound around two rotatable reels. The replaceable microbe sampling unit further includes a memory chip for storing location information. A microbe sample is collected on the adhesive microbe-capture region of the replaceable microbe sampling unit using a microbe sampling device. The replaceable microbe sampling unit including the microbe sample and location information stored in the memory chip is inserted into the receiving region of the analyzer.

The analyzer includes a motor, e.g., a DC brush motor, configured to drive rotation of at least one of the rotatable reels of the replaceable microbe sampling unit. Rotation of at least one of the rotatable reels moves the thin plastic strip from one position to the next during the analysis process.

The analyzer includes a sensor component configured to detect autofluorescence emitted from at least one type of microbe captured on the adhesive microbe-capture region of the inserted replaceable microbe sampling unit. The outer surface of the thin plastic strip including the adhesive is analyzed using a fluorescence spectrometer including a krypton ion laser, a color CCD camera, and a long-pass filter (cutoff wavelength, 550 nm) as described by Koenig & Schneckenburg (in *J. Fluorescence* (1994) 4:17-40, which is incorporated herein by reference). The excitation wavelength from the krypton laser is 407 nm. Fluorescent spots or regions of yellow and red corresponding to autofluorescence peak emissions associated with bacteria, e.g., *Propionibacterium acnes*, of about 580-600, 620, and about 640 nm are imaged using the CCD camera. Autofluorescence peaks at about 430-450 nm associated with sloughed off skin cells (see, e.g., Meerwaldt et al. (2005) *J. Am. Soc. Nephrol.* 16:3687-3693, which is incorporated herein by reference) that may have been captured on the adhesive microbe-capture region are filtered out by the long-pass filter.

The location information, e.g., one or more images of a skin surface, is retrieved from the memory chip using a location information reader associated with the analyzer. The location information reader generates a digital location output. The computing device receives sensor output as well as the location output.

The computing device is equipped with software such as that described by Selinummi et al. to assess both the intensity of the fluorescence as well as the quantity of spots. See, e.g., Selinummi et al. (2005) *BioTechniques* 39:859-863, which is incorporated herein by reference. The spatial distribution of the fluorescent spots or regions is digitally overlaid with the corresponding digital image skin surface using image registration software to create a microbe profile for the individual. A color scale is used to highlight the abundance of the bacteria detected on the skin surface. The microbe profile is exported to the individual's smart phone and includes a recommended treatment regimen including skin cleansing with gentle liquid cleanser, use of a non-prescription medication containing benzoyl peroxide, and recommended non-comedogenic cosmetic brands and/or moisturizers.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A microbe profiling device comprising:
a device head including an epidermis-engaging component and at least one access opening, the epidermis-engaging component configured to dislodge at least one type of microbe from a skin surface of an individual; and
a hand-held housing, at least a portion of the hand-held housing defining an opening aligned with the at least one access opening of the device head,
the hand-held housing including
at least one motivatable component;
a substrate disposed in relation to the at least one motivatable component and configured to be in operable communication with the opening defined by the hand-held housing, a surface of the substrate including a microbe-capture region, the microbe-capture region positioned to capture the at least one type of microbe dislodged by the epidermis-engaging component of the device head;
a location-capture component including circuitry to determine a location of one or more regions of the skin surface of the individual as the epidermis-engaging component of the device head contacts said one or more regions of the skin surface of the individual;
a reservoir including a plurality of at least one type of signal-generating element, the at least one type of signal-generating element configured to associate with the at least one type of microbe;
at least one sensor component including circuitry to detect one or more signals emitted or reflected from the at least one type of signal-generating element associated with the at least one type of microbe captured on the microbe-capture region of the substrate from said one or more regions of the skin surface of the individual and to transform the detected one or more signals into a sensor output; and
a computing component including a microprocessor, the computing component including
circuitry configured to receive information associated with the location of said one or more regions of the skin surface of the individual from the location-capture component;
circuitry configured to receive the sensor output from the at least one sensor component, the sensor output including information regarding the detected one or more signals;
circuitry configured to associate the location of said one or more regions of the skin surface of the individual with the detected one or more signals; and
circuitry configured to generate an output including information regarding an association between the location of said one or more regions of the skin surface of the individual and the detected one or more signals.

2. The device of claim 1, wherein the reservoir includes a controllable valve.

3. The device of claim 2, wherein the controllable valve is operably coupled to and controlled by the computing component.

4. The device of claim 2, wherein the controllable valve is operably coupled to a switch or button associated with the hand-held housing of the microbe profiling device.

5. The device of claim 1, wherein the reservoir is configured to controllably release at least a portion of the plurality of the at least one type of signal-generating element onto the skin surface of the individual.

6. The device of claim 1, wherein the reservoir is configured to controllably release at least a portion of the plurality of the at least one type of signal-generating element onto the microbe-capture region on the surface of the substrate.

7. The device of claim 1, wherein the reservoir includes at least one opening, the at least one opening adjacent to at least a portion of the substrate, and wherein the substrate is positioned to traverse the at least one opening defined by the reservoir to make contact with at least a portion of the plurality of the at least one type of signal-generating element.

8. The device of claim 1, wherein the epidermis-engaging component of the device head comprises a brush head.

9. The device of claim 1, wherein the epidermis-engaging component of the device head comprises at least one bladed surface.

10. The device of claim 1, wherein the epidermis-engaging component of the device head comprises at least one of a pad or abrasive surface.

11. The device of claim 1, wherein the at least one motivatable component of the hand-held housing comprises at least one rotatable disc or reel.

12. The device of claim 1, further comprising:
a motor operably coupled to the at least one motivatable component, the motor including circuitry to drive the at least one motivatable component.

13. The device of claim 1, wherein the substrate disposed in relation to the at least one motivatable component comprises an elongated flexible strip disposed in relation to the at least one motivatable component.

14. The device of claim 1, wherein the substrate disposed in relation to the at least one motivatable component comprises a disc shaped material disposed in relation to the at least one motivatable component.

15. The device of claim 1, wherein the substrate is disposed on an outer surface of at least one rotatable component and configured to move past the opening defined by the hand-held housing.

16. The device of claim 1, wherein the microbe capture region on the surface of the substrate includes at least one of an adhesive, an adsorbent, or an absorbent.

17. The device of claim 1, wherein the microbe capture region on the surface of the substrate includes a plurality of specific microbe-binding elements, wherein the specific microbe-binding elements specifically interact with at least one of the at least one type of microbe from the skin surface of the individual.

18. The device of claim 17, wherein the plurality of specific microbe-binding elements comprises at least one of a plurality of specific microbe-binding antibodies or a plurality of specific microbe-binding ligands.

19. The device of claim 17, wherein the plurality of specific microbe-binding elements comprises a plurality of specific 16S rRNA-binding elements.

20. The device of claim 1, wherein a first type of signal-generating element is configured to interact with a first type of microbe and a second type of signal-generating element is configured to interact with a second type of microbe, wherein the first type of signal-generating element emits or reflects a first signal type and the second type of signal-generating element emits or reflects a second signal type.

21. The device of claim 1, wherein the at least one type of signal-generating element comprises at least one type of chromogenic signal-generating element configured to emit or reflect a chromogenic signal.

22. The device of claim 1, wherein the at least one type of signal-generating element comprises at least one type of fluorogenic signal-generating element configured to emit a fluorescent signal.

23. The device of claim 1, wherein the at least one type of signal-generating element comprises at least one type of electromagnetic signal-generating element.

24. The device of claim 1, wherein the at least one type of signal-generating element comprises at least one type of radiofrequency signal-generating element.

25. The device of claim 1, wherein each of the at least one type of signal-generating element is coupled to at least one specific-microbe binding element.

26. The device of claim 1, wherein the location-capture component comprises an image capture device.

27. The device of claim 1, wherein the location-capture component comprises a fiducial reader.

28. The device of claim 1, wherein the at least one sensor component comprises at least one of an optical sensor component, a fluorescence sensor component, an electromagnetic energy sensor component, or a radiofrequency sensor component.

29. The device of claim 1, wherein the at least one sensor component includes a directed energy source, the directed energy source configured to emit directed energy to elicit one or more signals from the at least one type of signal-generating element.

30. The device of claim 1, wherein the computing device includes
circuitry configured to receive the sensor output from the at least one sensor component, the sensor output including information associated with at least one property of the detected one or more signals emitted or reflected from the at least one type of signal-generating element interacting with the at least one type of microbe captured on the microbe-capture region of the substrate from said one or more regions of the skin surface of the individual;
circuitry configured to generate a digital alignment between the location of said one or more regions of the skin surface of the individual and the detected one or more signals emitted or reflected from the at least one type of signal-generating element interacting with the at least one type of microbe captured on the microbe-capture region of the substrate from said one or more regions of the skin surface of the individual;
circuitry configured to generate a microbe profile of the individual based on the digital alignment, the microbe profile of the individual including a spatial distribution and an identity of the at least one type of microbe on the skin surface of the individual; and
circuitry configured to report the microbe profile of the individual to a user.

31. The device of claim 30, wherein the computing component includes
circuitry configured to generate a recommended treatment regimen based on the microbe profile of the individual; and
circuitry configured to report the recommended treatment regimen to the user.

32. The device of claim 30, wherein the computing component includes
circuitry configured to compare the microbe profile of the individual with a reference microbe profile;
circuitry configured to generate a recommended treatment regimen for the individual based on the comparison; and
circuitry configured to report the recommended treatment regimen to the user.

33. The device of claim 1, further comprising:
at least one second reservoir, the at least one second reservoir configured to hold and controllably release at least one agent.

34. The device of claim 33, wherein the at least one second reservoir is configured to controllably release the at least one agent onto the skin surface of the individual.

35. The device of claim 33, wherein the at least one agent comprises at least one therapeutic agent.

36. The device of claim 33, wherein the at least one agent comprises at least one lysing agent, the lysing agent configured to lyse the at least one type of microbe.

37. A method of profiling microbiota of a skin surface, comprising:
releasing at least one type of signal-generating element on to the skin surface of an individual, the at least one type of signal-generating element configured to associate with at least one type of microbe on the skin surface of the individual;
dislodging the at least one type of microbe from one or more regions of the skin surface of the individual with an epidermis-engaging component of a hand-held microbe profiling device, the hand-held microbe profiling device including
a device head including the epidermis-engaging component and at least one access opening; and
a hand-held housing, at least a portion of the hand-held housing defining an opening aligned with the at least one access opening of the device head, the hand-held housing including
at least one motivatable component;
a substrate disposed in relation to the at least one motivatable component and positioned in operable communication with the opening defined by the hand-held housing, a surface of the substrate including a microbe-capture region;
a location-capture component including circuitry to determine a location of said one or more regions of the skin surface of the individual;
at least one sensor component; and
a computing component including a microprocessor, the computing component including circuitry;
determining a location of said one or more regions of the skin surface of the individual with the location-capture component of the hand-held microbe profiling device as the epidermis-engaging component of the device head contacts said one or more regions of the skin surface of the individual and generating a location output, the location output including information associated with the location of said one or more regions of the skin surface of the individual;

capturing the dislodged at least one type of microbe through the at least one access opening of the device head and the aligned opening defined by the hand-held housing and onto a portion of the microbe-capture region of the substrate;

analyzing the microbe-capture region on the substrate with the at least one sensor component to detect one or more signals emitted or reflected from the at least one type of signal-generating element associated with the at least one type of microbe captured on the microbe-capture region from the skin surface of the individual and transforming the detected one or more signals into a sensor output;

receiving the location output with the computing component and generating a digital alignment of the location of said one or more regions of the skin surface of the individual with the one or more signals emitted or reflected from the at least one type of signal-generating element associated with the at least one type of microbe captured on the microbe-capture region from said one or more regions of the skin surface of the individual; and generating a microbe profile from the digital alignment with the computing component, the microbe profile including a spatial distribution and identity of the at least one type of microbe on the skin surface of the individual.

38. The device of claim 37, further comprising:

controllably releasing the at least one type of signal-generating element onto the skin surface of the individual from a reservoir incorporated into the hand-held microbe profiling device.

39. A method of profiling microbiota of a skin surface, comprising:

dislodging at least one type of microbe from one or more regions of the skin surface of an individual with an epidermis-engaging component of a hand-held microbe profiling device, the hand-held microbe profiling device including a device head including the epidermis-engaging component and at least one access opening; and a hand-held housing, at least a portion of the hand-held housing defining an opening aligned with the at least one access opening of the device head, the hand-held housing including at least one motivatable component;

a reservoir including a plurality of at least one type of signal-generating element, the at least one type of signal-generating element configured to associate with the at least one type of microbe;

a substrate disposed in relation to the at least one motivatable component and positioned in operable communication with the opening defined by the hand-held housing, a surface of the substrate including a microbe-capture region;

a location-capture component including circuitry to determine a location of said one or more regions of the skin surface of the individual;

at least one sensor component; and a computing component including a microprocessor, the computing component including circuitry;

determining a location of said one or more regions of the skin surface of the individual with the location-capture component of the hand-held microbe profiling device as the epidermis-engaging component of the device head contacts said one or more regions of the skin surface of the individual and generating a location output, the location output including information associated with the location of said one or more regions of the skin surface of the individual;

capturing the dislodged at least one type of microbe through the at least one access opening of the device head and the aligned opening defined by the hand-held housing and onto a portion of the microbe-capture region of the substrate;

releasing the at least one type of signal-generating element from the reservoir and onto the substrate including the microbe-capture region and the at least one type of microbe captured thereto;

analyzing the microbe-capture region on the substrate with the at least one sensor component to detect one or more signals emitted or reflected from the at least one type of signal-generating element associated with the at least one type of microbe captured on the microbe-capture region from the skin surface of the individual and transforming the detected one or more signals into a sensor output;

receiving the location output with the computing component and generating a digital alignment of the location of said one or more regions of the skin surface of the individual with the one or more signals emitted or reflected from the at least one type of signal-generating element associated with the at least one type of microbe captured on the microbe-capture region from said one or more regions of the skin surface of the individual; and generating a microbe profile from the digital alignment with the computing component, the microbe profile including a spatial distribution and identity of the at least one type of microbe on the skin surface of the individual.

40. The method of claim 39, further comprising:

releasing a lysing agent from a second reservoir incorporated into the hand-held microbe profiling device, the lysing agent configured to lyse the at least one type of microbe.

41. The method of claim 39, wherein releasing the lysing agent from the second reservoir comprises releasing the lysing agent from the second reservoir and onto the substrate including the microbe-capture region and the at least one type of microbe captured thereto.

* * * * *